(12) United States Patent
Shelton, IV et al.

(10) Patent No.: US 11,877,897 B2
(45) Date of Patent: Jan. 23, 2024

(54) SITUATIONAL AWARENESS OF INSTRUMENTS LOCATION AND INDIVIDUALIZATION OF USERS TO CONTROL DISPLAYS

(71) Applicant: Cilag GmbH International, Zug (CH)

(72) Inventors: Frederick E. Shelton, IV, New Vienna, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 438 days.

(21) Appl. No.: 17/062,513

(22) Filed: Oct. 2, 2020

(65) Prior Publication Data
US 2022/0104912 A1    Apr. 7, 2022

(51) Int. Cl.
| A61B 90/00 | (2016.01) |
| A61B 34/00 | (2016.01) |
| A61B 90/90 | (2016.01) |
| G16H 40/63 | (2018.01) |

(52) U.S. Cl.
CPC .............. *A61B 90/37* (2016.02); *A61B 34/25* (2016.02); *A61B 90/90* (2016.02); *G16H 40/63* (2018.01); *A61B 2034/258* (2016.02); *A61B 2090/368* (2016.02); *A61B 2090/372* (2016.02)

(58) Field of Classification Search
CPC ........ A61B 2034/258; A61B 2090/368; A61B 2090/372; A61B 34/25; A61B 90/37; A61B 90/90; G16H 20/40; G16H 40/20; G16H 40/40; G16H 40/63; Y02A 90/10
See application file for complete search history.

(56) References Cited

U.S. PATENT DOCUMENTS

| 5,754,192 A | 5/1998 | Sugaya |
| 6,451,015 B1 | 9/2002 | Rittman et al. |
| 6,847,336 B1 | 1/2005 | Lemelson et al. |
| 7,032,798 B2 | 4/2006 | Whitman et al. |
| 7,164,940 B2 | 1/2007 | Hareyama et al. |
| 7,496,395 B2 | 2/2009 | Serov et al. |
| 7,667,592 B2 | 2/2010 | Ohyama et al. |
| 7,670,334 B2 | 3/2010 | Hueil et al. |

(Continued)

FOREIGN PATENT DOCUMENTS

| CA | 3089858 A1 | 8/2019 |
| EP | 2491872 A1 | 8/2012 |

(Continued)

OTHER PUBLICATIONS

U.S. Appl. No. 16/729,747, filed Dec. 31, 2019, Ethicon LLC.
(Continued)

*Primary Examiner* — George Manuel
(74) *Attorney, Agent, or Firm* — Condo Roccia Koptiw LLP

(57) ABSTRACT

A surgical hub for controlling a display using situational awareness of a medical instrument may be provided. A user, a medical instrument, and a location within an operating room may be determined. Contextual data associated with the medical instrument may be determined based on the user, the medical instrument, and the location within the operating room. A display instruction may be sent to a display that may instruct the display to be configured in accordance with contextual data associated with the medical instrument.

19 Claims, 77 Drawing Sheets

(56) References Cited

U.S. PATENT DOCUMENTS

| | | |
|---|---|---|
| 7,803,151 B2 | 9/2010 | Whitman |
| 7,833,219 B2 | 11/2010 | Tashiro et al. |
| 7,839,354 B2 | 11/2010 | Moriwaki |
| 8,157,145 B2 | 4/2012 | Shelton et al. |
| 8,255,045 B2 | 8/2012 | Gharib et al. |
| 8,476,227 B2 | 7/2013 | Kaplan et al. |
| 8,523,043 B2 | 9/2013 | Ullrich et al. |
| 8,608,045 B2 | 12/2013 | Smith et al. |
| 8,851,354 B2 | 10/2014 | Swensgard et al. |
| 8,918,207 B2 | 12/2014 | Prisco |
| 8,960,519 B2 | 2/2015 | Whitman et al. |
| 9,011,427 B2 | 4/2015 | Price et al. |
| 9,072,535 B2 | 7/2015 | Shelton, IV et al. |
| 9,123,155 B2 | 9/2015 | Cunningham et al. |
| 9,250,172 B2 | 2/2016 | Harris et al. |
| 9,283,054 B2 | 3/2016 | Morgan et al. |
| 9,345,481 B2 | 5/2016 | Hall et al. |
| 9,516,239 B2 | 12/2016 | Blanquart et al. |
| 9,538,962 B1 | 1/2017 | Hannaford et al. |
| 9,582,055 B2 | 2/2017 | De Jong et al. |
| 9,743,016 B2 | 8/2017 | Nestares et al. |
| 9,777,913 B2 | 10/2017 | Talbert et al. |
| 9,913,642 B2 | 3/2018 | Leimbach et al. |
| 10,492,783 B2 | 12/2019 | Shelton, IV et al. |
| 10,639,037 B2 | 5/2020 | Shelton, IV et al. |
| 10,695,081 B2 | 6/2020 | Shelton, IV et al. |
| 10,881,399 B2 | 1/2021 | Shelton et al. |
| 10,912,567 B2 | 2/2021 | Shelton, IV et al. |
| 10,987,178 B2 | 4/2021 | Shelton, IV et al. |
| 11,123,074 B2 | 9/2021 | Adams et al. |
| 11,185,331 B2 | 11/2021 | Adams et al. |
| 11,284,963 B2 | 3/2022 | Shelton, IV et al. |
| 2004/0108825 A1 | 6/2004 | Lee et al. |
| 2005/0033117 A1 | 2/2005 | Ozaki et al. |
| 2005/0128184 A1 | 6/2005 | Mcgreevy |
| 2005/0134525 A1 | 6/2005 | Tanghe et al. |
| 2005/0206583 A1 | 9/2005 | Lemelson et al. |
| 2006/0004286 A1* | 1/2006 | Chang .......... A61B 90/16 606/198 |
| 2006/0076385 A1 | 4/2006 | Etter et al. |
| 2006/0082542 A1 | 4/2006 | Morita et al. |
| 2006/0109238 A1 | 5/2006 | Lau et al. |
| 2006/0184160 A1 | 8/2006 | Ozaki et al. |
| 2006/0273135 A1 | 12/2006 | Beetel |
| 2007/0013336 A1 | 1/2007 | Nowlin et al. |
| 2007/0055304 A1 | 3/2007 | Whitman |
| 2007/0151390 A1 | 7/2007 | Blumenkranz et al. |
| 2007/0173689 A1 | 7/2007 | Ozaki et al. |
| 2007/0225690 A1 | 9/2007 | Sekiguchi et al. |
| 2008/0319275 A1 | 12/2008 | Chiu et al. |
| 2009/0046146 A1 | 2/2009 | Hoyt et al. |
| 2009/0090763 A1 | 4/2009 | Zemlok et al. |
| 2009/0128084 A1 | 5/2009 | Johnson et al. |
| 2009/0248022 A1 | 10/2009 | Falkenstein et al. |
| 2010/0096431 A1 | 4/2010 | Smith et al. |
| 2010/0131482 A1 | 5/2010 | Linthicum et al. |
| 2011/0181394 A1 | 7/2011 | Blair |
| 2012/0069131 A1 | 3/2012 | Abelow |
| 2012/0116365 A1 | 5/2012 | Price et al. |
| 2012/0138658 A1 | 6/2012 | Ullrich et al. |
| 2012/0182409 A1 | 7/2012 | Moriyama et al. |
| 2012/0211542 A1 | 8/2012 | Racenet |
| 2012/0248167 A1 | 10/2012 | Flanagan et al. |
| 2012/0253329 A1 | 10/2012 | Zemlok et al. |
| 2013/0116218 A1 | 5/2013 | Kaplan et al. |
| 2013/0197531 A1 | 8/2013 | Boukhny et al. |
| 2013/0245456 A1 | 9/2013 | Ferguson et al. |
| 2014/0018637 A1 | 1/2014 | Bennett et al. |
| 2014/0066700 A1 | 3/2014 | Wilson et al. |
| 2014/0087999 A1 | 3/2014 | Kaplan et al. |
| 2014/0160002 A1 | 6/2014 | Dent |
| 2014/0160259 A1 | 6/2014 | Blanquart et al. |
| 2014/0160260 A1 | 6/2014 | Blanquart et al. |
| 2014/0160318 A1 | 6/2014 | Blanquart et al. |
| 2014/0160319 A1 | 6/2014 | Nestares et al. |
| 2014/0166728 A1 | 6/2014 | Swayze et al. |
| 2014/0201126 A1 | 7/2014 | Zadeh et al. |
| 2014/0214311 A1 | 7/2014 | Stevens et al. |
| 2014/0263541 A1 | 9/2014 | Leimbach et al. |
| 2014/0263551 A1 | 9/2014 | Hall et al. |
| 2014/0263552 A1 | 9/2014 | Hall et al. |
| 2014/0267655 A1 | 9/2014 | Richardson et al. |
| 2014/0268860 A1 | 9/2014 | Talbert et al. |
| 2015/0125447 A1 | 5/2015 | Heider |
| 2015/0157416 A1 | 6/2015 | Andersson |
| 2015/0182220 A1 | 7/2015 | Yates et al. |
| 2015/0223890 A1 | 8/2015 | Miller et al. |
| 2015/0342621 A1* | 12/2015 | Jackson, III ........ A61B 1/00087 600/595 |
| 2016/0066915 A1 | 3/2016 | Baber et al. |
| 2016/0066916 A1 | 3/2016 | Overmyer et al. |
| 2016/0100839 A1 | 4/2016 | Marczyk et al. |
| 2016/0148052 A1 | 5/2016 | Tsuda et al. |
| 2016/0154620 A1 | 6/2016 | Tsuda et al. |
| 2016/0171330 A1 | 6/2016 | Mentese et al. |
| 2016/0171947 A1 | 6/2016 | Chen |
| 2016/0249919 A1 | 9/2016 | Savage et al. |
| 2016/0253472 A1 | 9/2016 | Pedersen et al. |
| 2016/0256156 A1 | 9/2016 | Shelton, IV et al. |
| 2016/0256184 A1 | 9/2016 | Shelton, IV et al. |
| 2016/0265938 A1 | 9/2016 | Hryb et al. |
| 2016/0332296 A1 | 11/2016 | Kurnianto |
| 2017/0000551 A1 | 1/2017 | Ward et al. |
| 2017/0000575 A1 | 1/2017 | Griffiths et al. |
| 2017/0086914 A1 | 3/2017 | Wiener et al. |
| 2017/0172381 A1 | 6/2017 | Morimoto |
| 2017/0199632 A1 | 7/2017 | Ohmura et al. |
| 2017/0227754 A1 | 8/2017 | Huang |
| 2017/0249431 A1 | 8/2017 | Shelton, IV et al. |
| 2017/0272838 A1 | 9/2017 | Glazer et al. |
| 2017/0296169 A1 | 10/2017 | Yates et al. |
| 2017/0296178 A1 | 10/2017 | Miller et al. |
| 2017/0296213 A1 | 10/2017 | Swensgard et al. |
| 2017/0323062 A1 | 11/2017 | Djajadiningrat et al. |
| 2017/0333033 A1 | 11/2017 | Valentine et al. |
| 2018/0032130 A1 | 2/2018 | Meglan |
| 2018/0098049 A1 | 4/2018 | Sugano et al. |
| 2018/0098768 A1 | 4/2018 | Zhang et al. |
| 2018/0165051 A1 | 6/2018 | Kim et al. |
| 2018/0197624 A1 | 7/2018 | Baerenrodt et al. |
| 2018/0256025 A1 | 9/2018 | Yi et al. |
| 2018/0329504 A1 | 11/2018 | Ziraknejad et al. |
| 2018/0353186 A1 | 12/2018 | Mozdzierz et al. |
| 2018/0360449 A1 | 12/2018 | Shelton, IV et al. |
| 2018/0360452 A1 | 12/2018 | Shelton, IV et al. |
| 2018/0360460 A1 | 12/2018 | Mozdzierz et al. |
| 2019/0000446 A1 | 1/2019 | Shelton, IV et al. |
| 2019/0000464 A1 | 1/2019 | Shelton, IV et al. |
| 2019/0000478 A1 | 1/2019 | Messerly et al. |
| 2019/0020420 A1 | 1/2019 | Zocher et al. |
| 2019/0099180 A1 | 4/2019 | Leimbach et al. |
| 2019/0104919 A1 | 4/2019 | Shelton et al. |
| 2019/0117070 A1 | 4/2019 | Muhsin et al. |
| 2019/0125361 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0183591 A1 | 6/2019 | Johnson et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201025 A1 | 7/2019 | Shelton, IV et al. |
| 2019/0201029 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201044 A1 | 7/2019 | Shelton, IV et al. |
| 2019/0201102 A1 | 7/2019 | Shelton et al. |
| 2019/0201104 A1 | 7/2019 | Shelton et al. |
| 2019/0201115 A1 | 7/2019 | Shelton, IV et al. |
| 2019/0201119 A1 | 7/2019 | Harris et al. |
| 2019/0201122 A1 | 7/2019 | Shelton et al. |

(56) References Cited

U.S. PATENT DOCUMENTS

| | | |
|---|---|---|
| 2019/0201129 A1 | 7/2019 | Shelton et al. |
| 2019/0201136 A1 | 7/2019 | Shelton, IV et al. |
| 2019/0201137 A1 | 7/2019 | Shelton et al. |
| 2019/0201140 A1 | 7/2019 | Shelton et al. |
| 2019/0201141 A1 | 7/2019 | Shelton, IV et al. |
| 2019/0201144 A1 | 7/2019 | Shelton, IV et al. |
| 2019/0201146 A1 | 7/2019 | Shelton, IV et al. |
| 2019/0204201 A1 | 7/2019 | Shelton et al. |
| 2019/0205001 A1 | 7/2019 | Messerly et al. |
| 2019/0206003 A1 | 7/2019 | Harris et al. |
| 2019/0206050 A1 | 7/2019 | Yates et al. |
| 2019/0206555 A1 | 7/2019 | Morgan et al. |
| 2019/0206562 A1 | 7/2019 | Shelton et al. |
| 2019/0206563 A1 | 7/2019 | Shelton, IV et al. |
| 2019/0206564 A1 | 7/2019 | Shelton et al. |
| 2019/0206565 A1 | 7/2019 | Shelton, IV |
| 2019/0206569 A1 | 7/2019 | Shelton, IV et al. |
| 2019/0250873 A1 | 8/2019 | Blume et al. |
| 2019/0314015 A1 | 10/2019 | Shelton, IV et al. |
| 2019/0388137 A1 | 12/2019 | Henrywood |
| 2020/0030044 A1 | 1/2020 | Wang et al. |
| 2020/0046208 A1 | 2/2020 | Kasai et al. |
| 2020/0078078 A1 | 3/2020 | Henderson et al. |
| 2020/0078079 A1 | 3/2020 | Morgan et al. |
| 2020/0090412 A1 | 3/2020 | Harviainen |
| 2020/0120308 A1 | 4/2020 | Mcmillan et al. |
| 2020/0162664 A1 | 5/2020 | Maeda et al. |
| 2020/0188057 A1 | 6/2020 | Brandao et al. |
| 2020/0214571 A1 | 7/2020 | Bradbury et al. |
| 2020/0219319 A1 | 7/2020 | Lashmar et al. |
| 2020/0281790 A1 | 9/2020 | Augustine et al. |
| 2020/0342228 A1 | 10/2020 | Prevrhal et al. |
| 2020/0350063 A1 | 11/2020 | Thornton et al. |
| 2020/0356255 A1 | 11/2020 | Qing et al. |
| 2020/0405304 A1 | 12/2020 | Mozdzierz et al. |
| 2020/0405439 A1 | 12/2020 | Shelton, IV et al. |
| 2021/0007574 A1 | 1/2021 | Hirayama et al. |
| 2021/0015461 A1 | 1/2021 | Karasawa |
| 2021/0060243 A1 | 3/2021 | Dave et al. |
| 2021/0077110 A1 | 3/2021 | Adams et al. |
| 2021/0077111 A1 | 3/2021 | Adams et al. |
| 2021/0077112 A1 | 3/2021 | Adams et al. |
| 2021/0113269 A1 | 4/2021 | Vilsmeier et al. |
| 2021/0137581 A1 | 5/2021 | Reid et al. |
| 2021/0169578 A1 | 6/2021 | Calloway et al. |
| 2021/0196384 A1 | 7/2021 | Shelton, IV et al. |
| 2021/0196423 A1 | 7/2021 | Shelton, IV et al. |
| 2021/0196425 A1 | 7/2021 | Shelton, IV et al. |
| 2021/0205027 A1 | 7/2021 | Leist |
| 2021/0240279 A1 | 8/2021 | Harviainen et al. |
| 2021/0307833 A1 | 10/2021 | Farley et al. |
| 2021/0401533 A1 | 12/2021 | Im |
| 2022/0022982 A1 | 1/2022 | Hares et al. |
| 2022/0104694 A1 | 4/2022 | Shelton, IV et al. |
| 2022/0104713 A1 | 4/2022 | Shelton, IV |
| 2022/0104765 A1 | 4/2022 | Shelton, IV et al. |
| 2022/0104806 A1 | 4/2022 | Shelton, IV et al. |
| 2022/0104807 A1 | 4/2022 | Shelton, IV et al. |
| 2022/0104813 A1 | 4/2022 | Shelton, IV et al. |
| 2022/0104814 A1 | 4/2022 | Shelton, IV et al. |
| 2022/0104820 A1 | 4/2022 | Shelton, IV et al. |
| 2022/0104821 A1 | 4/2022 | Shelton, IV et al. |
| 2022/0104822 A1 | 4/2022 | Shelton, IV et al. |
| 2022/0104843 A1 | 4/2022 | Shelton, IV et al. |
| 2022/0104867 A1 | 4/2022 | Shelton, IV et al. |
| 2022/0104889 A1 | 4/2022 | Shelton, IV et al. |
| 2022/0104896 A1 | 4/2022 | Shelton, IV et al. |
| 2022/0104897 A1 | 4/2022 | Shelton, IV et al. |
| 2022/0104908 A1 | 4/2022 | Shelton, IV et al. |
| 2022/0104910 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0108783 A1 | 4/2022 | Shelton, IV et al. |
| 2022/0108788 A1 | 4/2022 | Shelton, IV et al. |
| 2022/0108789 A1 | 4/2022 | Shelton, IV et al. |
| 2022/0246287 A1 | 8/2022 | Dawson et al. |

FOREIGN PATENT DOCUMENTS

| | | |
|---|---|---|
| EP | 2659852 A2 | 11/2013 |
| EP | 3061405 A1 | 8/2016 |
| EP | 3064141 A1 | 9/2016 |
| EP | 3412225 A1 | 12/2018 |
| EP | 3449800 A1 | 3/2019 |
| EP | 3466348 A2 | 4/2019 |
| EP | 3506273 A1 | 7/2019 |
| EP | 3506299 A1 | 7/2019 |
| EP | 3547324 A1 | 10/2019 |
| EP | 3628207 A1 | 4/2020 |
| KR | 10-2001-0001630 A | 1/2001 |
| WO | 00/70529 A2 | 11/2000 |
| WO | 2008/135736 A1 | 11/2008 |
| WO | 2015/125447 A1 | 8/2015 |
| WO | 2016/171947 A1 | 10/2016 |
| WO | 2019/130108 A1 | 7/2019 |
| WO | 2019/133056 A1 | 7/2019 |
| WO | 2020/101283 A1 | 5/2020 |
| WO | 2020/154351 A1 | 7/2020 |

OTHER PUBLICATIONS

U.S. Appl. No. 16/729,778, filed Dec. 31, 2019, Ethicon LLC.
U.S. Appl. No. 16/729,807, filed Dec. 31, 2019, Ethicon LLC.
U.S. Appl. No. 17/062,504, filed Oct. 2, 2020, Shelton IV, et al..
U.S. Appl. No. 17/062,517, filed Oct. 2, 2020, Shelton IV, et al..
U.S. Appl. No. 17/062,520, filed Oct. 2, 2020, Shelton IV, et al..
U.S. Appl. No. 17/062,519, filed Oct. 2, 2020, Shelton IV, et al..
U.S. Appl. No. 17/062,516, filed Oct. 2, 2020, Shelton IV, et al..
"FPGA Fundamentals", Available at <https://www.ni.com/en-us/innovations/white-papers/08/fpga-fundamentals.html >, Jun. 17, 2020, pp. 1-9.
Alsos et al., "Interaction Techniques for Using Handhelds and PCs Together in a Clinical Setting", Dept of Computer and Information Science; Norwegian University of Science and Technology, Oct. 14-18, 2006, pp. 125-134.
Google Scholar, "Google Scholar", 2 pages.
Qamar, Rahil, "Semantic Mapping of Clinical Model Data To Biomedical Terminologies To Facilitate Interoperability", A these submitted to the University of Manchester, 2008, 260 pages.
Slade, William G., "The Fast Fourier Transform in Hardware: A Tutorial Based on an FPGA Implementation", Available at <http://web.mit.edu/>, Mar. 21, 2013, 27 pages.

\* cited by examiner

SITUATIONAL AWARENESS OF INSTRUMENTS LOCATION AND INDIVIDUALIZATION OF USERS TO CONTROL DISPLAYS

CROSS-REFERENCE TO RELATED APPLICATIONS

This application is related to the following, the contents of each of which are incorporated by reference herein:

U.S. patent application Ser. No. 17/062,513, filed Oct. 2, 2020, entitled "METHOD FOR OPERATING TIERED OPERATION MODES IN A SURGICAL SYSTEM," filed herewith;

U.S. patent application Ser. No. 17/062,517, filed Oct. 2, 2020, entitled "SHARED SITUATIONAL AWARENESS OF THE DEVICE ACTUATOR ACTIVITY TO PRIORITIZE CERTAIN ASPECTS OF DISPLAYED INFORMATION," filed herewith;

U.S. patent application Ser. No. 17/062,520, filed Oct. 2, 2020, entitled "MONITORING OF USER VISUAL GAZE TO CONTROL WHICH DISPLAY SYSTEM DISPLAYS THE PRIMARY INFORMATION," filed herewith;

U.S. patent application Ser. No. 17/062,519, filed Oct. 2, 2020, entitled "RECONFIGURATION OF DISPLAY SHARING," filed herewith; and U.S. patent application Ser. No. 17/062,516, filed Oct. 2, 2020, entitled "CONTROL A DISPLAY OUTSIDE THE STERILE FIELD FROM A DEVICE WITHIN THE STERILE FIELD," filed herewith.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cystoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

A surgical hub and/or medical instrument may be provided for controlling a display using situational awareness. The surgical hub and/or medical instrument may comprise a memory and a processor. The processor may be configured to perform a number of actions. A user, a medical instrument, and a location within an operating room may be determined. Contextual data (e.g. contextual information) associated with the medical instrument may be determined based on the user, the medical instrument, and the location within the operating room. A display instruction may be sent to a display that may instruct the display to be configured in accordance with contextual data (e.g. contextual information) associated with the medical instrument. The display may be a primary display or a secondary display.

A surgical hub and/or medical instrument may be provided for controlling a display using situational awareness. The surgical hub and/or medical instrument may comprise a memory and a processor. The processor may be configured to perform a number of actions. A first user, a medical instrument, and a location within an operating room may be determined. Contextual data (e.g. contextual information) associated with the medical instrument may be determined based on the first user, the medical instrument, and the location within the operating room. The surgical hub may determine that the medical instrument is being moved from a second user to the first user within or at a threshold distance of the location. The surgical hub may determine that that the location is near a patient. The surgical hub may set a display instruction to indicate that the first user is controlling the medical instrument and that the medical instrument will be used to perform a task of a surgical procedure. A display instruction may be sent to a display that may instruct the display to be configured in accordance with contextual data (e.g. contextual information) associated with the medical instrument. The primary display may be a primary display or a secondary display.

A surgical hub and/or medical instrument may be provided for controlling a display using situational awareness. The surgical hub may comprise a memory and a processor. The processor may be configured to perform a number of actions. A user, a first medical instrument, and a location within an operating room may be determined. A contextual data (e.g. contextual information) associated with the first medical instrument may be determined based on the user, the first medical instrument, and the location within the operating room. The surgical hub may determine that the first medical instrument, a second medical instrument, and the user within a threshold distance of the location. The surgical hub may determine that the user is exchanging the second medical instrument for the first medical instrument. The surgical hub may set the display instruction to indicate that the second medical instrument is being exchanged with the first medical instrument. In an example, a display instruction may be sent to the display that may instruct the display to be configured in accordance with contextual data (e.g. contextual information) associated with the medical instrument. The display may be a primary display or a secondary display.

A surgical hub and/or medical instrument may be provided for controlling a display using situational awareness. The surgical hub may comprise a memory and a processor. The processor may be configured to perform a number of actions. A user, a first medical instrument, and a location within an operating room may be determined. A first contextual data (e.g. contextual information) associated with the first medical instrument may be determined based on the user, the first medical instrument, and the location within the operating room. The surgical hub may determine that the first medical instrument, a second medical instrument, and the user within a threshold distance of the location. The surgical hub may determine that the user is exchanging the second medical instrument for the first medical instrument. The surgical hub may determine a second contextual data (e.g. contextual information) associated with the second medical instrument based on the user, the second medical instrument, and the location within the operating room. The surgical hub may set the first display instruction to indicate that the second medical instrument is being exchanged with the first medical instrument. A display instruction may be sent to the first display that may instruct the first display to be configured in accordance with first contextual data (e.g. contextual information) associated with the first medical instrument by displaying instrument data or an instruction for using the first medical instrument. The surgical hub send a second display instruction to a second display that instructs the second display to be configured in accordance with the second contextual data (e.g. contextual information) by turning off the second display or displaying one or more of a reloading instruction for the second medical instrument, a cleaning instruction for the second medical instrument, or an instrument instruction for the second medical instrument. The first display and the second display may be a primary display or a secondary display.

A surgical hub and/or medical instrument for prioritizing data on a display using situational awareness may be provided. The surgical hub and/or medical instrument may comprise a memory and a processor. The processor may be configured to perform a number of actions. A surgical procedure may be determined. A first surgical task that uses a medical instrument during a surgical procedure may be determined based on a contextual data. A second surgical task that uses the medical instrument may be determined based on the first surgical task and the contextual data. A message that may instruct a display to prioritize a display data associated with the second surgical task may be sent. The message may be a first message and a second message may be sent to the medical instrument to instruct the medical instrument to be configured in accordance with the second surgical task.

A surgical hub and/or medical instrument for prioritizing data on a display using situational awareness may be provided. The surgical hub and/or medical instrument may comprise a memory and a processor. The processor may be configured to perform a number of actions. A first surgical task that uses a medical instrument during a surgical procedure may be determined based on a contextual data. Instrument data may be received from the medical instrument and may be associated with the first surgical task. A second surgical task that uses the medical instrument may be determined based on the first surgical task, the instrument data, and the surgical procedure. A message may be sent that may instruct a display prioritize a display data associated with the second surgical task.

A surgical hub and/or medical instrument for prioritizing data on a display using situational awareness may be provided. The surgical hub and/or medical instrument may comprise a memory and a processor. The processor may be configured to perform a number of actions. A first surgical task that uses a medical instrument during a surgical procedure may be determined based on a contextual data. Instrument data may be received from the medical instrument and may be associated with the first surgical task. An error may be determined by analyzing the instrument data from the medical instrument using the contextual data. A second surgical task that uses the medical instrument may be determined based on the first surgical task, the instrument data, and the surgical procedure. A message may be sent that may instruct a display prioritize a display data associated with the second surgical task. The display data may indicate the error.

A surgical hub and/or medical instrument for prioritizing data on a display using situational awareness may be provided. The surgical hub and/or medical instrument may comprise a memory and a processor. A first surgical task that uses a medical instrument during a surgical procedure may be determined. An error that has occurred during the surgical procedure may be determined based on a contextual data. A second surgical task that uses the medical instrument may be determined based on the error, the contextual data, and the surgical procedure. A first message that may instruct a first display to display an indication of the error may be sent. A second message that may instruct a second display to a display data associated with the second surgical task may be sent. The first display may be a primary display, and the second display may be a secondary display associated with the medical instrument.

A surgical hub and/or medical instrument for prioritizing data on a display using situational awareness may be provided. The medical instrument may comprise a display and a memory. A contextual data may be determined. A surgical procedure may be determined. A surgical task that uses the medical instrument during a surgical procedure may be determined based on the contextual data. Display data may be determined. The display data may be associated with the surgical task and may be relevant to a user that may perform the surgical task that uses the medical instrument. A message may be sent. The message may instruct the display to prioritize the display data associated with the surgical task.

A surgical hub and/or medical instrument for prioritizing data on a display using situational awareness may be provided. The medical instrument may comprise a display and a memory. A first contextual data may be determined. A surgical procedure may be determined. A surgical task that uses the medical instrument during a surgical procedure may be determined based on the contextual data. A first display data may be determined. The first display data may be associated with the surgical task and may be relevant to a user that may perform the surgical task that uses the medical instrument. A first message may be sent. The first message may instruct the display to prioritize the first display data associated with the surgical task. An error that may have occurred during the surgical procedure may be determined based on a second contextual data. A second surgical task that uses the medical instrument may be determined based on the error. A second display data may be determined. The second display data that may be associated with the second surgical task and that may be relevant to the user that will perform the second surgical task that uses the medical instrument. A second message may be sent. The second message may instruct the display to reprioritize the second display data over the first display data.

A surgical hub and/or medical instrument for displaying information on a display based on a visual focus of a user may be provided. The surgical hub and/or medical instrument may comprise a memory and a processor. The processor may be configured to perform a number of actions. A display that is within a visual focus of the user may be determined. A surgical task that uses a medical instrument during a surgical procedure may be determined. Display data may be determined. The display data may be relevant to the user based on contextual data and the surgical task. A message may be sent that instructs the display to display the display data.

A surgical hub and/or medical instrument for displaying information on a display based on a visual focus of a user may be provided. The surgical hub and/or medical instrument may comprise a memory and a processor. The processor may be configured to perform a number of actions. A display that is within a visual focus of the user may be determined. An image or a video may be received from a camera. A geometric three-dimensional data set may be generated from the image or the video. One or more of a head orientation for the user and a line of sight for the user may be determined using the geometric three-dimensional data set. The visual focus of the user may be determined by using one or more of the head orientation for the user and the line of sight for the user. A surgical task that uses a medical instrument during a surgical procedure may be determined. Display data may be determined. The display data may be relevant to the user based on contextual data and the surgical task. A message may be sent that instructs the display to display the display data.

A surgical hub and/or medical instrument for displaying information on a display based on a visual focus of a user may be provided. The surgical hub and/or medical instrument may comprise a memory and a processor. The processor may be configured to perform a number of actions. A display that is within a visual focus of a first user may be determined. A surgical task that uses a medical instrument during a surgical procedure may be determined. Display data may be determined. The display data may be relevant to the first user based on contextual data and the surgical task. A message may be sent that instructs the display to display the display data.

A surgical hub and/or medical instrument for displaying information on a display based on a visual focus of a user may be provided. The surgical hub and/or medical instrument may comprise a memory and a processor. The processor may be configured to perform a number of actions. It may be determined that the display may be within a first focus of a first user and a second focus of a second user. Display data for the display may be determined based on a first surgical task for the first user and a second surgical task for the second user. A message instructing the display to display the display data may be sent.

A surgical hub and/or medical instrument for displaying information on a display based on a visual focus of a user may be provided. The surgical hub and/or medical instrument may comprise a memory and a processor. The processor may be configured to perform a number of actions. A first display and a second display that may be within a first focus of a first user and a second focus of a second user may be determined. It may be determined that that a first surgical task associated with the first user has a higher priority than a second surgical task associated with the second user. A first contextual data may be determined based on the first surgical task and a second contextual data may be determined based on the second surgical task. A first message instructing the first display to display the first contextual data may be sent and a second message instructing the second display to display the second contextual data may be sent.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first data based on the surgical task may be determined. A command from the user that indicates a preference for a second data may be determined. The command may be one or more of a voice command, a gesture, and a tactile control command. A display data may be determined. The display data may include the first data and the second data and may provide priority to the second data over the first data. A message comprising instructions for a display to display the display data may be sent. The message may be sent to the display. The display and/or an identity of the display may be determined based on the command from the user that indicates the preference for the second data. The first data may be a first contextual data and the second data may be a second contextual data.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first contextual data to be displayed on a first display may be determined. A command from a user may be determined. The command is one or more of a voice command, a command gesture, and a tactile control command. The command may indicate a preference for a second contextual data to be displayed on a second display.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first contextual data to be displayed on a first display may be determined. A command from a user may be determined. The command is one or more of a voice command, a command gesture, and a tactile control command. The command may indicate a preference for a second contextual data to be displayed on a second display. A visual focus of the user may be determined. It may be determined that the second display is within the visual focus of the user. A message instructing the second display to display the second contextual data may be sent.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first contextual data to be displayed on a first display may be determined. A command from a user may be determined. The command is one or more of a voice command, a command gesture, and a tactile control command. The command may indicate a preference for a second contextual data to be displayed on a second display.

An image or a video may be received from a camera. A geometric three-dimensional data may be generated from the image or the video. One or more of a head orientation for the user and a line of sight for the user using the geometric three-dimensional data may be determined. A visual focus of the user by using one or more of the head orientation for the user and the line of sight for the user may be determined. The second display may be determined using the visual focus. A message instructing the second display to display the second contextual data may be sent. It may be determined that the second display is displaying a third contextual data associated with a second user. The message may instruct the second display to remove the third contextual data and display the second contextual data.

A surgical hub and/or medical instrument for controlling a display outside a sterile field may be provided. The surgical hub and/or medical instrument may comprise a memory and a processor. A first message that instructs a first display that is located within the sterile field to display a first contextual data may be sent. A user gesture may be determined from a device associated with the first display. The user gesture may indicate that a second contextual data is to be displayed on a second display outside the sterile field. A second message that instructs the second display to show the second contextual data may be sent.

A surgical hub and/or medical instrument may be provided. The surgical hub and/or the medical instrument may comprise a memory and a processor. The processor may be configured to perform a number of actions. A user gesture may be determined. The user gesture may indicate a visual effect to be applied to a focal point on the display that is outside the sterile field. A focal point may be determined. For example, the focal point on the display may be a place on the display that a user is viewing or focusing upon. The focal point on the display may be associated with a contextual data that may be displayed on the display. A second message may be sent. A second message may be sent to the display that may instruct the display to apply the visual effect to the contextual data at the focal point on the display that is outside the sterile field.

A surgical hub and/or a medical instrument for controlling a display outside a sterile field may be provided. The surgical hub and/or medical instrument may comprise a memory and a processor. A user gesture may be provided. The user gesture may indicate that a visual effect is to be applied to a focal point on the display that is outside the sterile field. The focal point on the display may be determined. The focal point on the display may be associated with a first display data and may be determined based on a contextual data. A second display data may be generated by applying the visual effect to the first display data. A second message may be sent. The second message may instruct the display to display the second display data.

BRIEF DESCRIPTION OF THE DRAWINGS

FIG. 22A illustrates a single zone sterile field control and data input console;

FIG. 22B illustrates a multi zone sterile field control and data input console;

FIG. 22C illustrates a tethered sterile field control and data input console;

FIG. 22D illustrates a battery-operated sterile field control and data input console; and FIG. 22E illustrates a battery-operated sterile field control and data input console.

FIG. 23A shows the sterile field console positioned in the sterile field near two surgeons engaged in an operation; and FIG. 23B shows one of the surgeons tapping the touchscreen of the sterile field console.

FIG. 25A is a perspective view of the virtual anatomical detail;

FIG. 25B is a side view of the virtual anatomical detail;

FIG. 25C is a perspective view of the virtual anatomical detail; and

FIG. 25D is a side view of the virtual anatomical detail.

FIG. 26A illustrates an image of a surgical site displayed on a touchscreen display in portrait mode;

FIG. 26B shows the touchscreen display rotated in landscape mode and the surgeon uses his index finger to scroll the image in the direction of the arrows;

FIG. 26C shows the surgeon using his index finger and thumb to pinch open the image in the direction of the arrows to zoom in;

FIG. 26D shows the surgeon using his index finger and thumb to pinch close the image in the direction of the arrows to zoom out; and FIG. 26E shows the touchscreen display rotated in two directions indicated by arrows to enable the surgeon to view the image in different orientations.

DETAILED DESCRIPTION

Figure 1:
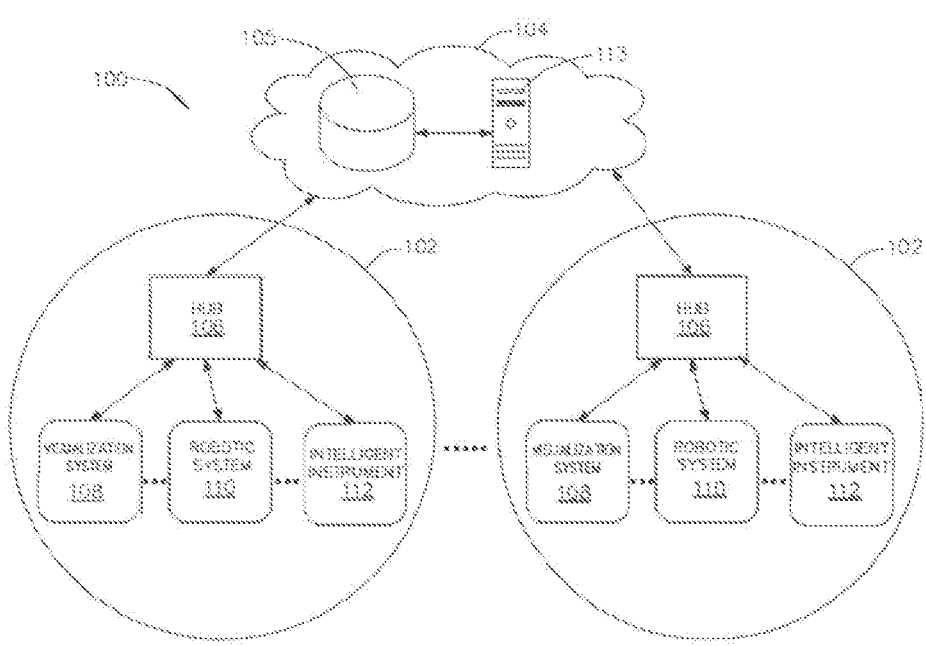
FIG. 1 is a block diagram of a computer-implemented interactive surgical system, in accordance with at least one aspect of the present disclosure.

Applicant of the present application owns the following U.S. patent applications, filed contemporaneously, each of which is herein incorporated by reference in its entirety:

U.S. patent application Ser. No. 16/209,416, titled "METHOD OF HUB COMMUNICATION, PROCESSING, DISPLAY, AND CLOUD ANALYTICS," filed Dec. 4, 2018;

U.S. patent application Ser. No. 15/940,671, titled "SURGICAL HUB SPATIAL AWARENESS TO DETERMINE DEVICES IN OPERATING THEATER," filed Mar. 29, 2018;

U.S. patent application Ser. No. 16/182,269, titled "IMAGE CAPTURING OF THE AREAS OUTSIDE THE ABDOMEN TO IMPROVE PLACEMENT AND CONTROL OF A SURGICAL DEVICE IN USE," filed Nov. 6, 2018;

U.S. patent application Ser. No. 16/729,747, titled "DYNAMIC SURGICAL VISUALIZATION SYSTEMS," filed Dec. 31, 2019;

U.S. patent application Ser. No. 16/729,778, titled "SYSTEM AND METHOD FOR DETERMINING, ADJUSTING, AND MANAGING RESECTION MARGIN ABOUT A SUBJECT TISSUE," filed Dec. 31, 2019;

U.S. patent application Ser. No. 16/729,807, titled "METHOD OF USING IMAGING DEVICES IN SURGERY," filed Dec. 31, 2019;

U.S. patent application Ser. No. 15/940,654, titled "SURGICAL HUB SITUATIONAL AWARENESS," filed Mar. 29, 2018;

U.S. patent application Ser. No. 15/940,704, titled "USE OF LASER LIGHT AND RED-GREEN-BLUE COLORATION TO DETERMINE PROPERTIES OF BACK SCATTERED LIGHT," which was filed on Mar. 29, 2018;

U.S. patent application Ser. No. 16/182,290, titled "SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION," filed Nov. 6, 2018;

U.S. Pat. No. 9,011,427, titled "SURGICAL INSTRUMENT WITH SAFETY GLASSES," issued on Apr. 21, 2015;

U.S. Pat. No. 9,123,155, titled "APPARATUS AND METHOD FOR USING AUGMENTED REALITY VISION SYSTEM IN SURGICAL PROCEDURES," which issued on Sep. 1, 2015;

U.S. patent application Ser. No. 16/209,478, titled "METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE," filed Dec. 4, 2018;

U.S. patent application Ser. No. 16/182,246, titled "ADJUSTMENTS BASED ON AIRBORNE PARTICLE PROPERTIES," filed Nov. 6, 2018;

U.S. patent application Ser. No. 16/209,385, titled "METHOD OF HUB COMMUNICATION, PROCESSING, STORAGE AND DISPLAY," filed Dec. 4, 2018;

U.S. patent application Ser. No. 16/209,407, titled "METHOD OF ROBOTIC HUB COMMUNICATION, DETECTION, AND CONTROL," filed Dec. 4, 2018;

U.S. patent application Ser. No. 16/182,231, titled "WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES," filed Nov. 6, 2018;

U.S. patent application Ser. No. 16/209,490, titled "METHOD FOR FACILITY DATA COLLECTION AND INTERPRETATION", filed Dec. 4, 2018;

U.S. Patent Application Publication No. 2014/0263552, titled "STAPLE CARTRIDGE TISSUE THICKNESS SENSOR SYSTEM," which published on Sep. 18, 2014;

U.S. patent application Ser. No. 15/628,175, titled "TECHNIQUES FOR ADAPTIVE CONTROL OF MOTOR VELOCITY OF A SURGICAL STAPLING AND CUTTING INSTRUMENT," filed Jun. 20, 2017;

U.S. Patent Application Publication No. 2009/0046146, titled "SURGICAL COMMUNICATION AND CONTROL SYSTEM," which published on Feb. 19, 2009; and U.S. Pat. No. 9,283,054, titled "SURGICAL APPARATUS WITH INDICATOR," which issued on Mar. 15, 2016.

Referring to FIG. 1, a computer-implemented interactive surgical system 100 may include one or more surgical systems 102 and a cloud-based system (e.g., the cloud 104 that may include a remote server 113 coupled to a storage device). Each surgical system 102 may include at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P may be integers greater than or equal to one.

Figure 2:
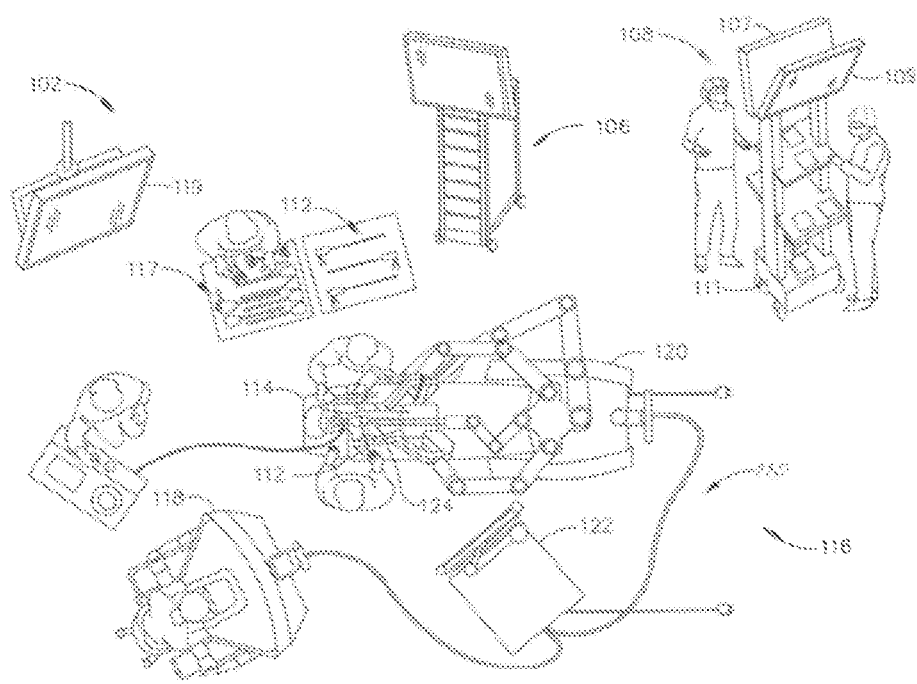
FIG. 2 is a surgical system being used to perform a surgical procedure in an operating room, in accordance with at least one aspect of the present disclosure.

In various aspects, the visualization system 108 may include one or more imaging sensors, one or more image-processing units, one or more storage arrays, and one or more displays that are strategically arranged with respect to the sterile field, as illustrated in FIG. 2. In one aspect, the visualization system 108 may include an interface for HL7, PACS, and EMR. Various components of the visualization system 108 are described in U.S. Patent Application Publication No. US 2019-0200844 A1, titled METHOD OF HUB COMMUNICATION, PROCESSING, STORAGE AND DISPLAY, filed Dec. 4, 2018, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 may include a first nonsterile display 107 and a second nonsterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a nonsterile display 107 or 109, while maintaining a live feed of the surgical site on the primary display 119. The snapshot on the nonsterile display 107 or 109 can permit a nonsterile operator to perform a diagnostic step relevant to the surgical procedure, for example.

In one aspect, the hub 106 may also be configured to route a diagnostic input or feedback entered by a nonsterile operator at the visualization tower 111 to the primary display 119 within the sterile field, where it can be viewed by a sterile operator at the operating table. In one example, the input can be in the form of a modification to the snapshot displayed on the nonsterile display 107 or 109, which can be routed to the primary display 119 by the hub 106.

Referring to FIG. 2, a surgical instrument 112 is being used in the surgical procedure as part of the surgical system 102. The hub 106 may also be configured to coordinate information flow to a display of the surgical instrument 112. For example, in U.S. Patent Application Publication No. US 2019-0200844 A1, titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a nonsterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Patent Application Publication No. US 2019-0200844 A1, titled METHOD OF HUB COMMUNICATION, PROCESSING, STORAGE AND DISPLAY, filed Dec. 4, 2018, the disclosure of which is herein incorporated by reference in its entirety, for example.

Figure 3:
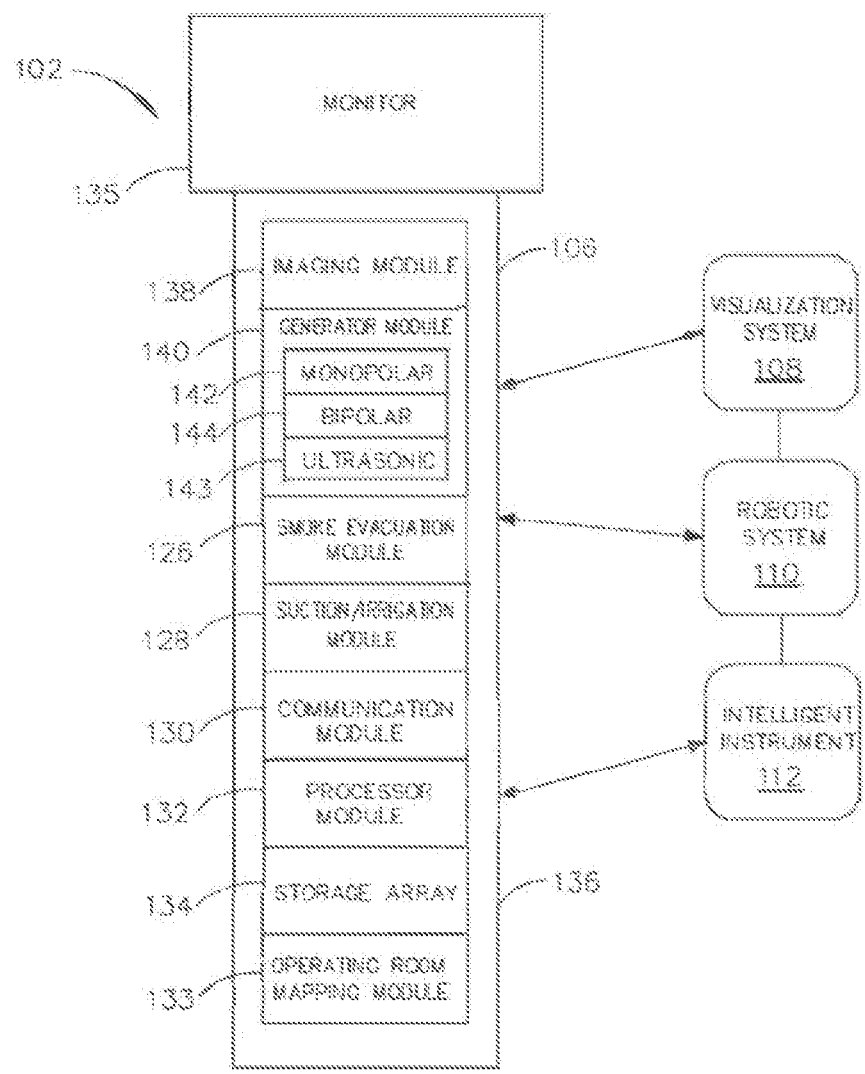
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 may be used in the surgical procedure as a part of the surgical system 102. The robotic system 110 may include a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Patent Application Publication No. US 2019-0201137 A1, titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud 104, and are suitable for use with the present disclosure, are described in U.S. Patent Application Publication No. US 2019-0206569 A1, titled METHOD OF CLOUD BASED DATA ANALYTICS FOR USE WITH THE HUB, filed Dec. 4, 2018, the disclosure of which is herein incorporated by reference in its entirety.

In various aspects, the imaging device 124 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cystoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail in U.S. Patent Application Publication No. US 2019-0200844 A1, titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 4:
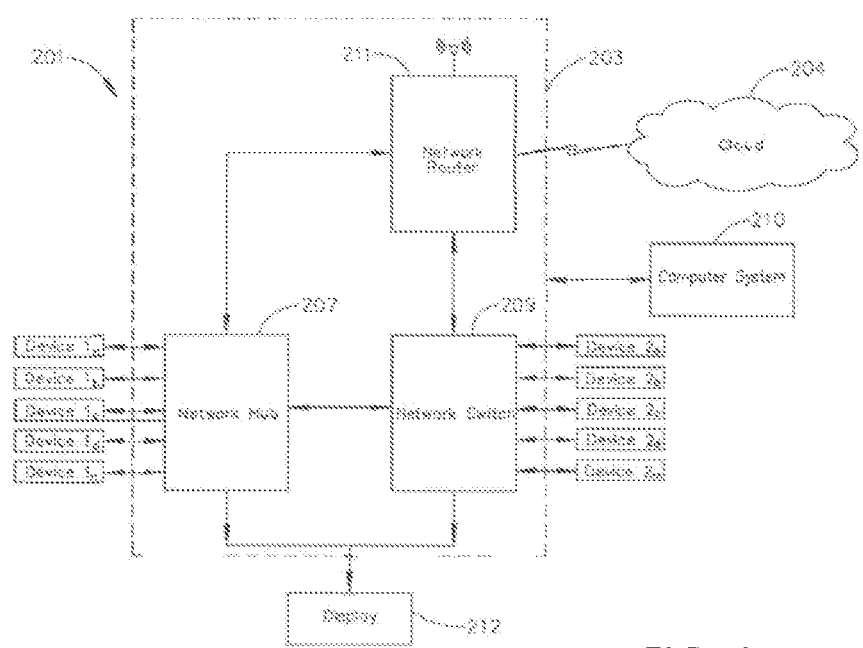
FIG. 4 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 4 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

The operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub may provide connectivity to the devices 1a-1n located in the same operating theater network. The network hub 207 may collect data in the form of packets and sends them to the router in half duplex mode. The network hub 207 may not store any media access control/Internet Protocol (MAC/IP) to transfer the device data. Only one of the devices 1a-1n can send data at a time through the network hub 207. The network hub 207 may not have routing tables or intelligence regarding where to send information and broadcasts all network data across each connection and to a remote server 213 (FIG. 4) over the cloud 204. The network hub 207 can detect basic network errors such as collisions but having all information broadcast to multiple ports can be a security risk and cause bottlenecks.

The operating theater devices 2a-2m may be connected to a network switch 209 over a wired channel or a wireless channel. The network switch 209 works in the data link layer of the OSI model. The network switch 209 may be a multicast device for connecting the devices 2a-2m located in the same operating theater to the network. The network switch 209 may send data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 may be coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 may send data in the form of packets to the cloud 204 and works in full duplex mode. Multiple devices can send data at the same time. The network router 211 uses IP addresses to transfer data.

In an example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and may handle a data type known as frames. Frames may carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 can be generally easy to install, configure, and maintain, making it a good option for networking the operating theater devices 1a-1n/2a-2m.

Figure 5:
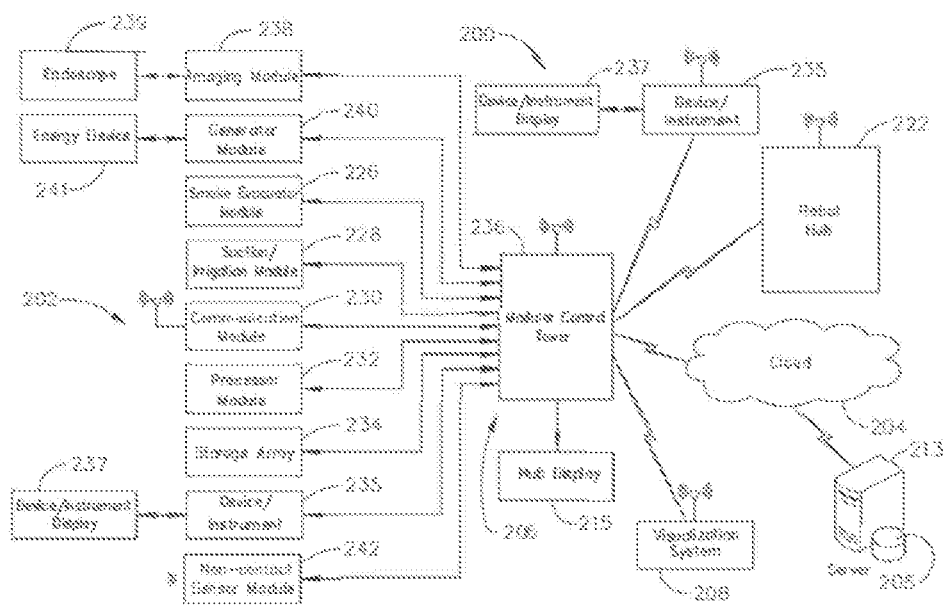
FIG. 5 illustrates a computer-implemented interactive surgical system, in accordance with at least one aspect of the present disclosure.
Figure 6:
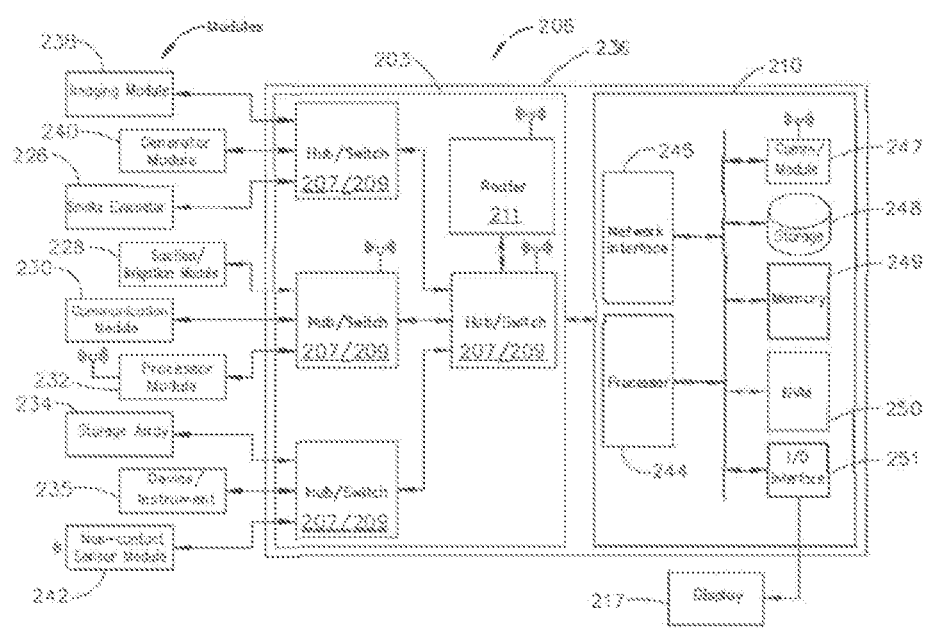
FIG. 6 illustrates a surgical hub comprising a plurality of modules coupled to the modular control tower, in accordance with at least one aspect of the present disclosure.

FIG. 5 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 6, the modular control tower 236 comprises a modular communication hub 203 coupled to a computer system 210.

As illustrated in the example of FIG. 5, the modular control tower 236 may be coupled to an imaging module 238 that may be coupled to an endoscope 239, a generator module 240 that may be coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices may be coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 6 illustrates a surgical hub 206 comprising a plurality of modules coupled to the modular control tower 236. The modular control tower 236 may comprise a modular communication hub 203, e.g., a network connectivity device, and a computer system 210 to provide local processing, visualization, and imaging, for example. As shown in FIG. 6, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 6, each of the network hubs/switches in the modular communication hub 203 may include three downstream ports and one upstream port. The upstream network hub/switch may be connected to a processor to provide a communication connection to the cloud computing resources and a local display 217. Communication to the cloud 204 may be made either through a wired or a wireless communication channel.

The surgical hub 206 may employ a non-contact sensor module 242 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described in U.S. Patent Application Publication No. US 2019-0200844 A1, titled METHOD OF HUB COMMUNICATION, PROCESSING, STORAGE AND DISPLAY, filed Dec. 4, 2018, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 may comprise a processor 244 and a network interface 245. The processor 244 can be coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory.

Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 210 through input device(s) coupled to the I/O interface 251. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 6, the imaging module 238 and/or visualization system 208, and/or the processor module 232 of FIGS. 5-6, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system 210. The hardware/software necessary for connection to the network interface may include, for illustrative purposes only, internal and external technologies such as modems, including regular telephone-grade modems, cable modems, and DSL modems, ISDN adapters, and Ethernet cards.

Figure 7:
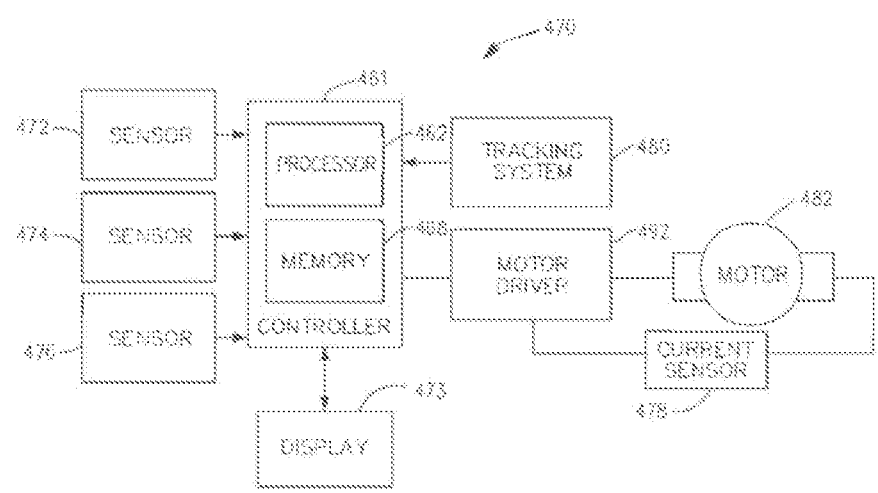
FIG. 7 illustrates a logic diagram of a control system of a surgical instrument or tool, in accordance with at least one aspect of the present disclosure.

FIG. 7 illustrates a logic diagram of a control system 470 of a surgical instrument or tool in accordance with one or more aspects of the present disclosure. The system 470 may comprise a control circuit. The control circuit may include a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 may be configured to determine the position of the longitudinally movable displacement member. The position information may be provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 may display a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 may include a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In some examples, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 may be a full-bridge controller for use with external N-channel power metal-oxide semiconductor field-effect transistors (MOSFETs) specifically designed for inductive loads, such as brush DC motors. The driver 492 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 may comprise a controlled motor drive circuit arrangement comprising a position sensor 472 according to one aspect of this disclosure. The position sensor 472 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 472 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches may be fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system may comprise a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 may be a low-voltage and low-power component and includes four Hall-effect elements in an area of the position sensor 472 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bitshift, and table lookup operations. The angle position, alarm bits, and magnetic field information may be transmitted over a standard serial communication interface, such as a serial peripheral interface (SPI) interface, to the microcontroller 461. The position sensor 472 may provide 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertial, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force may be converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 474, such as, for example, a micro-strain gauge, that can be configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain can be converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub 203 as shown in FIGS. 5 and 6.

Figure 8:
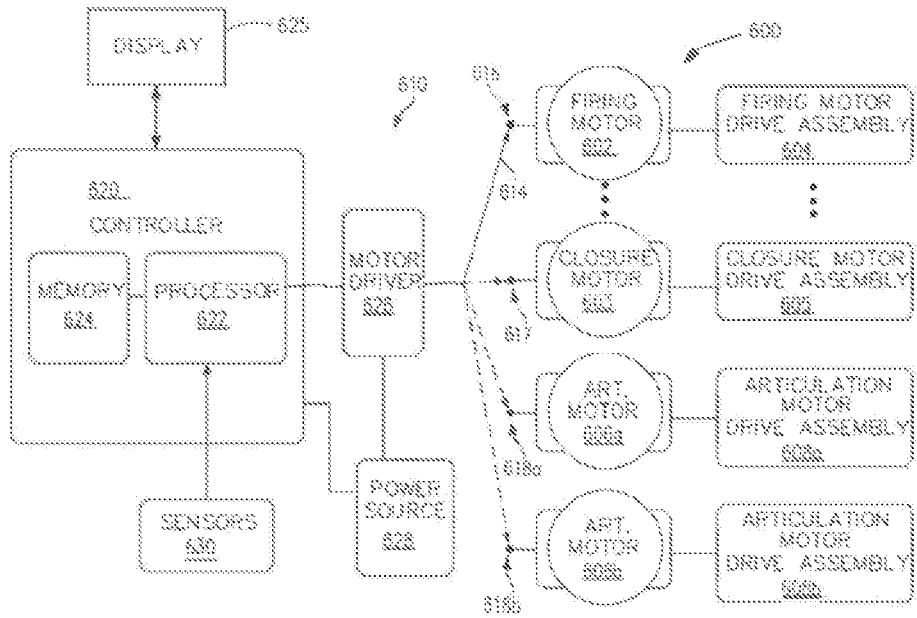
FIG. 8 illustrates a surgical instrument or tool comprising a plurality of motors which can be activated to perform various functions, in accordance with at least one aspect of the present disclosure.

FIG. 8 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described herein, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 8, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 8, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described herein.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor can be a multipurpose, programmable device that accepts digital data as input, processes it according to instructions stored in its memory, and provides results as output. It can be an example of sequential digital logic, as it may have internal memory. Processors may operate on numbers and symbols represented in the binary numeral system.

The processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

The memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

One or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 9:
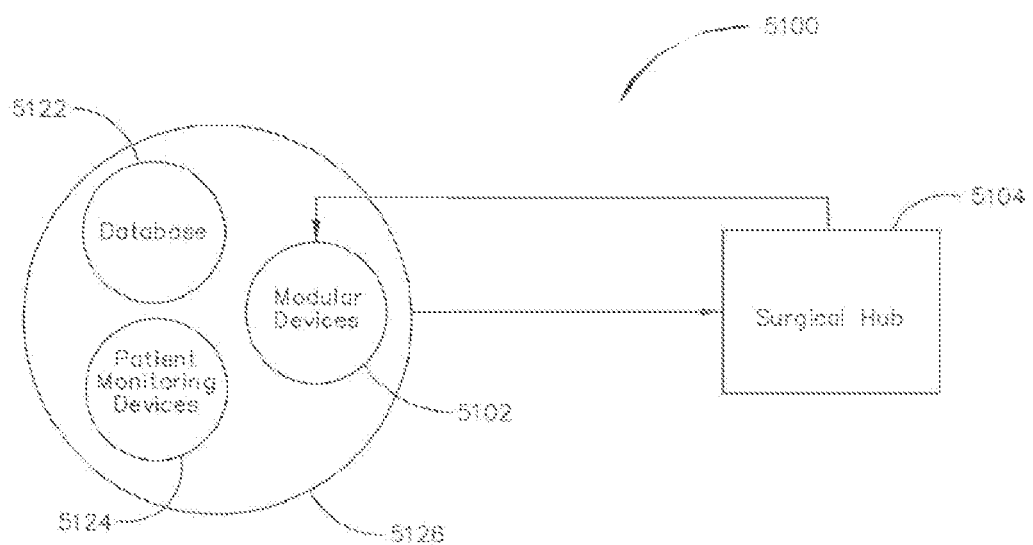
FIG. 9 illustrates a diagram of a situationally aware surgical system, in accordance with at least one aspect of the present disclosure.

FIG. 9 illustrates a diagram of a situationally aware surgical system 5100, in accordance with at least one aspect of the present disclosure. In some exemplifications, the data sources 5126 may include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In an exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In an exemplification, the situational awareness system can include a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in an exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use a soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can be configured to compare the list of items for the procedure and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In some exemplifications, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In some exemplifications, the surgical hub 5104 can be configured to provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 10:
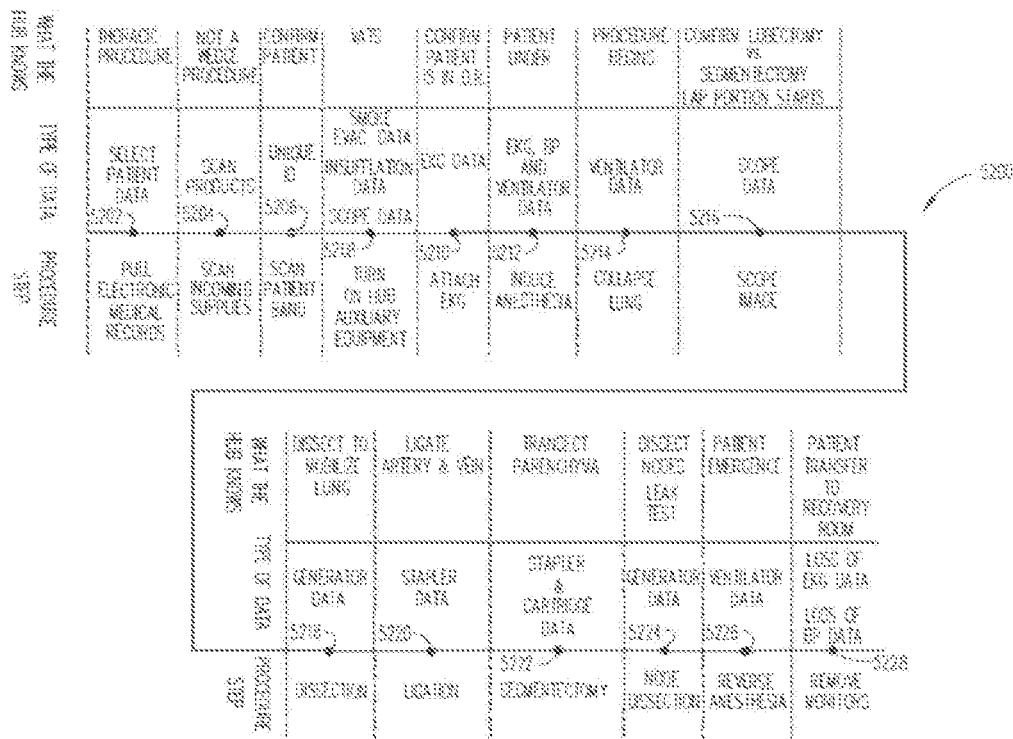
FIG. 10 illustrates a timeline of an illustrative surgical procedure and the inferences that the surgical hub can make from the data detected at each step in the surgical procedure, in accordance with at least one aspect of the present disclosure.

FIG. 10 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 9, reference should also be made to FIG. 9. The timeline 5200 may depict the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 may receive data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 can be able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described herein.

As the first step 5202 in this illustrative procedure, the hospital staff members may retrieve the patient's EMR from the hospital's EMR database. Based on select patient data in the EMR, the surgical hub 5104 determines that the procedure to be performed is a thoracic procedure. Second 5204, the staff members may scan the incoming medical supplies for the procedure. The surgical hub 5104 cross-references the scanned supplies with a list of supplies that can be utilized in various types of procedures and confirms that the mix of supplies corresponds to a thoracic procedure. Further, the surgical hub 5104 may also be able to determine that the procedure is not a wedge procedure (because the incoming supplies either lack certain supplies that are necessary for a thoracic wedge procedure or do not otherwise correspond to a thoracic wedge procedure). Third 5206, the medical personnel may scan the patient band via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that may be located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 may determine that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 may pair with the surgical hub 5104. As the surgical hub 5104 begins receiving data from the patient monitoring devices 5124, the surgical hub 5104 may confirm that the patient is in the operating theater, as described in the process 5207, for example. Sixth 5212, the medical personnel may induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof, for example. Upon completion of the sixth step 5212, the pre-operative portion of the lung segmentectomy procedure is completed and the operative portion begins.

Seventh 5214, the patient's lung that is being operated on may be collapsed (while ventilation is switched to the contralateral lung). The surgical hub 5104 can infer from the ventilator data that the patient's lung has been collapsed, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung can be the first operative step in this particular procedure. Eighth 5216, the medical imaging device 5108 (e.g., a scope) may be inserted and video from the medical imaging device may be initiated. The surgical hub 5104 may receive the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy may place the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. An example technique for performing a VATS lobectomy may utilize a single medical imaging device. An example technique for performing a VATS segmentectomy utilizes multiple cameras. An example technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team may begin the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team may proceed to the ligation step of the procedure. The surgical hub 5104 can infer that the surgeon is ligating arteries and veins because it may receive data from the surgical stapling and cutting instrument indicating that the instrument is being fired. Similar to the prior step, the surgical hub 5104 can derive this inference by cross-referencing the receipt of data from the surgical stapling and cutting instrument with the retrieved steps in the process. Eleventh 5222, the segmentectomy portion of the procedure can be performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed. Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (e.g., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure may begin.

Thirteenth 5226, the patient's anesthesia can be reversed. The surgical hub 5104 can infer that the patient is emerging from the anesthesia based on the ventilator data (i.e., the patient's breathing rate begins increasing), for example. Lastly, the fourteenth step 5228 may be that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 10, the patient data can also be utilized by a situationally aware surgical hub 5104 to generate control adjustments for the paired modular devices 5102.

Figure 11:
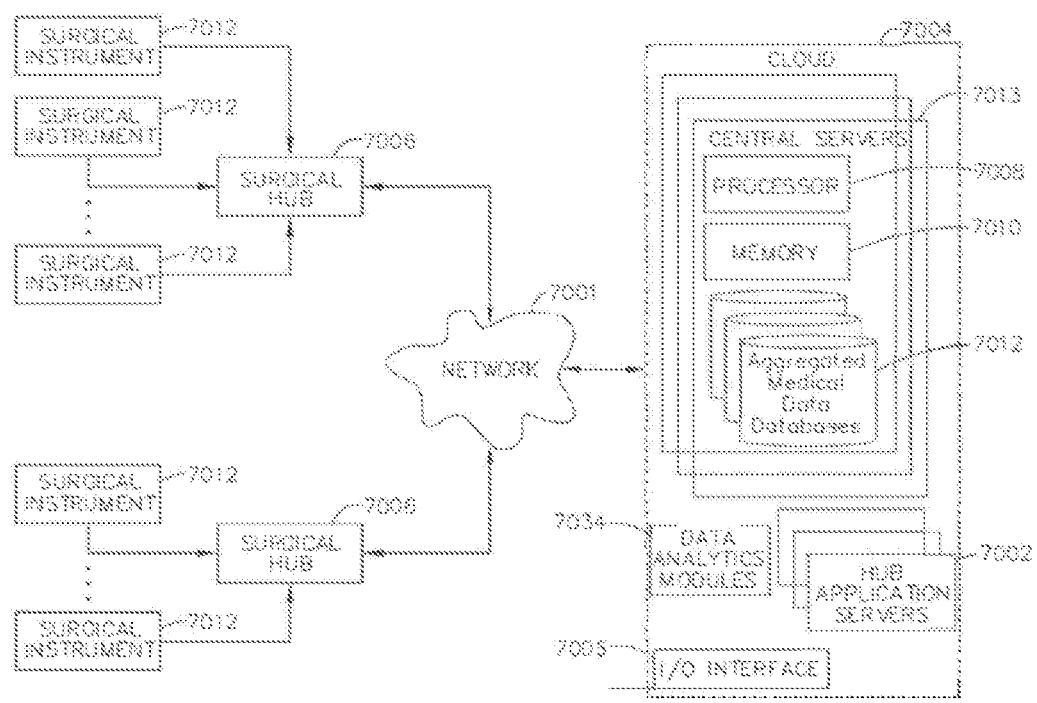
FIG. 11 is a block diagram of the computer-implemented interactive surgical system, in accordance with at least one aspect of the present disclosure.

FIG. 11 is a block diagram of the computer-implemented interactive surgical system, in accordance with at least one aspect of the present disclosure. In one aspect, the computer-implemented interactive surgical system may be configured to monitor and analyze data related to the operation of various surgical systems that include surgical hubs, surgical instruments, robotic devices and operating theaters or healthcare facilities. The computer-implemented interactive surgical system may comprise a cloud-based analytics system. Although the cloud-based analytics system may be described as a surgical system, it may not be necessarily limited as such and could be a cloud-based medical system generally. As illustrated in FIG. 11, the cloud-based analytics system may comprise a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 may be communicatively coupled to one or more surgical instruments 7012. The hubs 7006 may also be communicatively coupled to the cloud 7004 of the computer-implemented interactive surgical system via the network 7001. The cloud 7004 may be a remote centralized source of hardware and software for storing, manipulating, and communicating data generated based on the operation of various surgical systems. As shown in FIG. 11, access to the cloud 7004 may be achieved via the network 7001, which may be the Internet or some other suitable computer network. Surgical hubs 7006 that may be coupled to the cloud 7004 can be considered the client side of the cloud computing system (i.e., cloud-based analytics system). Surgical instruments 7012 may be paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 11, the cloud 7004 comprises central servers 7013 (may be same or similar to remote server 7013), hub application servers 7002, data analytics modules 7034, and an input/output ("I/O") interface 7006. The central servers 7013 of the cloud 7004 collectively administer the cloud computing system, which includes monitoring requests by client surgical hubs 7006 and managing the processing capacity of the cloud 7004 for executing the requests. Each of the central servers 7013 may comprise one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also may comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7011 of the cloud 7004. In particular, the cloud 7004 may advantageously perform data analysis and operations on the aggregated data to yield insights and/or perform functions that individual hubs 7006 could not achieve on their own. To this end, as shown in FIG. 11, the cloud 7004 and the surgical hubs 7006 are communicatively coupled to transmit and receive information. The I/O interface 7005 is connected to the plurality of surgical hubs 7006 via the network 7001. In this way, the I/O interface 7005 can be configured to transfer information between the surgical hubs 7006 and the aggregated medical data databases 7011. Accordingly, the I/O interface 7005 may facilitate read/write operations of the cloud-based analytics system. Such read/write operations may be executed in response to requests from hubs 7006. These requests could be transmitted to the hubs 7006 through the hub applications. The I/O interface 7005 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 may be configured to host and supply shared capabilities to software applications (e.g., hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 12.

The particular cloud computing system configuration described in the present disclosure may be specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch-controlled user interfaces such that clinicians may control aspects of interaction between the surgical instruments 7012 and the cloud 7004. Other suitable user interfaces for control such as auditory controlled user interfaces can also be used.

Figure 12:
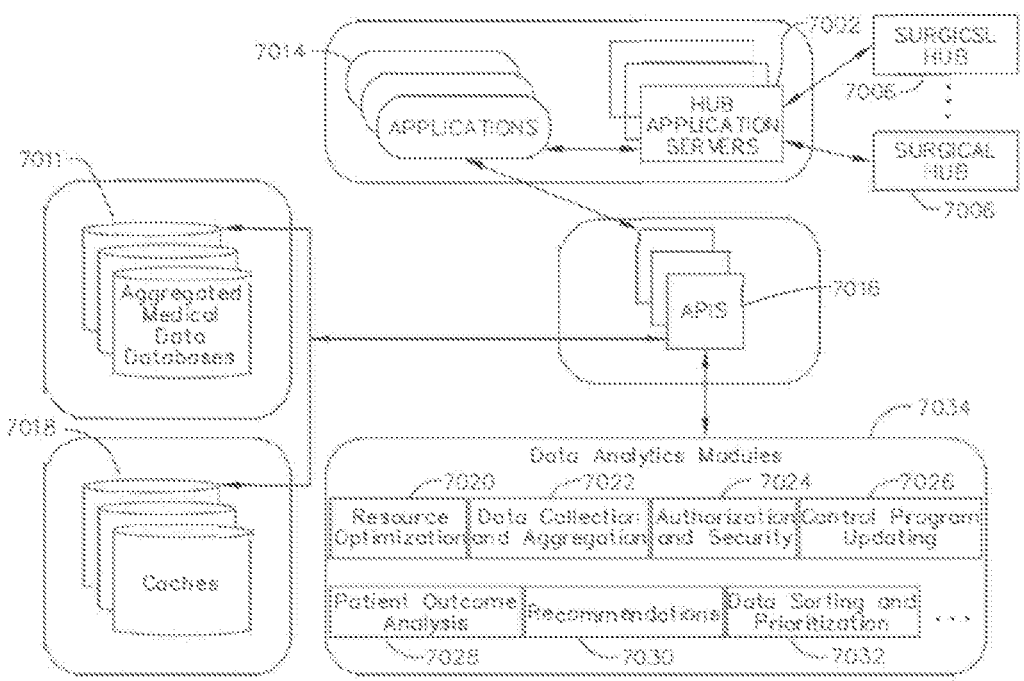
FIG. 12 is a block diagram which illustrates the functional architecture of the computer-implemented interactive surgical system, in accordance with at least one aspect of the present disclosure.

FIG. 12 is a block diagram which illustrates the functional architecture of the computer-implemented interactive surgical system, in accordance with at least one aspect of the present disclosure. The cloud-based analytics system may include a plurality of data analytics modules 7034 that may be executed by the processors 7008 of the cloud 7004 for providing data analytic solutions to problems specifically arising in the medical field. As shown in FIG. 12, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 may define the set of protocols and routines corresponding to the hub applications 7014. Additionally, the APIs 7016 may manage the storing and retrieval of data into and from the aggregated medical databases 7011 for the operations of the applications 7014. The caches 7018 may also store data (e.g., temporarily) and may be coupled to the APIs 7016 for more efficient retrieval of data used by the applications 7014. The data analytics modules 7034 in FIG. 12 may include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules may be used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical instruments 7012 for a group of healthcare facilities based on corresponding predicted demand of such surgical instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently. The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to surgical instruments 7012 that may be transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using surgical instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004. Furthermore, for security purposes, the cloud could maintain a database of hubs 7006, surgical instruments 7012, and other devices that may comprise a "blacklist" of prohibited devices. In particular, a surgical hubs 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally, or alternatively, the cloud 7004 may flag surgical instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash-based encryption. Upon transmitting proper authorization, the surgical instruments 7012 may transmit a signal to the corresponding hubs 7006 and ultimately the cloud 7004 to indicate that the surgical instruments 7012 are ready to obtain and transmit medical data. In response, the cloud 7004 may transition into a state enabled for receiving medical data for storage into the aggregated medical data databases 7011. This data transmission readiness could be indicated by a light indicator on the surgical instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described herein to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g., a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional example details for the various functions described are provided in the ensuing descriptions below. Each of the various descriptions may utilize the cloud architecture as described in FIGS. 11 and 12 as one example of hardware and software implementation.

Figure 13:
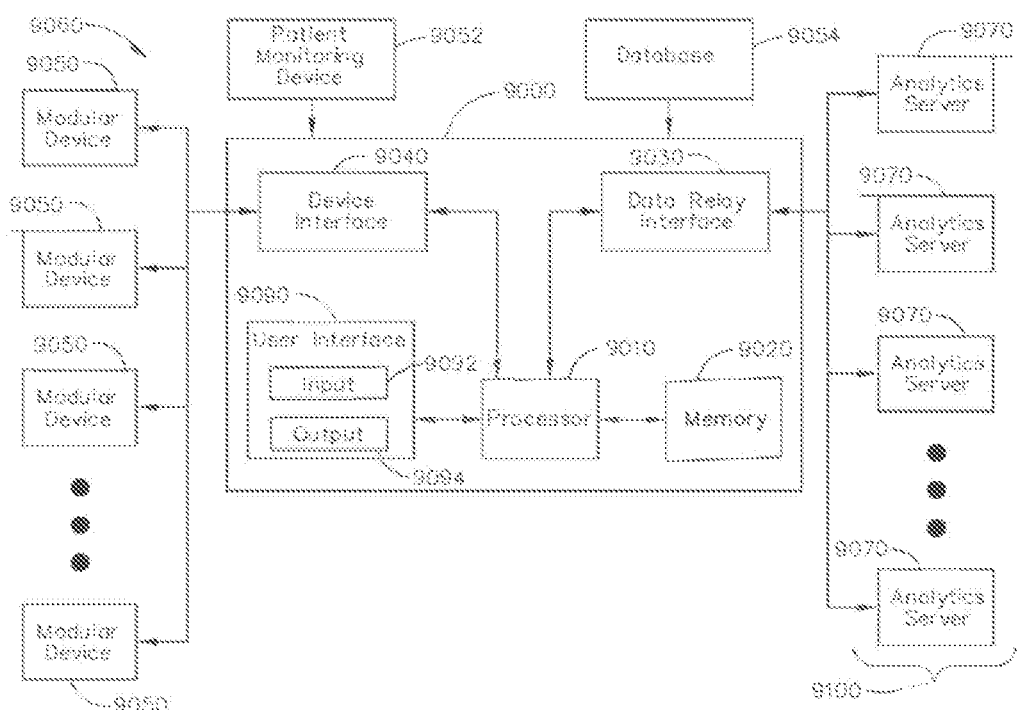
FIG. 13 illustrates a block diagram of a computer-implemented interactive surgical system that is configured to adaptively generate control program updates for modular devices, in accordance with at least one aspect of the present disclosure.

FIG. 13 illustrates a block diagram of a computer-implemented adaptive surgical system 9060 that is configured to adaptively generate control program updates for modular devices 9050, in accordance with at least one aspect of the present disclosure. In some exemplifications, the surgical system may include a surgical hub 9000, multiple modular devices 9050 communicably coupled to the surgical hub 9000, and an analytics system 9100 communicably coupled to the surgical hub 9000. Although a single surgical hub 9000 may be depicted, it should be noted that the surgical system 9060 can include any number of surgical hubs 9000, which can be connected to form a network of surgical hubs 9000 that are communicably coupled to the analytics system 9100. In some exemplifications, the surgical hub 9000 may include a processor 9010 coupled to a memory 9020 for executing instructions stored thereon and a data relay interface 9030 through which data is transmitted to the analytics system 9100. In some exemplifications, the surgical hub 9000 further may include a user interface 9090 having an input device 9092 (e.g., a capacitive touchscreen or a keyboard) for receiving inputs from a user and an output device 9094 (e.g., a display screen) for providing outputs to a user. Outputs can include data from a query input by the user, suggestions for products or mixes of products to use in a given procedure, and/or instructions for actions to be carried out before, during, or after surgical procedures. The surgical hub 9000 further may include an interface 9040 for communicably coupling the modular devices 9050 to the surgical hub 9000. In one aspect, the interface 9040 may include a transceiver that is communicably connectable to the modular device 9050 via a wireless communication protocol. The modular devices 9050 can include, for example, surgical stapling and cutting instruments, electro-surgical instruments, ultrasonic instruments, insufflators, respirators, and display screens. In some exemplifications, the surgical hub 9000 can further be communicably coupled to one or more patient monitoring devices 9052, such as EKG monitors or BP monitors. In some exemplifications, the surgical hub 9000 can further be communicably coupled to one or more databases 9054 or external computer systems, such as an EMR database of the medical facility at which the surgical hub 9000 is located.

When the modular devices 9050 are connected to the surgical hub 9000, the surgical hub 9000 can sense or receive perioperative data from the modular devices 9050 and then associate the received perioperative data with surgical procedural outcome data. The perioperative data may indicate how the modular devices 9050 were controlled during the course of a surgical procedure. The procedural outcome data includes data associated with a result from the surgical procedure (or a step thereof), which can include whether the surgical procedure (or a step thereof) had a positive or negative outcome. For example, the outcome data could include whether a patient suffered from postoperative complications from a particular procedure or whether there was leakage (e.g., bleeding or air leakage) at a particular staple or incision line. The surgical hub 9000 can obtain the surgical procedural outcome data by receiving the data from an external source (e.g., from an EMR database 9054), by directly detecting the outcome (e.g., via one of the connected modular devices 9050), or inferring the occurrence of the outcomes through a situational awareness system. For example, data regarding postoperative complications could be retrieved from an EMR database 9054 and data regarding staple or incision line leakages could be directly detected or inferred by a situational awareness system. The surgical procedural outcome data can be inferred by a situational awareness system from data received from a variety of data sources, including the modular devices 9050 themselves, the patient monitoring device 9052, and the databases 9054 to which the surgical hub 9000 is connected.

The surgical hub 9000 can transmit the associated modular device 9050 data and outcome data to the analytics system 9100 for processing thereon. By transmitting both the perioperative data indicating how the modular devices 9050 are controlled and the procedural outcome data, the analytics system 9100 can correlate the different manners of controlling the modular devices 9050 with surgical outcomes for the particular procedure type. In some exemplifications, the analytics system 9100 may include a network of analytics servers 9070 that are configured to receive data from the surgical hubs 9000. Each of the analytics servers 9070 can include a memory and a processor coupled to the memory that is executing instructions stored thereon to analyze the received data. In some exemplifications, the analytics servers 9070 may be connected in a distributed computing architecture and/or utilize a cloud computing architecture. Based on this paired data, the analytics system 9100 can then learn optimal or preferred operating parameters for the various types of modular devices 9050, generate adjustments to the control programs of the modular devices 9050 in the field, and then transmit (or "push") updates to the modular devices' 9050 control programs.

Additional detail regarding the computer-implemented interactive surgical system 9060, including the surgical hub 9000 and various modular devices 9050 connectable thereto, are described in connection with FIGS. 5-6.

Figure 14:
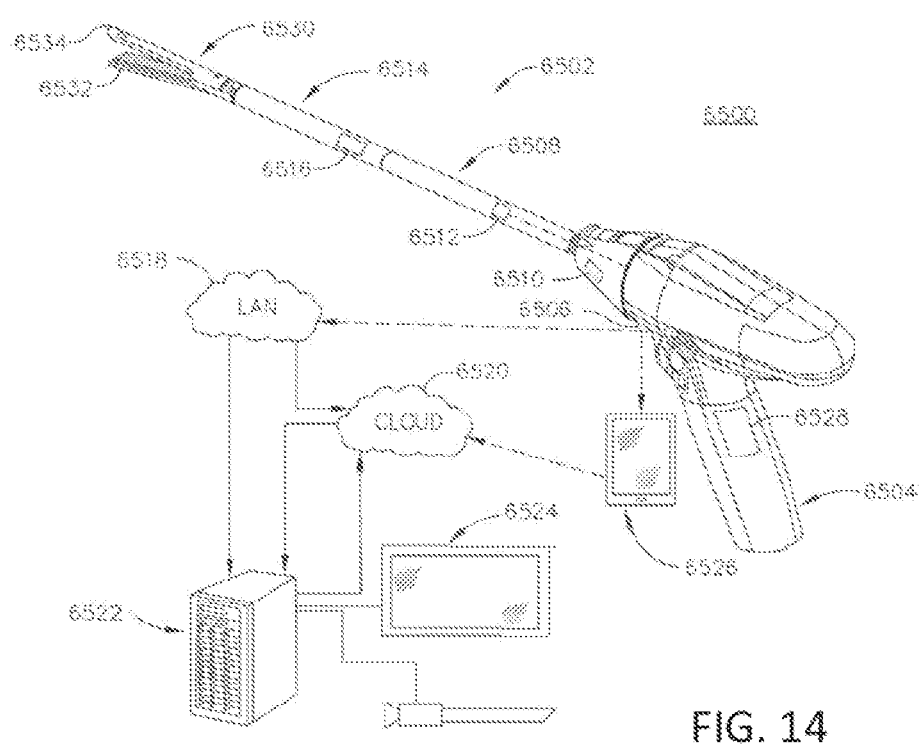
FIG. 14 illustrates a surgical system that includes a handle having a controller and a motor, an adapter releasably coupled to the handle, and a loading unit releasably coupled to the adapter, in accordance with at least one aspect of the present disclosure.

FIG. 14 provides a surgical system 6500 in accordance with the present disclosure and may include a surgical instrument 6502 that can be in communication with a console 6522 or a portable device 6526 through a local area network 6518 or a cloud network 6520 via a wired or wireless connection. In various aspects, the console 6522 and the portable device 6526 may be any suitable computing device. The surgical instrument 6502 may include a handle 6504, an adapter 6508, and a loading unit 6514. The adapter 6508 releasably couples to the handle 6504 and the loading unit 6514 releasably couples to the adapter 6508 such that the adapter 6508 transmits a force from a drive shaft to the loading unit 6514. The adapter 6508 or the loading unit 6514 may include a force gauge (not explicitly shown) disposed therein to measure a force exerted on the loading unit 6514. The loading unit 6514 may include an end effector 6530 having a first jaw 6532 and a second jaw 6534. The loading unit 6514 may be an in-situ loaded or multi-firing loading unit (MFLU) that allows a clinician to fire a plurality of fasteners multiple times without requiring the loading unit 6514 to be removed from a surgical site to reload the loading unit 6514.

The first and second jaws 6532, 6534 may be configured to clamp tissue therebetween, fire fasteners through the clamped tissue, and sever the clamped tissue. The first jaw 6532 may be configured to fire at least one fastener a plurality of times, or may be configured to include a replaceable multi-fire fastener cartridge including a plurality of fasteners (e.g., staples, clips, etc.) that may be fired more than one time prior to being replaced. The second jaw 6534 may include an anvil that deforms or otherwise secures the fasteners about tissue as the fasteners are ejected from the multi-fire fastener cartridge.

The handle 6504 may include a motor that is coupled to the drive shaft to affect rotation of the drive shaft. The handle 6504 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 6504 may be in communication with a controller 6528 of the handle 6504 to selectively activate the motor to affect rotation of the drive shafts. The controller 6528 may be disposed within the handle 6504 and is configured to receive input from the control interface and adapter data from the adapter 6508 or loading unit data from the loading unit 6514. The controller 6528 may analyze the input from the control interface and the data received from the adapter 6508 and/or loading unit 6514 to selectively activate the motor. The handle 6504 may also include a display that is viewable by a clinician during use of the handle 6504. The display may be configured to display portions of the adapter or loading unit data before, during, or after firing of the instrument 6502.

The adapter 6508 may include an adapter identification device 6510 disposed therein and the loading unit 6514 includes a loading unit identification device 6516 disposed therein. The adapter identification device 6510 may be in communication with the controller 6528, and the loading unit identification device 6516 may be in communication with the controller 6528. It will be appreciated that the loading unit identification device 6516 may be in communication with the adapter identification device 6510, which relays or passes communication from the loading unit identification device 6516 to the controller 6528.

The adapter 6508 may also include a plurality of sensors 6512 (one shown) disposed thereabout to detect various conditions of the adapter 6508 or of the environment (e.g., if the adapter 6508 is connected to a loading unit, if the adapter 6508 is connected to a handle, if the drive shafts are rotating, the torque of the drive shafts, the strain of the drive shafts, the temperature within the adapter 6508, a number of firings of the adapter 6508, a peak force of the adapter 6508 during firing, a total amount of force applied to the adapter 6508, a peak retraction force of the adapter 6508, a number of pauses of the adapter 6508 during firing, etc.). The plurality of sensors 6512 may provide an input to the adapter identification device 6510 in the form of data signals. The data signals of the plurality of sensors 6512 may be stored within, or be used to update the adapter data stored within, the adapter identification device 6510. The data signals of the plurality of sensors 6512 may be analog or digital. The plurality of sensors 6512 may include a force gauge to measure a force exerted on the loading unit 6514 during firing.

The handle 6504 and the adapter 6508 can be configured to interconnect the adapter identification device 6510 and the loading unit identification device 6516 with the controller 6528 via an electrical interface. The electrical interface may be a direct electrical interface (i.e., include electrical contacts that engage one another to transmit energy and signals therebetween). Additionally or alternatively, the electrical interface may be a non-contact electrical interface to wirelessly transmit energy and signals therebetween (e.g., inductively transfer). It is also contemplated that the adapter identification device 6510 and the controller 6528 may be in wireless communication with one another via a wireless connection separate from the electrical interface.

The handle 6504 may include a transmitter 6506 that is configured to transmit instrument data from the controller 6528 to other components of the system 6500 (e.g., the LAN 6518, the cloud 6520, the console 6522, or the portable device 6526). The transmitter 6506 also may receive data (e.g., cartridge data, loading unit data, or adapter data) from the other components of the system 6500. For example, the controller 6528 may transmit instrument data including a serial number of an attached adapter (e.g., adapter 6508) attached to the handle 6504, a serial number of a loading unit (e.g., loading unit 6514) attached to the adapter, and a serial number of a multi-fire fastener cartridge (e.g., multi-fire fastener cartridge), loaded into the loading unit, to the console 6522. Thereafter, the console 6522 may transmit data (e.g., cartridge data, loading unit data, or adapter data) associated with the attached cartridge, loading unit, and adapter, respectively, back to the controller 6528. The controller 6528 can display messages on the local instrument display or transmit the message, via transmitter 6506, to the console 6522 or the portable device 6526 to display the message on the display 6524 or portable device screen, respectively.

Figures 15A, 15B:
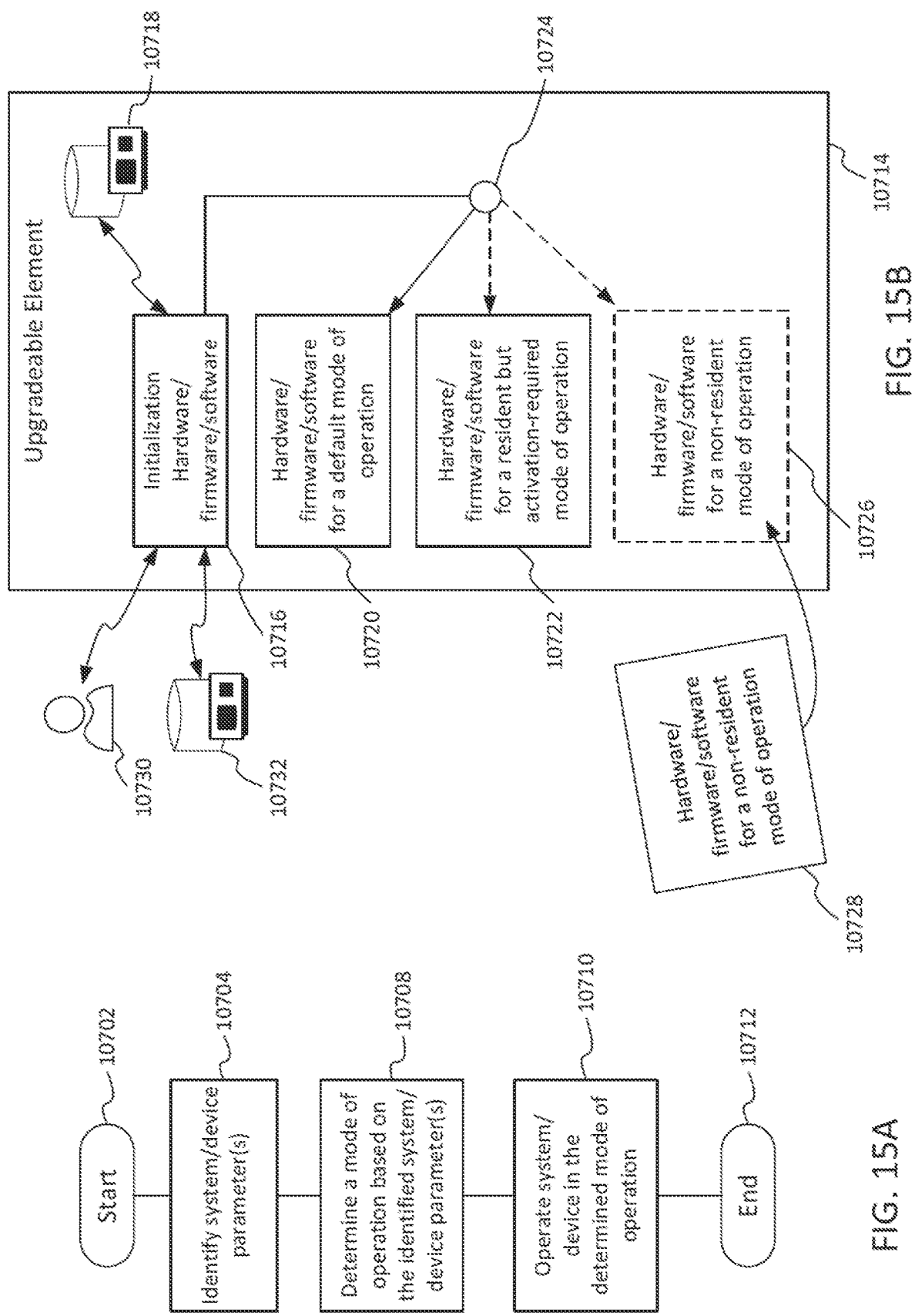
FIG. 15A illustrates an example flow for determining a mode of operation and operating in the determined mode.
FIG. 15B illustrates an example flow for changing a mode of operation.

FIG. 15A illustrates an example flow for determining a mode of operation and operating in the determined mode. The computer-implemented interactive surgical system and/or components and/or subsystems of the computer-implemented interactive surgical system may be configured to be updated. Such updates may include the inclusions of features and benefits that were not available to the user before the update. These updates may be established by any method of hardware, firmware, and software updates suitable for introducing the feature to the user. For example, replaceable/swappable (e.g., hot swappable) hardware components, flashable firmware devices, and updatable software systems may be used to update computer-implemented interactive surgical system and/or components and/or subsystems of the computer-implemented interactive surgical system.

The updates may be conditioned on any suitable criterion or set of criteria. For example, an update may be conditioned on one or more hardware capabilities of the system, such as processing capability, bandwidth, resolution, and the like. For example, the update may be conditioned on one or more software aspects, such as a purchase of certain software code. For example, the update may be conditioned on a purchased service tier. The service tier may represent a feature and/or a set of features the user is entitled to use in connection with the computer-implemented interactive surgical system. The service tier may be determined by a license code, an e-commerce server authentication interaction, a hardware key, a username/password combination, a biometric authentication interaction, a public/private key exchange interaction, or the like.

At 10704, a system/device parameter may be identified. The system/device parameter may be any element or set of elements on which an update in conditioned. For example, the computer-implemented interactive surgical system may detect a certain bandwidth of communication between a modular device and a surgical hub. For example, the computer-implemented interactive surgical system may detect an indication of the purchase of certain service tier.

At 10708, a mode of operation may be determined based on the identified system/device parameter. This determination may be made by a process that maps system/device parameters to modes of operation. The process may be a manual and/or an automated process. The process may be the result of local computation and/or remote computation. For example, a client/server interaction may be used to determine the mode of operation based on the on the identified system/device parameter. For example, local software and/or locally embedded firmware may be used to determine the mode of operation based on the identified system/device parameter. For example, a hardware key, such as a secure microprocessor for example, may be used to determine the mode of operation based on the identified system/device parameter.

At 10710, operation may proceed in accordance with the determined mode of operation. For example, a system or device may proceed to operate in a default mode of operation. For example, a system or device may proceed to operate in an alternate mode of operation. The mode of operation may be directed by control hardware, firmware, and/or software already resident in the system or device. The mode of operation may be directed by control hardware, firmware, and/or software newly installed/updated.

FIG. 15B illustrates an example functional block diagram for changing a mode of operation. An upgradeable element 10714 may include an initialization component 10716. The initialization component 10716 may include any hardware, firmware, and/or software suitable determining a mode of operation. For example, the initialization component 10716 may be portion of a system or device start-up procedure. The initialization component 10716 may engage in an interaction to determine a mode of operation for the upgradeable element 10714. For example, the initialization component 10716 may interact with a user 10730, an external resource 10732, and/or a local resource 10718 for example. For example, the initialization component 10716 may receive a licensing key from the user 10730 to determine a mode of operation. The initialization component 10716 may query an external resource 10732, such as a server for example, with a serial number of the upgradable device 10714 to determine a mode of operation. For example, the initialization component 10716 may query a local resource 10718, such as a local query to determine an amount of available bandwidth and/or a local query of a hardware key for example, to determine a mode of operation.

The upgradeable element 10714 may include one or more operation components 10720, 10722, 10726, 10728 and an operational pointer 10724. The initialization component 10716 may direct the operational pointer 10724 to direct the operation of the upgradable element 10741 to the operation component 10720, 10722, 10726, 10728 that corresponds with the determined mode of operation. The initialization component 10716 may direct the operational pointer 10724 to direct the operation of the upgradable element to a default operation component 10720. For example, the default operation component 10720 may be selected on the condition of no other alternate mode of operation being determined. For example, the default operation component 10720 may be selected on the condition of a failure of the initialization component and/or interaction failure. The initialization component 10716 may direct the operational pointer 10724 to direct the operation of the upgradable element 10714 to a resident operation component 10722. For example, certain features may be resident in the upgradable component 10714 but require activation to be put into operation. The initialization component 10716 may direct the operational pointer 10724 to direct the operation of the upgradable element 10714 to install a new operation component 10728 and/or a new installed operation component 10726. For example, new software and/or firmware may be downloaded. The new software and or firmware may contain code to enable the features represented by the selected mode of operation. For example, a new hardware component may be installed to enable the selected mode of operation.

Cooperation between a primary display and/or a secondary display may be provided. For example, cooperation between a local instrument displays and paired imaging device display may be provided.

An instrument may be provided that may include a local display, a hub having an operating room (OR), or operating theater, display separate from the instrument display. When the instrument is linked to the surgical hub, the secondary display on the device reconfigures to display different information than when it may be independent of the surgical hub connection. A portion of the information on the secondary display of the instrument may be displayed on the primary display of the surgical hub. An image fusion may occur which may allow for the overlay of one or more of the status of a device, the integration landmarks being used to interlock several images, and a guidance feature. The image fusion may be provided on the surgical hub and/or instrument display. As disclosed herein, a number of techniques may be used for overlaying or augmenting images and/or text from multiple image/text sources to present composite images on one or more displays.

Cooperation between one or more local instrument displays and a paired laparoscope display may be provided. The behavior of a local display of an instrument may change when it senses the connectable presence of a display (e.g. a global display) that may be coupled to the surgical hub. The present disclosure may provide a $360^{-\infty}$ composite top visual field of view of a surgical site, which may assist in avoiding collateral structures.

During a surgical procedure, the surgical site may be displayed on a remote surgical hub display. The remote surgical hub display may be referred to as a primary display. During a surgical procedure, surgical devices may track and record surgical data and variables (e.g., surgical parameters) that may be stored in the instrument (see FIGS. 1-13 for instrument architectures comprising processors, memory, control circuits, storage, and the like). The surgical parameters may include force-to-fire (FTF), force-to-close (FTC), firing progress, tissue gap, power level, impedance, tissue compression stability (creep), and the like. Providing image/text overlay may be provided, for example, to allow a surgeon to watch a display that may present the overlaid image/text information.

When a surgical device (e.g., an instrument) is connected to the surgical hub, a composite image may be displayed on the primary display that may include a field of view of the surgical site received from a first instrument (e.g., medical imaging device such as, e.g., laparoscope, endoscope, thoracoscope, and the like) that may be augmented by surgical data and variables received from a second instrument (e.g., a surgical stapler) to provide pertinent images and data on the primary display.

During a surgical procedure the surgical site may be displayed as a narrow field of view of a medical imaging device on the primary surgical hub display. Items outside the current field of view, collateral structures, may not be viewed without moving the medical imaging device.

An embodiment may provide a narrow field of view of the surgical site in a first window of the display augmented by a wide field of view of the surgical site in a separate window of the display. This provides a composite overhead field of view mapped using two or more imaging arrays to provide an augmented image of multiple perspective views of the surgical site.

An embodiment may provide a wide field of view of the surgical site on a first display, which may be primary display. And a narrow field of view of the surgical side may be provided on a second display, which may be a secondary display.

A surgical hub may be provided that may comprising a processor and a memory coupled to the processor. The memory may stores instructions executable by the processor to detect a surgical device connection to the surgical hub, transmit a control signal to the detected surgical device to transmit to the surgical hub surgical parameter data associated with the detected device, receive the surgical parameter data, receive image data from an image sensor, and display, on a display coupled to the surgical hub, an image received from the image sensor in conjunction with the surgical parameter data received from the surgical device.

In another aspect, the present disclosure provides a surgical hub, comprising a processor and a memory coupled to the processor. The memory may store instructions executable by the processor to receive first image data from a first image sensor, receive second image data from a second image sensor, and display, on a display coupled to the surgical hub, a first image corresponding to the first field of view and a second image corresponding to the second field of view. The first image data represents a first field of view and the second image data represents a second field of view. The display may be a primary display and/or a secondary display. This display may be inside a sterile field or may be outside the sterile field.

The first field of view may be a narrow angle field of view and the second field of view may be a wide-angle field of view. The first image may be augmented with the second image on the display. The first image may be fused with the second image into a third image and display a fused image on the display. The fused image data may comprise instrument data which may include status information associated with a surgical device, an image data integration landmark to interlock a plurality of images, a guidance parameter, and the like. The first image sensor may capture the first image data at a first time and the second image data at a second time.

A third image data may be received from a third image sensor, wherein the third image data may represent a third field of view. A composite image data may be generated comprising the second and third image data. The first image may be displayed on the first display and/or in a first window of the display. The first image may correspond to the first image data. A third image may be displayed on a second display and/or in a second window of the first display. The third image may correspond to the composite image data. The display may be a primary display and/or a secondary display. This display may be inside a sterile field or may be outside the sterile field.

The third image data may represent a third field of view. The second image data may be fused with the third image data to generate fused image data. The first image may be displayed on a first display and/or in a first window of the display. The first image may correspond to the first image data. A third image may be displayed on a second display and/or in a second window of the first display. The third image may correspond to the fused image data.

Displaying endoscope images augmented with surgical device images on a primary surgical hub display may enable the surgeon to focus on a display to obtain a field of view of the surgical site augmented with surgical device data associated with the surgical procedure such as force-to-fire, force-to-close, firing progress, tissue gap, power level, impedance, tissue compression stability (creep), and the like. An endoscope image may be augmented with surgical devices images and may be displayed on primary display and/or a secondary display. For example, a primary display may display an endoscope image augmented with a surgical device image while a secondary display may display the surgical device image. As described herein, a user may gesture and/or issue a command to change primary display and/or secondary display. For example, a user may move the images display on the secondary display to the primary display or vice versa. Displaying a narrow field of view image in a first window of a display and a composite image of several other perspectives such as wider fields of view enables the surgeon to view a magnified image of the surgical site simultaneously with wider fields of view of the surgical site without moving the scope.

Both a global display and a local display of a device, e.g., a surgical instrument, may be provided. The local display may be coupled to the surgical hub. The global display may be associated with a primary display. The local display may be associated with a secondary display. The device may display one or more (e.g. all) of its relevant menus and displays on a local display until it senses a connection to the surgical hub at which point a sub-set of the information may be displayed on a primary display, for example, a monitor through the surgical hub. Information may or may not be mirrored on the device display. Information may be removed from the device screen. This technique frees up the device display to show different information or display larger font information on the surgical hub display.

An instrument may have a local display, which may be a secondary display. A surgical hub may be associated with an operating theater (e.g., operating room or OR) display that may be separate from the instrument display and may be a primary display. When an instrument is linked to the surgical hub, the instrument local display may become the secondary display and the instrument may reconfigure to display different information than when it may be operating independent of the surgical hub connection. In another aspect, some portion of the information on the secondary display may be displayed on the primary display in the operating theater through the surgical hub.

Figure 16:
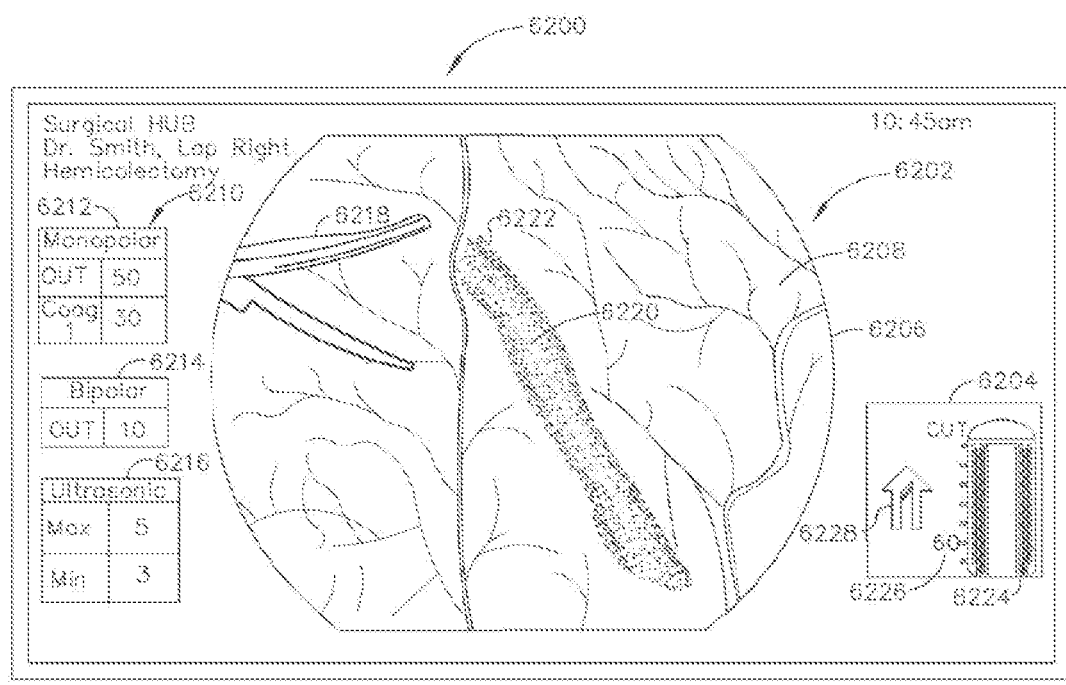
FIG. 16 illustrates a primary display of the surgical hub.

FIG. 16 illustrates a primary display of a surgical hub. For example, FIG. 16 illustrates an example primary display 6200 associate with the surgical hub 206 comprising a global display window 6202 and a local instrument display window 6204, according to one aspect of the present disclosure. With continued reference to FIGS. 1-11 to show interaction with an interactive surgical system 100 environment including a surgical hub 106, 206 and FIGS. 12-14 for surgical hub connected instruments together, the local instrument display 6204 behavior may be displayed when the instrument 235 senses the connectable presence of a global display window 6202 through the surgical hub 206. The global display window 6202 may show a field of view 6206 of a surgical site 6208, as viewed through a medical imaging device such as, for example, a laparoscope/endoscope 219 coupled to an imaging module 238, at the center of the surgical hub display 215, referred to herein also as a monitor, for example. The end effector 6218 portion of the connected instrument 235 may be shown in the field of view 6206 of the surgical site 6208 in the global display window 6202. The images shown on the display 237 located on an instrument 235 coupled to the surgical hub 206 is shown, or mirrored, on the local instrument display window 6204 located in the lower right corner of the monitor 6200 as shown in FIG. 16, for example.

During operation, relevant instrument and information and menus may be displayed on the display 237 located on the instrument 235 until the instrument 235 senses a connection of the instrument 235 to the surgical hub 206 at which point all or some sub-set of the information presented on the instrument display 237 may be displayed (e.g., only) on the local instrument display window 6204 portion of the surgical hub display 6200 through the surgical hub 206. The information displayed on the local instrument display window 6204 may be mirrored on the display 237 located on the instrument 235 or may be no longer accessible on the instrument display 237 detonated screen. This technique frees up the instrument 235 to show different information or to show larger font information on the surgical hub display 6200.

The primary display 6200 may provide perioperative visualization of the surgical site 6208. Advanced imaging may identify and visually highlight 6222 critical structures such as the ureter 6220 (or nerves, etc.) and may track instrument proximity displays 6210 and shown on the left side of the display 6200. In the illustrated example, the instrument proximity displays 6210 may show instrument specific settings. For example, the top instrument proximity display 6212 may show settings for a monopolar instrument, the middle instrument proximity display 6214 may show settings for a bipolar instrument, and the bottom instrument proximity display 6212 may show settings for an ultrasonic instrument.

One or more secondary displays, which may be dedicated local displays, may be linked to the surgical hub 206 to provide both an interaction portal via a touchscreen display and/or a secondary screen that may display any number of surgical hub 206 tracked data feeds to provide a status. The secondary screen may display force to fire (FTF), tissue gap, power level, impedance, tissue compression stability (creep), etc., while the primary screen may display key variables (e.g. only key variables) to keep the feed free of clutter. The interactive display may be used to move the display of information to the primary display to a desired location, size, color, and the like. For example, a user may user the interactive display to move information to a primary display where it may be highlighted and/or shown more prominently than other data.

As shown in FIG. 16, the secondary screen displays the instrument proximity displays 6210 on the left side of the display 6200 and the local instrument display 6204 on the bottom right side of the display 6200. The local instrument display 6204 presented on the surgical hub display 6200 displays an icon of the end effector 6218, such as the icon of a staple cartridge 6224 currently in use, the size 6226 of the staple cartridge 6224 (e.g., 60 mm), and an icon of the current position of the knife 6228 of the end effector.

The display 237 located on the instrument 235 may display the wireless or wired attachment of the instrument 235 to the surgical hub 206 and the instrument's communication/recording on the surgical hub 206. A setting may be provided on the instrument 235 to enable the user to select mirroring or extending the display to both monitoring devices. The instrument controls may be used to interact with the surgical hub display of the information being sourced on the instrument. As disclosed herein, the instrument 235 may comprise wireless communication circuits to communicate wirelessly with the surgical hub 206.

A first instrument coupled to the surgical hub 206 may pair to a screen of a second instrument coupled to the surgical hub 206 allowing both instruments to display some hybrid combination of information from the two devices of both becoming mirrors of portions of the primary display.

The primary display 6200 of the surgical hub 206 may provide a 360° composite top visual view of the surgical site 6208 to avoid collateral structures. For example, a secondary display of the end-effector surgical stapler may be provided within the primary display 6200 of the surgical hub 206 or on another display in order to provide better perspective around the areas within a current the field of view 6206.

Figure 17:
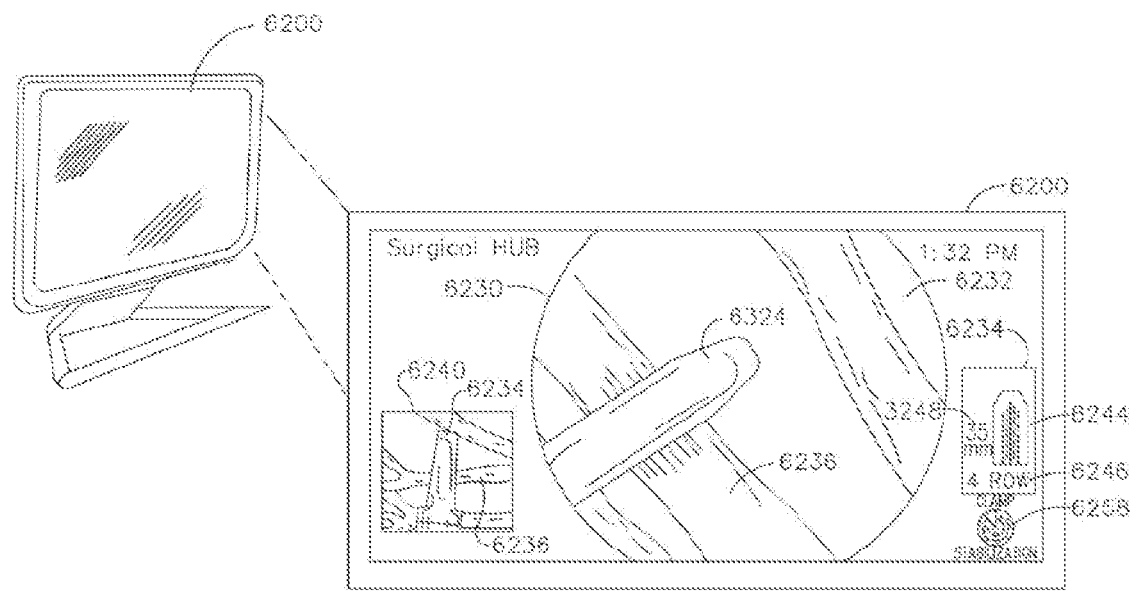
FIG. 17 illustrates an example a primary display of the surgical hub.

FIG. 17 illustrates an example a primary display of the surgical hub. For example, FIG. 17 may illustrate an example primary display having a composite overhead views of an end-effector 6234 portion of a surgical stapler mapped using two or more imaging arrays or one array and time to provide multiple perspective views of the end-effector 6234 to enable the composite imaging of an overhead field of view. The techniques described herein may be applied to ultrasonic instruments, electrosurgical instruments, combination ultrasonic/electrosurgical instruments, and/or combination surgical stapler/electrosurgical instruments. Several techniques may be performed for overlaying or augmenting images and/or text from multiple image/text sources to present composite images on a display (e.g., a single display).

As shown in FIG. 17, a primary display 6200 of the surgical hub 206 may display a primary window 6230. The primary window 6230 may be located at the center of the screen shows a magnified or exploded narrow angle view of a surgical field of view 6232. The primary window 6230 located in the center of the screen shows a magnified or narrow angle view of an end-effector 6234 of the surgical stapler grasping a vessel 6236. The primary window 6230 may display knitted images to produce a composite image that enables visualization of structures adjacent to the surgical field of view 6232. A second window 6240 may be shown in the lower left corner of the primary display 6200. The second window 6240 displays a knitted image in a wide-angle view at standard focus of the image shown in the primary window 6230 in an overhead view. The overhead view provided in the second window 6240 can enable the viewer to easily see items that are out of the narrow field surgical field of view 6232 without moving the laparoscope, or other imaging device coupled to the imaging module 238 of the surgical hub 206. A third window 6242 can be shown in the lower right corner of the primary display 6200 shows an icon 6244 representative of the staple cartridge of the end-effector 6234 (e.g., a staple cartridge in this instance) and additional information such as "4 Row" indicating the number of staple rows 6246 and "35 mm" indicating the distance 6248 traversed by the knife along the length of the staple cartridge. Below the third window 6242 is displayed an icon 6258 of a frame of the current state of a clamp stabilization sequence 6250 that indicates clamp stabilization.

In an example visualization control mode, display may be controlled by the user, for example, via motion tracking (e.g., head orientation relative to a monitor), hand gestures, voice activation and other means within the sterile field. A user may use gestures, motion tracking commands, voice activation, and the like to move data from one display to another display. For example, a user may use a gesture to move data from a first display to a second display. The gesture may be detected by the hub and the hub may instruct the first display to remove the data or stop displaying the data and may instruct the second display to display the data.

Figure 18:
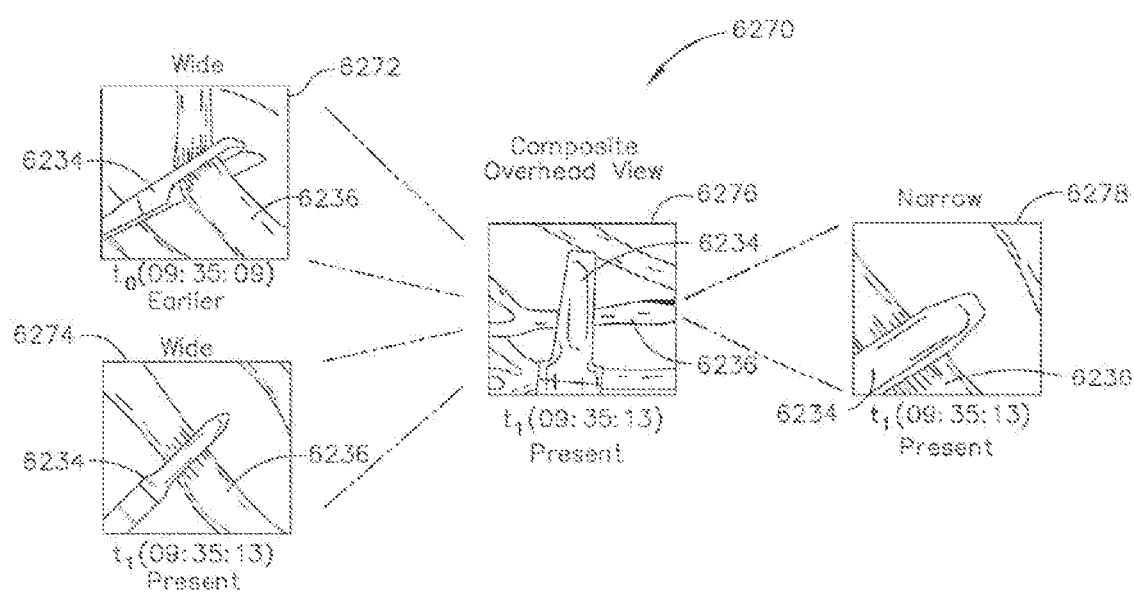
FIG. 18 illustrates a diagram of four wide angle view images of a surgical site at four separate times during the procedure.

FIG. 18 illustrates a diagram of four wide angle view images of a surgical site at four separate times during the procedure. For example, FIG. 18 illustrates a diagram 6270 of four separate wide-angle view images 6272, 6274, 6276, 6278 of a surgical site at four separate times during the procedure, according to an aspect of the present disclosure.

The sequence of images shows the creation of an overhead composite image in wide and narrow focus over time. A first image 6272 is a wide-angle view of the end-effector 6234 clamping the vessel 6236 taken at an earlier time to (e.g., 09:35:09). A second image 6274 is another wide-angle view of the end-effector 6234 clamping the vessel 6236 taken at the present time t1 (e.g., 09:35:13). A third image 6276 is a composite image of an overhead view of the end-effector 6234 clamping the vessel 6236 taken at present time t1. The third image 6276 may be displayed in the second window 6240 of the primary display 6200 of the surgical hub 206 as shown in FIG. 17. A fourth image 6278 is a narrow angle view of the end-effector 6234 clamping the vessel 6236 at present time t1 (e.g., 09:35:13). The fourth image 6278 is the narrow angle view of the surgical site shown in the primary window 6230 of the primary display 6200 of the surgical hub 206 as shown in FIG. 17.

In an aspect of the present disclosure, the primary display and/or the secondary display may display one or more of the first image, the second image, the third image, and/or the fourth image. For example, the primary display may display the third image and the secondary display may display the fourth image. As another example, the primary display may display the fourth image and the second display may display the third image.

Figure 19:
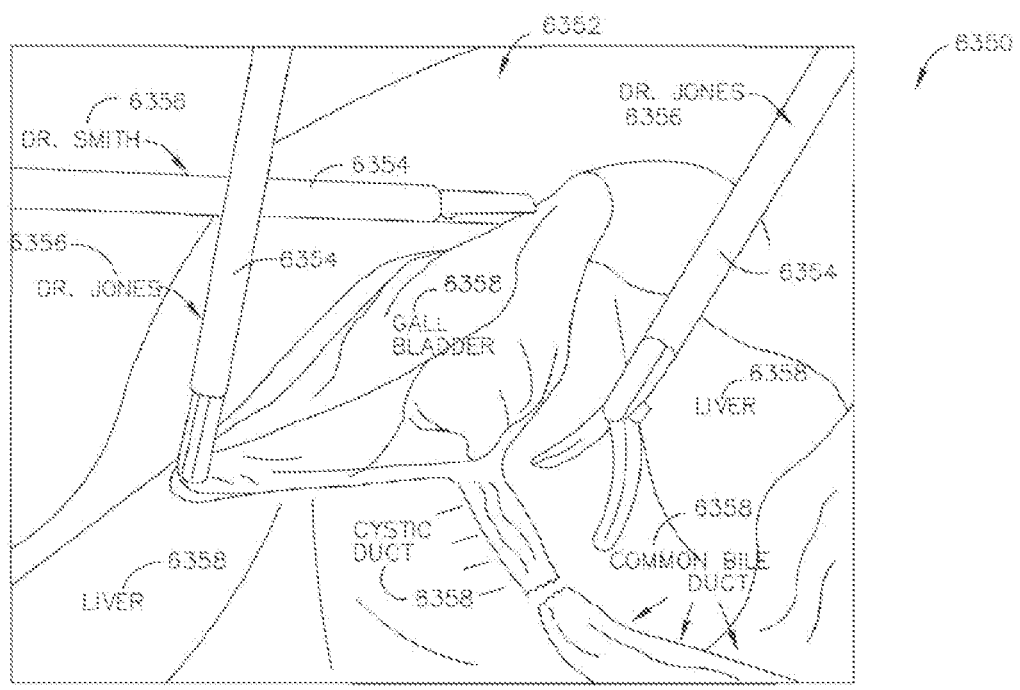
FIG. 19 illustrates an example of an augmented video image of a pre-operative video image augmented with data identifying displayed elements.

FIG. 19 illustrates an example of an augmented video image of a pre-operative video image augmented with data identifying displayed elements. The pre-operative video image that may be augmented with data may be displayed on a primary display and/or a secondary display. For example, an augmented video image may be displayed on the primary display while a video image may be displayed on the secondary display. As another example, the augmented video image may be displayed on the secondary display while the video image may be displayed on the primary display.

For example, FIG. 19 illustrates an example of an augmented video image 6350 comprising a pre-operative video image 6352 augmented with data (e.g. 6354, 6356, 6358 identifying displayed elements). An augmented reality vision system may be employed in surgical procedures to implement a method for augmenting data onto a pre-operative image 6352. The method includes generating a pre-operative image 6352 of an anatomical section of a patient and generating an augmented video image of a surgical site within the patient. The augmented video image 6350 may include an image of at least a portion of a surgical tool 6354 operated by a user 6456. The method may further include processing the pre-operative image 6352 to generate data about the anatomical section of the patient. The data may include a label 6358 for the anatomical section and a peripheral margin of at least a portion of the anatomical section. The peripheral margin may be configured to guide a surgeon to a cutting location relative to the anatomical section, embedding the data and an identity of the user 6356 within the pre-operative image 6350 to display an augmented video image 6350 to the user about the anatomical section of the patient. The method may further include sensing a loading condition on the surgical tool 6354, generating a feedback signal based on the sensed loading condition, and updating, in real time, the data and a location of the identity of the user operating the surgical tool 6354 embedded within the augmented video image 6350 in response to a change in a location of the surgical tool 6354 within the augmented video image 6350. Further examples are disclosed in U.S. Pat. No. 9,123,155, titled APPARATUS AND METHOD FOR USING AUGMENTED REALITY VISION SYSTEM IN SURGICAL PROCEDURES, which issued on Sep. 1, 2015, which is herein incorporated by reference in its entirety.

In an aspect, radiographic integration techniques may be employed to overlay the pre-operative image 6352 with data obtained through live internal sensing or pre-procedure techniques. Radiographic integration may include marker and landmark identification using surgical landmarks, radiographic markers placed in or outside the patient, identification of radio—opaque staples, clips or other tissue-fixated items. Digital radiography techniques may be employed to generate digital images for overlaying with a pre-operative image 6352. Digital radiography is a form of X-ray imaging that employs a digital image capture device with digital X-ray sensors instead of traditional photo graphic film. Digital radiography techniques provide immediate image preview and availability for overlaying with the pre-operative image 6352. In addition, special image processing techniques can be applied to the digital X-ray images to enhance the overall display quality of the image.

Digital radiography techniques may employ image detectors that include flat panel detectors (FPDs), which may be classified in two categories indirect FPDs and direct FPDs. Indirect FPDs may include amorphous silicon (a-Si) combined with a scintillator in the detector's outer layer, which is made from cesium iodide (CSI) or gadolinium oxy-sulfide (Gd2O2S), converts X-rays to light. The light may be channeled through the a-Si photodiode layer where it is converted to a digital output signal. The digital signal may then read out by thin film transistors (TFTs) or fiber—coupled charge coupled devices (CODs). Direct FPDs include amorphous selenium (a-Se) FPDs that convert X-ray photons directly into charge. The outer layer of a flat panel in this design may be a high voltage bias electrode. X-ray photons may create electron hole pairs in a-Se, and the transit of these electrons and holes may depend on the potential of the bias voltage charge. As the holes may be replaced with electrons, the resultant charge pattern in the selenium layer may be read out by a TFT array, active matrix array, electrometer probes or micro plasma line addressing. Other direct digital detectors may be based on CMOS and CCD technology. Phosphor detectors also may be employed to record the X-ray energy during exposure and may be scanned by a laser diode to excite the stored energy which may be released and read out by a digital image capture array of a CCD.

Figure 20:
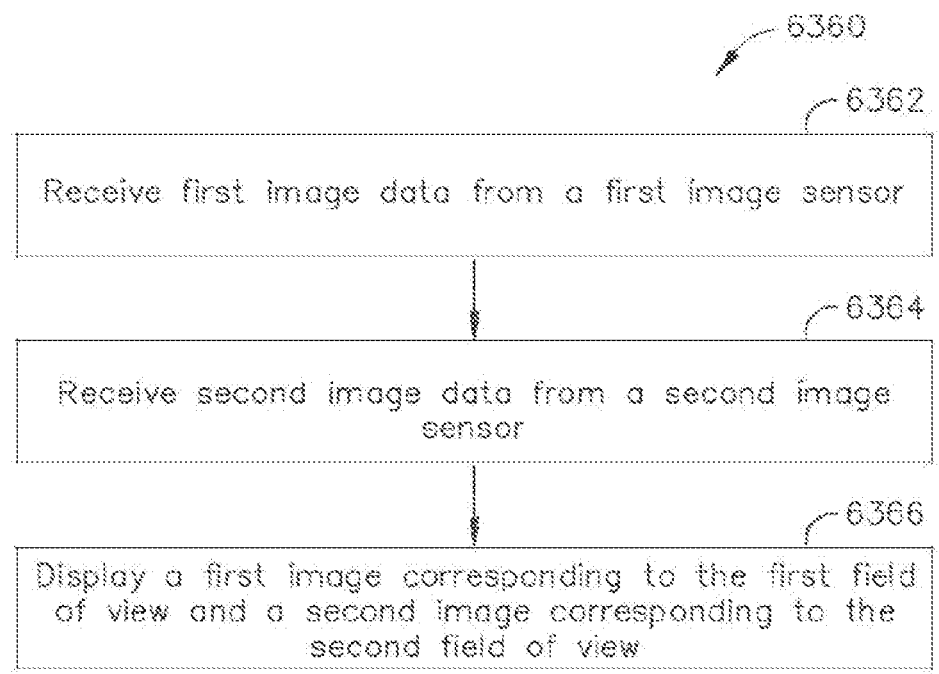
FIG. 20 illustrates an example flow diagram of a process for displaying one or more images.

FIG. 20 illustrates an example flow diagram of a process for displaying one or more images. For example, FIG. 20 illustrates a logic flow diagram 6360 of a process depicting a control program or a logic configuration to display images, according to one aspect of the present disclosure. With reference also to FIGS. 1-11 to show interaction with an interactive surgical system 100 environment including a surgical hub 106, 206, the present disclosure provides, in an aspect, a surgical hub 206, comprising a processor 244 and a memory 249 coupled to the processor 244. The memory 249 stores instructions executable by the processor 244 to receive 6362 first image data from a first image sensor, receive 6364 second image data from a second image sensor, and display 6366, on a display, a first image corresponding to the first field of view and a second image corresponding to the second field of view. The first image data may represent a first field of view and the second image data represents a second field of view. The display may be a primary display and/or a secondary display. The display may be display 217 coupled to the surgical hub 206.

In an aspect, the first field of view may be a narrow angle field of view and the second field of view is a wide-angle field of view. In another aspect, the memory 249 stores instructions executable by the processor 244 to augment the first image with the second image on the display. The display may be a primary display and/or a secondary display.

In another aspect, the memory 249 stores instructions executable by the processor 244 to fuse the first image and the second image into a third image and display a fused image on a display. The display may be a primary display and/or a secondary display. The display may be display 217. The first image, second image, and/or third image may be displayed on the secondary display, while the fused image may be displayed on the primary display. The first image, second image, and/or third image may be displayed on the primary display, while the fused image may be displayed on the secondary display.

In another aspect, the fused image data comprises status information associated with a surgical device 235, an image data integration landmark to interlock a plurality of images, and at least one guidance parameter. In another aspect, the first image sensor is the same as the same image sensor and wherein the first image data is captured as a first time and the second image data is captured at a second time. One or more images may be displayed on a primary display and/or a secondary display.

In another aspect, the memory 249 stores instructions executable by the processor 244 to receive third image data from a third image sensor, wherein the third image data represents a third field of view, generate composite image data comprising the second and third image data, display the first image in a first window of the display, wherein the first image corresponds to the first image data, and display a third image in a second window of the display 215, wherein the third image corresponds to the composite image data. In another aspect, the first image, second image, and/or third image may be displayed on the primary display and/or the secondary display. For example, the user may indicate that the primary display and/or secondary may display at one of the first image, second image, and third image.

In another aspect, the memory 249 stores instructions executable by the processor 244 to receive third image data from a third image sensor, wherein the third image data represents a third field of view, fuse the second and third image data to generate fused image data, display the first image in a first window of the display 217, wherein the first image corresponds to the first image data, and display a third image in a second window of the display 217, wherein the third image corresponds to the fused image data. In another aspect, the first image, second image, and/or third image may be displayed on the primary display and/or the secondary display. For example, the user may indicate that the primary display and/or secondary may display at one of the first image, second image, and third image.

Figure 21:
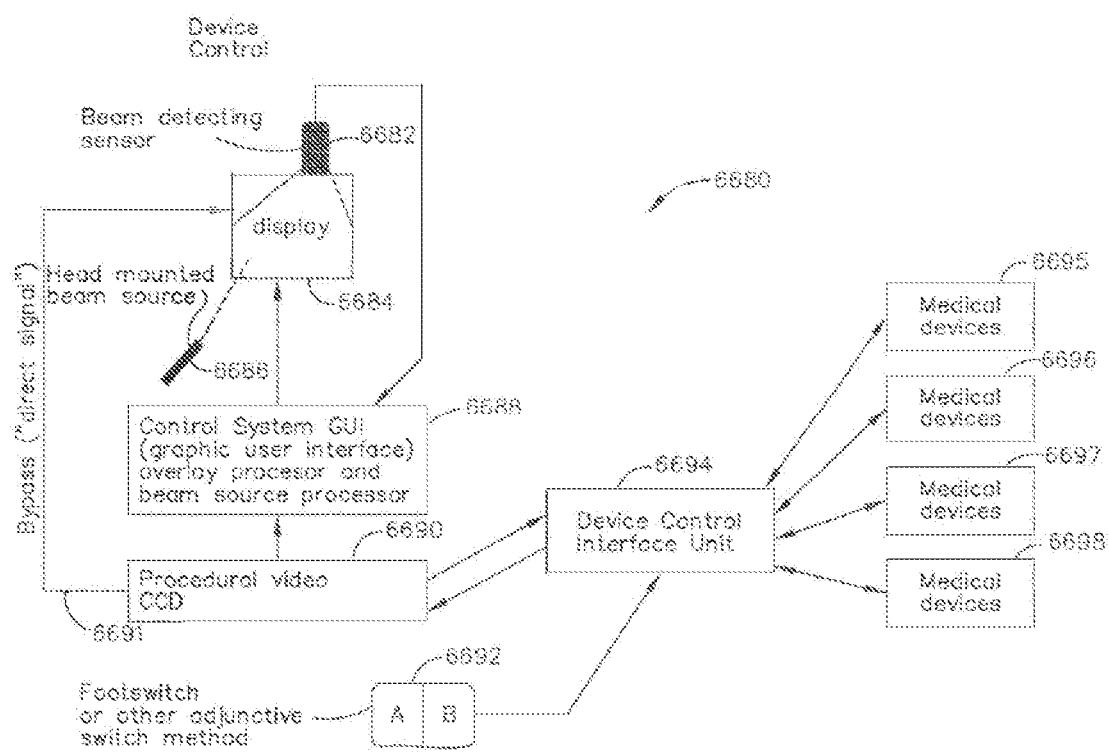
FIG. 21 illustrates a diagram of a beam source and combined beam detector system utilized as a device control mechanism in an operating theater, in accordance with at least one aspect of the present disclosure.

In an aspect, the present disclosure provides illustrates a surgical communication and control headset that interfaces with the surgical hub 206 described in connection with FIGS. 1-11. Further examples are disclosed in U.S. Patent Application Publication No. 2009/0046146, titled SURGICAL COMMUNICATION AND CONTROL SYSTEM, which published on Feb. 19, 2009, which is herein incorporated by reference in its entirety. FIG. 21 illustrates a diagram of a beam source and combined beam detector system utilized as a device control mechanism in an operating theater, in accordance with at least one aspect of the present disclosure. For example, FIG. 21 illustrates a diagram of a beam source and combined beam detector system utilized as a device control mechanism in an operating theater. The system 6680 may be configured and wired to allow for device control with the overlay generated on a primary display (e.g. a primary procedural display) and/or a secondary display. A footswitch shows a method to allow the user to click on command icons that would appear on the screen while the beam source is used to aim at the particular desired command icon to be clicked. The beam source may also be used to indicate where the user may be looking. The beam source may also be used by a user to indicate where data may be displayed. For example, a user may direct the beam source at the primary display and/or the secondary display to indicate which display should be used to display data.

The control system graphic user interface (GUI) and device control processor communicate, and parameters are changed using the system. The system may comprise a display that may be coupled to a beam detecting sensor. The display may be a primary display and/or a secondary display. For example, the system 6680 includes a display 6684 coupled to a beam detecting sensor 6682. The system may include a head mounted source 6686. The beam detecting sensor 6682 may be in communication with a control system GUI overlay processor and beam source processor 6688. The surgeon may operate a footswitch 6692 or other adjunctive switch, which provides a signal to a device control interface unit 6694.

The system 6680 may provide a means for a sterile clinician to control procedural devices in an easy and quick, yet hands free and centralized fashion. The ability to maximize the efficiency of the operation and minimize the time a patient is under anesthesia is important to the best patient outcomes. It is common for surgeons, cardiologists or radiologists to verbally request adjustments be made to certain medical devices and electronic equipment used in the procedure outside the sterile field. It is typical that he or she must rely on another staff member to make the adjustments he or she needs to settings on devices such as cameras, bovies, surgical beds, shavers, insufflators, injectors, to name a few. In many circumstances, having to command a staff member to make a change to a setting can slow down a procedure because the nonsterile staff member is busy with another task. The sterile physician cannot adjust nonsterile equipment without compromising sterility, so he or she must often wait for the nonsterile staff member to make the requested adjustment to a certain device before resuming the procedure.

The system 6680 allows a user to use a beam source and beam detector to regenerate a pointer overlay coupled with a GUI and a concurrent switching method (i.e., a foot switch, etc.) to allow the clinician to click through commands on a primary display and/or secondary display. In one aspect, a GUI could appear on the procedural video display, which may be a primary display and/or secondary display, when activated, such as when the user tilts his or her head twice to awaken it or steps on a foot switch provided with the system. Or it is possible that a gesture, such as a right head tilt wakes up the system, and another gesture, such as a left head tilt simply activates the beam source. When the overlay (called device control GUI overlay) appears on the screen it may show button icons representing various surgical devices and the user may use the beam source, in this case a laser beam, to aim at the button icons. Once the laser is over the proper button icon, a foot switch, or other simultaneous switch method can be activated, effectively acting like a mouse click on a computer. For example, a user can "wake up" the system, causing a device control GUI overlay to pop up that lists button icons on the screen, each one labeled as a corresponding procedural medical device. The user may point the laser at the correct box or device and click a foot pedal (or some other concurrent control—like voice control, waistband button, etc.) to make a selection, much like clicking a mouse on a computer. The sterile physician can then select "insufflator, for example" The subsequent screen shows arrow icons that can be clicked for various settings for the device that need to be adjusted (pressure, rate, etc.). In one iteration, the user can then may point the laser at the up arrow and click the foot pedal repeatedly until the desired setting is attained.

In an aspect, a user, such as the sterile physician, may use the beam to indicate where data may be displayed. For example, the user may be able to view a primary display and/or a secondary display. The user may wish to see contextual data, such a data related to the operation, on one of more of the displays. The user may use the beam to indicate that the contextual data should appear on the primary display. The user may use the beam to indicate that the contextual data should appear on the secondary display. The user may use the beam to indicate that data from the primary display should be moved to the secondary display, or that the data should be moved from the secondary display to the primary display.

A surgical hub may provide an interface control with one or more primary displays and/or one or more secondary displays, which may be secondary surgeon display units. The primary display and/or secondary display may be designed to be within the sterile field.

Figure 22A:
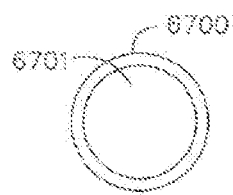
FIGS. 22A-E illustrate various types of sterile field control and data input consoles, in accordance with at least one aspect of the present disclosure, where.
Figure 22B:
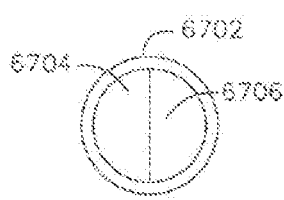
Figure 22C:
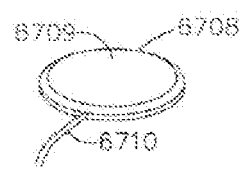
Figure 22D:
Figure 22E:
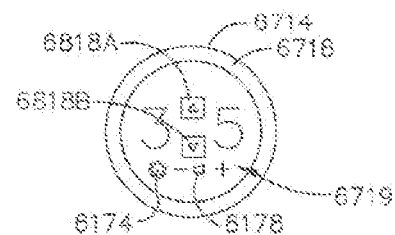

FIGS. 22A-E illustrate various types of sterile field control and data input consoles, in accordance with at least one aspect of the present disclosure. FIG. 22A illustrates a single zone sterile field control and data input console. FIG. 22B illustrates a multi zone sterile field control and data input console. FIG. 22C illustrates a tethered sterile field control and data input console. FIG. 22D illustrates a battery-operated sterile field control and data input console. FIG. 22E illustrates a battery-operated sterile field control and data input console.

In an aspect, the surgical hub 206 may provide a secondary user interface that may enable display and control of surgical hub 206 functions from with the sterile field. The secondary display may be used to change display locations, what information is displayed where, pass off control of specific functions or devices. For example, the secondary display may be used by a user to move data display on a secondary display to a primary display. As another example, the secondary display may be used by a user to move data from a primary display to a secondary display. The secondary display may be internal to a medical instrument, external to a medical instrument, or associated with a medical instrument.

A display unit, which may be a primary display and/or a secondary display, may be designed to be used within the sterile field and may be accessible for input and display by a surgeon to allow the surgeon to have interactive input control from the sterile field to control other surgical devices that may be coupled to the surgical hub. The display unit may be sterile and located within the sterile field to allow the surgeons to interface with the display unit and the surgical hub to directly interface and configure instruments as necessary without leaving the sterile field. The display unit may be used for display, control, interchanges of tool control, allowing feeds from other surgical hubs without the surgeon leaving the sterile field. The display unit may allow a user, such as the surgeon to control a primary display and/or secondary display that may be outside the sterile field. The display unit may allow the user to control a primary and/or secondary display that may be within the sterile field.

In an aspect, the present disclosure provides a control unit, comprising an interactive touchscreen display, an interface configured to couple the interactive touchscreen display to a surgical hub, a processor, and a memory coupled to the processor. The memory stores instructions executable by the processor to receive input commands from the interactive touchscreen display located inside a sterile field and transmits the input commands to a surgical hub to control devices coupled to the surgical hub located outside the sterile field.

In an aspect, the present disclosure provides a control unit, comprising an interactive touchscreen display, an interface configured to couple the interactive touchscreen display to a surgical hub, and a control circuit configured to receive input commands from the interactive touchscreen display located inside a sterile field and transmit the input commands to a surgical hub to control devices coupled to the surgical hub located outside the sterile field.

A display unit may be provided that may be used within the sterile field and may be accessible for input and display by a surgeon. For example, the display unit may provide the surgeon interactive input control from the sterile field to control other surgical devices coupled to the surgical hub. This display unit within the sterile field is sterile and allows the surgeons to interface with it and the surgical hub. This gives the surgeon control of the instruments coupled to the surgical hub and allows the surgeon to directly interface and configure the instruments as necessary without leaving the sterile field. The display unit may be used for display, control, interchanges of tool control, allowing feeds from other surgical hubs without the surgeon leaving the sterile field. For example, the display unit may be a primary display and/or a secondary display, and the display unit may be used to control the display of data on another primary display and/or secondary display. In another example, the display unit may be used to move data being displayed on one display to another display.

A secondary user interface may be used to enable display and control of surgical hub functions from within a sterile field. This control may a primary display and/or a secondary display and may be a display device like an I-pad, e.g., a portable interactive touchscreen display device configured to be introduced into the operating theater in a sterile manner. It may be paired like any other device or it may be location sensitive. The display device may be allowed to function in this manner whenever the display device is placed over a location (e.g. a specific location). For example, the display device may be allowed to function in this manner whenever the display device is placed over a location of the draped abdomen of the patient during a surgical procedure.

In an aspect, the present disclosure provides a secondary user interface to enable display and control of surgical hub functions from within the sterile field. In an aspect, the secondary display may be used to change display locations, determine what information and where the information is displayed, and pass off control of specific functions or devices. For example, the secondary display may be used to send data to be displayed on a primary display.

There may be a number of different types of secondary surgical display. For example, one type of secondary display may be designed to be used within the sterile field and may be accessible for input and display by the surgeon within the sterile field interactive control displays. Sterile field interactive control displays may be shared or common sterile field input control displays. A sterile field display may be a primary display and/or a secondary display.

A sterile field display may be mounted on the operating table, on a stand, or merely laying on the abdomen or chest of the patient. The sterile field display is sterile and allows the surgeons to interface with the sterile field display and the surgical hub. This may give the surgeon control of the system and may allow them to interface and configure the sterile field display as necessary. The sterile field display may be configured as a master device and may be used for display, control, interchanges of tool control, allowing feeds from other surgical hubs, etc. For example, the sterile field display may be a primary display and/or a secondary display and may allow the surgeon to control one or more primary displays and/or secondary displays.

In an aspect, the sterile field display may be employed to re-configure the wireless activation devices within the operating theater (OR) and their paired energy device if a surgeon hands the device to another. FIGS. 22A-22E illustrate various types of sterile field control and data input consoles 6700, 6702, 6708, 6712, 6714 according to various aspects of the present disclosure. Each of the disclosed sterile field control and data input consoles 6700, 6702, 6708, 6712, 6714 comprise at least one touchscreen 6701, 6704/6706, 6709, 6713, 6716 input/output device layered on the top of an electronic visual display of an information processing system. The sterile field control and data input consoles 6700, 6702, 6708, 6712, 6714 may include batteries as a power source. Some include a cable 6710 to connect to a separate power source or to recharge the batteries. A user can give input or control the information processing system through simple or multi-touch gestures by touching the touchscreen 6701, 6704/6706, 6709, 6713, 6716 with a stylus, one or more fingers, or a surgical tool. The sterile field control and data input consoles 6700, 6702, 6708, 6712, 6714 may be used to re-configure wireless activation devices within the operating theater and a paired energy device if a surgeon hands the device to another surgeon. For example, the sterile field display may be a primary display and/or a secondary display and may allow the surgeon to control one or more primary displays and/or secondary displays.

The sterile field control and data input consoles 6700, 6702, 6708, 6712, 6714 may be used to accept consult feeds from another operating theater where it would then configure a portion of the operating theater screens or all of them to mirror the other operating theater so the surgeon is able to see what is needed to help. The sterile field control and data input consoles 6700, 6702, 6708, 6712, 6714 are configured to communicate with the surgical hub 206. Accordingly, the description of the surgical hub 206 discussed in connection with FIGS. 1-11 is incorporated in this section by reference.

FIG. 22A illustrates a single zone sterile field control and data input console 6700, according to one aspect of the present disclosure. The single zone console 6700 is configured for use in a single zone within a sterile field. The single zone console 6700 may be a secondary display. Once deployed in a sterile field, the single zone console 6700 can receive touchscreen inputs from a user in the sterile field. The touchscreen 6701 enables the user to interact directly with what is displayed, rather than using a mouse, touchpad, or other such devices (other than a stylus or surgical tool). The single zone console 6700 includes wireless communication circuits to communicate wirelessly to the surgical hub 206. The single zone console 6700 may allow a user to control a primary display and/or another secondary display.

FIG. 22B illustrates a multi zone sterile field control and data input console 6702, according to one aspect of the present disclosure. The multi zone console 6702 comprises a first touchscreen 6704 to receive an input from a first zone of a sterile field and a second touchscreen 6706 to receive an input from a second zone of a sterile field. The multi zone console 6702 may be a secondary display. The multi zone console 6702 is configured to receive inputs from multiple users in a sterile field. The multi zone console 6702 includes wireless communication circuits to communicate wirelessly to the surgical hub 206. Accordingly, the multi zone sterile field control and data input console 6702 comprises an interactive touchscreen display with multiple input and output zones. The multi zone console 6702 may allow a user to control a primary display and/or another secondary display.

FIG. 22C illustrates a tethered sterile field control and data input console 6708, according to one aspect of the present disclosure. The tethered console 6708 includes a cable 6710 to connect the tethered console 6708 to the surgical hub 206 via a wired connection. The cable 6710 enables the tethered console 6708 to communicate over a wired link in addition to a wireless link. The cable 6710 also enables the tethered console 6708 to connect to a power source for powering the console 6708 and/or recharging the batteries in the console 6708. The tethered console 6708 may be a secondary display. The tethered console 6708 may allow a user to control a primary display and/or another secondary display.

FIG. 22D illustrates a battery-operated sterile field control and data input console 6712, according to one aspect of the present disclosure. The sterile field console 6712 is battery operated and includes wireless communication circuits to communicate wirelessly with the surgical hub 206. In an aspect, the sterile field console 6712 may be configured to communicate with any of the modules coupled to the hub 206 such as the generator module 240. Through the sterile field console 6712, the surgeon may adjust the power output level of a generator using the touchscreen 6713 interface. An example is described below in connection with FIG. 22E. The sterile field console 6712 may be a secondary display. The sterile field console 6712 may allow a user to control a primary display and/or another secondary display.

FIG. 22E illustrates a battery-operated sterile field control and data input console 6714, according to one aspect of the present disclosure. The sterile field console 6714 may include a user interface displayed on the touchscreen of a generator. The surgeon may thus control the output of the generator by touching the up/down arrow icons 6718A, 6718B that increase/decrease the power output of the generator module 240. Additional icons 6719 enable access to the generator module settings 6174, volume 6178 using the +/− icons, among other features directly from the sterile field console 6714. The sterile field console 6714 may be employed to adjust the settings or reconfigure other wireless activations devices or modules coupled to the hub 206 within the operating theater and their paired energy device when the surgeon hands the sterile field console 6714 to another. The sterile field console 6714 may be a secondary display. The sterile field console 6714 may allow a user to control a primary display and/or another secondary display.

Figures 23A, 23B:
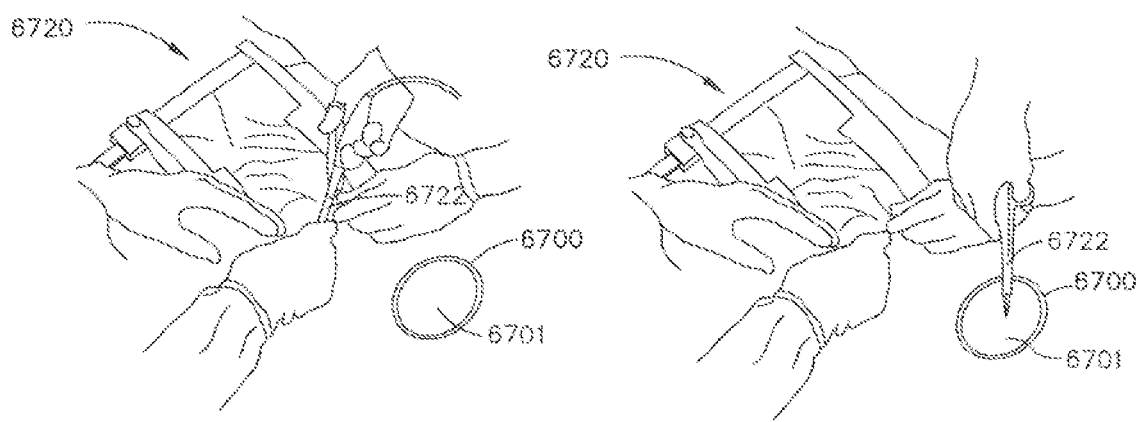
FIGS. 23A-23B illustrate a sterile field console in use in a sterile field during a surgical procedure, in accordance with at least one aspect of the present disclosure, where.

FIGS. 23A-23B illustrate a sterile field console 6700 in use in a sterile field during a surgical procedure, according to one aspect of the present disclosure. FIG. 23 shows the sterile field console 6714 positioned in the sterile field near two surgeons engaged in an operation. In FIG. 23, one of the surgeons is shown tapping the touchscreen 6701 of the sterile field console with a surgical tool 6722 to adjust the output of a modular device coupled to the surgical hub 206, reconfigure the modular device, or an energy device paired with the modular device coupled to the surgical hub 206.

The sterile field display may be employed as an interactable scalable secondary display allowing the surgeon to overlay other feeds or images like laser Doppler scanning arrays. In an aspect, the sterile field display may be employed to call up a pre-operative scan or image to review. Once vessel path and depth and device trajectory are estimated, the surgeon employs a sterile field interactable scalable secondary display allowing the surgeon to overlay other feeds or images.

Figure 24:
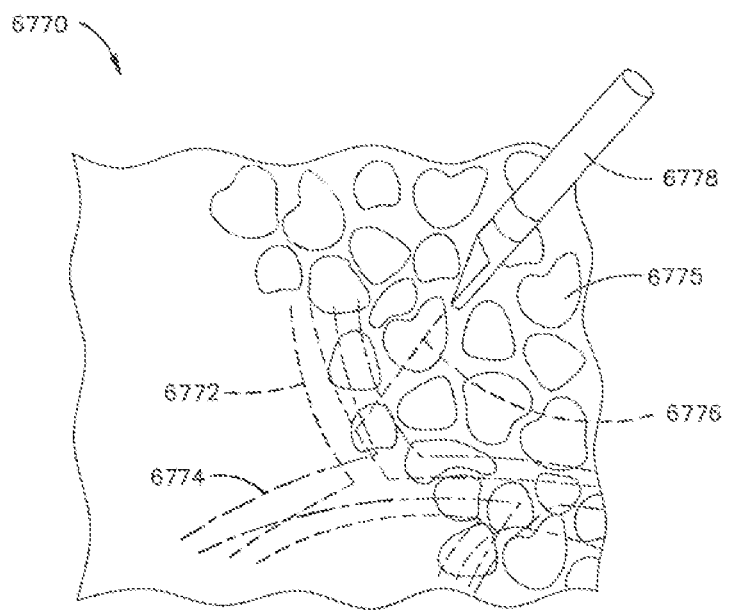
FIG. 24 illustrates a standard technique for estimating vessel path and depth and device trajectory, in accordance with at least one aspect of the present disclosure.

FIG. 24 is a diagram 6770 that illustrates a technique for estimating vessel path, depth, and device trajectory. Prior to dissecting a vessel 6772, 6774 located below the surface of the tissue 6775 using a standard approach, the surgeon estimates the path and depth of the vessel 6772, 6774 and a trajectory 6776 of a surgical device 6778 will take to reach the vessel 6772, 6774. It is often difficult to estimate the path and depth 6776 of a vessel 6772, 6774 located below the surface of the tissue 6775 because the surgeon cannot accurately visualize the location of the vessel 6772, 6774 path and depth 6776.

Figure 25A:
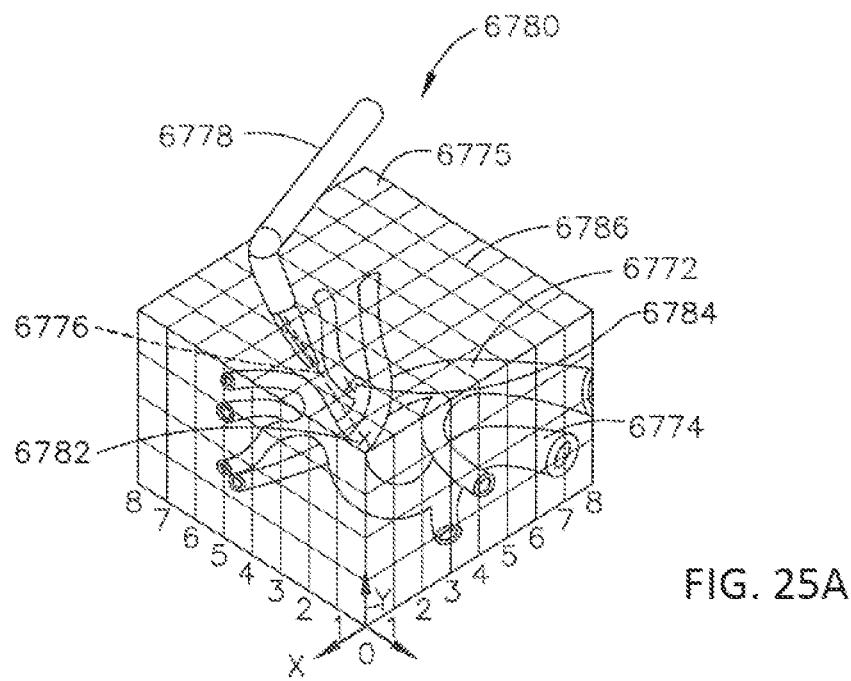
FIGS. 25A-25D illustrate multiple real time views of images of a virtual anatomical detail for dissection, in accordance with at least one aspect of the present disclosure, where.
Figure 25B:
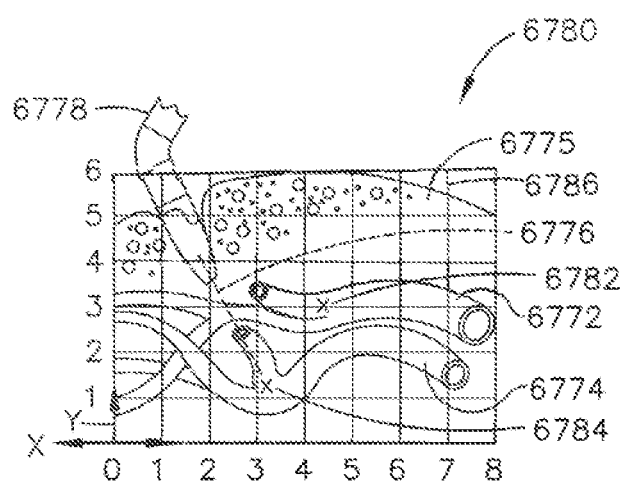
Figure 25C:
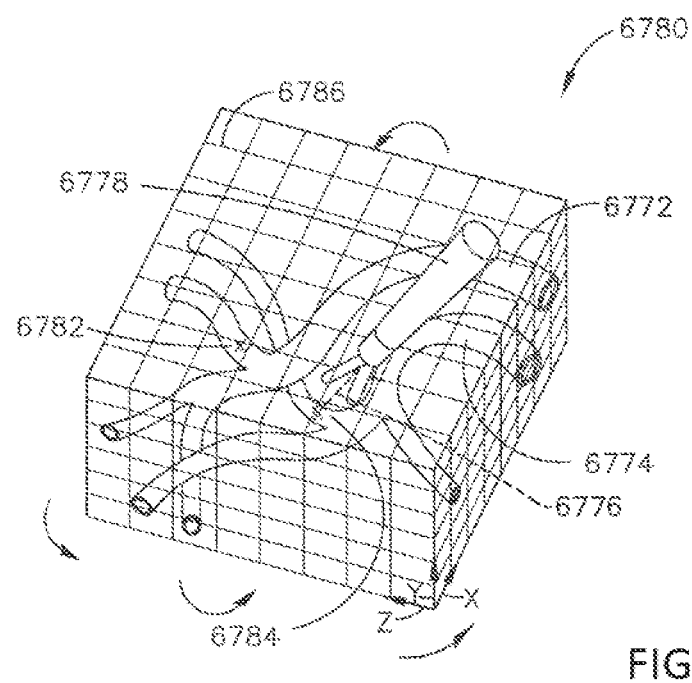
Figure 25D:
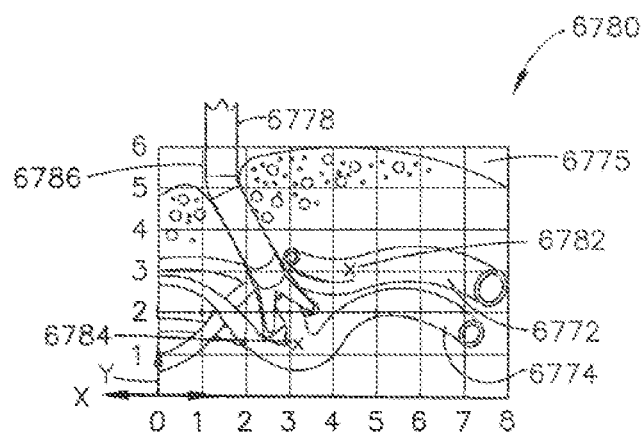

FIGS. 25A-25D illustrate multiple real time views of images of a virtual anatomical detail for dissection including perspective views (FIGS. 25A, 25C) and side views (FIGS. 25B, 25D). The images may be displayed on a primary display and/or a secondary display. For example, the images may be displayed on a sterile field display of tablet computer or sterile field control and data input console employed as an interactable scalable secondary display allowing the surgeon to overlay other feeds or images, according to an aspect of the present disclosure. The images of the virtual anatomy may enable the surgeon to more accurately predict the path and depth of a vessel 6772, 6774 located below the surface of the tissue 6775 as shown in FIG. 24 and the best trajectory 6776 of the surgical device 6778.

FIG. 25A is a perspective view of a virtual anatomy 6780 displayed on a secondary device, such as a tablet computer or sterile field control and data input console. FIG. 25B is a side view of the virtual anatomy 6780 shown in FIG. 25A, according to one aspect of the present disclosure. With reference to FIGS. 25A-25B, in one aspect, the surgeon uses a smart surgical device 6778 and a tablet computer to visualize the virtual anatomy 6780 in real time and in multiple views. The smart surgical device 6778 may include a display, which may be a secondary display. The tablet computer may include a display that may be a primary display and/or a secondary display. The three-dimensional perspective view includes a portion of tissue 6775 in which the vessels 6772, 6774 are located below surface. The portion of tissue is overlaid with a grid 6786 to enable the surgeon to visualize a scale and gauge the path and depth of the vessels 6772, 6774 at target locations 6782, 6784 each marked by an X. The grid 6786 also assists the surgeon determine the best trajectory 6776 of the surgical device 6778. As illustrated, the vessels 6772, 6774 have an unusual vessel path.

FIG. 25C illustrates a perspective view of the virtual anatomy 6780 for dissection, according to one aspect of the present disclosure. FIG. 25D is a side view of the virtual anatomy 6780 for dissection, according to one aspect of the present disclosure. With reference to FIGS. 25C-25D, using the tablet computer, the surgeon can zoom and pan $360^{-\infty}$ to obtain an optimal view of the virtual anatomy 6780 for dissection. The surgeon then determines the best path or trajectory 6776 to insert the surgical device 6778 (e.g., a dissector in this example). The surgeon may view the anatomy in a three-dimensional perspective view or any one of six views. See for example the side view of the virtual anatomy in FIG. 25D and the insertion of the surgical device 6778 (e.g., the dissector).

In another aspect, a sterile field control and data input console may allow live chatting between different departments, such as, for example, with the oncology or pathology department, to discuss margins or other particulars associated with imaging. The sterile field control and data input console may allow the pathology department to tell the surgeon about relationships of the margins within a specimen and show them to the surgeon in real time using the sterile field console.

In another aspect, a sterile field control and data input console may be used to change the focus and field of view of its own image or control that of any of the other monitors coupled to the surgical hub. For example, the sterile field control and data input console may be a primary display and/or a secondary display that may be used to control another primary display and/or secondary display.

In another aspect, a sterile field control and data input console may be used to display the status of any of the equipment or modules coupled to the surgical hub 206. Knowledge of which device coupled to the surgical hub 206 is being used may be obtained via information such as the device is not on the instrument pad or on-device sensors. Based on this information, the sterile field control and data input console may change display, configurations, switch power to drive one device, and not another, one cord from capital to instrument pad and multiple cords from there. Device diagnostics may obtain knowledge that the device is inactive or not being used. Device diagnostics may be based on information such as the device is not on the instrument pad or based on-device sensors.

In another aspect, a sterile field control and data input console may be used as a learning tool. The console may display checklists, procedure steps, and/or sequence of steps. A timer/clock may be displayed to measure time to complete steps and/or procedures. The console may display room sound pressure level as indicator for activity, stress, etc.

FIGS. 26A-26E illustrate a touchscreen display 6890 that may be used within the sterile field, according to an aspect of the present disclosure. The touch screen display 6890 may be a primary display and/or a secondary display. Using the touchscreen display 6890, a surgeon may manipulate images 6892 displayed on the touchscreen display 6890 using a variety of gestures such as, for example, drag and drop, scroll, zoom, rotate, tap, double tap, flick, drag, swipe, pinch open, pinch close, touch and hold, two-finger scroll, among others. Using the touchscreen display 6890, a surgeon may manipulate images 6892 that may be displayed on another primary display and/or secondary display using a variety of gestures such as, for example, drag and drop, scroll, zoom, rotate, tap, double tap, flick, drag, swipe, pinch open, pinch close, touch and hold, two-finger scroll, among others. A surgeon may also use a gesture, such as a gesture on the touch screen display 6890, to move an image or data being displayed on touch screen display 6890 to another primary display and/or secondary display. A surgeon may also use a gesture, such as a gesture on the touchscreen display 6890, to move an image or data being displayed on a primary display and/or secondary display to the touchscreen display 6890.

Figure 26A:
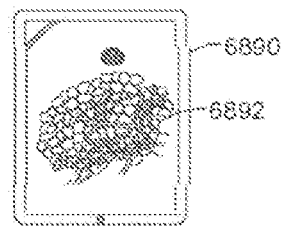
FIGS. 26A-26E illustrate a touchscreen display that may be used within the sterile field, in accordance with an aspect of the present disclosure, where.
Figure 26B:
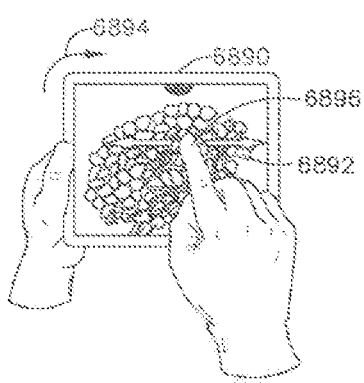
Figure 26E:
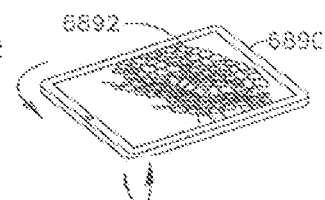
Figure 26C:
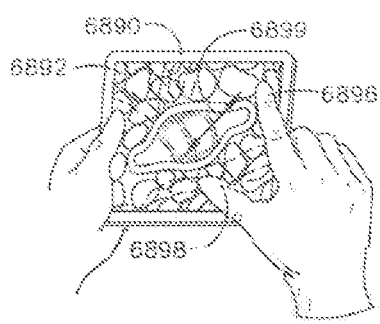
Figure 26D:
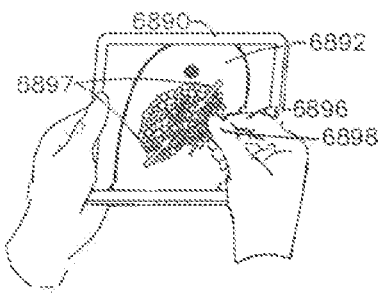

FIG. 26A illustrates an image 6892 of a surgical site displayed on a touchscreen display 6890 in portrait mode. FIG. 26B shows the touchscreen display 6890 rotated (e.g. arrow 6894) to landscape mode and the surgeon uses his index finger 6896 to scroll the image 6892 in the direction of the arrows. FIG. 26C shows the surgeon using his index finger 6896 and thumb 6898 to pinch open the image 6892 in the direction of the arrows 6899 to zoom in. FIG. 26D shows the surgeon using his index finger 6896 and thumb 6898 to pinch close the image 6892 in the direction of the arrows 6897 to zoom out. FIG. 26E shows the touchscreen display 6890 rotated in two directions indicated by arrows 6894, 6896 to enable the surgeon to view the image 6892 in different orientations.

Outside the sterile field, control and static displays are used that may be different from the control and static displays used inside the sterile field. The control and static displays located outside the sterile field provide interactive and static displays for operating theater (OR) and device control. The control and static displays located outside the sterile field may be primary displays and/or secondary displays. The control and static displays located outside the sterile field may include secondary displays, such as secondary static displays and secondary touchscreens for input and output.

Nonsterile displays 107, 109, 119 (FIG. 2) may be used outside the sterile field and may include monitors placed on a wall of the operating theater, on a rolling stand, or on capital equipment. A display may be presented with a feed from the control device to which they are attached and may display what is presented to it.

One or more secondary displays, which may be secondary touch input screens located outside the sterile field, may be part of the visualization system 108 (FIG. 2), part of the surgical hub 106 (FIG. 2), or may be fixed placement touch monitors on the walls or rolling stands. A difference between a touch input screen and a static display may be that a user may interact with the touch input screen by changing what may be displayed on that specific monitor or others. For capital equipment applications, it may be the interface to control the setting of the connected capital equipment. Primary displays and/or secondary displays outside the sterile field may be used to preload a surgeon's preferences. For example, the touch input screens and the static displays outside the sterile field may be used to preload the surgeon's preferences (instrumentation settings and modes, lighting, procedure and preferred steps and sequence, music, etc.).

Secondary displays, such as secondary surgeon displays may include personal input displays with a personal input device that may function similarly to a sterile field input display device but may be controlled by a surgeon. Secondary displays, such as personal secondary displays, may be implemented in many form factors such as, for example, a watch, a small display pad, interface glasses, etc. A personal secondary display may include control capabilities of a display device and may be located on or controlled by a surgeon. The personal secondary display may be keyed to the surgeon (e.g. specifically keyed to the surgeon) and may indicate that to one or more users, itself, one or more primary displays, one or more secondary displays, and/or other devices. A personal secondary display may be used to grant permission for release of a device. A personal secondary display may be used to control one or more primary displays and/or secondary displays. For example, the personal secondary display may be used to control what is displayed on a primary display and/or secondary display. As another example, the personal secondary display may be used to move data from one display to another display.

A personal secondary display may be used to provide dedicated data to one of several surgical personnel that may want to monitor something that the others may not want to monitor. A personal secondary display may be used as a command module. A personal secondary display may be held by a chief surgeon in the operating theater and may give the surgeon the control to override any of the other inputs from anyone else. A personal secondary display may be coupled to a short-range wireless (e.g., Bluetooth) microphone and/or earpiece allowing the surgeon to have discrete conversations or calls or the personal secondary display may be used to broadcast to all the others in the operating theater or other department. The surgeon may also use the microphone and/or earpiece to issue verbal commands to the personal secondary display. The surgeon may also use gestures to provide one or more commands to the personal secondary display.

Figure 27:
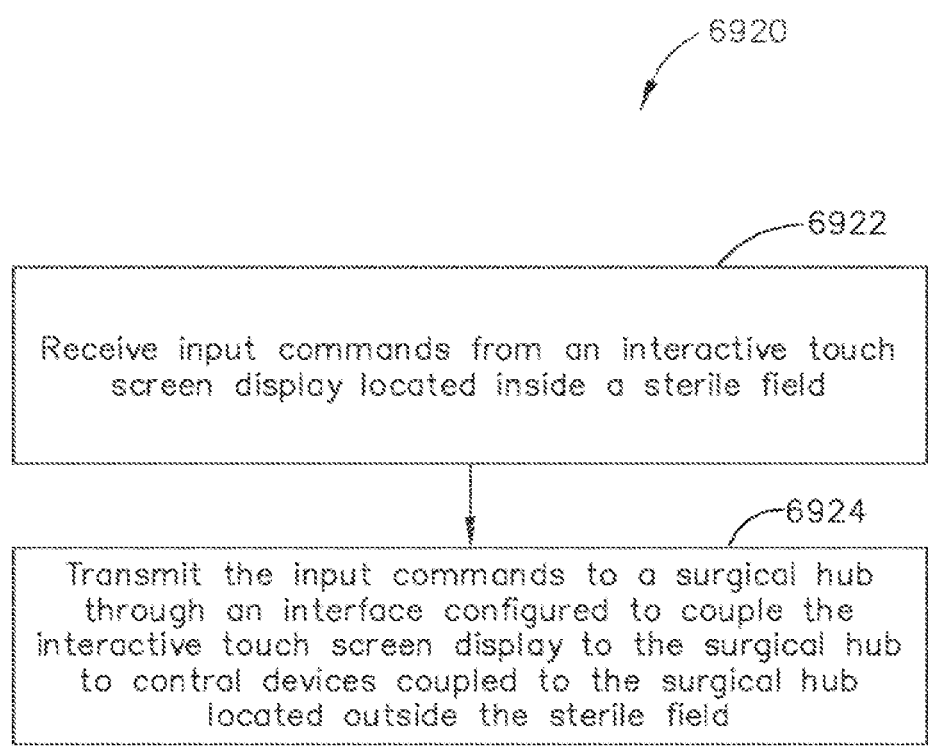
FIG. 27 is a logic flow diagram of a process depicting a control program or a logic configuration to communicate from inside a sterile field to a device located outside the sterile field, in accordance with at least one aspect of the present disclosure.

FIG. 27 is a logic flow diagram 6920 of a process depicting a control program or a logic configuration to communicate from inside a sterile field to a device located outside the sterile field, according to an aspect of the present disclosure. In an aspect, a control unit may comprise an interactive touchscreen display, an interface configured to couple the interactive touchscreen display to a surgical hub, a processor, and a memory coupled to the processor. The memory may store instructions executable by the processor to receive 6922 input commands from the interactive touchscreen display located inside a sterile field and may transmit 6924 the input commands to a surgical hub to control devices coupled to the surgical hub located outside the sterile field.

Figure 28:
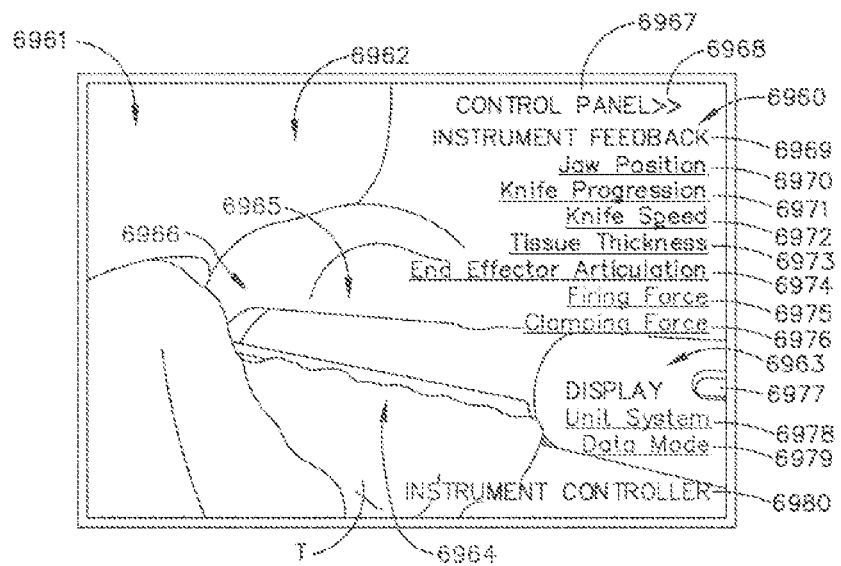
FIG. 28 illustrates a second layer of information overlaying a first layer of information, in accordance with at least one aspect of the present disclosure.

FIG. 28 illustrates a second layer of information overlaying a first layer of information. The second layer of information includes a symbolic representation of the knife overlapping the detected position of the knife in the disposable loading unit (DLU) depicted in the first layer of information. Further examples are disclosed in U.S. Pat. No. 9,283,054, titled SURGICAL APPARATUS WITH INDICATOR, which issued on Mar. 15, 2016, which is herein incorporated by reference in its entirety.

Referring to FIG. 28, the second layer of information 6963 can overlay at least a portion of the first layer of information 6962 on the display 6960. Furthermore, the touch screen 6961, which may be a primary display and/or a secondary display, may allow a user to manipulate the second layer of information 6963 relative to the video feedback in the underlying first layer of information 6962 on the display 6960. For example, a user may operate the touch screen 6961 to select, manipulate, reformat, resize, and/or otherwise modify the information displayed in the second layer of information 6963. In an aspect, the user may move the first layer of information and/or the second layer information one or more displays that may include a primary display and/or a secondary display. In an aspect, the user can may the touch screen 6961 to manipulate the second layer of information 6963 relative to the surgical instrument 6964 depicted in the first layer of information 6962 on the display 6960. A user may select a menu, category and/or classification of the control panel 6967 thereof, for example, and the second layer of information 6963 and/or the control panel 6967 may be adjusted to reflect the user's selection. In various aspects, a user may select a category from the instrument feedback category 6969 that corresponds to a specific feature or features of the surgical instrument 6964 depicted in the first layer of information 6962. Feedback corresponding to the user-selected category can move, locate itself, and/or "snap" to a position on the display 6960 relative to the specific feature or features of the surgical instrument 6964. For example, the selected feedback may move to a position near and/or overlapping the specific feature or features of the surgical instrument 6964 depicted in the first layer of information 6962.

The instrument feedback menu 6969 may include a plurality of feedback categories, and can relate to the feedback data measured and/or detected by the surgical instrument 6964 during a surgical procedure. As described herein, the surgical instrument 6964 may detect and/or measure the position 6970 of a moveable jaw between an open orientation and a closed orientation, the thickness 6973 of clamped tissue, the clamping force 6976 on the clamped tissue, the articulation 6974 of the DLU 6965, and/or the position 6971, velocity 6972, and/or force 6975 of the firing element, for example. Furthermore, the feedback controller in signal communication with the surgical instrument 6964 may provide the sensed feedback to the display 6960, which can display the feedback in the second layer of information 6963. As described herein, the selection, placement, and/or form of the feedback data displayed in the second layer of information 6963 can be modified based on the user's input to the touch screen 6961, for example.

When the knife of the DLU 6965 is blocked from view by the end effector jaws 6966 and/or tissue T, for example, the operator may track and/or approximate the position of the knife in the DLU 6965 based on the changing value of the feedback data and/or the shifting position of the feedback data relative to the DLU 6965 depicted in the underlying first layer of information 6962.

In various aspects, the display menu 6977 of the control panel 6967 may relate to a plurality of categories, such as unit systems 6978 and/or data modes 6979, for example. In certain aspects, a user may select the unit systems category 6978 to switch between unit systems, such as between metric and U.S. customary units, for example. Additionally, a user can select the data mode category 6979 to switch between types of numerical representations of the feedback data and/or types of graphical representations of the feedback data, for example. The numerical representations of the feedback data can be displayed as numerical values and/or percentages, for example. Furthermore, the graphical representations of the feedback data can be displayed as a function of time and/or distance, for example. As described herein, a user may select the instrument controller menu 6980 from the control panel 6967 to input directives for the surgical instrument 6964, which may be implemented via the instrument controller and/or the microcontroller, for example. A user may minimize or collapse the control panel 6967 by selecting the minimize/maximize icon 6968, and may maximize or un-collapse the control panel 6967 by re-selecting the minimize/maximize icon 6968.

Figure 29:
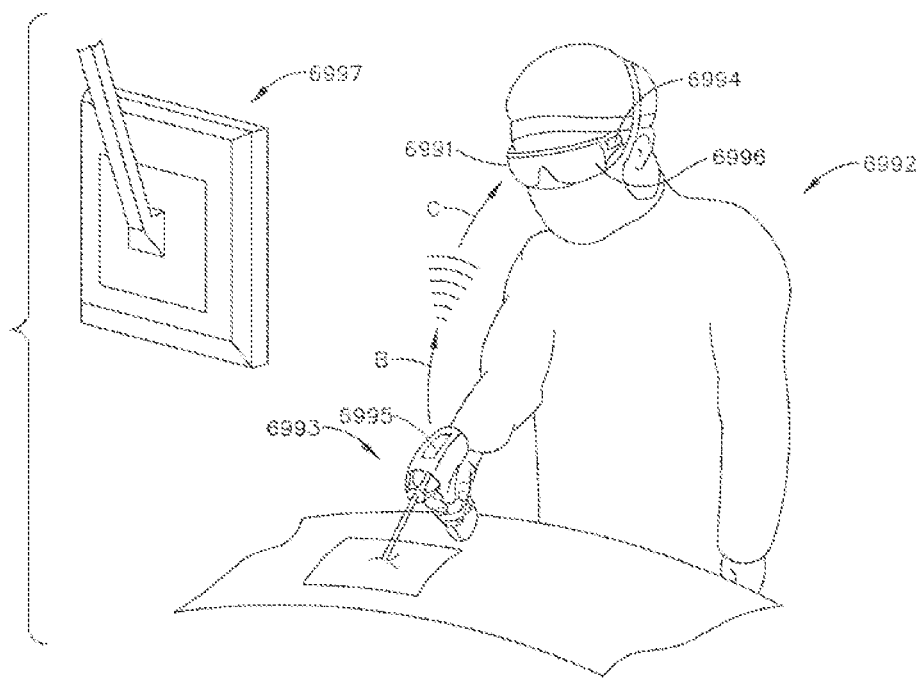
FIG. 29 depicts a perspective view of a surgeon using a surgical instrument that includes a handle assembly housing and a wireless circuit board during a surgical procedure, with the surgeon wearing a set of safety glasses, in accordance with at least one aspect of the present disclosure.

FIG. 29 depicts a perspective view of a surgeon using a surgical instrument that includes a handle assembly housing and a wireless circuit board during a surgical procedure, with the surgeon wearing a set of safety glasses. The wireless circuit board transmits a signal to a set of safety glasses worn by a surgeon using the surgical instrument during a procedure. The signal is received by a wireless port on the safety glasses. One or more lighting devices on a front lens of the safety glasses change color, fade, or glow in response to the received signal to indicate information to the surgeon about the status of the surgical instrument. The lighting devices are disposable on peripheral edges of the front lens to not distract the direct line of vision of the surgeon. Further examples are disclosed in U.S. Pat. No. 9,011,427, titled SURGICAL INSTRUMENT WITH SAFETY GLASSES, which issued on Apr. 21, 2015, which is herein incorporated by reference in its entirety.

FIG. 29 shows a version of safety glasses 6991 that may be worn by a surgeon 6992 during a surgical procedure while using a medical device. The safety glasses 6991 may be a primary display and/or a secondary display. The safety glasses 6991 may be used to determine a direction in which the surgeon 6992 is looking. For example, the safety glasses 6991 may analyze the pupil movements of the surgeon 6992 (e.g. using an internal or external camera) and may determine that the surgeon is viewing the monitor 6997. As another example, the safety glasses 6991 may use one or more sensors to track the head movement of the surgeon to determine where the surgeon is viewing (e.g. the surgeon is viewing the monitor 6997).

In use, a wireless communications board housed in a surgical instrument 6993 may communicate with a wireless port 6994 on safety glasses 6991. Exemplary surgical instrument 6993 is a battery-operated device, though instrument 6993 could be powered by a cable or otherwise. Instrument 6993 includes an end effector. Particularly, wireless communications board 6995 transmits one or more wireless signals indicated by arrows (B, C) to wireless port 6994 of safety glasses 6991. Safety glasses 6991 receive the signal, analyze the received signal, and display indicated status information received by the signal on lenses 6996 to a user, such as surgeon 6992, wearing safety glasses 6991.

Wireless communications board 6995 may transmit a wireless signal to surgical monitor 6997 such that surgical monitor 6997 may display received indicated status information to surgeon 6992, as described herein. Surgical monitor 6997 may be a primary display and/or a secondary display.

A version of the safety glasses 6991 may include lighting device on peripheral edges of the safety glasses 6991. A lighting device provides peripheral-vision sensory feedback of instrument 6993, with which the safety glasses 6991 communicate to a user wearing the safety glasses 6991. The lighting device may be, for example, a light-emitted diode ("LED"), a series of LEDs, or any other suitable lighting device known to those of ordinary skill in the art and apparent in view of the teachings herein.

LEDs may be located at edges or sides of a front lens of the safety glasses 6991 so not to distract from a user's center of vision while still being positioned within the user's field of view such that the user does not need to look away from the surgical site to see the lighting device. Displayed lights may pulse and/or change color to communicate to the wearer of the safety glasses 6991 various aspects of information retrieved from instrument 6993, such as system status information or tissue sensing information (i.e., whether the end effector has sufficiently severed and sealed tissue). Feedback from housed wireless communications board 6995 may cause a lighting device to activate, blink, or change color to indicate information about the use of instrument 6993 to a user. For example, a device may incorporate a feedback mechanism based on one or more sensed tissue parameters. In this case, a change in the device output(s) based on this feedback in synch with a tone change may submit a signal through wireless communications board 6995 to the safety glasses 6991 to trigger activation of the lighting device. Such described means of activation of the lighting device should not be considered limiting as other means of indicating status information of instrument 6993 to the user via the safety glasses 6991 are contemplated. Further, the safety glasses 6991 may be single-use or reusable eyewear. Button-cell power supplies such as button-cell batteries may be used to power wireless receivers and LEDs of versions of safety glasses 6991, which may also include a housed wireless board and tri-color LEDs. Such button-cell power supplies may provide a low-cost means of providing sensory feedback of information about instrument 6993 when in use to surgeon 6992 wearing safety glasses 6991.

It is an unfortunate reality that the outcomes of all surgical procedures are not always optimal and/or successful. For instances where a failure event is detected and/or identified, a communication method may be utilized to isolate surgical data which may be associated with the failure event (e.g., failure event surgical data) from surgical data which may not be associated with the failure event (e.g., non-failure event surgical data) and may communicate the surgical data which may be associated with the failure event (e.g., failure event data) from the surgical hub 206 to the cloud-based system 205 on a prioritized basis for analysis. According to an aspect of the present disclosure, failure event surgical data may be communicated from the surgical hub 206 to the cloud-based system 205 on a prioritized basis relative to non-failure event surgical data.

Figure 30:
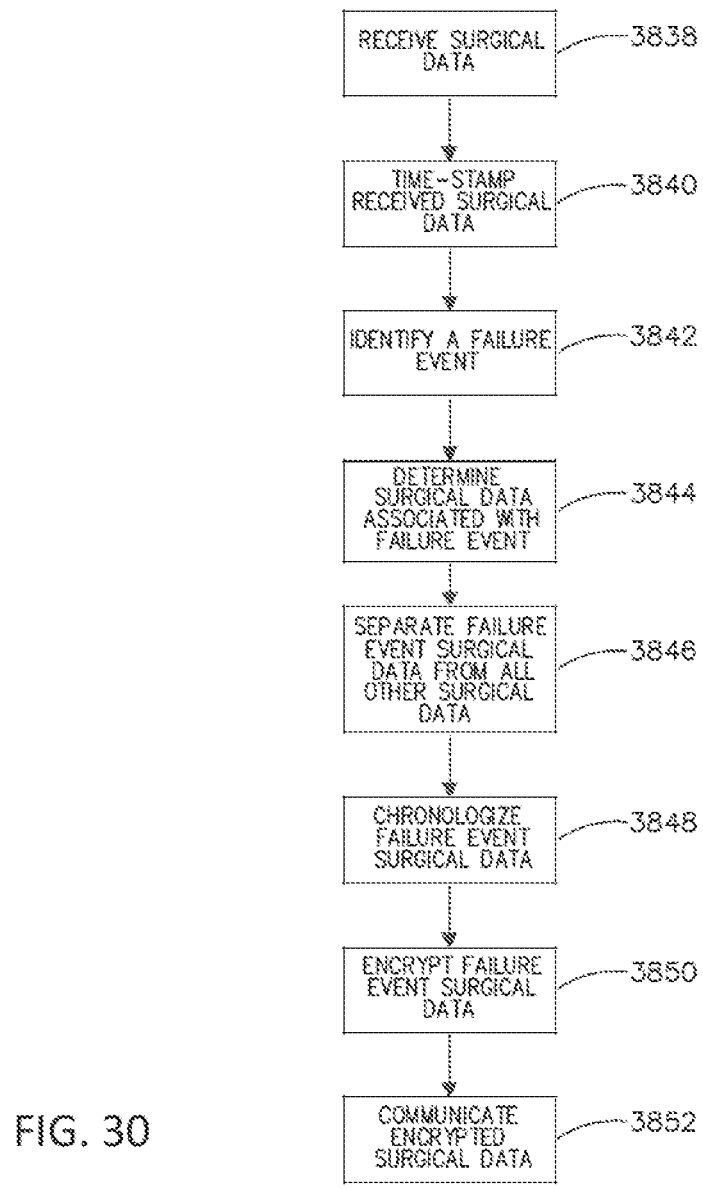
FIG. 30 illustrates a method of identifying surgical data associated with a failure event and communicating the identified surgical data to a cloud-based system on a prioritized basis, in accordance with at least one aspect of the present disclosure.

FIG. 30 illustrates various aspects of a system-implemented method of identifying surgical data associated with a failure event (e.g., failure event surgical data) and communicating the identified surgical data to a cloud-based system 205 on a prioritized basis. The method comprises receiving 3838 surgical data at a surgical hub 206, wherein the surgical data is associated with a surgical procedure; time-stamping 3840 the surgical data; identifying 3842 a failure event associated with the surgical procedure; determining 3844 which of the surgical data is associated with the failure event (e.g., failure event surgical data); separating 3846 the surgical data associated with the failure event from all other surgical data (e.g., non-failure event surgical data) received at the surgical hub 206; chronologizing 3848 the surgical data associated with the failure event; encrypting 3850 the surgical data associated with the failure event; and communicating 3852 the encrypted surgical data to a cloud-based system 205 on a prioritized basis.

More specifically, various surgical data may be captured during a surgical procedure and the captured surgical data, as well as other surgical data associated with the surgical procedure, may be communicated to the surgical hub 206. The surgical data may include, for example, data associated with a surgical device/instrument (e.g., FIG. 5, surgical device/instrument 235) utilized during the surgery, data associated with the patient, data associated with the facility where the surgical procedure was performed, and data associated with the surgeon. Either prior to or subsequent to the surgical data being communicated to and received by the surgical hub 206, the surgical data can be time-stamped and/or stripped of all information which could identify the specific surgery, the patient, or the surgeon, so that the information is essentially anonymized for further processing and analysis by the cloud-based system 205.

When a failure event has been detected and/or identified (e.g., which can be either during or after the surgical procedure), the surgical hub 206 may determine which of the surgical data is associated with the failure event (e.g., failure event surgical data) and which of the surgical data may not be associated with the surgical event (e.g., non-failure event surgical data). According to an aspect of the present disclosure, a failure event may include, for example, a detection of one or more misfired staples during a stapling portion of a surgical procedure. For example, in one aspect, referring to FIG. 5, an endoscope 239 may take snapshots while a surgical device/instrument 235 comprising an end effector including a staple cartridge performs a stapling portion of a surgical procedure. In such an aspect, an imaging module 238 may compare the snapshots to stored images and/or images downloaded from the cloud-based system 205 that convey correctly fired staples to detect a misfired staple and/or evidence of a misfired staple (e.g., a leak). In another aspect, the imaging module 238 may analyze the snapshots themselves to detect a misfired staple and/or evidence of a misfired staple. In one alternative aspect, the surgical hub 206 may communicate the snapshots to the cloud-based system 205, and a component of the cloud-based system 205 may perform the various imaging module functions described above to detect a misfired staple and/or evidence of a misfired staple and to report the detection to the surgical hub 206. According to another aspect of the present disclosure, a failure event may include a detection of a tissue temperature which is below the expected temperature during a tissue-sealing portion of a surgical procedure and/or a visual indication of excessive bleeding or oozing following a surgical procedure (e.g., FIG. 5, via endoscope 239). For example, in one aspect, referring to FIG. 5, the surgical device/instrument 235 may comprise an end effector, including a temperature sensor and the surgical hub 206, and/or the cloud-based system may compare at least one temperature detected by the temperature sensor (e.g., during a tissue-sealing portion of a surgical procedure) to a stored temperature and/or a range of temperatures expected and/or associated with that surgical procedure to detect an inadequate/low sealing temperature. In another aspect, an endoscope 239 may take snapshots during a surgical procedure. In such an aspect, an imaging module 238 may compare the snapshots to stored images and/or images downloaded from the cloud-based system 205 that convey tissue correctly sealed at expected temperatures to detect evidence of an improper/insufficient sealing temperature (e.g., charring, oozing/bleeding). Further, in such an aspect, the imaging module 238 may analyze the snapshots themselves to detect evidence of an improper/insufficient sealing temperature (e.g., charring, oozing/bleeding). As another example, the surgical hub 206 may communicate the snapshots to the cloud-based system 205, and a component of the cloud-based system 205 may perform the various imaging module functions described above to detect evidence of an improper/insufficient sealing temperature and to report the detection to the surgical hub 206. According to the various aspects described herein, in response to the detected and/or identified failure event, the surgical hub 206 may download a program from the cloud-based system 205 for execution by the surgical device/instrument 235 that corrects the detected issue (e.g., program that alters surgical device/instrument parameters to prevent misfired staples, program that alters surgical device/instrument parameters to ensure correct sealing temperature).

In some aspects, a failure event may be deemed to cover a certain time period, and one or more (e.g. all) surgical data associated with that time period may be deemed to be associated with the failure event.

After the surgical data associated with the failure event has been identified, the identified surgical data (e.g., failure event surgical data) may be separated or isolated from some or all of the other surgical data associated with the surgical procedure (e.g., non-failure event surgical data). The separation may be realized, for example, by tagging or flagging the identified surgical data, by storing the identified surgical data apart from all of the other surgical data associated with the surgical procedure, or by storing only the other surgical data while continuing to process the identified surgical data for subsequent prioritized communication to the cloud-based system 205. According to various aspects, the tagging or flagging of the identified surgical data can occur during the communication process when the datagram is generated as described in more detail below.

The timestamping of the surgical data (e.g., either before or after the surgical data is received at the surgical hub) may be utilized by a component of the surgical hub 206 to chronologize the identified surgical data associated with the failure event. The component of the surgical hub 206 which utilizes the timestamping to chronologize the identified surgical data may be, for example, the processor module 232, the processor 244 of the computer system 210, and/or combinations thereof. By chronologizing the identified surgical data, the cloud-based system 205 and/or other interested parties can subsequently better understand the conditions which were present leading up to the occurrence of the failure event and possibly pinpoint the exact cause of the failure event, thereby providing the knowledge to potentially mitigate a similar failure event from occurring during a similar surgical procedure performed at a future date.

When the identified surgical data has been chronologized, the chronologized surgical data may be encrypted in a manner similar to that described above with respect to the encryption of the generator data. Thus, the identified surgical data may be encrypted to help ensure the confidentiality of the identified surgical data, either while it is being stored at the surgical hub 206 or while it is being transmitted to the cloud-based system 205 using the Internet or other computer networks. According to various aspects, a component of the surgical hub 206 utilizes an encryption algorithm to convert the identified surgical data from a readable version to an encoded version, thereby forming the encrypted surgical data associated with the failure event. The component of the surgical hub which utilizes the encryption algorithm may be, for example, the processor module 232, the processor 244 of the computer system 210, and/or combinations thereof. The utilized encryption algorithm can be a symmetric encryption algorithm or an asymmetric encryption algorithm.

After the identified surgical data has been encrypted, a component of the surgical hub may communicate the encrypted surgical data associated with the failure event (e.g., encrypted failure event surgical data) to the cloud-based system 205. The component of the surgical hub which communicates the encrypted surgical data to the cloud-based system 205 may be, for example, the processor module 232, a hub/switch 207/209 of the modular communication hub 203, the router 211 of the modular communication hub 203, or the communication module 247 of the computer system 210. According to various aspects, the communication of the encrypted surgical data (e.g., encrypted failure event surgical data) through the Internet can follow an IP which: may provide datagrams that encapsulate the encrypted surgical data to be delivered, and may provide addressing methods that are used to label the datagram with source and destination information. The datagram may include a field which includes a flag or a tag which identifies the encrypted surgical data (e.g., encrypted failure event surgical data) as being prioritized relative to other non-prioritized surgical data (e.g., encrypted non-failure event surgical data).

In some aspects, once a failure event associated with a surgical procedure has been identified, the surgical hub 206 and/or the cloud-based system 205 can subsequently flag or tag a surgical device/instrument 235 which was utilized during the surgical procedure for inoperability and/or removal. For example, in one aspect, information (e.g., serial number, ID) associated with the surgical device/instrument 235 and stored at the surgical hub 206 and/or the cloud-based system 205 can be utilized to effectively block the surgical device/instrument 235 from being used again (e.g., blacklisted). In another aspect, information (e.g., serial number, ID) associated with the surgical device/instrument can initiate the printing of a shipping slip and shipping instructions for returning the surgical device/instrument 235 back to a manufacturer or other designated party so that a thorough analysis/inspection of the surgical device/instrument 235 can be performed (e.g., to determine the cause of the failure). According to various aspects described herein, once the cause of a failure is determined (e.g., via the surgical hub 206 and/or the cloud-based system 205), the surgical hub 206 may download a program from the cloud-based system 205 for execution by the surgical device/instrument 235 that corrects the determined cause of the failure (i.e., program that alters surgical device/instrument parameters to prevent the failure from occurring again).

In some aspects, the primary display and/or the secondary display may be used to provide or display a notification that an operation error has occurred. For example, when a failure event associated with a surgical procedure has been identified, the surgical hub 206 and/or the cloud-based system 205 may send an error message to be displayed on one or more primary displays and/or secondary displays. The error message may indicate to a user that a failure event has occurred, may indicate instructions for correcting the error, may indicate recommendations for correcting the error, may indicate instructions that may alter the surgical procedure, and the like. For example, an error message on the primary display may provide instruction to a surgical error that may have occurred to a patient due to the failure event. As another example, an error message on a secondary display may provide instructions to a user on how to clear a misfired staple and reload a staple cartridge.

According to some aspects, the surgical hub 206 and/or the cloud-based system 205 can also provide/display a reminder (e.g., via hub display 215 and/or surgical device/instrument display 237) to administrators, staff, and/or other personnel to physically remove the surgical device/instrument 235 from the operating room (e.g., if detected as still present in the operating room) and/or to send the surgical device/instrument 235 to the manufacturer or the other designated party. In one aspect, the reminder may be set up to be provided/displayed periodically until an administrator can remove the flag or tag of the surgical device/instrument 235 from the surgical hub 206 and/or the cloud-based system 205. According to various aspects, an administrator may remove the flag or tag once the administrator can confirm (e.g., system tracking of the surgical device/instrument 235 via its serial number/ID) that the surgical device/instrument 235 has been received by the manufacturer or the other designated party. By using the methods described herein to flag and/or track surgical data associated with a failure event, a closed loop control of the surgical data associated with the failure event and/or with a surgical device/instrument 235 may be realized. It will be appreciated that the surgical hub 206 can be utilized to effectively manage the utilization (or non-utilization) of surgical devices/instruments 235 which have or potentially could be utilized during a surgical procedure.

In various aspects of the present disclosure, the surgical hub 206 and/or cloud-based system 205 may want to control which components (e.g., surgical device/instrument 235, energy device 241) are being utilized in its interactive surgical system 100/200 to perform surgical procedures (e.g., to minimize future failure events, to avoid the use of unauthorized or knock-off components).

As such, in various aspects of the present disclosure, since an interactive surgical system 100 may comprise a plurality of surgical hubs 106, a cloud-based system 105 and/or each surgical hub 106 of the interactive surgical system 100 may want to track component-surgical hub combinations utilized over time. In one aspect, upon/after a component (See FIG. 5, e.g., surgical device/instrument 235, energy device 241) is connected to/used with a particular surgical hub 106 (e.g., surgical device/instrument 235 wired/wirelessly connected to the particular surgical hub 106, energy device 241 connected to the particular surgical hub 106 via generator module 240), the particular surgical hub 106 may communicate a record/block of that connection/use (e.g., linking respective unique identifiers of the connected devices) to the cloud-based system 105 and/or to the other surgical hubs 106 in the interactive surgical system 100. For example, upon/after the connection/use of an energy device 241, a particular surgical hub 106 may communicate a record/block (e.g., linking a unique identifier of the energy device 241 to a unique identifier of a generator module 240 to a unique identifier of the particular surgical hub 106) to the cloud-based system 105 and/or other surgical hubs 106 in the interactive surgical system 100. In such an aspect, if this is the first time the component (e.g., energy device) is connected to/used with a surgical hub 106 in the interactive surgical system 100, the cloud-based system 105 and/or each surgical hub 106 of the interactive surgical system 100 may store the record/block as a genesis record/block. In such an aspect, the genesis record/block stored at the cloud-based system 105 and/or each surgical hub 106 may comprise a time stamp. However, in such an aspect, if this is not the first time the component (e.g., energy device 241) has been connected to/used with a surgical hub 106 in the interactive surgical system 100, the cloud-based system 105 and/or each surgical hub 106 of the interactive surgical system may store the record/block as a new record/block in a chain of record/blocks associated with the component. In such an aspect, the new record/block may comprise a cryptographic hash of the most recently communicated record/block stored at the cloud-based system 105 and/or each surgical hub 106, the communicated linkage data, and a time stamp. In such an aspect, each cryptographic hash links each new record/block (e.g., each use of the component) to its prior record/block to form a chain confirming the integrity of each prior record/block(s) back to an original genesis record/block (e.g., first use of the component). According to such an aspect, this blockchain of records/blocks may be developed at the cloud-based system 105 and/or each surgical hub 106 of the interactive surgical system 100 to permanently and verifiably tie usage of a particular component to one or more than one surgical hub 106 in the interactive surgical system 100 over time. Here, according to another aspect, this approach may be similarly applied to sub-components (e.g., handle, shaft, end effector, cartridge) of a component when/after the component is connected to/used with a particular surgical hub 106 of an interactive surgical system 100.

According to various aspects of the present disclosure, the cloud-based system 105 and/or each surgical hub 106 may utilize such records/blocks to trace usage of a particular component and/or a sub-component back to its initial usage in the interactive surgical system 100. For example, if a particular component (e.g., surgical device/instrument 235) is flagged/tagged as related to a failure event, the cloud-based system 105 and/or a surgical hub 106 may analyze such records/blocks to determine whether past usage of that component and/or a sub-component of that component contributed to or caused the failure event (e.g., overused). In one example, the cloud-based system 105 may determine that a sub-component (e.g., end effector) of that component may actually be contributing/causing the failure event and then tag/flag that component for inoperability and/or removal based on the determination.

According to another aspect, the cloud-based system 205 and/or surgical hub 206 may control which components (e.g., surgical device/instrument 235, energy device 241) are being utilized in an interactive surgical system 200 to perform surgical procedures by authenticating the component and/or its supplier/manufacturer. In one aspect, the supplier/manufacturer of a component may associate a serial number and a source ID with the component. In such an aspect, the supplier/manufacturer may create/generate a private key for the serial number, encrypt the serial number with the private key, and store the encrypted serial number and the source ID on an electronic chip (e.g., memory) in the component prior to shipment to a surgical site. Here, upon/after connection of the component to a surgical hub 206, the surgical hub 206 may read the encrypted serial number and the source ID from the electronic chip. In response, the surgical hub 206 may send a message (i.e., comprising the encrypted serial number) to a server of the supplier/manufacturer associated with the source ID (e.g., directly or via the cloud-based system 205). In such an aspect, the surgical hub 206 may encrypt the message using a public key associated with that supplier/manufacturer. In response, the surgical hub 206 may receive a message (i.e., comprising the private key the supplier/manufacturer generated for/associated with that encrypted serial number) from the supplier/manufacturer server (e.g., directly or via the cloud-based system 205). In such an aspect, the supplier/manufacturer server may encrypt the message using a public key associated with the surgical hub 206. Further, in such an aspect, the surgical hub 206 may then decrypt the message (e.g., using a private key paired to the public key used to encrypt the message) to reveal the private key associated with the encrypted serial number. The surgical hub 206 may then decrypt the encrypted serial number, using that private key, to reveal the serial number. Further, in such an aspect, the surgical hub 206 may then compare the decrypted serial number to a comprehensive list of authorized serial numbers (e.g., stored at the surgical hub 206 and/or the cloud-based system and/or downloaded from the cloud-based system, e.g., received separately from the supplier/manufacturer) and permit use of the connected component if the decrypted serial number matches an authorized serial number. Initially, such a process permits the surgical hub 206 to authenticate the supplier/manufacturer. In particular, the surgical hub 206 encrypted the message comprising the encrypted serial number using a public key associated with the supplier/manufacturer. As such, receiving a response message (i.e., comprising the private key) authenticates the supplier/manufacturer to the surgical hub 206 (i.e., otherwise the supplier/manufacturer would not have access to the private key paired to the public key used by the surgical hub 206 to encrypt the message, and the supplier/manufacturer would not have been able to associate the encrypted serial number received in the message to its already generated private key). Furthermore, such a process permits the surgical hub 206 to authenticate the connected component/device itself. In particular, the supplier/manufacturer (e.g., just authenticated) encrypted the serial number of the component using the delivered private key. Upon secure receipt of the private key, the surgical hub 206 is able to decrypt the encrypted serial number (i.e., read from the connected component), which authenticates the component and/or its association with the supplier/manufacturer (i.e., only that private key as received from that supplier/manufacturer would decrypt the encrypted serial number). Nonetheless, the surgical hub 206 further verifies the component as authentic (e.g., compares the decrypted serial number to a comprehensive list of authorized serial numbers received separately from the supplier/manufacturer). Notably, such aspects as described above can alternatively be performed by the cloud-based system 205 and/or a combination of the cloud-based system 205 and the surgical hub 206 to control which components (e.g., surgical device/instrument 235, energy device 241) are being utilized in an interactive surgical system 200 (e.g., to perform surgical procedures) by authenticating the component and/or its supplier/manufacturer. In one aspect, such described approaches may prevent the use of knock-off component(s) within the interactive surgical system 200 and ensure the safety and well-being of surgical patients.

According to another aspect, the electronic chip of a component (e.g., surgical device/instrument 235, energy device 241) may store (e.g., in memory) data associated with usage of that component (i.e., usage data, e.g., number of uses with a limited use device, number of uses remaining, firing algorithms executed, designation as a single-use component). In such an aspect, the surgical hub 206 and/or the cloud-based system 205, upon/after connection of the component to the interactive surgical system, may read such usage data from the memory of a component and write back at least a portion of that usage data for storage (e.g., in memory 249) at the surgical hub 206 and/or for storage at the cloud-based system 205 (e.g., individually and/or under a blockchain approach discussed herein). According to such an aspect, the surgical hub 206 and/or the cloud-based system 205, upon/after a subsequent connection of that component to the interactive surgical system, may again read such usage data and compare that usage to previously stored usage data. Here, if a discrepancy exists or if a predetermined/authorized usage has been met, the surgical hub 206 and/or the cloud-based system 205 may prevent use of that component (e.g., blacklisted, rendered inoperable, flagged for removal) on the interactive surgical system 200. In various aspects, such an approach prevents bypass of the encryption chip systems. If the component's electronic chip/memory has been tampered with (e.g., memory reset, number of uses altered, firing algorithms altered, single-use device designated as a multi-use device), a discrepancy will exist, and the component's use will be controlled/prevented.

Additional details are disclosed in U.S. Pat. No. 9,011,427, titled SURGICAL INSTRUMENT WITH SAFETY GLASSES, which issued on Apr. 21, 2015, which is herein incorporated by reference in its entirety.

A surgical hub that may provide coordination of device pairing in an operating room may be provided. One of the functions of the surgical hub 106 is to pair (also referred to herein as "connect" or "couple") with other components of the surgical system 102 to control, gather information from, or coordinate interactions between the components of the surgical system 102. Since the operating rooms of a hospital are likely in close physical proximity to one another, a surgical hub 106 of a surgical system 102 may unknowingly pair with components of a surgical system 102 in a neighboring operating room, which would significantly interfere with the functions of the surgical hub 106. For example, the surgical hub 106 may unintentionally activate a surgical instrument in a different operating room or record information from a different ongoing surgical procedure in a neighboring operating room.

Aspects of the present disclosure present a surgical hub 106 that may pair with detected devices of the surgical system 102 that are located within the bounds of its operating room. The surgical hub 106 may avoid incorrectly pairing with devices in another operating room.

Furthermore, the surgical hub 106 may rely on its knowledge of the location of other components of the surgical system 102 within its operating room in making decisions about, for example, which surgical instruments should be paired with one another or activated. A change in the position of the surgical hub 106 or another component of the surgical system 102 can be problematic.

Aspects of the present disclosure further present a surgical hub 106 that may be configured to reevaluate or redetermine the bounds of its operating room upon detecting that the surgical hub 106 has been moved.

Aspects of the present disclosure further present a surgical hub 106 that may be configured to redetermine the bounds of its operating room upon detection of a potential device of the surgical system 102, which can be an indication that the surgical hub 106 has been moved.

In various aspects, a surgical hub 106 may be used with a surgical system 102 in a surgical procedure performed in an operating room. The surgical hub 106 may comprise a control circuit configured to determine the bounds of the operating room, determine devices of the surgical system 102 located within the bounds of the operating room, and pair the surgical hub 106 with the devices of the surgical system 102 located within the bounds of the operating room.

In an aspect, the control circuit may be configured to determine the bounds of the operating room after activation of the surgical hub 106. In one aspect, the surgical hub 106 includes a communication circuit configured to detect and pair with the devices of the surgical system located within the bounds of the operating room. In an aspect, the control circuit is configured to redetermine the bounds of the operating room after a potential device of the surgical system 102 is detected. In one aspect, the control circuit is configured to periodically determine the bounds of the operating room.

In an aspect, the surgical hub 106 may comprise an operating room mapping circuit that includes a plurality of non-contact sensors configured to measure the bounds of the operating room.

In various aspects, the surgical hub 106 includes a processor and a memory coupled to the processor. The memory stores instructions executable by the processor to pair the surgical hub with devices of the surgical system 102 located within the bounds of the operating room, as described above. In various aspects, the present disclosure provides a non-transitory computer-readable medium storing computer-readable instructions which, when executed, cause a machine to pair the surgical hub 106 with devices of the surgical system 102 located within the bounds of the operating room, as described herein.

Figure 32:
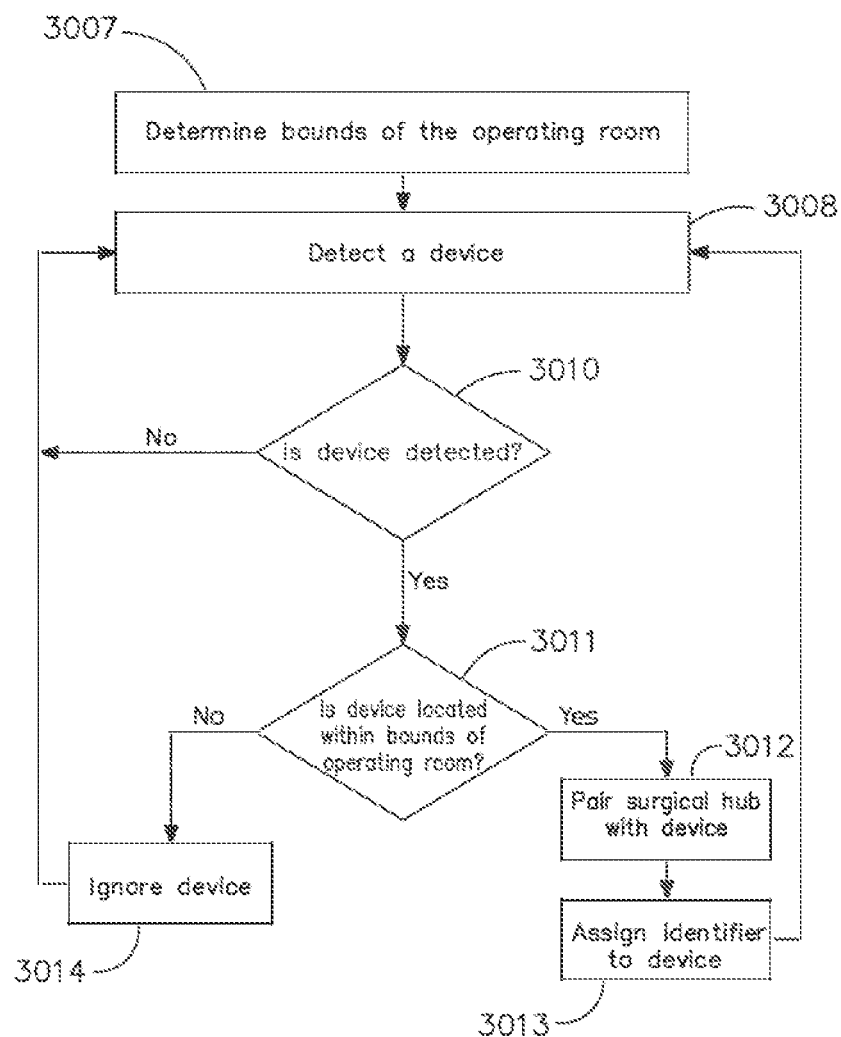
FIG. 32 is a logic flow diagram of a process depicting a control program or a logic configuration for surgical hub pairing with surgical devices of a surgical system that are located within the bounds of an operating room, in accordance with at least one aspect of the present disclosure.
Figure 33:
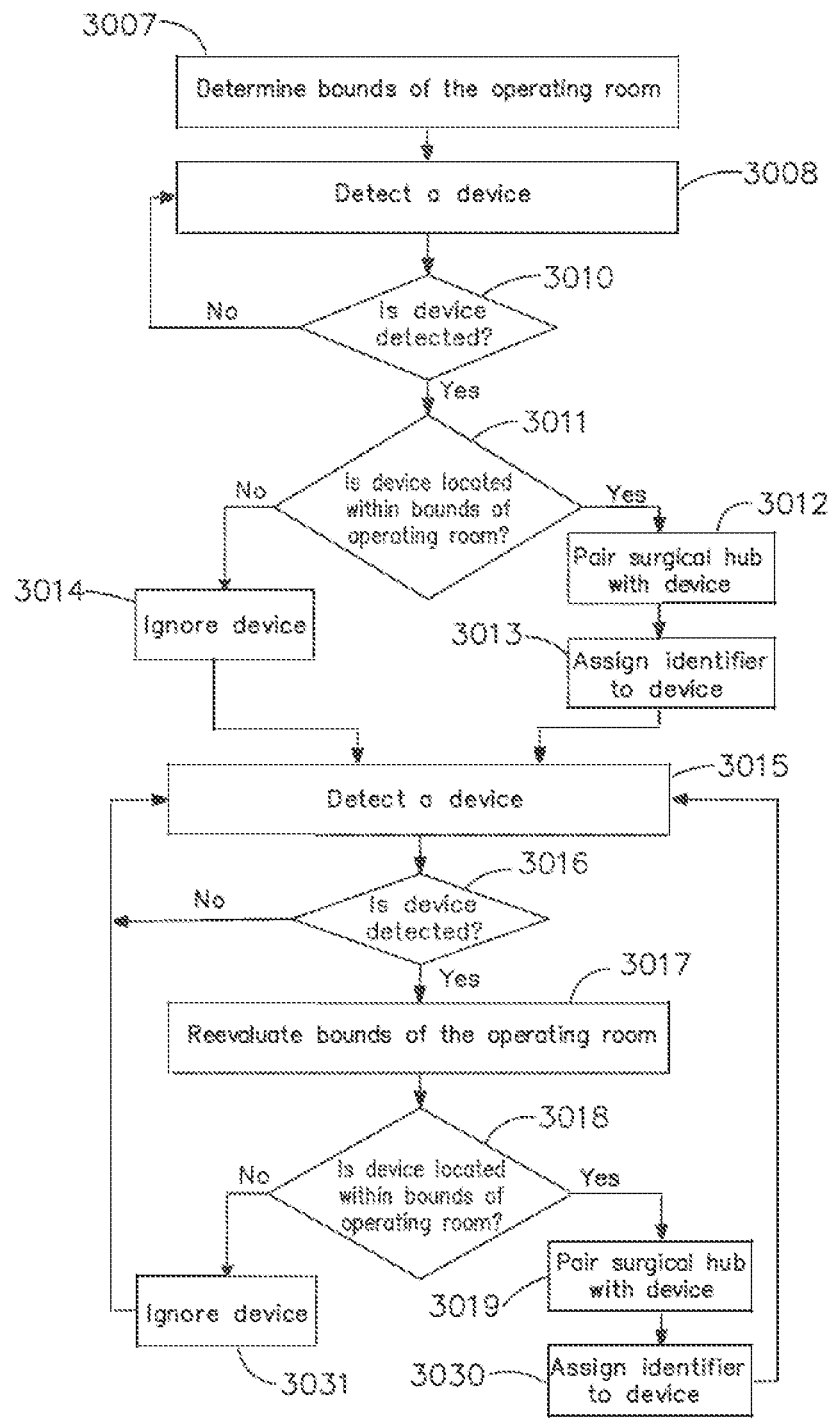
FIG. 33 is a logic flow diagram of a process depicting a control program or a logic configuration for selectively forming and severing connections between devices of a surgical system, in accordance with at least one aspect of the present disclosure.

FIGS. 32 and 33 are logic flow diagrams of processes depicting control programs or logic configurations for pairing the surgical hub 106 with devices of the surgical system 102 located within the bounds of the operating room, as described herein.

The surgical hub 106 performs a wide range of functions that may use short- and long-range communication, such as assisting in a surgical procedure, coordinating between devices of the surgical system 102, and gathering and transmitting data to the cloud 104. To perform its functions, the surgical hub 106 may be equipped with a communication module 130 capable of short-range communication with other devices of the surgical system 102. The communication module 130 is also capable of long-range communication with the cloud 104.

The surgical hub 106 may also be equipped with an operating room mapping module 133 which may be capable of identifying the bounds of an operating room, and identifying devices of the surgical system 102 within the operating room. The surgical hub 106 may be configured to identify the bounds of an operating room, and only pair with or connect to potential devices of the surgical system 102 that are detected within the operating room.

In an aspect, the pairing may comprise establishing a communication link or pathway. In another aspect, the pairing may comprise establishing a control link or pathway.

Figure 34:
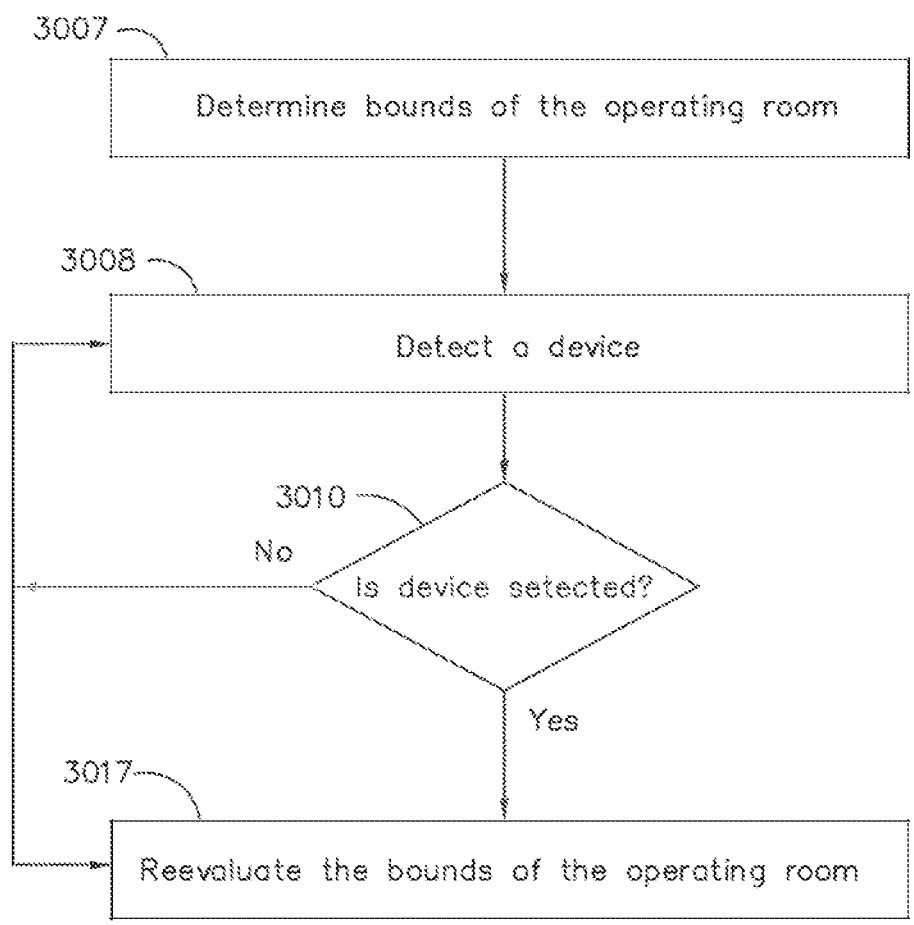
FIG. 34 is a logic flow diagram of a process depicting a control program or a logic configuration for selectively reevaluating the bounds of an operating room after detecting a new device, in accordance with at least one aspect of the present disclosure.
Figure 35:
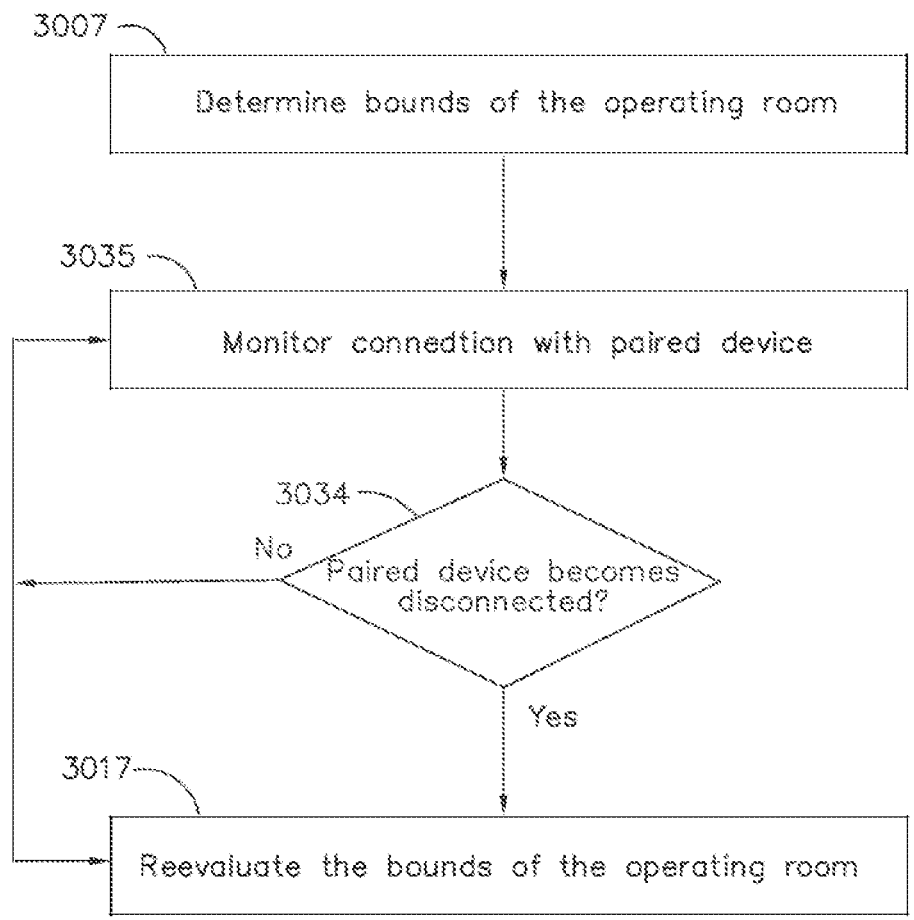
FIG. 35 is a logic flow diagram of a process depicting a control program or a logic configuration for selectively reevaluating the bounds of an operating room after disconnection of a paired device, in accordance with at least one aspect of the present disclosure.
Figure 36:
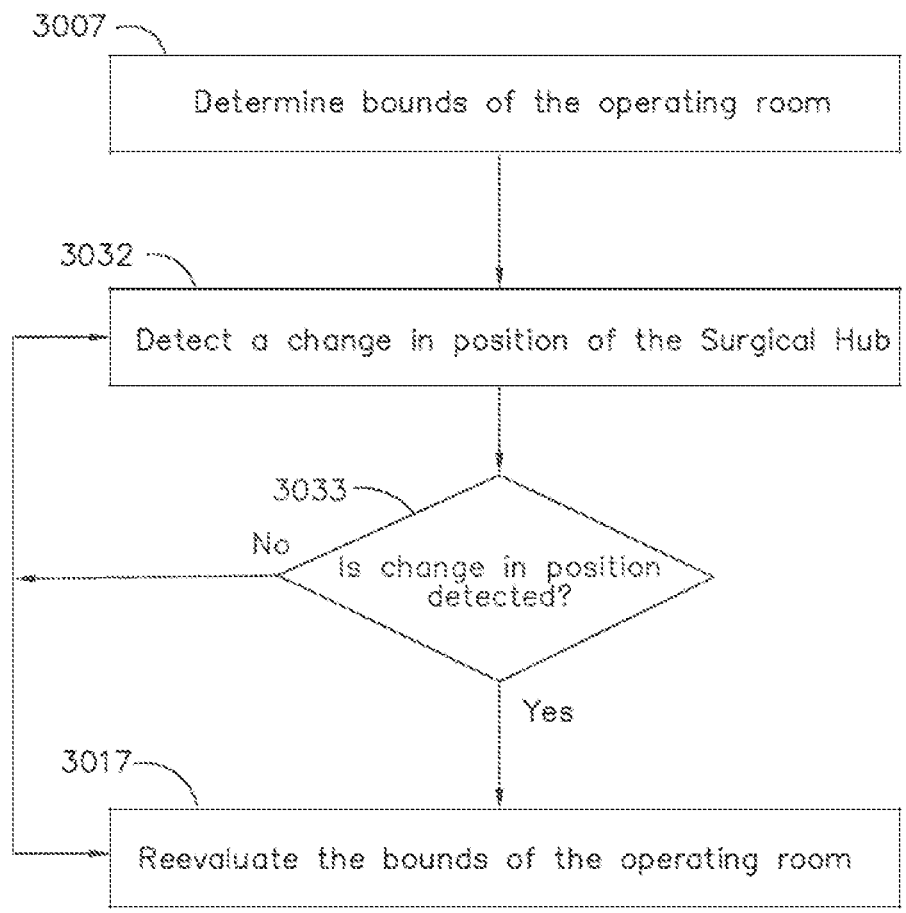
FIG. 36 is a logic flow diagram of a process depicting a control program or a logic configuration for reevaluating the bounds of an operating room by a surgical hub after detecting a change in the position of the surgical hub, in accordance with at least one aspect of the present disclosure.

A mapping or evaluation of the bounds of the operating room takes place during an activation (e.g. initial activation) of the surgical hub 106. The surgical hub 106 may be configured to maintain spatial awareness during operation by periodically mapping its operating room, which can be helpful in determining if the surgical hub 106 has been moved. The reevaluation 3017 may be performed periodically or it may be triggered by an event such as observing a change in the devices of the surgical system 102 that are deemed within the operating room. In an aspect, the change is detection 3010 of a device (e.g. a new device) that was not previously deemed as within the bounds of the operating room, as illustrated in FIG. 34. In another aspect, the change may be a disappearance, disconnection, or un-pairing of a paired device that was previously deemed as residing within the operating room, as illustrated in FIG. 35. The surgical hub 106 may continuously monitor 3035 the connection with paired devices to detect 3034 the disappearance, disconnection, or un-pairing of a paired device.

In other aspects, reevaluation triggering events may be, for example, changes in surgeons' positions, instrument exchanges, or sensing of a new set of tasks being performed by the surgical hub 106.

In one aspect, the evaluation of the bounds of the room by the surgical hub 106 is accomplished by activation of a sensor array of the operating-room mapping module 133 within the surgical hub 106 which enables it to detect the walls of the operating room.

Other components of the surgical system 102 may be made to be spatially aware in the same, or a similar, manner as the surgical hub 106. For example, a robotic hub 122 may also be equipped with an operating room mapping module 133. A primary display and/or a secondary display may also be equipped with an operating room mapping module.

The spatial awareness of the surgical hub 106 and its ability to map an operating room for potential components of the surgical system 102 allows the surgical hub 106 to make autonomous decisions about whether to include or exclude such potential components as part of the surgical system 102, which may relieve the surgical staff from dealing with such tasks. Furthermore, the surgical hub 106 is configured to make inferences about, for example, the type of surgical procedure to be performed in the operating room based on information gathered prior to, during, and/or after the performance of the surgical procedure. Examples of gathered information include the types of devices that are brought into the operating room, time of introduction of such devices into the operating room, and/or the devices sequence of activation. The spatial awareness of the surgical hub 106 may also be used to update one of more displays within an operating room. For example, the spatial awareness of the surgical hub 106 may display data on a primary display, may display data on a secondary display, and/or may move data between the primary display and secondary display based on at least one of a detection of an instrument, a mapping of the operating room, a detection of a user, a change in a location of the surgical hub, a disconnection of an instrument, and the like.

In one aspect, the surgical hub 106 employs the operating-room mapping module 133 to determine the bounds of the surgical theater (e.g., a fixed, mobile, or temporary operating room or space) using either ultrasonic or laser non-contact measurement devices.

Figure 31:
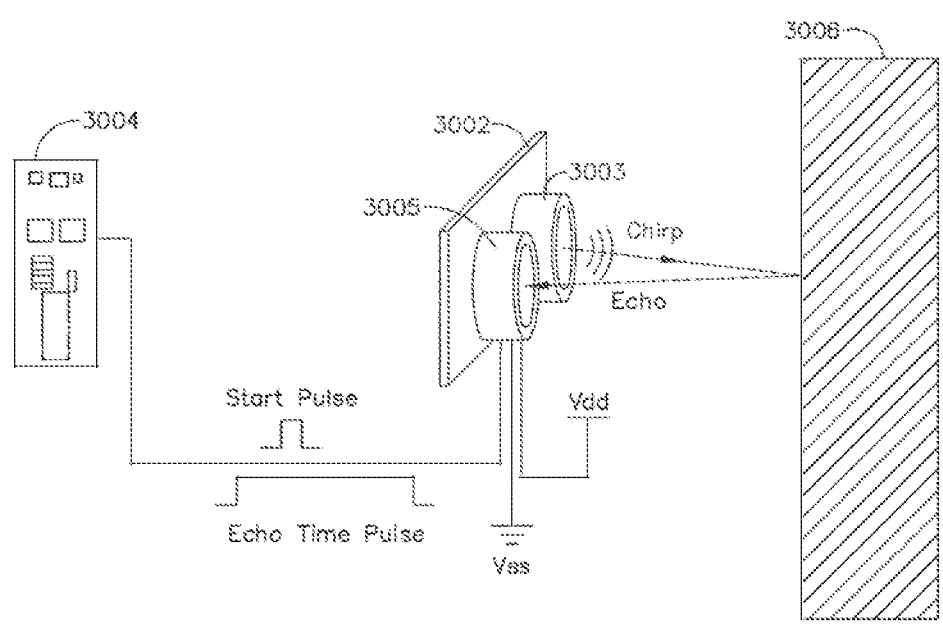
FIG. 31 illustrates ultrasonic pinging of an operating room wall to determine a distance between a surgical hub and the operating room wall, in accordance with at least one aspect of the present disclosure.

Referring to FIG. 31, ultrasound based non-contact sensors 3002 can be employed to scan the operating theater by transmitting a burst of ultrasound and receiving the echo when it bounces off a perimeter wall 3006 of an operating theater to determine the size of the operating theater and to adjust Bluetooth pairing distance limits. In one example, the non-contact sensors 3002 can be ping ultrasonic distance sensors, as illustrated in FIG. 31.

FIG. 31 shows how an ultrasonic sensor 3002 sends a brief chirp with its ultrasonic speaker 3003 and makes it possible for a micro-controller 3004 of the operating-room mapping module 133 to measure how long the echo takes to return to the ultrasonic sensor's ultrasonic microphone 3005. The micro-controller 3004 has to send the ultrasonic sensor 3002 a pulse to begin the measurement. The ultrasonic sensor 3002 then waits long enough for the micro-controller program to start a pulse input command. Then, at about the same time the ultrasonic sensor 3002 chirps a 40 kHz tone, it sends a high signal to the micro-controller 3004. When the ultrasonic sensor 3002 detects the echo with its ultrasonic microphone 3005, it changes that high signal back to low. The micro-controller's pulse input command measures the time between the high and low changes and stores its measurement in a variable. This value can be used along with the speed of sound in air to calculate the distance between the surgical hub 106 and the operating-room wall 3006.

In an example, as illustrated in FIG. 31, a surgical hub 106 can be equipped with four ultrasonic sensors 3002, wherein each of the four ultrasonic sensors is configured to assess the distance between the surgical hub 106 and a wall of the operating room 3000. A surgical hub 106 can be equipped with more or less than four ultrasonic sensors 3002 to determine the bounds of an operating room.

Other distance sensors may be employed by the operating-room mapping module 133 to determine the bounds of an operating room. In an example, the operating-room mapping module 133 may be equipped with one or more photoelectric sensors that can be employed to assess the bounds of an operating room. In one example, suitable laser distance sensors can also be employed to assess the bounds of an operating room. Laser-based non-contact sensors may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits.

Figure 47:
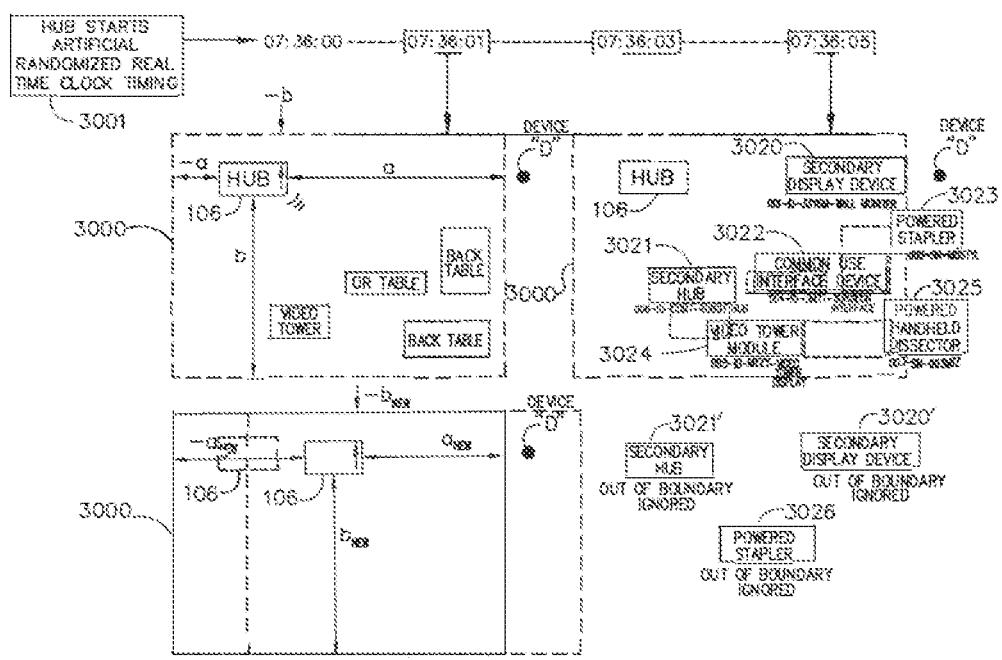
FIG. 47 illustrates a partial artificial timeline of a surgical procedure performed in an operating room via a surgical system, in accordance with at least one aspect of the present disclosure.

Referring to the top left corner of FIG. 47, a surgical hub 106 is brought into an operating room 3000. The surgical hub 106 is activated at the beginning of the set-up that occurs prior to the surgical procedure. In the example of FIG. 47, the set-up starts at an actual time of 11:31:14 (EST) based on a real-time clock. However, at the stated procedure set-up start time, the surgical hub 106 starts 3001 an artificial randomized real-time clock timing scheme at artificial real time 07:36:00 to protect private patient information.

At artificial real time 07:36:01, the operating-room mapping module 133 employs the ultrasonic distance sensors to ultrasonically ping the room (e.g., sends out a burst of ultrasound and listens for the echo when it bounces off the perimeter walls of the operating room as described above) to verify the size of the operating room and to adjust pairing distance limits.

At artificial real time 07:36:03, the data is stripped and time stamped. At artificial real time 07:36:05, the surgical hub 106 begins pairing devices located only within the operating room 3000 as verified using ultrasonic distance sensors 3002 of the operating-room mapping module 133. The top right corner of FIG. 33 illustrates several example devices that are within the bounds of the operating room 3000 and are paired with the surgical hub 106, including a secondary display device 3020, a secondary hub 3021, a common interface device 3022, a powered stapler 3023, a video tower module 3024, and a powered handheld dissector 3025. On the other hand, secondary hub 3021', secondary display device 3020', and powered stapler 3026 are all outside the bounds of the operating room 3000 and, accordingly, are not paired with the surgical hub 106.

In addition to establishing a communication link with the devices of the surgical system 102 that are within the operating room, the surgical hub 106 also assigns a unique identification and communication sequence or number to each of the devices. The unique sequence may include the device's name and a time stamp of when the communication was first established. Other suitable device information may also be incorporated into the unique sequence of the device.

As illustrated in the top left corner of FIG. 47, the surgical hub 106 has determined that the operating room 3000 bounds are at distances a, −a, b, and −b from the surgical hub 106. Since Device "D" is outside the determined bounds of its operating room 3000, the surgical hub 106 will not pair with the Device "D." FIG. 32 is an example algorithm illustrating how the surgical hub 106 may pair (e.g. may only pair) with devices within the bounds of its operating room. After activation, the surgical hub 106 determines 3007 bounds of the operating room using the operating-room mapping module 133, as described above. After the initial determination, the surgical hub 106 continuously searches for or detects 3008 devices within a pairing range. If a device is detected 3010, the surgical hub 106 then determines 3011 whether the detected device is within the bounds of the operating room. The surgical hub 106 pairs 3012 with the device if it is determined that the device is within the bounds of the operating room. The surgical hub 106 may display data associated with the paired device on a primary display and/or a secondary display. In certain instances, the surgical hub 106 will also assign 3013 an identifier to the device. If, however, the surgical hub 106 determines that the detected device is outside the bounds of the operating room, the surgical hub 106 will ignore 3014 the device.

Referring to FIG. 33, after an initial determination of the bounds of the room, and after an initial pairing of devices located within such bounds, the surgical hub 106 continues to detect 3015 new devices that become available for pairing. If a new device is detected 3016, the surgical hub 106 is configured to reevaluate 3017 the bounds of the operating room prior to pairing with the new device. If the new device is determined 3018 to be within the newly determined bounds of the operating room, then the surgical hub 106 pairs with the device 3019 and assigns 3030 a unique identifier to the new device. If, however, the surgical hub 106 determines that the new device is outside the newly determined bounds of the operating room, the surgical hub 106 will ignore 3031 the device.

For pairing, the operating-room mapping module 133 may contain a compass and integrated Bluetooth transceiver. Other communication mechanisms, which are not significantly affected by the hospital environment or geographical location, may be employed. Bluetooth Low Energy (BLE) beacon technology can currently achieve indoor distance measurements with accuracy of about 1-2 meters, with improved accuracy in closer proximities (within 0-6 meters). To improve the accuracy of the distance measurements, a compass is used with the BLE. The operating-room mapping module 133 utilizes the BLE and the compass to determine where modules are located in relation to the patient. For example, two modules facing each other (detected by compass) with greater than one meter distance between them may clearly indicate that the modules are on opposite sides of the patient. The more "Hub"-enabled modules that reside in the operating room, the greater the achievable accuracy becomes due to triangulation techniques.

In the situations where multiple surgical hubs 106, modules, and/or other peripherals are present in the same operating room, as illustrated in the top right corner of FIG. 47, the operating-room mapping module 133 is configured to map the physical location of each module that resides within the operating room. This information could be used by the user interface to display a virtual map of the room, enabling the user to more easily identify which modules are present and enabled, as well as their current status. In one aspect, the mapping data collected by surgical hubs 106 are uploaded to the cloud 104, where the data are analyzed for identifying how an operating room is physically setup, for example.

The surgical hub 106 is configured to determine a device's location by assessing transmission radio signal strength and direction. For Bluetooth protocols, the Received Signal Strength Indication (RSSI) is a measurement of the received radio signal strength. In one aspect, the devices of the surgical system 102 can be equipped with USB Bluetooth dongles. The surgical hub 106 may scan the USB Bluetooth beacons to get distance information. In another aspect, multiple high-gain antennas on a Bluetooth access point with variable attenuators can produce more accurate results than RSSI measurements. In one aspect, the hub is configured to determine the location of a device by measuring the signal strength from multiple antennas. Alternatively, in some examples, the surgical hub 106 can be equipped with one or more motion sensor devices configured to detect a change in the position of the surgical hub 106.

Referring to the bottom left corner of FIG. 47, the surgical hub 106 has been moved from its original position, which is depicted in dashed lines, to a new position closer to the device "D," which is still outside the bounds of the operating room 3000. The surgical hub 106 in its new position, and based on the previously determined bounds of the operating room, would naturally conclude that the device "D" is a potential component of the surgical system 102. However, the introduction of a new device is a triggering event for reevaluation 3017 of the bounds of the operating room, as illustrated in the example algorithm of FIGS. 32, 34. After performing the reevaluation, the surgical hub 106 determines that the operating room bounds have changed. Based on the new bounds, at distances anew, –a new, bnew, and –bnew, the surgical hub 106 concludes that it has been moved and that the Device "D" is outside the newly determined bounds of its operating room. Accordingly, the surgical hub 106 will still not pair with the Device "D." The surgical hub 106 may also update a primary display and/or a secondary display to reflect the change.

In one aspect, one or more of the processes depicted in FIGS. 32-36 can be executed by a control circuit of a surgical hub 106, as depicted in FIG. 6 (processor 244). In another aspect, one or more of the processes depicted in FIGS. 32-36 may be executed by a cloud computing system 104, as depicted in FIG. 1. In yet another aspect, one or more of the processes depicted in FIGS. 32-36 can be executed by at least one of the aforementioned cloud computing systems 104 and/or a control circuit of a surgical hub 106 in combination with a control circuit of a modular device, such as the microcontroller 461 of the surgical instrument depicted in FIG. 7, the microcontroller 620 of the surgical instrument depicted in FIG. 16, the control circuit 710 of the robotic surgical instrument 700 depicted in FIG. 8, the control circuit 760 of the surgical instruments 750, and/or any other suitable microcontroller.

During a surgical procedure, a surgical instrument such as an ultrasonic or an RF surgical instrument can be coupled to a generator module 140 of the surgical hub 106. In addition, a separate surgical instrument controller such as a foot, or hand, switch or activation device can be used by an operator of the surgical instrument to activate the energy flow from the generator to the surgical instrument. Multiple surgical instrument controllers and multiple surgical instruments can be used concurrently in an operating room. Pressing or activating the wrong surgical instrument controller can lead to undesirable consequences. Aspects of the present disclosure present a solution in which the surgical hub 106 coordinates the pairing of surgical instrument controllers and surgical instruments to ensure patient and operator safety.

Aspects of the present disclosure are presented for a surgical hub 106 configured to establish and sever pairings between components of the surgical system 102 within the bounds of the operating room to coordinate flow of information and control actions between such components. The surgical hub 106 can be configured to establish a pairing between a surgical instrument controller and a surgical instrument that reside within the bounds of an operating room of surgical hub 106.

In various aspects, the surgical hub 106 can be configured to establish and sever pairings between components of the surgical system 102 based on operator request or situational and/or spatial awareness. The hub situational awareness is described in greater detail herein with respect to FIG. 10.

Aspects of the present disclosure are presented for a surgical hub for use with a surgical system in a surgical procedure performed in an operating room. The surgical hub includes a control circuit that selectively forms and severs pairings between devices of the surgical system. The surgical hub may update a primary display and/or a secondary display to reflect formed or severed pairings. In one aspect, the hub includes a control circuit is configured to pair the hub with a first device of the surgical system, assign a first identifier to the first device, pair the hub with a second device of the surgical system, assign a second identifier to the second device, and selectively pair the first device with the second device. In one aspect, the surgical hub includes a storage medium, wherein the control circuit is configured to store a record indicative of the pairing between the first device and the second device in the storage medium. In one aspect, the pairing between the first device and the second device defines a communication pathway therebetween. In one aspect, the pairing between the first device and the second device defines a control pathway for transmitting control actions from the second device to the first device.

Further to the above, in one aspect, the control circuit is further configured to pair the hub with a third device of the surgical system, assign a third identifier to the third device, sever the pairing between the first device and the second device, and selectively pair the first device with the third device. In one aspect, the control circuit is further configured to store a record indicative of the pairing between the first device and the third device in the storage medium. In one aspect, the pairing between the first device and the third device defines a communication pathway therebetween. In one aspect, the pairing between the first device and the third device defines a control pathway for transmitting control actions from the third device to the first device.

Figure 37:
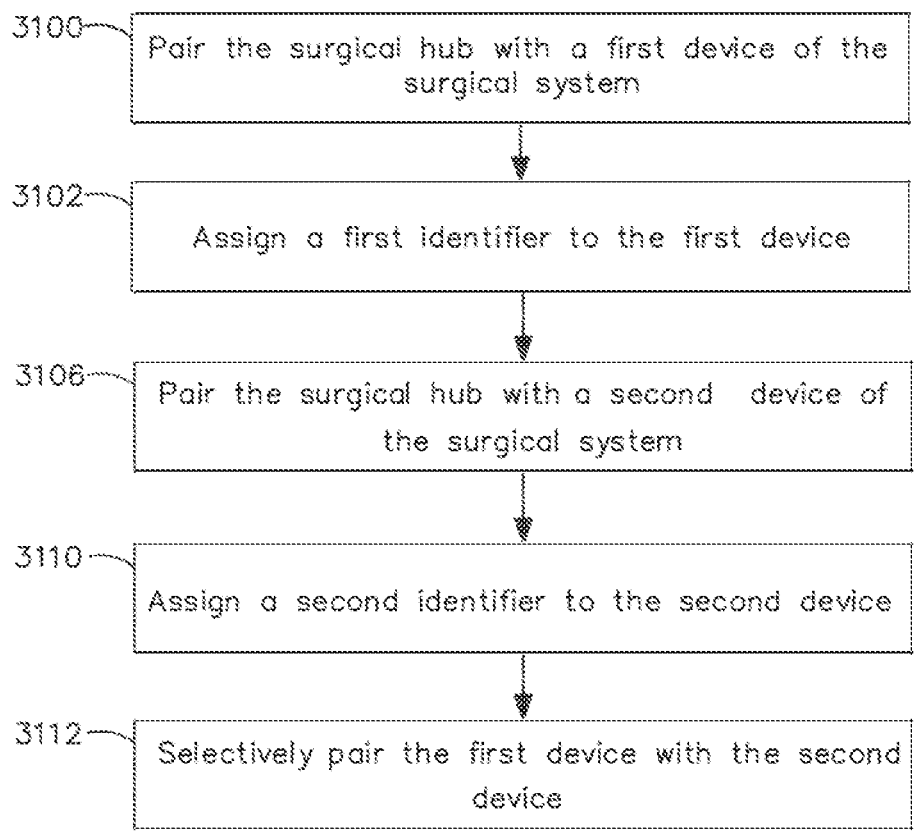
FIG. 37 is a logic flow diagram of a process depicting a control program or a logic configuration for selectively forming connections between devices of a surgical system, in accordance with at least one aspect of the present disclosure.
Figure 38:
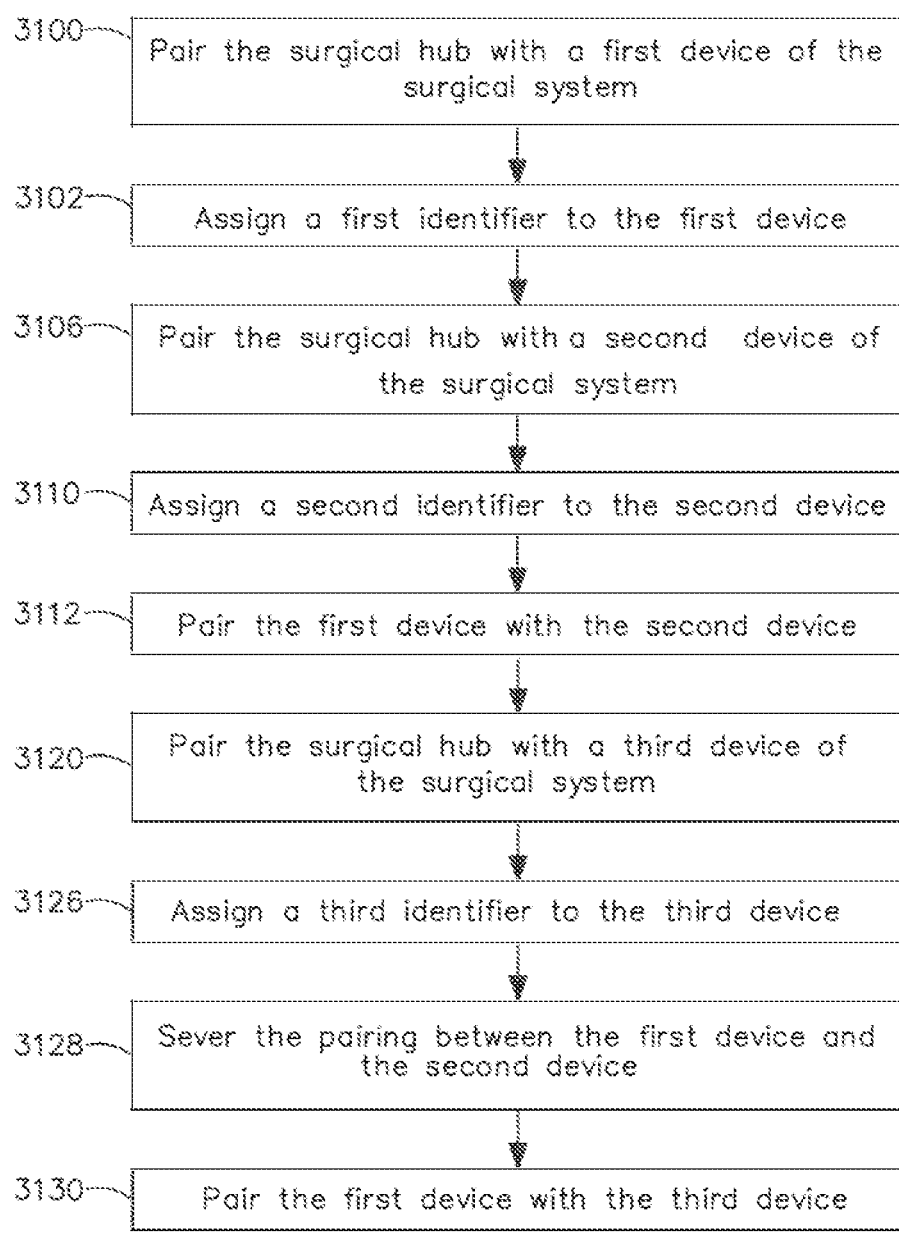
FIG. 38 is a logic flow diagram of a process depicting a control program or a logic configuration for selectively forming and severing connections between devices of a surgical system, in accordance with at least one aspect of the present disclosure.

In various aspects, the surgical hub includes a processor and a memory coupled to the processor. The memory stores instructions executable by the processor to selectively form and sever pairings between the devices of the surgical system, as described above. In various aspects, the present disclosure provides a non-transitory computer-readable medium storing computer-readable instructions which, when executed, cause a machine to selectively form and sever pairings between the devices of the surgical system, as described above. FIGS. 37 and 38 are logic flow diagrams of processes depicting control programs or logic configurations for selectively forming and severing pairings between the devices of the surgical system, as described herein.

In one aspect, the surgical hub 106 establishes a first pairing with a surgical instrument and a second pairing with the surgical instrument controller. The surgical hub 106 then links the pairings together allowing the surgical instrument and the surgical instrument controller to operate with one another. The surgical hub 106 may update the display of a primary display and/or a secondary display to reflect the linked pairings. In another aspect, the surgical hub 106 may sever an existing communication link between a surgical instrument and a surgical instrument controller, then link the surgical instrument to another surgical instrument controller that is linked to the surgical hub 106. The surgical hub 106 may update the display of a primary display and/or a secondary display to reflect the severed communication link and/or the link to another surgical instrument controller.

In one aspect, the surgical instrument controller is paired to two sources. The surgical instrument controller is paired to the surgical hub 106, which includes the generator module 140, for control of its activation. The surgical instrument controller is also paired to a specific surgical instrument to prevent inadvertent activation of the wrong surgical instrument.

Figure 39:
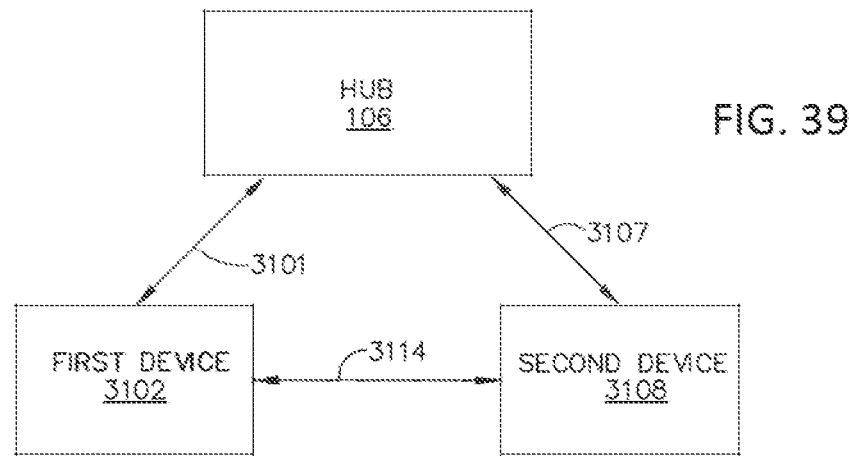
FIG. 39 illustrates a surgical hub pairing a first device and a second device of a surgical system in an operating room, in accordance with at least one aspect of the present disclosure.

Referring to FIGS. 37 and 39, the surgical hub 106 may cause the communication module 130 to pair 3100 or establish a first communication link 3101 with a first device 3102 of the surgical system 102, which can be a first surgical instrument. Then, the huh may assign 3104 a first identification number to the first device 3102. This is a unique identification and communication sequence or number that may include the device's name and a time stamp of when the communication was first established.

In addition, the surgical hub 106 may then cause the communication module 130 to pair 3106 or establish a second communication link 3107 with a second device 3108 of the surgical system 102, which can be a surgical instrument controller. The surgical hub 106 then assigns 3110a second identification number to the second device 3108.

In various aspects, the pairing a surgical hub 106 with a device may include detecting the presence of a new device, determining that the new device is within bounds of the operating room, as described herein, and pairing (e.g. only pairing) with the new device if the new device is located within the bounds of the operating room.

The surgical hub 106 may then pair 3112 or authorize a communication link 3114 to be established between the first device 3102 and the second device 3108, as illustrated in FIG. 39. A record indicative of the communication link 3114 is stored by the surgical hub 106 in the storage array 134. In one aspect, the communication link 3114 is established through the surgical hub 106. In another aspect, as illustrated in FIG. 39, the communication link 3114 is a direct link between the first device 3102 and the second device 3108. The surgical hub 106 may update a primary display and/or a secondary display to reflect the direct link between the first device 3102 and the second device 3108.

Figure 40:
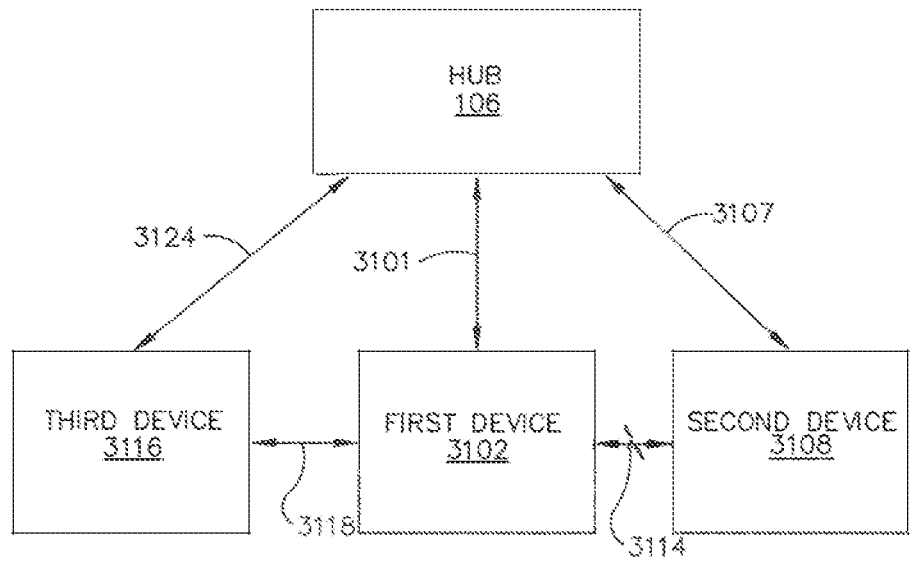
FIG. 40 illustrates a surgical hub unpairing a first device and a second device of a surgical system in an operating room, and pairing the first device with a third device in the operating room, in accordance with at least one aspect of the present disclosure.
Figure 41:
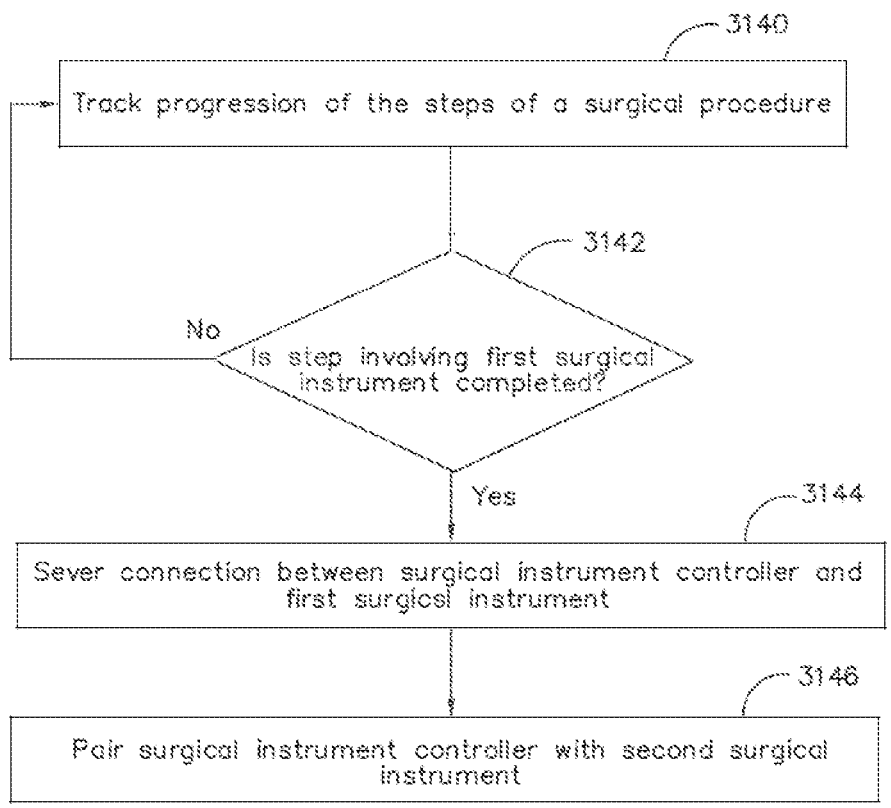
FIG. 41 is a logic flow diagram of a process depicting a control program or a logic configuration for forming a severing connections between devices of a surgical system in an operating room during a surgical procedure based on progression of the steps of the surgical procedure, in accordance with at least one aspect of the present disclosure.

Referring to FIGS. 38 and 40, the surgical hub 106 may detect and pair 3120 or establish a third communication link 3124 with a third device 3116 of the surgical system 102, which may be another surgical instrument controller, for example. The surgical hub 106 may then assign 3126a third identification number to the third device 3116. The surgical hub 106 may update a primary display and/or a secondary display to indicate that the third device has been detected and/or paired.

In certain aspects, as illustrated in FIG. 40, the surgical hub 106 may then pair 3130 or authorize a communication link 3118 to be established between the first device 3102 and the third device 3116, while causing the communication link 3114 to be severed 3128, as illustrated in FIG. 40. A record indicative of the formation of the communication link 3118 and severing of the communication link 3114 is stored by the surgical hub 106 in the storage array 134. In one aspect, the communication link 3118 is established through the surgical hub 106. In another aspect, as illustrated in FIG. 40, the communication link 3118 is a direct link between the first device 3102 and the third device 3116.

As described above, the surgical hub 106 can manage an indirect communication between devices of the surgical system 102. For example, in situations where the first device 3102 is a surgical instrument and the second device 3108 is a surgical instrument controller, an output of the surgical instrument controller can be transmitted through the communication link 3107 to the surgical hub 106, which may then transmit the output to the surgical instrument through the communication link 3101.

In making a decision to connect or sever a connection between devices of the surgical system 102, the surgical hub 106 may rely on perioperative data received or generated by the surgical hub 106. Perioperative data includes operator input, hub-situational awareness, hub-spatial awareness, and/or cloud data. For example, a request can be transmitted to the surgical hub 106 from an operator user-interface to assign a surgical instrument controller to a surgical instrument. If the surgical hub 106 determines that the surgical instrument controller is already connected to another surgical instrument, the surgical hub 106 may sever the connection and establish a new connection per the operator's request. The surgical hub 106 may update the display of a primary display and/or a secondary display to reflect the decision to connect or sever a connection.

In certain examples, the surgical hub 106 may establish a first communication link between the visualization system 108 and the primary display 119 to transmit an image, or other information, from the visualization system 108, which resides outside the sterile field, to the primary display 119, which is located within the sterile field. The surgical hub 106 may then sever the first communication link and establish a second communication link between a robotic hub 122 and the primary display 119 to transmit another image, or other information, from the robotic hub 122 to the primary display 119, for example. The ability of the surgical hub 106 to assign and reassign the primary display 119 to different components of the surgical system 102 allows the surgical hub 106 to manage the information flow within the operating room, particularly between components inside the sterile field and outside the sterile field, without physically moving these components.

In another example that involves the hub-situational awareness, the surgical hub 106 may selectively connect or disconnect devices of the surgical system 102 within an operating room based on the type of surgical procedure being performed or based on a determination of an upcoming task of the surgical procedure that requires the devices to be connected or disconnected. The hub situational awareness is described herein, for example with respect to FIG. 10.

Referring to FIG. 31, the surgical hub 106 may track 3140 the progression of surgical tasks in a surgical procedure and may coordinate pairing and unpairing of the devices of the surgical system 102 based upon such progression. For example, the surgical hub 106 may determine that a first surgical task requires use of a first surgical instrument, while a second surgical task, occurring after completion of the first surgical task, requires use of a second surgical instrument. Accordingly, the surgical hub 106 may assign a surgical instrument controller to the first surgical instrument for the duration of the first surgical task. After detecting completion 3142 of the first surgical task, the surgical hub 106 may cause the communication link between the first surgical instrument and the surgical instrument controller to be severed 3144. The surgical hub 106 may then assign the surgical instrument controller to the second surgical instrument by pairing 3146 or authorizing the establishment of a communication link between the surgical instrument controller and the second surgical instrument. The surgical hub 106 may update a primary display and/or a secondary display data associated with the progression of the surgical tasks. For example, the surgical hub 106 may display data associated with the first surgical instrument when connected for the first surgical task and may display data associated with the second surgical instrument when connected for the second surgical task.

Various other examples of the hub-situational awareness, which may influence the decision to connect or disconnect devices of the surgical system 102, are described herein, for example, with respect to FIG. 10. The hub-situational awareness may also be reflected by displaying data on a primary display and/or a secondary display.

The surgical hub 106 may utilize its spatial awareness capabilities, as described herein, to track progression of the surgical tasks of a surgical procedure and autonomously reassign a surgical instrument controller from one surgical instrument to another surgical instrument within the operating room of the surgical hub 106. In one aspect, the surgical hub 106 uses Bluetooth pairing and compass information to determine the physical position of the components of the surgical system 102. The surgical hub 106 may update a primary display and/or a secondary display when the surgical instrument controller is reassigned from one surgical instrument to another surgical instrument within the operating room of the surgical hub 106.

In the example illustrated in FIG. 2, the surgical hub 106 is paired with a first surgical instrument held by a surgical operator at the operating table and a second surgical instrument positioned on a side tray. A surgical instrument controller can be selectively paired with either the first surgical instrument or the second surgical instrument. Utilizing the Bluetooth pairing and compass information, the surgical hub 106 autonomously assigns the surgical instrument controller to the first surgical instrument because of its proximity to the patient. The surgical hub 106 may update the primary display and/or secondary display with data to reflect the assignment of the surgical instrument controller to the first surgical instrument.

After completion of the surgical task that involved using the first surgical instrument, the first surgical instrument may be returned to the side tray or otherwise moved away from the patient. Detecting a change in the position of the first surgical instrument, the surgical hub 106 may sever the communication link between the first surgical instrument and the surgical instrument controller to protect against unintended activation of the first surgical instrument by the surgical instrument controller. The surgical hub 106 may also reassign the surgical instrument controller to another surgical instrument if the surgical hub 106 detects that it has been moved to a new position at the operating table. The surgical hub 106 may update the primary display and/or the secondary display to reflect that the surgical instrument controller has been assigned to a second surgical instrument. For example, the surgical hub 106 may update a primary display to display data associated with the second medical instrument. As another example, the surgical hub 106 may update a secondary display to display instruction for cleaning and/or reloading of the first medical instrument. As another example, the surgical hub 106 may update a secondary display to display one or more settings for the second medical instrument.

In various aspects, devices of the surgical system 102 may be equipped with an easy hand-off operation mode that would allow one user to give activation control of a device they currently control to another surgical instrument controller within reach of another operator. In one aspect, the devices are equipped to accomplish the hand-off through a predetermined activation sequence of the devices that causes the devices that are activated in the predetermined activation sequence to pair with one another. Primary display and/or secondary displays may be updated accordingly.

In an aspect, the activation sequence may be accomplished by powering on the devices to be paired with one another in a particular order. Primary displays and/or secondary display may be updated accordingly. In another aspect, the activation sequence is accomplished by powering on the devices to be paired with one another within a predetermined time period. In one aspect, the activation sequence is accomplished by activating communication components, such as Bluetooth, of the devices to be paired with one another in a particular order. In another aspect, the activation sequence is accomplished by activating communication components, such as Bluetooth, of the devices to be paired within one another within a predetermined time period.

A hand-off may be accomplished by a selection of a device through one of the surgical-operator input devices. After the selection is completed, the next activation by another controller would allow the new controller to take control.

In various aspects, the surgical hub 106 may be configured to directly identify components of the surgical system 102 as they are brought into an operating room. In one aspect, the devices of the surgical system 102 can be equipped with an identifier recognizable by the surgical hub 106, such as, for example, a bar code or an RFID tag. NFC can also be employed. The surgical hub 106 can be equipped with a suitable reader or scanner for detecting the devices brought into the operating room. The surgical hub 106 may update a primary display and/or a secondary display to indicate that the components of the surgical system 102 have been identified.

The surgical hub 106 may also be configured to check and/or update various control programs of the devices of the surgical system 102. Upon detecting and establishing a communication link of a device of the surgical system 102, the surgical hub 106 may check if its control program is up to date. If the surgical hub 106 determines that a later version of the control program is available, the surgical hub 106 may download the latest version from the cloud 104 and may update the device to the latest version. The surgical hub 106 may issue a sequential identification and communication number to each paired or connected device.

Cooperative utilization of data derived from secondary sources by intelligent surgical hubs may be provided. In a surgical procedure, the attention of a surgical operator must be focused on the tasks at hand. Receiving information from multiple sources, such as, for example, multiple displays, although helpful, may also be distracting. The imaging module 138 of the surgical hub 106 is configured to intelligently gather, analyze, organize/package, and disseminate relevant information to the surgical operator in a manner that minimizes distractions.

Aspects of the present disclosure are presented for cooperative utilization of data derived from multiple sources, such as, for example, an imaging module 138 of the surgical hub 106. In one aspect, the imaging module 138 is configured to overlay data derived from one or more sources onto a livestream destined for the primary display 119, for example. In one aspect, the overlaid data may be derived from one or more frames acquired by the imaging module 138. The imaging module 138 may commandeer image frames on their way for display on a local display such as, for example, the primary display 119. The imaging module 138 also comprises an image processor that may perform an array of local image processing on the commandeered images. The overlaid data may be displayed on a primary display and/or a secondary display.

Furthermore, a surgical procedure generally includes a number of surgical tasks which can be performed by one or more surgical instruments guided by a surgical operator or a surgical robot, for example. Success or failure of a surgical procedure depends on the success or failure of each of the surgical tasks. Without relevant data on the individual surgical tasks, determining the reason for a failed surgical procedure is a question of probability.

Aspects of the present disclosure are presented for capturing one or more frames of a livestream of a surgical procedure for further processing and/or pairing with other data. The frames may be captured at the completion of a surgical task (also referred to elsewhere herein as "surgical step") to assess whether the surgical task was completed successfully. Furthermore, the frames, and the paired data, can be uploaded to the cloud for further analysis.

In one aspect, one or more captured images are used to identify at least one previously completed surgical task to evaluate the outcome of the surgical task. In one aspect, the surgical task is a tissue-stapling task. In another aspect, the surgical task is an advanced energy transection.

Figure 42:
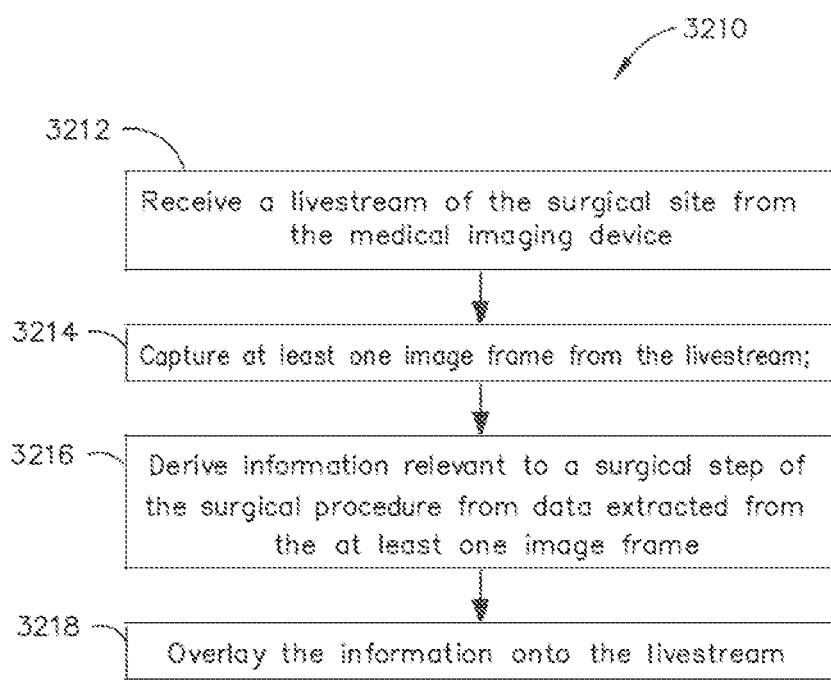
FIG. 42 is a logic flow diagram of a process depicting a control program or a logic configuration for overlaying information derived from one or more still frames of a livestream of a remote surgical site onto the livestream, in accordance with at least one aspect of the present disclosure.

FIG. 42 is a logic flow diagram of a process 3210 depicting a control program or a logic configuration for overlaying information derived from one or more still frames of a livestream of a remote surgical site onto the livestream. The process 3210 includes receiving 3212a livestream of a remote surgical site from a medical imaging device 124, for example, capturing 3214 at least one image frame of a surgical task of the surgical procedure from the livestream, deriving 3216 information relevant to the surgical task from data extracted from the at least one image frame, and overlaying 3218 the information onto the livestream. The livestream may be displayed on a primary display and/or a secondary display.

In one aspect, the still frames can be of a surgical task performed at the remote surgical site. The still frames can be analyzed for information regarding completion of the surgical task. In one aspect, the surgical task comprises stapling tissue at the surgical site. In another aspect, the surgical task comprises applying energy to tissue at the surgical site.

Figure 43:
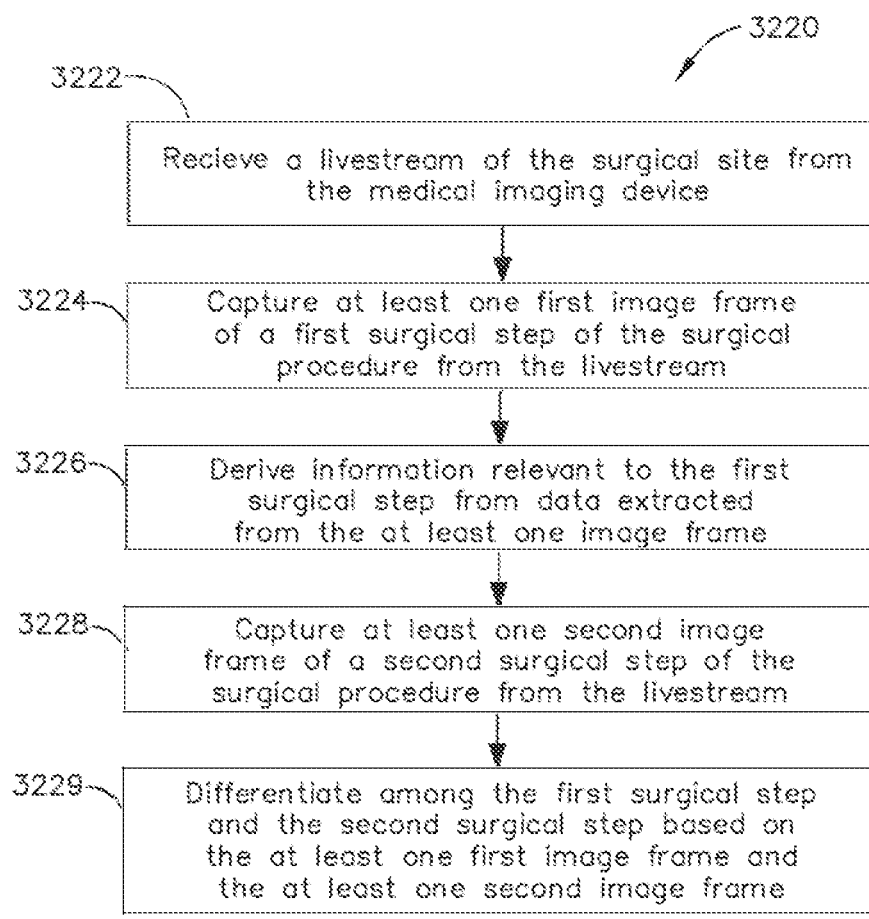
FIG. 43 is a logic flow diagram of a process depicting a control program or a logic configuration for differentiating among surgical steps of a surgical procedure, in accordance with at least one aspect of the present disclosure.

FIG. 43 is a logic flow diagram of a process 3220 depicting a control program or a logic configuration for differentiating among surgical tasks of a surgical procedure. The process 3220 includes receiving 3222a livestream of a surgical site from a medical imaging device 124, for example, capturing 3224 at least one first image frame of a first surgical task of the surgical procedure from the livestream, deriving 3226 information relevant to the first surgical task from data extracted from the at least one image frame, capturing 3228 at least one second image frame of a second surgical task of the surgical procedure from the live stream, and differentiating 3229 among the first surgical task and the second surgical task based on the at least one first image frame and the at least one second image frame.

Figure 44:
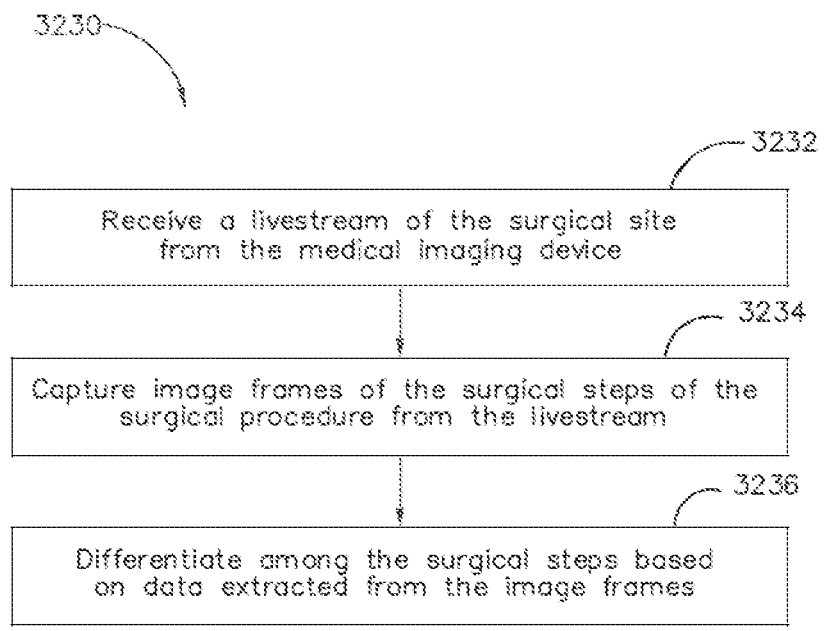
FIG. 44 is a logic flow diagram of a process depicting a control program or a logic configuration for differentiating among surgical steps of a surgical procedure, in accordance with at least one aspect of the present disclosure.

FIG. 44 is a logic flow diagram of a process 3230 depicting a control program or a logic configuration for differentiating among surgical tasks of a surgical procedure. The process 3232 includes receiving 3232a livestream of the surgical site from a medical imaging device 124, for example, capturing 3234 image frames of the surgical tasks of the surgical procedure from the livestream and differentiating 3236 among the surgical tasks based on data extracted from the image frames.

Figure 45:
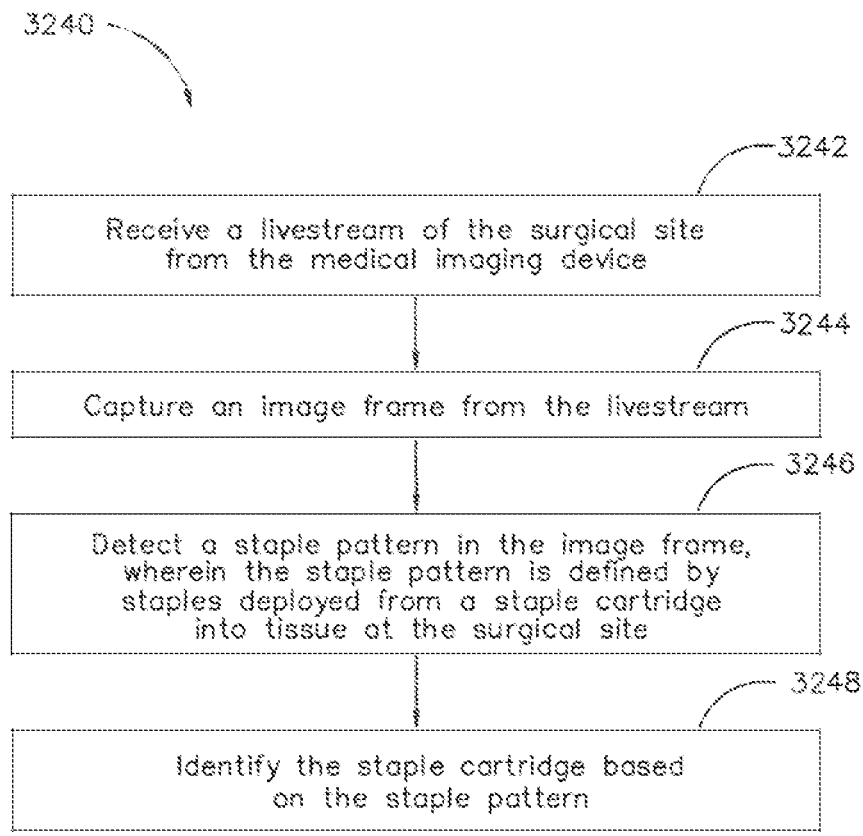
FIG. 45 is a logic flow diagram of a process depicting a control program or a logic configuration for identifying a staple cartridge from information derived from one or more still frames of staples deployed from the staple cartridge into tissue, in accordance with at least one aspect of the present disclosure.

FIG. 45 is a logic flow diagram of a process 3240 depicting a control program or a logic configuration for identifying a staple cartridge from information derived from one or more still frames of staples deployed from the staple cartridge into tissue. The process 3240 includes receiving 3242a livestream of the surgical site from medical imaging device 124, for example, capturing 3244 an image frame from the livestream, detecting 3246a staple pattern in the image frame, wherein the staple pattern is defined by staples deployed from a staple cartridge into tissue at the surgical site. The process 3240 further includes identifying 3248 the staple cartridge based on the staple pattern.

Figure 46:
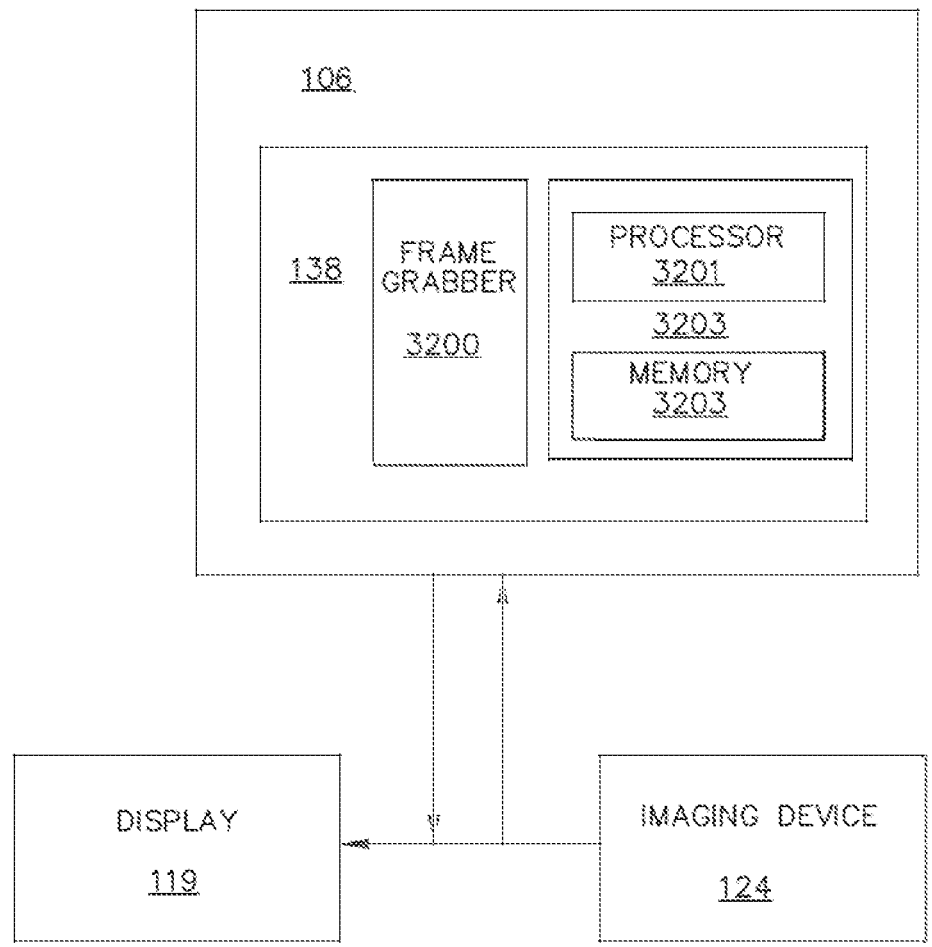
FIG. 46 is a partial view of a surgical system in an operating room, the surgical system including a surgical hub that has an imaging module in communication with an imaging device at a remote surgical site, in accordance with at least one aspect of the present disclosure.

Referring to FIGS. 31 and 46, a surgical hub 106 is in communication with a medical imaging device 124 located at a remote surgical site during a surgical procedure. The imaging module 138 receives a livestream of the remote surgical site transmitted by the imaging device 124 to a primary display 119, for example, in accordance with tasks 3212, 3222, 3232, 3242.

Further to the above, the imaging module 138 of the surgical hub 106 includes a frame grabber 3200. The frame grabber 3200 is configured to capture (i.e., "grabs") individual, digital still frames from the livestream transmitted by the imaging device 124, for example, to a primary display 119, for example, during a surgical procedure, in accordance with tasks 3214, 3224, 3234, 3244. The captured still frames are stored and processed by a computer platform 3203 (FIG. 46) of the imaging module 138 to derive information about the surgical procedure. Processing of the captured frames may include performance of simple operations, such as histogram calculations, 2D filtering, and arithmetic operations on arrays of pixels to the performance of more complex tasks, such as object detection, 3D filtering, and the like.

In one aspect, the derived information can be overlaid onto the livestream. In one aspect, the still frames and/or the information resulting from processing the still frames can be communicated to a cloud 104 for data aggregation and further analysis.

In various aspects, the frame grabber 3200 may include a digital video decoder and a memory for storing the acquired still frames, such as, for example, a frame buffer. The frame grabber 3200 may also include a bus interface through which a processor can control the acquisition and access the data and a general purpose I/O for triggering image acquisition or controlling external equipment.

As described above, the imaging device 124 can be in the form of an endoscope, including a camera and a light source positioned at a remote surgical site, and configured to provide a livestream of the remote surgical site at the primary display 119, for example.

In various aspects, image recognition algorithms can be implemented to identify features or objects in still frames of a surgical site that are captured by the frame grabber 3200. Useful information pertaining to the surgical tasks associated with the captured frames can be derived from the identified features. For example, identification of staples in the captured frames indicates that a tissue-stapling surgical task has been performed at the surgical site. The type, color, arrangement, and size of the identified staples can also be used to derive useful information regarding the staple cartridge and the surgical instrument employed to deploy the staples. As described above, such information can be overlaid on a livestream directed to a primary display 119 in the operating room.

The image recognition algorithms can be performed at least in part locally by the computer platform 3203 (FIG. 46) of the imaging module 138. In certain instances, the image recognition algorithms can be performed at least in part by the processor module 132 of the surgical hub 106. An image database can be utilized in performance of the image recognition algorithms and can be stored in a memory 3202 of the computer platform 3203. In an aspect, the imaging database can be stored in the storage array 134 (FIG. 3) of the surgical hub 106. The image database may be updated from the cloud 104.

An example image recognition algorithm that can be executed by the computer platform 3203 may include a key points-based comparison and a region-based color comparison. The algorithm includes: receiving an input at a processing device, such as, for example, the computer platform 3203; the input, including data related to a still frame of a remote surgical site; performing a retrieving task, including retrieving an image from an image database and, until the image is either accepted or rejected, designating the image as a candidate image; performing an image recognition task, including using the processing device to perform an image recognition algorithm on the still frame and candidate images in order to obtain an image recognition algorithm output; and performing a comparison task, including: if the image recognition algorithm output is within a pre-selected range, accepting the candidate image as the still frame and if the image recognition algorithm output is not within the pre-selected range, rejecting the candidate image and repeating the retrieving, image recognition, and comparison tasks.

Referring generally to FIGS. 48-53, the interaction between surgical hubs may be extended beyond the bounds of the operating room. In various aspects, surgical hubs in separate operating rooms may interact with one another within predefined limits. Depending on their relative proximity, surgical hubs in separate operating rooms may interact through any suitable wired or wireless data communication network such as Bluetooth and WiFi. As used here, a "data communication network" represents any number of physical, virtual, or logical components, including hardware, software, firmware, and/or processing logic configured to support data communication between an originating component and a destination component, where data communication is carried out in accordance with one or more designated communication protocols over one or more designated communication media.

In various aspects, a first surgical operator in a first operating room may wish to consult a second surgical operator in a second operating room, such as in case of an emergency. A temporary communication link may be established between the surgical hubs of the first and second operating room to facilitate the consult while the first and second surgical operators remain in their respective operating rooms.

The surgical operator being consulted may be presented with a consult request through the surgical hub in his/her operating room. If the surgical operator accepts, he/she will have access to some or all the data compiled by the surgical hub requesting the consult. The surgical operator may access all previously stored data, including a full history of the procedure. In addition, a livestream of the surgical site at the requesting operating room may be transmitted through the surgical hubs to a display, such as a primary display and/or secondary display, at the receiving operating room. A user may determine which display may receive the livestream. For example, a user may instruct the surgical hub to display the livestream on the primary display and/or the secondary display. The user may instruct the surgical display to move the livestream from a primary display to a secondary display, or from a secondary display to a primary display.

When a consult request begins, the receiving surgical hub begins to record some or all received information in a temporarily storage location, which may be a dedicated portion of the storage array of the surgical hub. At the end of the consult, the temporary storage location may be purged from all the information. In one aspect, during a consult, the surgical hub records some or all accessible data, including blood pressure, ventilation data, oxygen stats, generator settings and uses, and all patient electronic data. The recorded data may likely be more than the data stored by the surgical hub during normal operation, which may be helpful in providing the surgical operator being consulted with as much information as possible for the consult.

Figure 48:
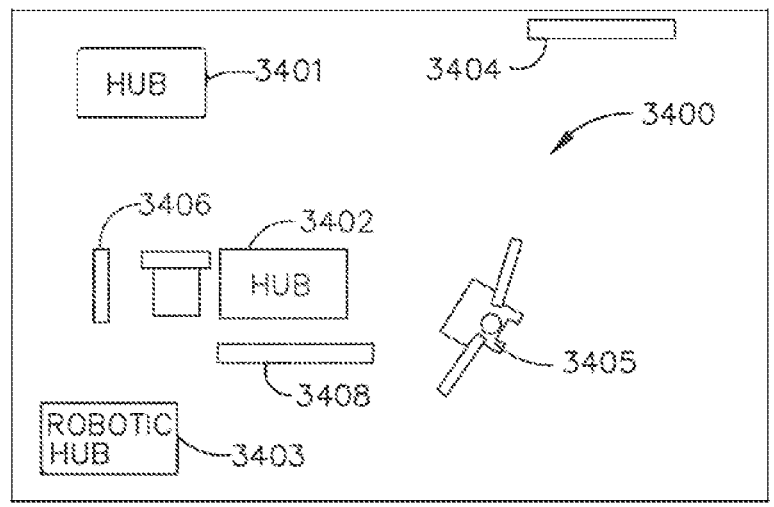
FIG. 48 illustrates an interaction between two surgical hubs in different operating rooms ("OR1" and "OR3"), in accordance with at least one aspect of the present disclosure.
Figure 48:
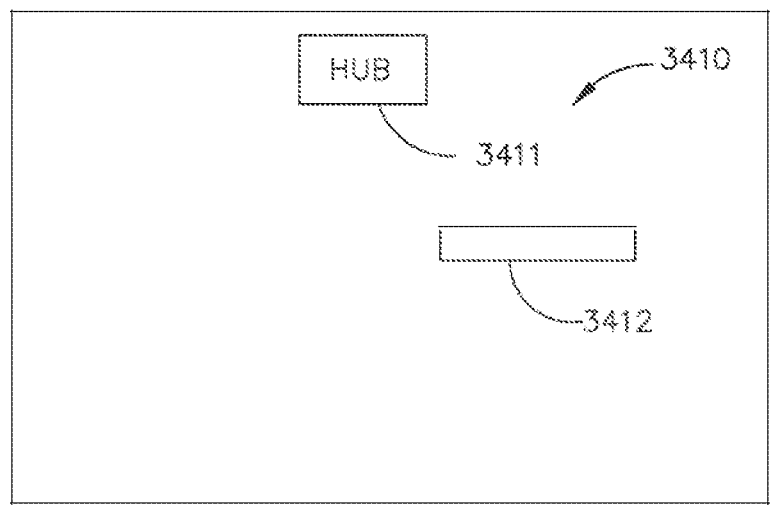

Referring to FIG. 48, a non-limiting example of an interaction between surgical hubs in different operating rooms is depicted. FIG. 48 depicts an operating room OR 1 that may include a surgical system 3400 supporting a thoracic segmentectomy and a second operating room OR 3 that includes a surgical system 3410 supporting a colorectal procedure. The surgical system 3400 includes surgical hub 3401, surgical hub 3402, and robotic surgical hub 3403. The surgical system 3400 further includes a personal interface 3406, a primary display 3408, and secondary displays 3404, 3405. The surgical system 3410 includes a surgical hub 3411 and a secondary display 3412. For clarity, several components of the surgical systems 3400, 3410 are removed.

In the example of FIG. 48, the surgical operator of OR 3 may request a consult from the surgical operator of OR 1. A surgical hub 3411 of the OR 3 transmits the consult request to one of the surgical hubs of the OR 1, such as the surgical hub 3401. In OR 1, the surgical hub 3401 presents the request at a personal interface 3406, which may be a secondary display, held by the surgical operator. The consult is regarding selecting an optimal location of a colon transection. The surgical operator of OR 1, through a personal interface 3406, recommends an optimal location for the transection site that avoids a highly vascular section of the colon. The recommendation may be transmitted in real time through the surgical hubs 3401, 3411. Accordingly, the surgical operator is able to respond to the consult request in real time without having to leave the sterile field of his own operating room. The surgical operator requesting the consult also did not have to leave the sterile field of OR 3. In an example, the consult request may be moved from the secondary display, such as personal interface 3406 to a primary display, such as 3408, and/or secondary display 3404.

If the surgical hub 3401 is not in communication with the personal interface 3406, it may relay the message to another surgical hub such as, for example, the surgical hub 3402 or the robotic surgical hub 3403. The surgical hub 3401 may request control of the personal interface 3406 from another surgical hub.

Figure 49:
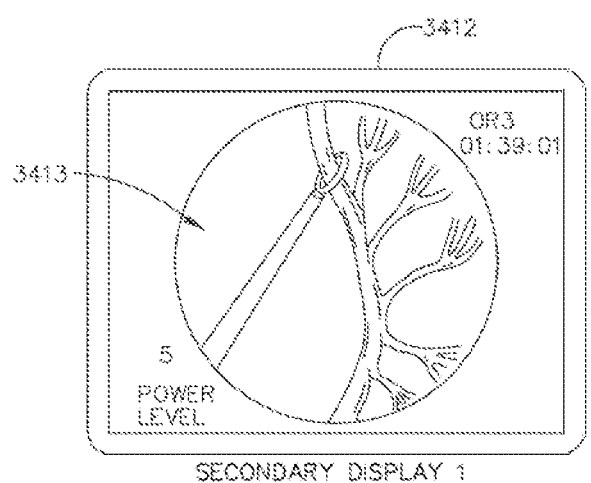
FIG. 49 illustrates a secondary display in an operating room ("OR3") showing a surgical site in a colorectal procedure, in accordance with at least one aspect of the present disclosure.
Figure 50:
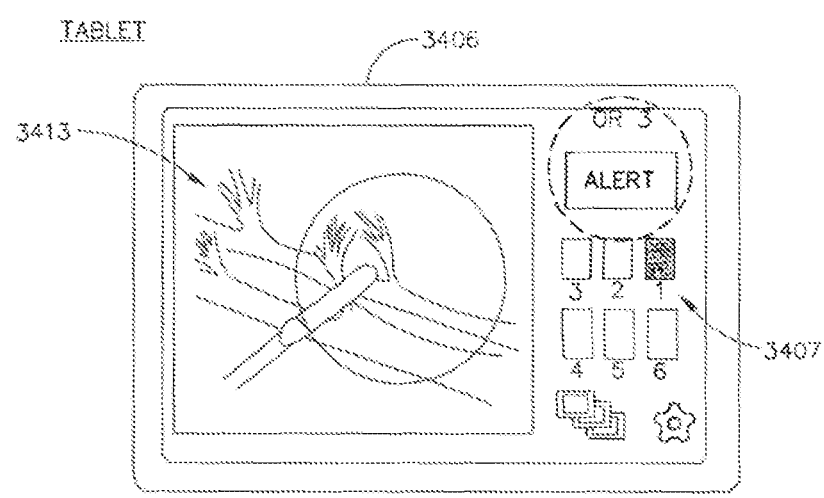
FIG. 50 illustrates a personal interface or tablet in OR1 displaying the surgical site of OR3, in accordance with at least one aspect of the present disclosure.

If the surgical operator of OR 1 decides to accept the consult request, a livestream, or frames, of a surgical site 3413 of the colorectal procedure of OR 3 is transmitted to OR 1 through a connection established between the surgical hubs 3401, 3411, for example. FIG. 49 illustrates a livestream of the surgical site 3413 displayed on a secondary display of OR 3. The surgical hubs 3401, 3411 cooperate to transmit the livestream of the surgical site of OR 3 to the personal interface 3406 of the OR 1, as illustrated in FIG. 50.

Figure 51:
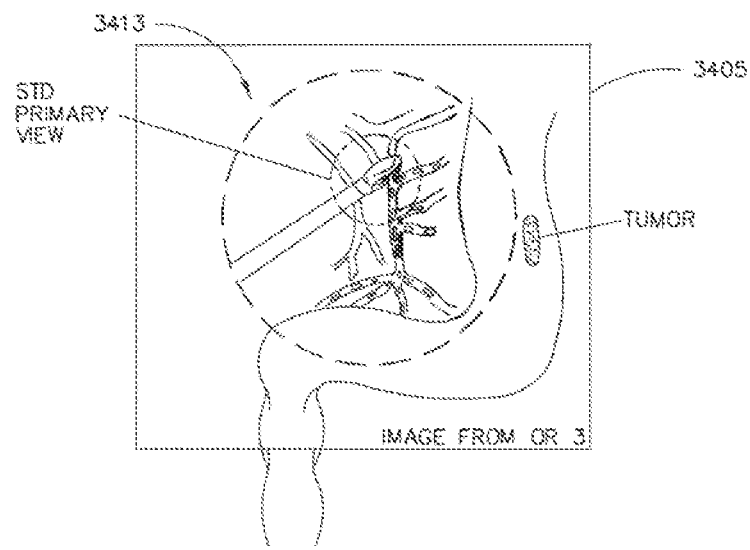
FIG. 51 illustrates an expanded view of the surgical site of OR3 displayed on a primary display of OR1, in accordance with at least one aspect of the present disclosure.
Figure 52:
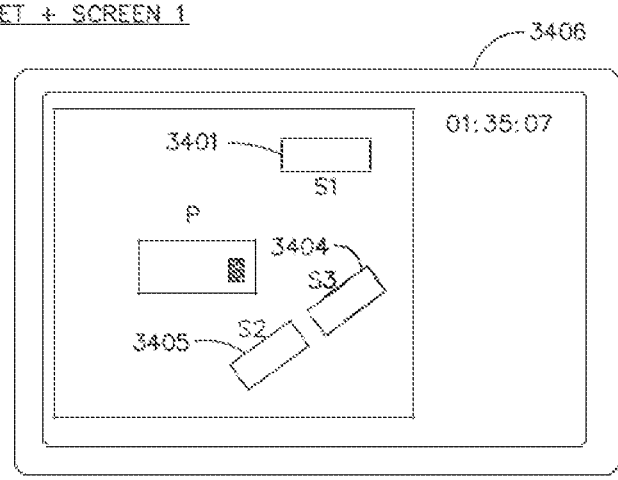
FIG. 52 illustrates a personal interface or tablet displaying a layout of OR1 that shows available displays, in accordance with at least one aspect of the present disclosure.
Figure 53:
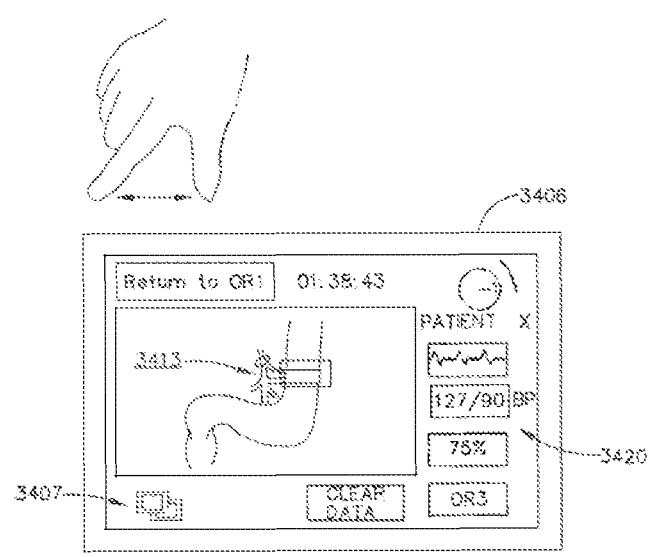
FIG. 53 illustrates a recommendation of a transection location of a surgical site of OR3 made by a surgical operator in OR1 via a personal interface or tablet in OR1, in accordance with at least one aspect of the present disclosure.

Referring to FIGS. 51-53, the surgical operator may expand the laparoscopic livestream from OR 3 onto the primary display 3408 in OR 1, for example, through the controls of the personal interface 3406, which may be a secondary display. The personal interface 3406 may allow the surgical operator to select a destination for the livestream by presenting the surgical operator with icons that represent the displays that may be available in OR 1, as illustrated in FIG. 52. Other navigation controls 3407 may be available to the surgical operator through the personal interface 3406, as illustrated in FIG. 53. For example, the personal interface 3406 includes navigation controls for adjusting the livestream of the surgical site of OR 3 in OR 1 by the surgical operator moving his or her fingers on the livestream displayed on the personal interface 3406. To visualize the high vasculature regions, the consulted surgical operator may change the view of the livestream from OR 3 through the personal interface 3406 to an advanced imaging screen. The surgical operator may then manipulate the image in multiple planes to see the vascularization using a wide-angle multi-spectral view, for example. In an example, the surgeon may give instruct the personal interface 3406 to adjust the livestream or select a destination for the livestream using one or more of a gesture, a hand motion, a voice command, a head motion, and the like.

As illustrated in FIG. 53, the surgical operator also may have access to an array of relevant information 3420, such as, for example, heart rate, blood pressure, ventilation data, oxygen stats, generator settings and uses, and all patient electronic data of the patient in OR 3. Surgical hub situational awareness may be provided. Although an "intelligent" device including control algorithms that respond to sensed data may be an improvement over a "dumb" device that operates without accounting for sensed data, some sensed data may be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or sub optimally given the particular context-free sensed data. For example, the optimal manner for a control algorithm to control a surgical instrument in response to a particular sensed parameter may vary according to the particular tissue type being operated on. This may be due to the fact that different tissue types have different properties (e.g., resistance to tearing) and thus respond differently to actions taken by surgical instruments. It may be desirable for a surgical instrument to take different actions even when the same measurement for a particular parameter is sensed. As a specific example, the optimal manner in which to control a surgical stapling and cutting instrument in response to the instrument sensing an unexpectedly high force to close its end effector will vary depending upon whether the tissue type is susceptible or resistant to tearing. For tissues that may be susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

A surgical hub may include a system that may be configured to derive information about the surgical procedure being performed based on data received from various data sources and may control the paired modular devices accordingly. In other words, the surgical hub may be configured to infer information about the surgical procedure from received data and then control the modular devices paired to the surgical hub based upon the inferred context of the surgical procedure. The surgical hub may display the data received and/or the configuration settings on one or more primary displays and/or secondary displays.

As another example, a situationally aware surgical hub, such as situationally aware surgical hub 5104 show in FIG. 9, may determine whether the current or subsequent task of a surgical procedure requires a different view or degree of magnification on a display according to the feature(s) at the surgical site that the surgeon is expected to need to view. The surgical hub may then proactively change the displayed view on a primary display and/or a secondary display accordingly so that the display automatically adjusts throughout the surgical procedure.

As yet another example, a situationally aware surgical hub may determine which task of the surgical procedure is being performed or will subsequently be performed and whether particular data or comparisons between data will be requested for that task of the surgical procedure. The surgical hub may be configured to automatically call up data screens based upon the task of the surgical procedure being performed, without waiting for the surgeon to ask for the particular information. For example, the surgical hub may instruct a primary display to display a first set of data and may instruct a secondary display to display a second set of data.

A situationally aware surgical hub may determine whether the operating theater is setup properly or optimally for the surgical procedure to be performed. The surgical hub may be configured to determine the type of surgical procedure being performed, retrieve the corresponding checklists, product location, or setup needs (e.g., from a memory), and then compare the current operating theater layout to the standard layout for the type of surgical procedure that the surgical hub determines is being performed. The surgical hub may display instructions to the staff as to how to set up the operating theater on a primary display and/or a secondary display.

The surgical hub may be configured to compare the list of items for the procedure and/or a list of devices paired with the surgical hub to a recommended or anticipated manifest of items and/or devices for the given surgical procedure. If there are any discontinuities between the lists, the surgical hub may be configured to provide an alert to a user using a primary display and/or a secondary display.

A situationally aware surgical hub may determine whether the surgeon (or other medical personnel) was making an error or otherwise deviating from the expected course of action during the course of a surgical procedure. For example, the surgical hub may be configured to determine the type of surgical procedure being performed, retrieve the corresponding list of tasks or order of equipment usage (e.g., from a memory), and then compare the tasks being performed or the equipment being used during the course of the surgical procedure to the expected tasks or equipment for the type of surgical procedure that the surgical hub determined is being performed. The surgical hub may provide an alert using a primary display and/or a secondary display indicating that an unexpected action is being performed or an unexpected device is being utilized at the particular task in the surgical procedure. The surgical hub may provide remedial instructions to correct the error using a primary display and/or a secondary display.

The situational awareness system for the surgical hub may improve surgical procedure outcomes by adjusting the surgical instruments, primary displays, and/or secondary displays for the particular context of each surgical procedure (such as adjusting to different tissue types) and validating actions during a surgical procedure. The situational awareness system also improves surgeons' efficiency in performing surgical procedures by automatically suggesting next tasks, providing data, and adjusting displays (e.g. primary displays and/or secondary displays) and other modular devices in the surgical theater according to the context of the procedure.

Figure 54A:
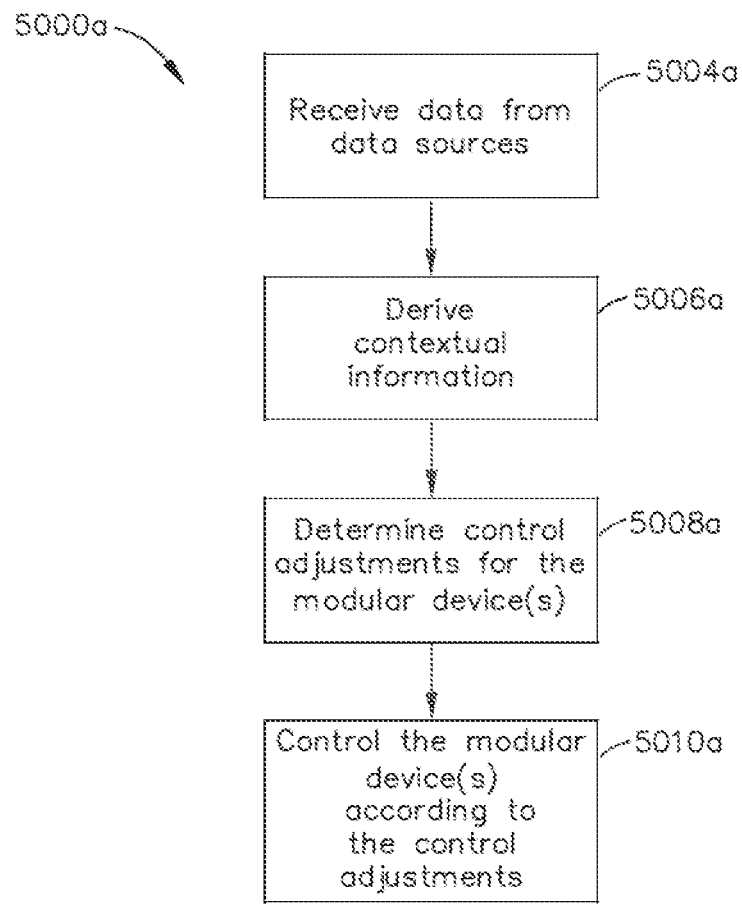
FIG. 54A illustrates a logic flow diagram of a process for controlling a modular device according to contextual information derived from received data, in accordance with at least one aspect of the present disclosure.

FIG. 54A illustrates a logic flow diagram of a process 5000 *a* for controlling a modular device 5102 according to contextual information (e.g. contextual data) derived from received data, in accordance with at least one aspect of the present disclosure. The phrase "contextual information" may be used interchangeably with the phrase "contextual data" herein.

A situationally aware surgical hub 5104 may execute the process 5000 *a* to determine appropriate control adjustments for modular devices 5102 paired with the surgical hub 5104 before, during, or after a surgical procedure as dictated by the context of the surgical procedure. In the following description of the process 5000 *a*, reference should also be made to FIG. 9. In an example, the process 5000 *a* may be executed by a control circuit of a surgical hub 5104, as depicted in FIG. 6 (processor 244). In another example, the process 5000 *a* may be executed by a cloud computing system 104, as depicted in FIG. 1. In another example, the process 5000 *a* may be executed by a distributed computing system including at least one of the aforementioned cloud computing system 104 and/or a control circuit of a surgical hub 5104 in combination with a control circuit of a modular device, such as the microcontroller 461 of the surgical instrument depicted in FIG. 7. For economy, the following description of the process 5000 *a* will be described as being executed by the control circuit of a surgical hub 5104; however, it should be understood that the description of the process 5000 *a* encompasses all of the aforementioned example.

The control circuit of the surgical hub 5104 executing the process 5000 *a* receives 5004 *a* data from one or more data sources 5126 to which the surgical hub 5104 is communicably connected. The data sources 5126 include, for example, databases 5122, patient monitoring devices 5124, and modular devices 5102. In one exemplification, the databases 5122 may include a patient EMR database associated with the medical facility at which the surgical procedure is being performed. The data received 5004 *a* from the data sources 5126 may include perioperative data, which includes preoperative data, intraoperative data, and/or postoperative data associated with the given surgical procedure. The data received 5004 *a* from the databases 5122 may include the type of surgical procedure being performed or the patient's medical history (e.g., medical conditions that may or may not be the subject of the present surgical procedure).

As the process 5000 *a* continues, the control circuit of the surgical hub 5104 may derive 5006 *a* contextual information (e.g. contextual data) from the data received 5004 *a* from the data sources 5126. The contextual information (e.g. contextual data) may include, for example, the type of procedure being performed, the particular task being performed in the surgical procedure, the patient's state (e.g., whether the patient is under anesthesia or whether the patient is in the operating room), or the type of tissue being operated on. The control circuit may derive 5006 *a* contextual information according to data from ether an individual data source 5126 or combinations of data sources 5126. The control circuit may derive 5006 *a* contextual information according to, for example, the type(s) of data that it receives, the order in which the data is received, or particular measurements or values associated with the data. For example, if the control circuit receives data from an RF generator indicating that the RF generator has been activated, the control circuit could thus infer that the RF electrosurgical instrument is now in use and that the surgeon is or will be performing a task of the surgical procedure utilizing the particular instrument. As another example, if the control circuit receives data indicating that a laparoscope imaging device has been activated and an ultrasonic generator is subsequently activated, the control circuit may infer that the surgeon is on a laparoscopic dissection task of the surgical procedure due to the order in which the events occurred. As another example, if the control circuit receives data from a ventilator indicating that the patient's respiration is below a particular rate, then the control circuit may determine that the patient is under anesthesia.

The control circuit may then determine 5008 *a* what control adjustments are necessary (if any) for one or more modular devices 5102 according to the derived 5006 *a* contextual information (e.g. contextual data). After determining 5008 the control adjustments, the control circuit of the surgical hub 5104 may then control 5010 the modular devices according to the control adjustments (if the control circuit determined 5008 *a* that any were necessary). For example, if the control circuit determines that an arthroscopic procedure is being performed and that the next task in the procedure utilizes an RF or ultrasonic surgical instrument in a liquid environment, the control circuit may determine 5008 *a* that a control adjustment for the generator of the RF or ultrasonic surgical instrument is necessary to preemptively increase the energy output of the instrument (because such instruments require increased energy in liquid environments to maintain their effectiveness). The control circuit may then control 5010 the generator and/or the RF or ultrasonic surgical instrument accordingly by causing the generator to increase its output and/or causing the RF or ultrasonic surgical instrument to increase the energy drawn from the generator. The control circuit may control 5010 the modular devices 5102 according to the determined 5008 *a* control adjustment by, for example, transmitting the control adjustments to the particular modular device to update the modular device's 5102 programming. In an example wherein the modular device(s) 5102 and the surgical hub 5104 are executing a distributed computing architecture, the control circuit may control 5010 the modular device 5102 according to the determined 5008 *a* control adjustment by updating the distributed program.

The surgical hub may also display what control adjustments may have been made. For example, the control circuit of the surgical hub may determine what control adjustments are to be made, and may display those adjustments to a user via a primary display and/or a secondary display. In another example, the control circuit of the surgical hub may highlight or make the data related to the adjustments more prominent on a primary screen and/or a secondary screen.

Figure 54B:
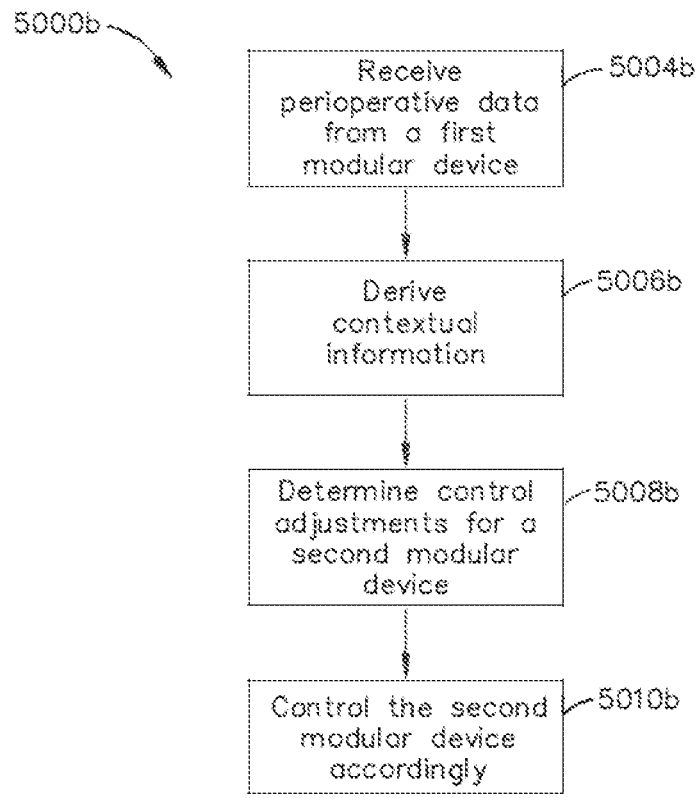
FIG. 54B illustrates a logic flow diagram of a process for controlling a second modular device according to contextual information derived from perioperative data received from a first modular device, in accordance with at least one aspect of the present disclosure.
Figure 54C:
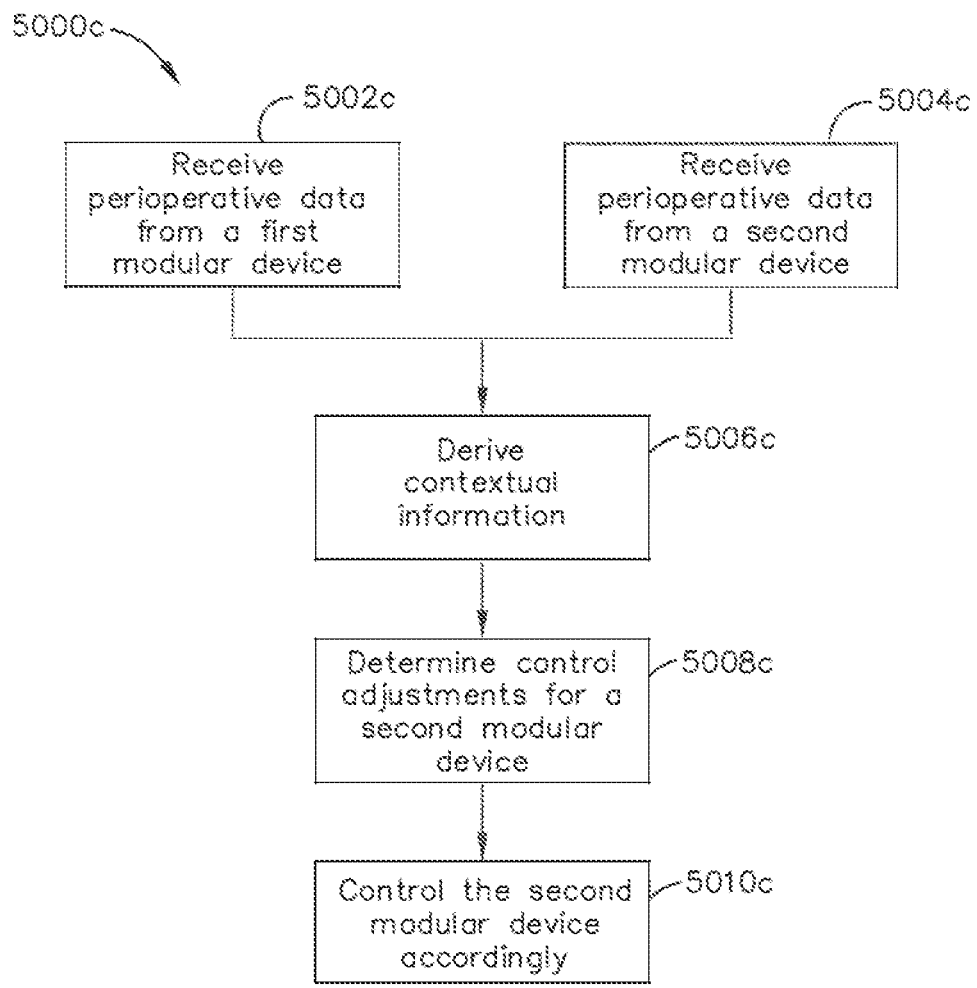
FIG. 54C illustrates a logic flow diagram of a process for controlling a second modular device according to contextual information derived from perioperative data received from a first modular device and the second modular device, in accordance with at least one aspect of the present disclosure.
Figure 54D:
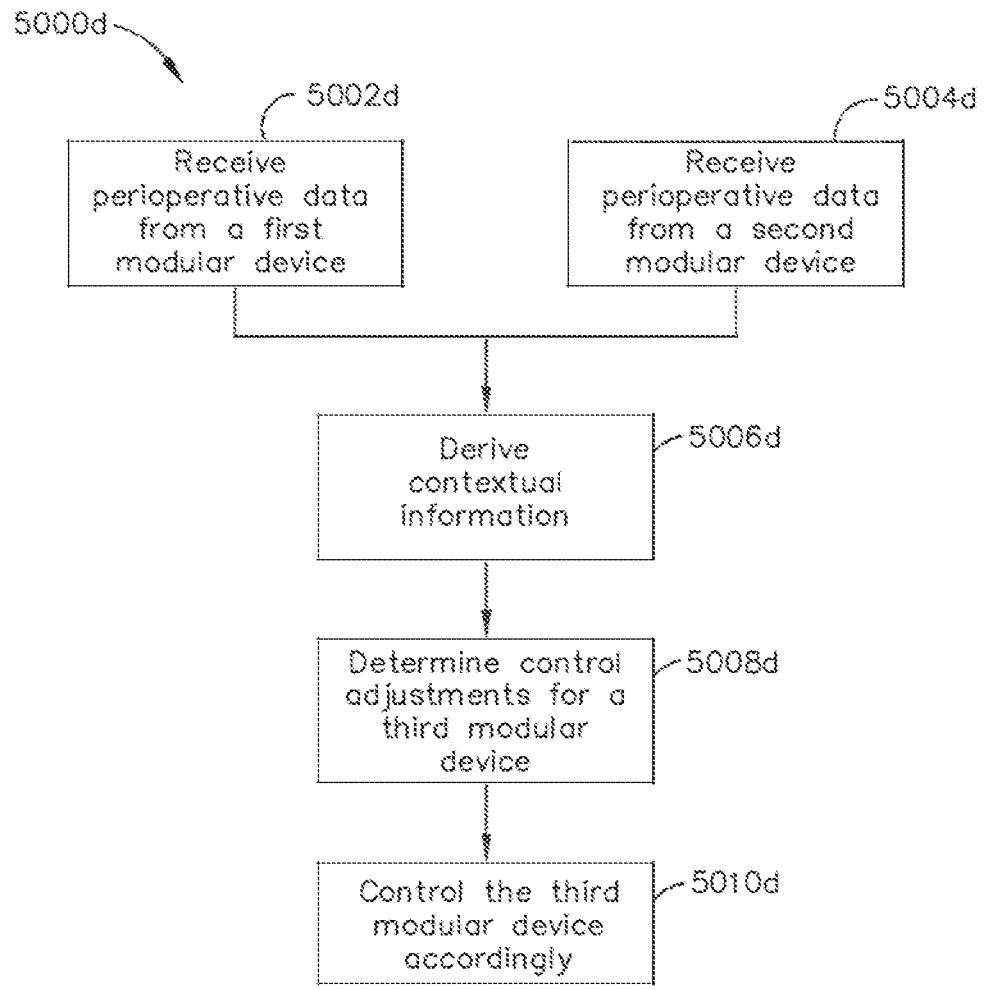
FIG. 54D illustrates a logic flow diagram of a process for controlling a third modular device according to contextual information derived from perioperative data received from a first modular device and a second modular device, in accordance with at least one aspect of the present disclosure.

FIGS. 54B-D illustrate representative implementations of the process 5000 *a* depicted in FIG. 54A. As with the process 5000 *a* depicted in FIG. 54A, the processes illustrated in FIGS. 54B-D may, in one exemplification, be executed by a control circuit of the surgical hub 5104. FIG. 54B illustrates a logic flow diagram of a process 5000 *b* for controlling a second modular device according to contextual information (e.g. contextual information) derived from perioperative data received from a first modular device, in accordance with at least one aspect of the present disclosure. In the illustrated example, the control circuit of the surgical hub 5104 receives 5004 *b* perioperative data from a first modular device. The perioperative data may include, for example, data regarding the modular device 5102 itself (e.g., pressure differential, motor current, internal forces, or motor torque) or data regarding the patient with which the modular device 5102 is being utilized (e.g., tissue properties, respiration rate, airway volume, or laparoscopic image data). The perioperative data may be displayed on a primary display and/or a secondary display. After receiving 5004 *b* the perioperative data, the control circuit of the surgical hub 5104 derives 5006 *b* contextual information (e.g. contextual data) from the perioperative data. The contextual information may include, for example, the procedure type, the task of the procedure being performed, or the status of the patient. The contextual information (e.g. contextual information) may be displayed on a primary display and/or a secondary display. The control circuit of the surgical hub 5104 then determines 5008 *b* control adjustments for a second modular device based upon the derived 5006 *b* contextual information and then controls 5010 *b* the second modular device accordingly. The control adjustments may be displayed on a primary display and/or a secondary display. For example, the surgical hub 5104 may receive 5004 *b* perioperative data from a ventilator indicating that the patient's lung has been deflated, derive 5006 *b* the contextual information therefrom that the subsequent task in the particular procedure type utilizes a medical imaging device (e.g., a scope), determine 5008 *b* that the medical imaging device should be activated and set to a particular magnification, and then control 5010 *b* the medical imaging device accordingly.

FIG. 54C illustrates a logic flow diagram of a process 5000 *c* for controlling a second modular device according to contextual information (e.g. contextual data) derived from perioperative data received from a first modular device and the second modular device. In the illustrated example, the control circuit of the surgical hub 5104 receives 5002 *c* perioperative data from a first modular device and receives 5004 *c* perioperative data from a second modular device. The perioperative data from the first modular device and/or the second modular device may be displayed on a primary display and/or a secondary display. After receiving 5002 *c*, 5004 *c* the perioperative data, the control circuit of the surgical hub 5104 derives 5006 *c* contextual information from the perioperative data. The contextual information may be displayed on a primary display and/or a secondary display. The control circuit of the surgical hub 5104 then determines 5008 *c* control adjustments for the second modular device based upon the derived 5006 *c* contextual information and then controls 5010 *c* the second modular device accordingly. The control adjustments may be displayed on a primary display and/or a secondary display. For example, the surgical hub 5104 may receive 5002 *c* perioperative data from a RF electrosurgical instrument indicating that the instrument has been fired, receive 5004 *c* perioperative data from a surgical stapling instrument indicating that the instrument has been fired, derive 5006 *c* the contextual information therefrom that the subsequent task in the particular procedure type requires that the surgical stapling instrument be fired with a particular force (because the optimal force to fire may vary according to the tissue type being operated on), determine 5008 *c* the particular force thresholds that should be applied to the surgical stapling instrument, and then control 5010 *c* the surgical stapling instrument accordingly.

FIG. 54D illustrates a logic flow diagram of a process 5000 *d* for controlling a third modular device according to contextual information derived from perioperative data received from a first modular device and a second modular device. In the illustrated exemplification, the control circuit of the surgical hub 5104 receives 5002 *d* perioperative data from a first modular device and receives 5004 *d* perioperative data from a second modular device. The perioperative data may be displayed on a primary display and/or a secondary display. After receiving 5002 *d*, 5004 *d* the perioperative data, the control circuit of the surgical hub 5104 derives 5006 *d* contextual information from the perioperative data. The contextual information may be displayed on the primary display and/or the secondary display. The control circuit of the surgical hub 5104 then determines 5008 *d* control adjustments for a third modular device based upon the derived 5006 *d* contextual information and then controls 5010 *d* the third modular device accordingly. For example, the surgical hub 5104 may receive 5002 *d*, 5004 *d* perioperative data from an insufflator and a medical imaging device indicating that both devices have been activated and paired to the surgical hub 5104, derive 5006 *d* the contextual information therefrom that a video-assisted thoracoscopic surgery (VATS) procedure is being performed, determine 5008 *d* that the displays connected to the surgical hub 5104 should be set to display particular views or information associated with the procedure type, and then control 5010 *d* the displays accordingly. For example, the surgical hub 5104 may display a first image (e.g. a wide view image) from the medical imaging device on a primary display and may display a second image (e.g. a narrow view image) from the medical imaging device on a secondary display.

In an example, a surgical hub 5706 (e.g. each surgical hub) may be configured to determine when one or more operating theater events occur (e.g., via a situational awareness system) and may track the length of time spent on the one or more events (e.g. each event). An operating theater event may be an event that a surgical hub 5706 may detect or infer the occurrence of. An operating theater event may include, for example, a particular surgical procedure, a task or portion of a surgical procedure, or downtime between surgical procedures, an error with a device, and the like. The operating theater events may be categorized according to an event type, such as a type of surgical procedure being performed, so that the data from individual procedures may be aggregated together to form searchable data sets.

In an exemplification, the surgical hub 5706 is configured to determine whether a surgical procedure is being performed and then track both the length of time spent between procedures (i.e., downtime) and the time spent on the procedures themselves. The surgical hub 5706 may further be configured to determine and track the time spent on each of the individual tasks taken by the medical personnel (e.g., surgeons, nurses, orderlies) either between or during the surgical procedures. The surgical hub may determine when surgical procedures or different tasks of surgical procedures are being performed via a situational awareness system, which is described in further detail above.

Figure 55:
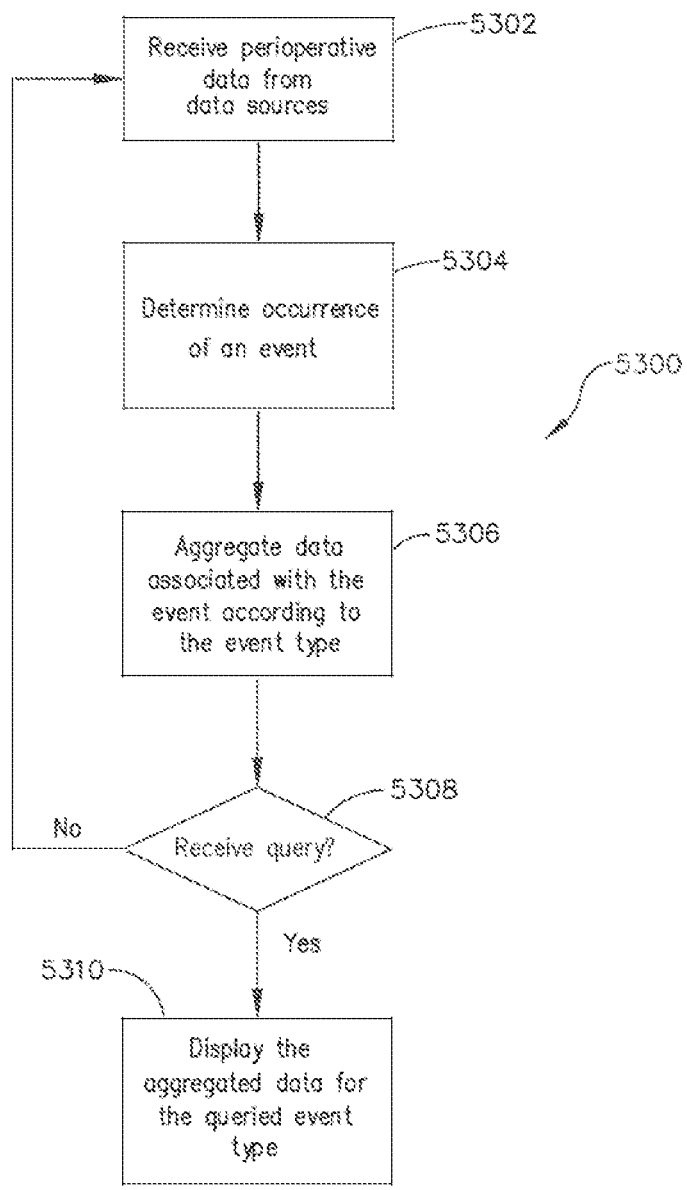
FIG. 55 illustrates a logic flow diagram of tracking data associated with an operating theater event, in accordance with at least one aspect of the present disclosure.

FIG. 55 illustrates a logic flow diagram of a process 5300 for tracking data associated with an operating theater event. The control circuit of the surgical hub 5706 executing the process 5300 receives 5302 perioperative data from the modular devices and other data sources (e.g., databases and patient monitoring devices) that are communicably coupled to the surgical hub 5706. The control circuit then determines 5304 whether an event has occurred via, for example, a situational awareness system that derives contextual information from the received 5302 data. The event may be associated with an operating theater in which the surgical hub 5706 in being used. The event may include, for example, a surgical procedure, a task or portion of a surgical procedure, or downtime between surgical procedures or tasks of a surgical procedure. Furthermore, the control circuit tracks data associated with the particular event, such as the length of time of the event, the surgical instruments and/or other medical products utilized during the course of the event, and the medical personnel associated with the event. The surgical hub 5706 may further determine this information regarding the event via, for example, the situational awareness system. The surgical hub 5706 may display the event or information regarding the event on a primary display and/or a secondary display.

For example, the control circuit of a situationally aware surgical hub 5706 could determine that anesthesia is being induced in a patient through data received from one or more modular devices 5102 (FIG. 9) and/or patient monitoring devices 5124 (FIG. 9). The control circuit may then determine that the operative portion of the surgical procedure has begun upon detecting that an ultrasonic surgical instrument or RF electrosurgical instrument has been activated. The control circuit could thus determine the length of time for the anesthesia inducement task according to the difference in time between the beginning of that particular task and the beginning of the first task in the operative portion of the surgical procedure. Likewise, the control circuit could determine how long the particular operative task in the surgical procedure took according to when the control circuit detects the subsequent task in the procedure begins. Further, the control circuit could determine how long the overall operative portion of the surgical procedure took according to when the control circuit detects that the final operative task in the procedure ends. The control circuit may also determine what surgical instruments (and other modular devices 5102) are being utilized during the course of each task in the surgical procedure by tracking the activation and/or use of the instruments during each of the tasks. The control circuit may also detect the completion of the surgical procedure by, for example, detecting when the patient monitoring devices 5124 have been removed from the patient (as in task fourteen 5228 of FIG. 86). The control circuit may then track the downtime between procedures according to when the control circuit infers that the subsequent surgical procedure has begun. The surgical hub 5706 may use a primary display and/or a secondary display to display information regarding a task performed, a surgical instrument that was used, a length of time, a subsequent task, a previous task, and the like.

The control circuit executing the process 5300 then aggregates 5306 the data associated with the event according to the event type. The aggregated data or a subset of the aggregated data may be displayed on a primary display and/or a secondary display. In an example, the aggregated 5306 data may be stored in a memory 249 (FIG. 6) of the surgical hub 5706. In another exemplification, the control circuit is configured to upload the data associated with the event to the cloud 5702, whereupon the data is aggregated 5306 according to the event type for all of the data uploaded by each of the surgical hubs 5706 connected to the cloud 5702. In another example, the control circuit is configured to upload the data associated with the event to a database associated with a local network of the surgical hubs 5706, whereupon the data is aggregated 5306 according to the event type for all of the data uploaded across the local network of surgical hubs 5706.

In an example, the control circuit is further configured to compare the data associated with the event type to baseline data associated with the event type. The baseline data may correspond to, for example, average values associated with the particular event type for a particular hospital, network of hospitals, or across the entirety of the cloud 5702. The baseline data may be stored on the surgical hub 5706 or retrieved by the surgical 5706 as the perioperative data is received 5302 thereby.

Aggregating 5306 the data from one or more (e.g. each) of the events according to the event type may allow individual incidents of the event type to thereafter be compared against the historical or aggregated data to determine when deviations from the norm for an event type occur. The control circuit further determines 5308 whether it has received a query. If the control circuit does not receive a query, then the process 5300 continues along the NO branch and loops back to continue receiving 5302 data from the data sources. If the control circuit does receive a query for a particular event type, the process 5300 continues along the YES branch and the control circuit then retrieves the aggregated data for the particular event type and displays 5310 the appropriate aggregated data corresponding to the query. In various exemplifications, the control circuit may retrieve the appropriate aggregated data from the memory of the surgical hub 5706, the cloud 5702, or a local database 5708 a, 5708 b.

In one example, the surgical hub 5706 is configured to determine a length of time for a procedure via the aforementioned situational awareness system according to data received from one or more modular devices utilized in the performance of the surgical procedure (and other data sources). When a time a surgical procedure is completed, the surgical hub 5706 uploads or stores the length of time required to complete the particular type of surgical procedure, which may then be aggregated with the data from every other instance of the type of procedure. In some aspects, the surgical hub 5706, cloud 5702, and/or local database 5708a, 5708 b may then determine an average or expected procedure length for the particular type of procedure from the aggregated data. When the surgical hub 5706 receives a query as to the particular type of procedure thereafter, the surgical hub 5706 may then provide feedback as to the average (or expected) procedure length or compare an individual incidence of the procedure type to the average procedure length to determine whether the particular incidence deviates therefrom.

In some aspects, the surgical hub 5706 may be configured to automatically compare each incidence of an event type to average or expected norms for the event type and then provide feedback (e.g., display a report) when a particular incidence of the event type deviates from the norm. For example, the surgical hub 5706 may be configured to provide feedback whenever a surgical procedure (or a task of the surgical procedure) deviates from the expected length of time to complete the surgical procedure (or the task of the surgical procedure) by more than a set amount.

Figure 56:
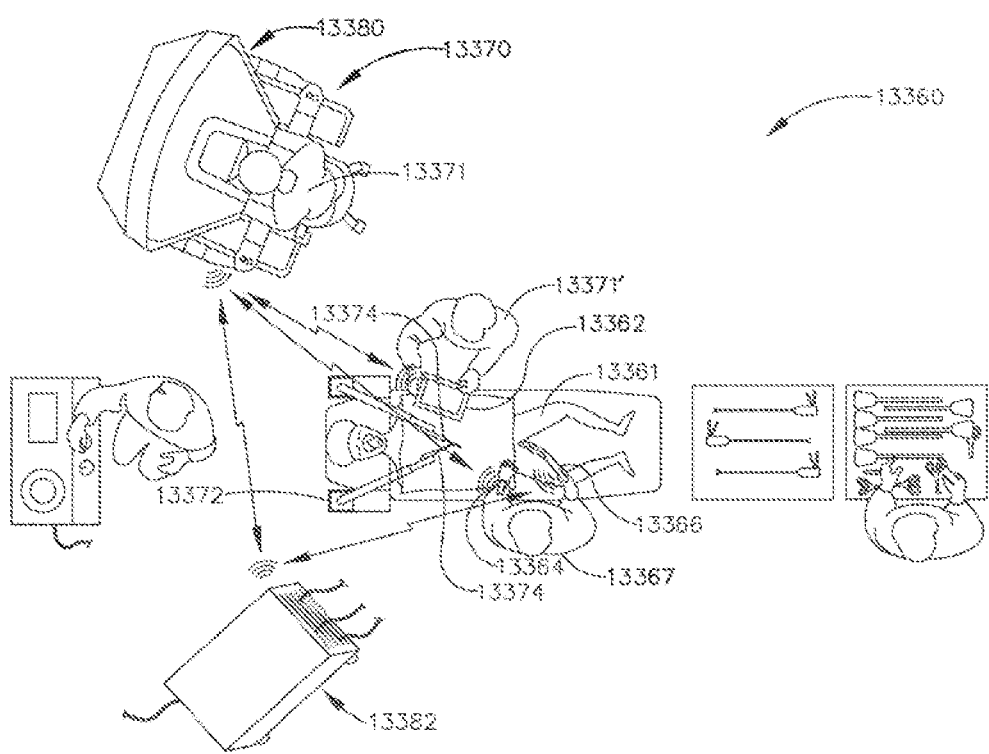
FIG. 56 is a schematic of a robotic surgical system during a surgical procedure including a plurality of hubs and interactive secondary displays, in accordance with at least one aspect of the present disclosure.
Figure 57:
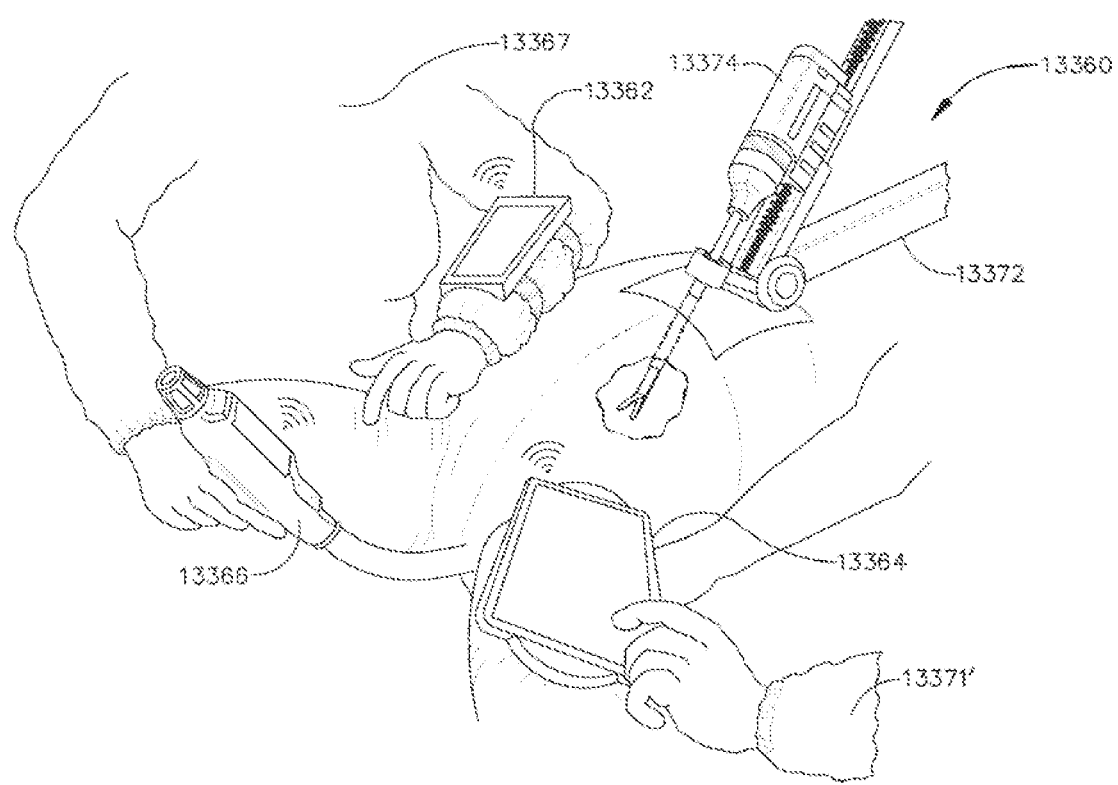
FIG. 57 is a detail view of the interactive secondary displays of FIG. 57, in accordance with at least one aspect of the present disclosure.

FIG. 56 is a schematic of a robotic surgical system during a surgical procedure including a plurality of hubs and interactive secondary displays, in accordance with at least one aspect of the present disclosure. FIG. 57 is a detail view of the interactive secondary displays of FIG. 57, in accordance with at least one aspect of the present disclosure.

Referring primarily to FIG. 57, hubs 13380, 13382 include wireless communication modules such that a wireless communication link is established between the two hubs 13380, 13382. Additionally, the robotic hub 13380 is in signal communication with the interactive secondary displays 13362, 13364 within the sterile field. The hub 13382 is in signal communication with the handheld surgical instrument 13366. If the surgeon 13371 moves over towards the patient 13361 and within the sterile field (as indicated by the reference character 13371'), the surgeon 13371 can use one of the wireless interactive displays 13362, 13364 to operate the robot 13372 away from the remote command console 13370. The plurality of secondary displays 13362, 13364 within the sterile field allows the surgeon 13371 to move away from the remote command console 13370 without losing sight of important information for the surgical procedure and controls for the robotic tools utilized therein.

The interactive secondary displays 13362, 13364 permit the clinician to step away from the remote command console 13370 and into the sterile field while maintaining control of the robot 13372. For example, the interactive secondary displays 13362, 13364 allow the clinician to maintain cooperative and/or coordinated control over the powered handheld surgical instrument(s) 13366 and the robotic surgical system at the same time. In various instances, information is communicated between the robotic surgical system, one or more powered handheld surgical instruments 13366, surgical hubs 13380, 13382, and the interactive secondary displays 13362, 13364. Such information may include, for example, the images on the display of the robotic surgical system and/or the powered handheld surgical instruments, a parameter of the robotic surgical system and/or the powered handheld surgical instruments, and/or a control command for the robotic surgical system and/or the powered handheld surgical instruments.

In various instances, the control unit of the robotic surgical system (e.g. the control unit 13113 of the robotic surgical system 13110) is configured to communicate at least one display element from the surgeon's command console (e.g. the console 13116) to an interactive secondary display (e.g. the display 13130). In other words, a portion of the display at the surgeon's console is replicated on the display of the interactive secondary display, integrating the robot display with the interactive secondary display. The replication of the robot display on to the display of the interactive secondary display allows the clinician to step away from the remote command console without losing the visual image that is displayed there. For example, at least one of the interactive secondary displays 13362, 13364 can display information from the robot, such as information from the robot display and/or the surgeon's command console 13370.

In various instances, the interactive secondary displays 13362, 13364 are configured to control and/or adjust at least one operating parameter of the robotic surgical system. Such control can occur automatically and/or in response to a clinician input. Interacting with a touch-sensitive screen and/or buttons on the interactive secondary display(s) 13362, 13364, the clinician is able to input a command to control movement and/or functionality of the one or more robotic tools. For example, when utilizing a handheld surgical instrument 13366, the clinician may want to move the robotic tool 13374 to a different position. To control the robotic tool 13374, the clinician applies an input to the interactive secondary display(s) 13362, 13364, and the respective interactive secondary display(s) 13362, 13364 communicates the clinician input to the control unit of the robotic surgical system in the robotic hub 13380.

In various instances, a clinician positioned at the remote command console 13370 of the robotic surgical system can manually override any robot command initiated by a clinician input on the one or more interactive secondary displays 13362, 13364. For example, when a clinician input is received from the one or more interactive secondary displays 13362, 13364, a clinician positioned at the remote command console 13370 can either allow the command to be issued and the desired function performed or the clinician can override the command by interacting with the remote command console 13370 and prohibiting the command from being issued.

In certain instances, a clinician within the sterile field can be required to request permission to control the robot 13372 and/or the robotic tool 13374 mounted thereto. The surgeon 13371 at the remote command console 13370 can grant or deny the clinician's request. For example, the surgeon can receive a pop-up or other notification indicating the permission is being requested by another clinician operating a handheld surgical instrument and/or interacting with an interactive secondary display 13362, 13364.

In various instances, the processor of a robotic surgical system and/or the surgical hub 13380, 13382, for example, may be programmed with pre-approved functions of the robotic surgical system. For example, if a clinician input from the interactive secondary display 13362, 13364 corresponds to a pre-approved function, the robotic surgical system allows for the interactive secondary display 13362, 13364 to control the robotic surgical system and/or does not prohibit the interactive secondary display 13362, 13364 from controlling the robotic surgical system. If a clinician input from the interactive secondary display 13362, 13364 does not correspond to a pre-approved function, the interactive secondary display 13362, 13364 is unable to command the robotic surgical system to perform the desired function. In one instance, a situational awareness module in the robotic hub 13370 and/or the surgical hub 13382 is configured to dictate and/or influence when the interactive secondary display can issue control motions to the robot surgical system.

In various instances, an interactive secondary display 13362, 13364 has control over a portion of the robotic surgical system upon making contact with the portion of the robotic surgical system. For example, when the interactive secondary display 13362, 13364 is brought into contact with the robotic tool 13374, control of the contacted robotic tool 13374 is granted to the interactive secondary display 13362, 13364. A clinician can then utilize a touch-sensitive screen and/or buttons on the interactive secondary display 13362, 13364 to input a command to control movement and/or functionality of the contacted robotic tool 13374. This control scheme allows for a clinician to reposition a robotic arm, reload a robotic tool, and/or otherwise reconfigure the robotic surgical system. In a similar manner as discussed above, the clinician 13371 positioned at the remote command console 13370 of the robotic surgical system can manually override any robot command initiated by the interactive secondary display 13362, 13364.

In various aspects, the present disclosure provides a control circuit to receive a first user input from a console and to receive a second user input from a mobile wireless control module for controlling a function of a robotic surgical tool, as described herein. For example, a first user may provide input using a secondary display and a second user may provide input using another secondary display. In various aspects, the present disclosure provides a non-transitory computer readable medium storing computer readable instructions which, when executed, cause a machine to receive a first user input from a console and to receive a second user input from a mobile wireless control module for controlling a function of a robotic surgical tool, as described herein.

Figure 58:
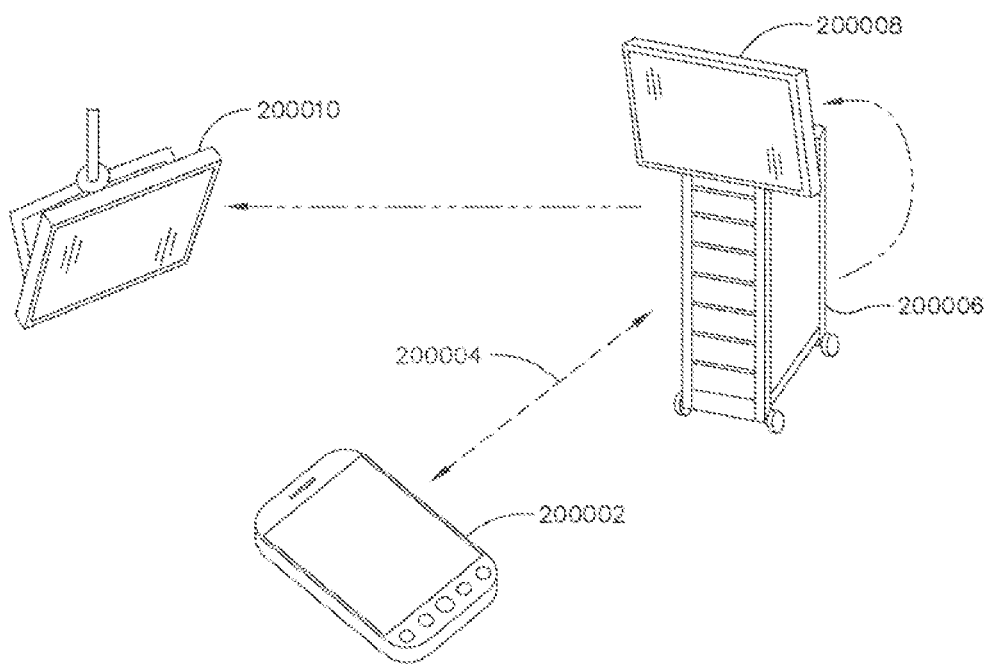
FIG. 58 is a diagram of a pairing of a personally owned wireless device with a surgical hub, in accordance with at least one aspect of the present disclosure.

FIG. 58 depicts an example of a pairing of a personally owned wireless device 200002, which may be secondary displays, with a surgical hub 200006. The wireless device 200002 and the surgical hub 200006 may communicate with each other over a wireless link 200004. As disclosed herein, the surgical hub 200006 may display imported data received from the wireless device 200002 on one or more displays visible to the members of the surgical team. In one aspect, the surgical hub 200006 may cause the imported data to be displayed on a primary or in-use display monitor 200008. In another aspect, the surgical hub 200006 may cause the imported data to be displayed on a secondary display monitor 200010.

In some aspects, the computer systems described herein may be programmed to evaluate the surgical staff during the course of a surgical procedure (e.g., how they are using surgical instruments) and propose suggestions to improve the surgical staff members' techniques or actions. In one aspect, the computer systems described herein, such as the surgical hubs 106, 206 (FIGS. 1-11), can be programmed to analyze the techniques, physical characteristics, and/or performances of a surgeon and/or the other surgical staff members relative to a baseline. Further, the computer system can be programmed to provide notifications or prompts that indicate when the surgical staff is deviating from the baseline so that the surgical staff can alter their actions and optimize their performance or technique. In some aspects, the notifications can include warnings that the surgical staff is not utilizing proper technique (which can further include recommendations on corrective actions that the surgical staff can take to address their technique), suggestions for alternative surgical products, statistics regarding correlations between procedural variables (e.g., time taken to complete the procedure) and the monitored physical characteristics of the surgical staff, comparisons between surgeons, and so on. In various aspects, the notifications or recommendations can be provided either in real time (e.g., in the OR during the surgical procedure) or in a post-procedure report. Accordingly, the computer system can be programmed to automatically analyze and compare staff members' techniques and instrument usage skills.

Figure 59:
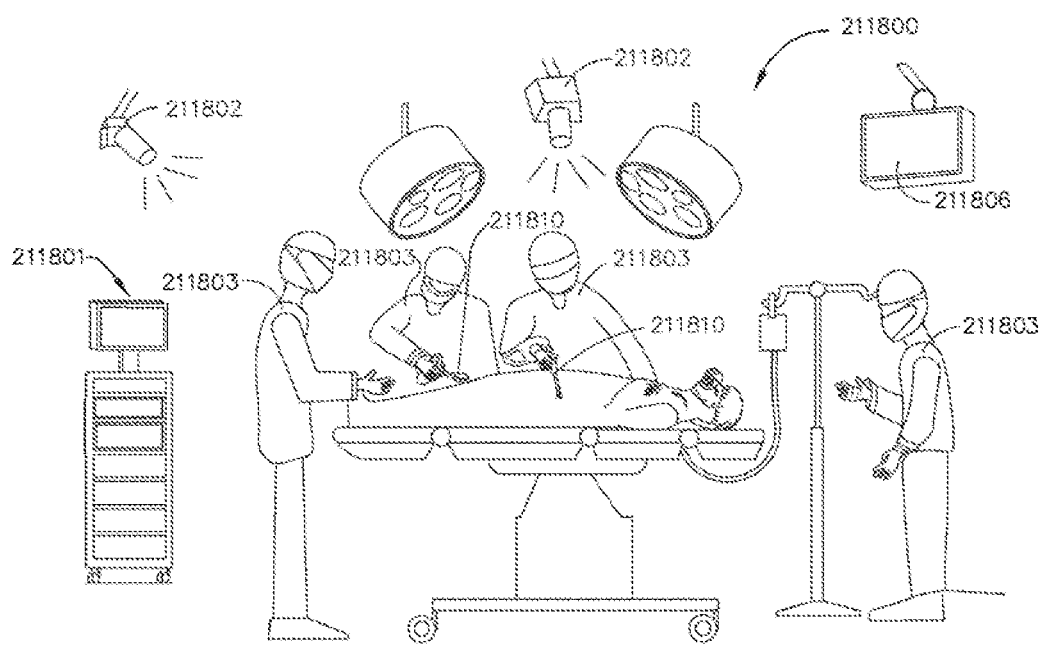
FIG. 59 is a diagram of an illustrative operating room (OR) setup, in accordance with at least one aspect of the present disclosure.

FIG. 59 is a diagram of an illustrative OR setup, in accordance with at least one aspect of the present disclosure. In various implementations, the surgical hub 211801 can be connected to various one or more cameras 211802, surgical instruments 211810, displays 211806, and other surgical devices within the OR 211800 via a communications protocol (e.g., Bluetooth), as described above under the heading SURGICAL HUBS. The cameras 211802 can be oriented in order to capture images and/or video of the surgical staff members 211803 during the course of a surgical procedure. Accordingly, the surgical hub 211801 can receive the captured image and/or video data from the cameras 211802 to visually analyze the techniques or physical characteristics of the surgical staff members 211803 during the surgical procedure.

Figure 60:
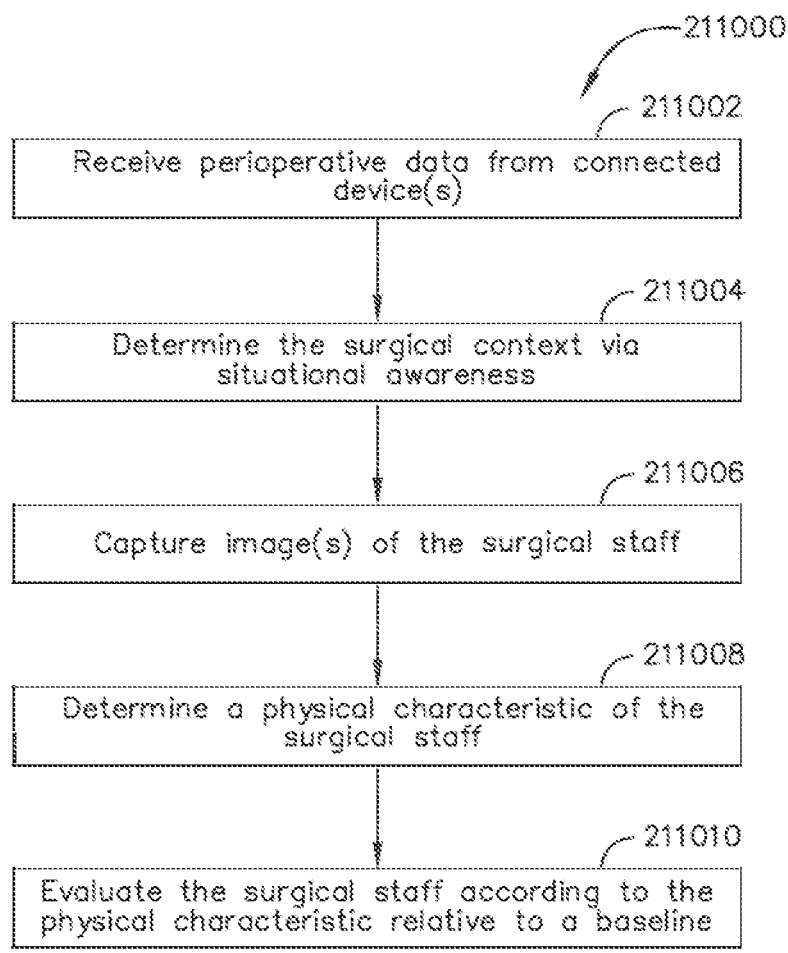
FIG. 60 is a logic flow diagram of a process for visually evaluating surgical staff members, in accordance with at least one aspect of the present disclosure.

FIG. 60 is a logic flow diagram of a process 211000 for visually evaluating surgical staff members, in accordance with at least one aspect of the present disclosure. In the following description of the process 211000, reference should also be made to FIGS. 6 and 59. The process 211000 can be executed by a processor or control circuit of a computer system, such as the processor 244 of the surgical hub 206 illustrated in FIG. 6. Accordingly, the process 211000 can be embodied as a set of computer-executable instructions stored in a memory 249 that, when executed by the processor 244, cause the computer system (e.g., a surgical hub 211801) to perform the described steps.

As described above under the heading SURGICAL HUBS, computer systems, such as surgical hubs 211801, can be connected to or paired with a variety of surgical devices, such as surgical instruments, generators, smoke evacuators, displays, and so on. Through their connections to these surgical devices, the surgical hubs 211801 can receive an array of perioperative data from these paired surgical devices while the devices are in use during a surgical procedure. Further, as described above under the heading SITUATIONAL AWARENESS, surgical hubs 211801 can determine the context of the surgical procedure being performed (e.g., the procedure type or the step of the procedure being performed) based, at least in part, on perioperative data received from these connected surgical devices.

Accordingly, the processor 244 executing the process 211000 receives 211002 perioperative data from the surgical device(s) connected or paired with the surgical hub 211801 and determines 211004 the surgical context based at least in part on the received perioperative data utilizing situational awareness. The surgical context determined by the surgical hub 211801 through situational awareness can be utilized to inform evaluations of the surgical staff performing the surgical procedure.

Accordingly, the processor 244 captures 211006 image(s) of the surgical staff performing the surgical procedure via, for example, cameras 211802 positioned within the OR 211800. The captured image(s) can include static images or moving images (i.e., video). The images of the surgical staff can be captured at a variety of angles and magnifications, utilize different filters, and so on. In one implementation, the cameras 211802 are arranged within the OR 211800 so that they can collectively visualize each surgical staff member performing the procedure.

Accordingly, the processor 244 determines 211008 a physical characteristic of one or more surgical staff members from the captured image(s). For example, the physical characteristic can include posture, as discussed in connection with FIGS. 61-62, or wrist angle, as discussed in connection with FIGS. 63-64. In other implementations, the physical characteristic can include the position, orientation, angle, or rotation of an individual's head, shoulders, torso, elbows, legs, hips, and so on. The physical characteristic can be determined 211008 utilizing a variety of machine vision, image processing, object recognition, and optical tracking techniques. In one aspect, the physical characteristic can be determined 211008 by processing the captured images to detect the edges of the objects in the images and comparing the detected images to a template of the body part being evaluated. Once the body part being evaluated has been recognized, its position, orientation, and other characteristics can be tracked by comparing the movement of the tracked body part relative to the known positions of the cameras 211802. In another aspect, the physical characteristic can be determined 211008 utilizing marker-based optical systems (e.g., active markers embedded in the surgical staff members' uniforms emitting electromagnetic radiation or other signals that can be received by the cameras 211802 or other sensors connected to the surgical hubs 211801). By tracking the movement of the markers relative to the cameras 211802, the processor 244 can thus determine the corresponding position and orientation of the body part.

Accordingly, the processor 244 evaluates 211010 the determined physical characteristic of the surgical staff member to a baseline. In one aspect, the baseline can correspond to the surgical context determined via situational awareness. The processor 244 can retrieve the baselines for various physical characteristics from a memory (e.g., the memory 249 illustrated in FIG. 6) according to the given surgical context, for example. The baseline can include values or ranges of values for particular physical characteristics to be tracked during particular surgical contexts. The types of physical characteristics evaluated in different surgical contexts can be the same or unique to each particular surgical context.

In one aspect, the processor 244 can provide feedback to the surgical staff members in real time during the surgical procedure. The real-time feedback can include a graphical notification or recommendation displayed on a display 211806 within the OR 211800, audio feedback emitted by the surgical hub 211801 or a surgical instrument 211810, and so on. Further, the feedback can include suggestions that trocar port placements be shifted, that a surgical instrument be moved from one trocar port to another port, that the positioning of the patient being operated on be adjusted (e.g., situated at an increased table angle or rolled), and other such suggestions to improve access to the surgical site and minimize non-ideal surgical technique exhibited by the surgical staff. In another aspect, the processor 244 can provide postoperative feedback to the surgical staff members. The postoperative feedback can include graphical overlays or notifications displayed on the captured video of the procedure that can be reviewed by the surgical staff for learning purposes, a post-surgery report indicating times or particular surgical steps where the surgical staff deviated from the baselines, and so on. Any visually identifiable physical characteristic (or combination of physical characteristics) can be utilized as the basis for suggesting improvements in the technique exhibited by the surgical staff.

In one aspect, one or more of the steps of the process 211000 can be executed by a second or remote computer system, such as the cloud computing systems described under the heading CLOUD SYSTEM HARDWARE AND FUNCTIONAL MODULES. For example, the surgical hub 211801 can receive 211002 perioperative data from the connected surgical devices, determine 211004 the surgical context based at least in part on the perioperative data, capture 211006 or receive images of a surgical staff member 211803 via the cameras 211802, and determine 211008 a physical characteristic of the surgical staff member 211803, as described above. However, in this aspect, instead of performing the evaluation onboard the surgical hub 211801, the surgical hub 211801 can instead transmit data regarding the physical characteristic and the determined surgical context to a second computer system, such as a cloud computing system. The cloud computing system can then perform the evaluation by determining whether the determined physical characteristic deviates from the baseline physical characteristic that corresponds to the surgical context. In some aspects, the baseline physical characteristic can be determined or calculated from data aggregated from all of the surgical hubs 211801 that are communicably connected to the cloud computing system, which allows for the cloud computing system to compare surgical staff members' 211803 techniques across a number of medical facilities. Accordingly, the cloud computing system can transmit the results of the comparison between the physical characteristic determined by the surgical hub 211801 and the corresponding baseline stored on or determined by the cloud computing system. Upon receiving the results, the surgical hub 211801 can then take appropriate action (e.g., displaying a notification if the surgical staff members' 211803 technique is deviating from the baseline, as described above). In other aspects, one or more additional or different steps of the process 211000 can be performed by other computing systems that are communicably coupled to the first computing system. Such connected computer systems can, in some aspects, be embodied as distributed computing systems.

Figure 61:
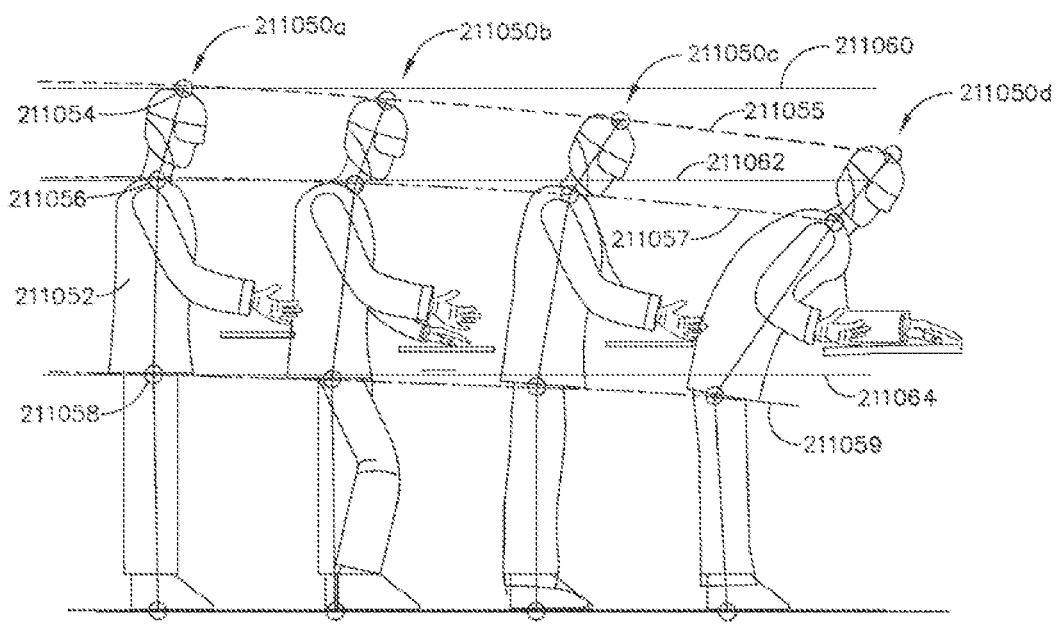
FIG. 61 is a diagram illustrating a series of models of a surgical staff member during the course of a surgical procedure, in accordance with at least one aspect of the present disclosure.
Figure 62:
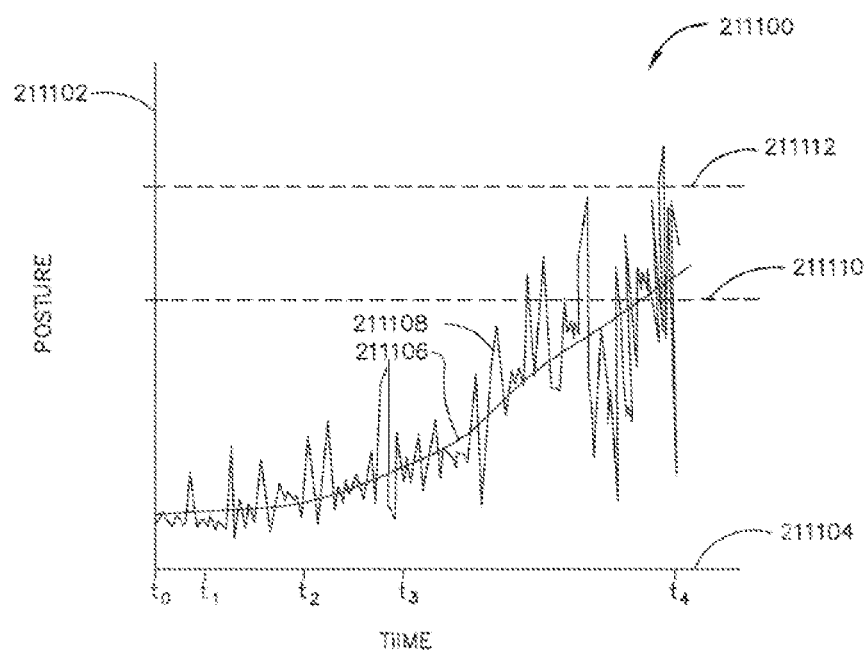
FIG. 62 is a graph depicting the measured posture of the surgical staff member illustrated in FIG. 61 over time, in accordance with at least one aspect of the present disclosure.

FIGS. 61-62 illustrate a prophetic implementation of the process 211000 illustrated in FIG. 60 where the physical characteristic being evaluated is the posture of a surgical staff member. FIG. 61 is a diagram illustrating a series of models 211050 $a$, 211050 $b$, 211050 $c$, 211050 $d$ of a surgical staff member 211052 during the course of a surgical procedure, in accordance with at least one aspect of the present disclosure. Correspondingly, FIG. 62 is a graph 211100 depicting the measured posture of the surgical staff member illustrated in FIG. 61 over time, in accordance with at least one aspect of the present disclosure. FIGS. 59-60 should also be referenced in the following description of FIGS. 61-62. Accordingly, the surgical hub 211801 executing the process 211000 can analyze the posture of a surgical staff member and provide recommendations if the staff member's posture deviates from the baseline. Poor, unexpected, or otherwise improper posture can indicate, for example, that the surgeon is fatigued, is having difficulty with a particular surgical step, is utilizing the surgical instrument incorrectly, has positioned the surgical instrument incorrectly, or is otherwise acting in a potentially risky manner that could create danger. Therefore, monitoring the surgical staff members' postures during the course of a surgical procedure and providing notifications when a staff member is deviating from a baseline posture can be beneficial to alert unaware users as to their risky conduct so that they can take corrective actions or allow other individuals to take corrective actions (e.g., swap a fatigued staff member for a fresher individual).

Referring to FIG. 62, the vertical axis 211102 of the graph 211100 represents the posture of an individual and the horizontal axis 211104 represents time. The first model 211050 $a$ in FIG. 61 corresponds to time t1 in FIG. 62 during the surgical procedure, the second model 211050 $b$ corresponds to time t2, the third model 211050 $c$ corresponds to time t3, and the fourth model 211050 $d$ corresponds to time t4. In tandem, FIGS. 61 and 62 illustrate that the posture of the individual being evaluated increasingly deviates from the baseline position(s) during the course of the surgical procedure.

In one aspect, the posture of the individual being evaluated by the computer system can be quantified as a metric corresponding to the deviation in position of one or more locations of the individual's body from corresponding initial or threshold positions. For example, FIG. 61 illustrates the change in a head position 211054, a shoulder position 211056, and a hip position 211058 of the modeled individual over time by a first line 211055, a second line 211057, and a third line 211059, respectively. In an aspect utilizing a marker-based optical system, the surgeon's uniform can have a marker located at one or more of these locations that can be tracked by the optical system, for example. In an aspect utilizing a markerless optical system, the optical system can be configured to identify the surgical staff member and optically track the location and movement of one or more body parts or body locations of the identified surgical staff member. Further, the head, shoulder, and hip positions 211054, 211056, 211058 can be compared to a baseline head position 211060, a baseline shoulder position 211062, and a baseline hip position 211064, respectively. The baseline positions 211060, 211062, 211064 can correspond to the initial positions of the respective body parts (i.e., the positions at time t0 in FIG. 62) or can be predetermined thresholds against which the positions of the body parts are compared. In one aspect, the posture metric (as represented by the vertical axis 211102 of the graph 211100) can be equal to the distance between one of the body positions 211054, 211056, 211058 and its corresponding baseline positions 211060, 211062, 211064. In another aspect, the posture metric can be equal to the cumulative distance between more than one of the body positions 211054, 211056, 211058 and their corresponding baseline positions 211060, 211062, 211064. The first line 211108 in the graph 211100 represents the raw posture metric values over time, and the second line 211106 represents the normalized posture metric values over time. In various aspects, the process 211000 can evaluate 211010 whether the physical characteristic (in this case, posture) has deviated from the baseline according to raw or mathematically manipulated (e.g., normalized) data.

In one aspect, the surgical hub 211801 executing the process 211000 can compare the calculated posture metric to one or more thresholds and then take various actions accordingly. In the depicted implementation, the surgical hub 211801 compares the posture metric to a first threshold 211110 and a second threshold 211112. If the normalized posture metric, represented by the second line 211106, exceeds the first threshold 211110, then the surgical hub 211801 can be configured to provide a first notification or warning to the surgical staff in the OR 211800 that indicates that there is a potential risk with the particular individual's form. Further, if the normalized posture metric, represented by the second line 211106, exceeds the second threshold 211112, then the surgical hub 211801 can be configured to provide a second notification or warning to the users in the OR 211800 that indicates that there is a high degree of risk with the particular individual's form. For example, at time t4, the posture metric for the evaluated surgical staff member, as represented by the fourth model 211050 *d*, exceeds the first threshold 211110; accordingly, the surgical hub 211801 can be configured to provide a first or initial warning to the surgical staff.

Figure 63:
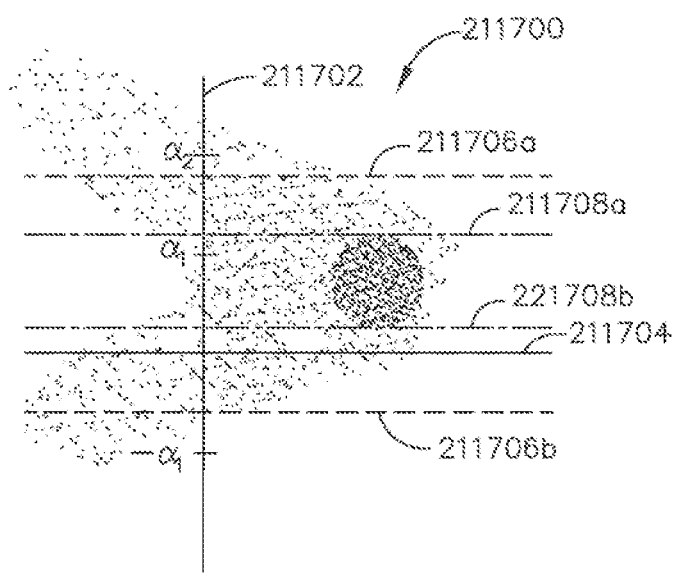
FIG. 63 is a depiction of a surgeon holding a surgical instrument, in accordance with at least one aspect of the present disclosure.
Figure 64:
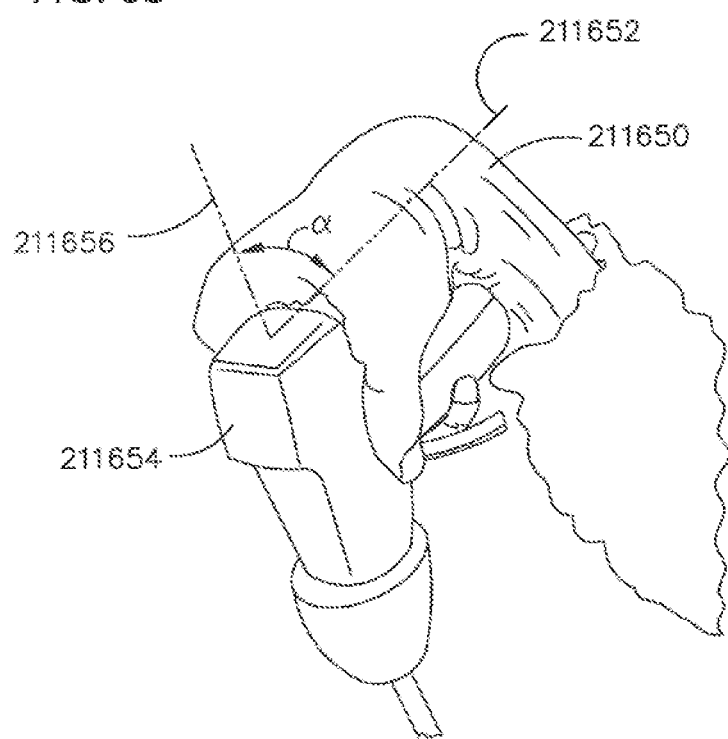
FIG. 64 is a scatterplot of wrist angle verses surgical procedure outcomes, in accordance with at least one aspect of the present disclosure.

FIGS. 63-64 illustrate a prophetic implementation of the process 211000 illustrated in FIG. 60 where the physical characteristic being evaluated is the wrist angle of a surgical staff member. FIG. 63 is a depiction of a surgeon holding a surgical instrument 211654, in accordance with at least one aspect of the present disclosure. Correspondingly, FIG. 64 is a scatterplot 211700 of wrist angle verses surgical procedure outcomes, in accordance with at least one aspect of the present disclosure. FIGS. 59-60 should also be referenced in the following description of FIGS. 63-64. Accordingly, the surgical hub 211801 executing the process 211000 can analyze the wrist angle of a surgical staff member's hand holding a surgical instrument 211654 and provide recommendations if the staff member's wrist angle deviates from the baseline. Awkwardly holding a surgical instrument, as evidenced by an extreme wrist angle relative to the surgical instrument, can indicate, for example, that the surgeon is utilizing the surgical instrument incorrectly, has positioned the surgical instrument incorrectly, is utilizing an incorrect surgical instrument for the particular procedural step, or is otherwise acting in a potentially risky manner that could create danger.

In this particular implementation, the angle of the individual's wrist 211650 is defined as the angle $\alpha$ between the longitudinal axis 211656 of the surgical instrument 211654 being held by the surgeon and the longitudinal axis 211652 (i.e., the proximal-to-distal axis) of the individual's hand In other implementations, wrist angle can be defined as the angle between the individual's hand and forearm, for example. In the scatterplot 211700 of FIG. 64, the vertical axis 211702 represents wrist angle $\alpha$ and the horizontal axis 211704 represents procedural outcomes. The portions of the horizontal axis 211704 to the right and left of the vertical axis 211702 can correspond to positive and negative procedural outcomes, respectively, for example. A variety of different procedural outcomes can be compared to the wrist angle $\alpha$ of the surgeon, such as whether a particular procedural step or firing of the surgical instrument 211654 resulted in excessive bleeding, the incidence of reoperation for the surgical procedure, and so on. Further, procedural outcomes can be quantified in a variety of different manners depending upon the particular type of procedural outcome that is being compared with the wrist angle $\alpha$ of the surgeon. For example, if the procedural outcome is bleeding occurring after a particular firing of the surgical instrument 211654, the horizontal axis 211704 can represent the degree or amount of blood along the incision line from the firing of the surgical instrument 211654. Further, the wrist angle $\alpha$ of each plotted point in the scatterplot 211700 can represent the wrist angle $\alpha$ at a particular instant in the surgical procedure, the average wrist angle $\alpha$ during a particular step of the surgical procedure, the overall average wrist angle during the surgical procedure, and so on. Further, whether the wrist angle $\alpha$ corresponds to an average wrist angle $\alpha$ or a wrist angle $\alpha$ at a particular instant in time can correspond to the type of procedural outcome against which the wrist angle $\alpha$ is being compared. For example, if the procedural outcome represented by the horizontal axis 211704 is the amount of bleeding from a firing of the surgical instrument 211654, the vertical axis 211702 can represent the wrist angle $\alpha$ at the instant that the surgical instrument 211654 was fired. As another example, if the procedural outcome represented by the horizontal axis 211704 is the incidence of reoperation for a particular procedure type, the vertical axis 211702 can represent the average wrist angle $\alpha$ during the surgical procedure.

In one aspect, the surgical hub 211801 executing the process 211000 can compare the calculated wrist angle $\alpha$ to one or more thresholds and then take various actions accordingly. In the depicted implementation, the surgical hub 211801 determines whether the surgeon's wrist angle $\alpha$ falls within a first zone, which is delineated by a first threshold 211708 *a* and a second threshold 211708 *b*, within a second zone, which is delineated by a third threshold 211706 *a* and a fourth threshold 211706 *b*, or outside the second zone. If the wrist angle $\alpha$ measured by the surgical hub 211801 during the course of a surgical procedure falls between the first and second thresholds 221708 *a*, 221708 *b* then the surgical hub 211801 can be configured to determine that the wrist angle $\alpha$ is within acceptable parameters and take no action. If the surgeon's wrist angle $\alpha$ falls between the first and second thresholds 221708 *a*, 221708 *b* and third and fourth thresholds 221706 *a*, 221706 *b*, then the surgical hub 211801 can be configured to provide a first notification or warning to the surgical staff in the OR 211800 that indicates that there is a potential risk with the particular individual's form. Further, if the surgeon's wrist angle α falls outside of the third and fourth thresholds 221706 *a*, 221706 *b*, then the surgical hub 211801 can be configured to provide a second notification or warning to the users in the OR 211800 that indicates that there is a high degree of risk with the particular individual's form.

In some aspects, the various thresholds or baselines against which the monitored physical characteristic is compared can be determined empirically. The surgical hubs 211801 and/or cloud computing system described above under the heading CLOUD SYSTEM HARDWARE AND FUNCTIONAL MODULES can capture data related to various physical characteristics of the surgical staff members from a sample population of surgical procedures for analysis. In one aspect, the computer system can correlate those physical characteristics with various surgical outcomes and then set the thresholds or baselines according to the particular physical characteristics of the surgeon or other surgical staff members that are correlated most highly with positive surgical outcomes. Accordingly, a surgical hub 211801 executing the process 211000 can provide notifications or warnings when the surgical staff members are deviating from best practices. In another aspect, the computer system can set the thresholds or baselines according to the physical characteristics that are exhibited most often within the sample population. Accordingly, a surgical hub 211801 executing the process 211000 can provide notifications or warnings when the surgical staff members are deviating from the most common practices. For example, in FIG. 64 the first and second thresholds 211708 *a*, 211708 *b* can be set so that they correspond to the most common wrist angle α exhibited by a surgeon when performing the particular surgical procedure (i.e., the densest portion of the scatterplot 211700). Accordingly, when a surgical hub 211801 executing the process 211000 determines that the surgeon's wrist angle α is deviating from the empirically determined baseline defined by the first and second thresholds 211708 *a*, 211708 *b*, the surgical hub 211801 can provide a notification to the surgical staff or take other actions, as discussed above.

In one aspect, the physical characteristic being tracked by the surgical hub 211801 can be differentiated according to product type. Accordingly, the surgical hub 211801 can be configured to notify the surgical staff members when the particular physical characteristic being tracked corresponds to a different product type. For example, the surgical hub 211801 can be configured to notify the surgeon when the surgeon's arm and/or wrist posture deviates from the baseline for the particular surgical instrument currently being utilized and thus indicates that a different surgical instrument would be more appropriate.

In one aspect, the surgical hub 211801 can be configured to compare the external orientation of a surgical instrument 211810 to the internal access orientation of its end effector. The external orientation of the surgical instrument 211810 can be determined via the cameras 211802 and optical systems described above. The internal orientation of the end effector of the surgical instrument 211810 can be determined via an endoscope or another scope utilized to visualize the surgical site. By comparing the external and internal orientations of the surgical instrument 211810, the surgical hub 211801 can then determine whether a different type of surgical instrument 211810 would be more appropriate. For example, the surgical hub 211801 can be configured to provide a notification to the surgical staff if the external orientation of the surgical instrument 211810 deviates from the internal orientation of the end effector of the surgical instrument 211810 to more than a threshold degree.

In sum, computer systems, such as a surgical hub 211801, can be configured to provide recommendations to a surgical staff member (e.g., a surgeon) as the surgical staff member's technique starts to drift from best or common practices. In some aspects, the computer system can be configured to only provide notifications or feedback when the individual has repeatedly exhibited suboptimal behavior during the course of a given surgical procedure. The notifications provided by the computer systems can suggest, for example, that the surgical staff member adjust their technique to coincide with the optimal technique for the procedure type, utilize a more appropriate instrument, and so on.

In one aspect, the computer system (e.g., a surgical hub 211801) can be configured to allow surgical staff members to compare their technique to themselves, rather than to the baselines established by the sampled population or pre-programmed into the computer system. In other words, the baseline against which the computer system compares a surgical staff member can be the surgical staff member's prior performance in a particular surgical procedure type or a prior instance of utilizing a particular type of surgical instrument. Such aspects can be useful to allow surgeons to track improvements in their surgical techniques or document trial periods for new surgical products. Accordingly, the surgical hub 211801 can be configured to evaluate products during a trial period and provide highlights of the use of the products during the given period. In one aspect, the surgical hub 211801 can be programmed to be especially sensitive to deviations between the surgical staff members performance and the corresponding baselines so that the surgical hub 211801 can reinforce the proper techniques for using the surgical device when the trial period is ongoing. In one aspect, the surgical hub 211801 could be configured to record the use of the new surgical products and compare and contrast the new products with the previous baseline product use. The surgical hub 211801 could further provide a post-analysis review to highlight similarities and differences noted between the surgeon's tracked physical characteristics when utilizing the two different products. Further, the surgical hub 211801 can allow the surgeon to compare populations of procedures between the new and old surgical products. The recommendations provided by the surgical hub 211801 can include, for example, comparative videos demonstrating the use of the new products.

In one aspect, the computer system (e.g., a surgical hub 211801) can be configured to allow surgical staff members to compare their technique directly to other surgeons, rather than to the baselines established by the sampled population or pre-programmed into the computer system.

In one aspect, the computer system (e.g., a surgical hub 211801) can be configured to analyze trends in surgical device usage as surgeons become more experienced in performing particular surgical procedures (or performing surgical procedures generally) or using new surgical instruments. For example, the computer system could identify motions, behaviors, and other physical characteristics that change dramatically as the surgeons become more experienced. Accordingly, the computer system can recognize when a surgeon is exhibiting suboptimal techniques early in the surgeon's learning curve and can provide recommendations about the optimal approach, prior to the suboptimal technique becoming ingrained in the surgeon.

Figure 65A:
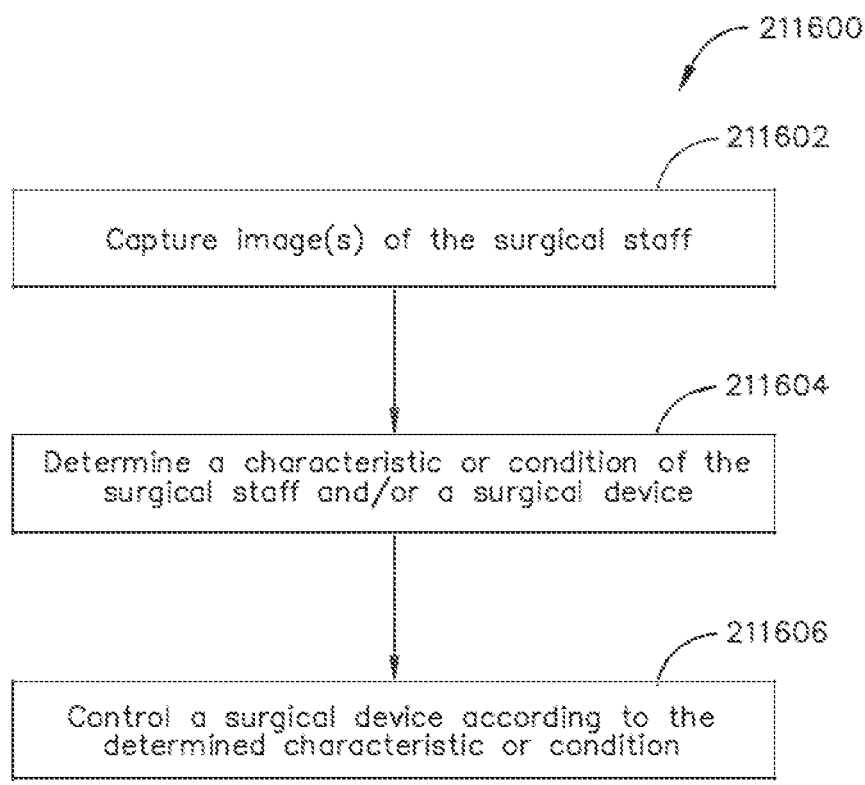
FIG. 65A is a logic flow diagram of a process for controlling a surgical device, in accordance with at least one aspect of the present disclosure.

FIG. 65A is a logic flow diagram of a process 211600 for controlling a surgical device, in accordance with at least one aspect of the present disclosure. The process 211600 can be executed by a processor or control circuit of a computer system, such as the processor 244 of the surgical hub 206 illustrated in FIG. 6. Accordingly, the process 211600 can be embodied as a set of computer-executable instructions stored in a memory 249 that, when executed by the processor 244, cause the computer system (e.g., a surgical hub 211801) to perform the described steps.

Accordingly, the processor 244 executing the process 211600 captures 211602 image(s) (which can include static images or video) of the OR 211800 via an assembly of cameras 211802 situated therein. Any captured images that include surgical staff members 211803 and/or surgical devices can be analyzed by the process 211600 to ascertain information about the surgical staff members 211803 and/or surgical devices for controlling the surgical devices. Targets to be tracked or monitored (i.e., the surgical staff members 211803 and surgical devices) can be recognized from images captured by the assembly of cameras 211802 utilizing a variety of image or object recognition techniques, including appearance and feature-based techniques. For example, the captured images can be processed utilizing an edge detection algorithm (e.g., a Canny edge detector algorithm) to generate outlines of the various objects within each image. An algorithm can then compare the templates of target objects to the images containing the outlined objects to determine whether any of the target objects are located within the images. As another example, an algorithm can extract features from the captured images. The extracted features can be then be fed to a machine learning model (e.g., an artificial neural network or a support vector machine) trained via supervised or unsupervised learning techniques to correlate a feature vector to the targets. The features can include edges (extracted via a Canny edge detector algorithm, for example), curvature, corners (extracted via a Harris & Stephens corner detector algorithm, for example), and so on.

Accordingly, the processor 244 determines 211604 a characteristic or condition of the surgical staff and/or surgical devices captured by the images. Such characteristics or conditions can include physical properties, actions, interactions between other objects or individuals, and so on. More particularly, characteristics or conditions of the surgical staff members 211803 can include whether a surgical staff member 211803 is performing a gesture 211804 (as shown in FIG. 59), whether a surgical staff member 211803 is holding a given surgical instrument 211810, where a surgical staff member 211803 is located, the number of surgical staff members 211803 within the OR, whether a surgical staff member 211803 is interacting with a surgical device (and which surgical device is being interacted with), whether a surgical staff member 211803 is passing a surgical instrument 211810 or another surgical device to another surgical staff member 211803, physical properties associated with a surgical staff member 211803 (e.g., posture, arm position, wrist angle), and so on. Characteristics or conditions of the surgical devices can include their poses, whether they are actively being used (e.g., whether a generator is actively supplying energy to a connected surgical instrument 211810), whether a surgical instrument 211810 is being inserted through a trocar (and the location or identity of that trocar), and so on.

Accordingly, the processor 244 controls 211606 a surgical device that is paired with the surgical hub 211801 in a manner that depends upon the particular determined characteristic or condition. For example, if the processor 244 determines 211604 that a surgical staff member 211803 is making a "change instrument mode" gesture, then the processor 244 can transmit a signal to or otherwise control 211606 a particular surgical instrument 211810 (or its associated generator) connected to the surgical hub 211801 to change the operational mode of the surgical instrument 211810 (e.g., change an electrosurgical surgical instrument from a sealing mode to a cutting mode). This would allow the surgical staff to control the surgical instruments 211810 without the need to directly interact with the surgical instruments 211810 themselves. As another example, if the processor 244 determines 211604 that a surgical instrument 211810 is being passed (or is being prepared to be passed) from one surgical staff member 211803 (e.g., a nurse) to another surgical staff member 211803 (e.g., a surgeon), then the processor 244 can transmit a signal to or otherwise control 211606 the energy generator to activate and begin supplying energy to the connected surgical instrument 211810. This would allow the surgical hub 211801 to preemptively activate surgical instruments 211810 so that they are ready for use without the surgeon needing to take any affirmative action. As yet another example, if the processor 244 determines 211604 that a surgical instrument 211810 is at a particular orientation when being (or as it is about to be) fired, the processor 244 can transmit a signal to or otherwise control 211606 the surgical instrument 211810 to modify the operational parameters of the surgical instrument 211810 (e.g., force to fire or maximum permitted articulation angle) accordingly. This would allow the surgical hub 211801 to control the functions of the surgical instruments 211810 to account for differences in placements and orientations of the surgical instruments 211810.

In another aspect, the surgical hub 211801 can include a voice recognition system in addition to or in lieu of the gesture recognition system 211500, described below. In this aspect, the surgical hub 211801 can be programmed to identify and respond to a variety of voice commands and control the functions of any connected surgical devices accordingly.

Figure 65B:
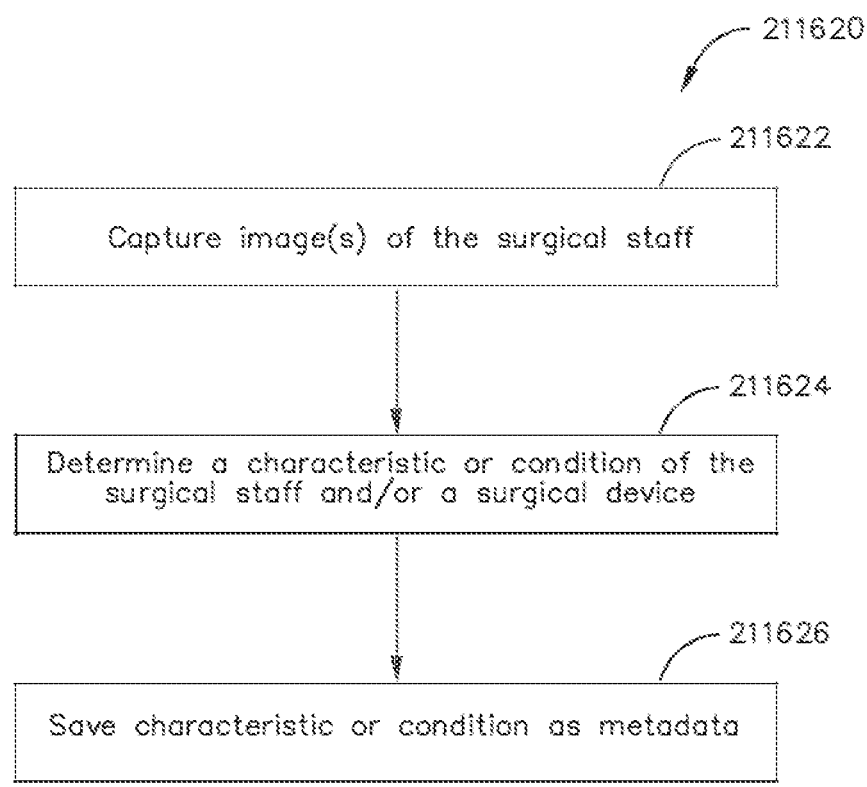
FIG. 65B is a logic flow diagram of a process for generating surgical metadata, in accordance with at least one aspect of the present disclosure.

In another aspect, FIG. 65B is a logic flow diagram of a process 211620 for generating surgical metadata, in accordance with at least one aspect of the present disclosure. As described above in connection with FIG. 65A, the process 211620 can be executed by a processor 244. Accordingly, the processor 244 executing the process 211620 can capture 211622 image/video data and determine 211624 a characteristic of the surgical staff members 211803 and/or surgical instruments 211810, as described above in connection with FIG. 65A. However, in this aspect, the processor 244 saves 211626 the characteristic or condition as metadata that is associated with or linked to the perioperative data generated by the surgical devices during the course of the surgical procedure. As noted above, the characteristics or conditions saved 211626 as metadata can include a wide range of physical properties of, actions by, and interactions between the surgical staff members 211803 and surgical instruments 211810 within the OR 211800.

Figure 66:
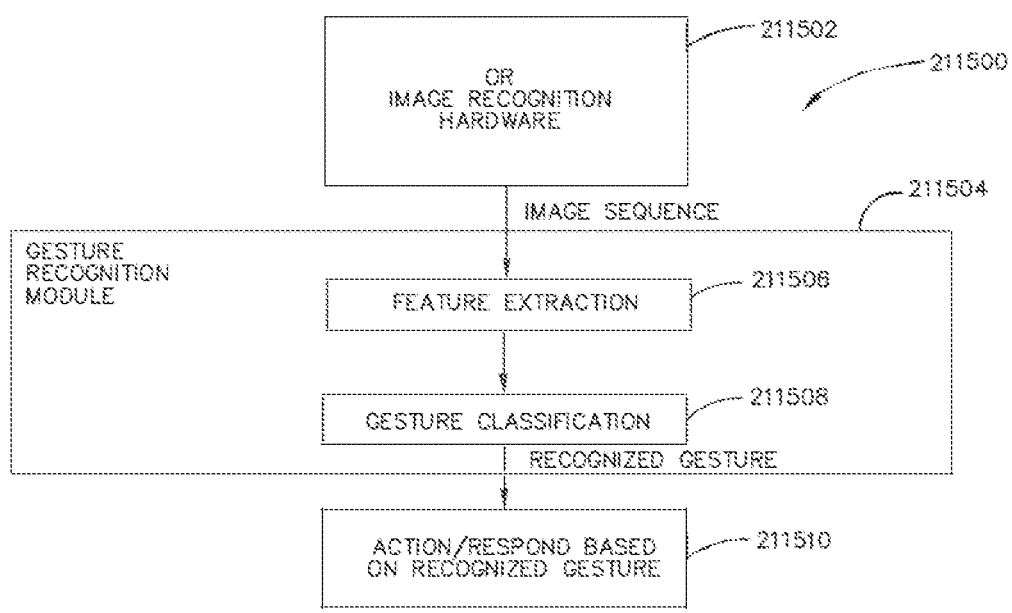
FIG. 66 is a block diagram of a gesture recognition system, in accordance with at least one aspect of the present disclosure.

In one implementation of the processes 211600, 211620 described in connection with FIGS. 61A and 61B, the surgical hub 211801 can be configured to recognize and respond to gestures performed by individuals within the OR 211800. For example, FIG. 66 is a block diagram of a gesture recognition system 211500, in accordance with at least one aspect of the present disclosure. In the following description of FIG. 66, reference should also be made to FIGS. 10 and 16. The gesture recognition system 211500 includes a gesture recognition module 211504 that can be executed by a processor or control circuit of a computer system, such as the processor 244 of the surgical hub 206 illustrated in FIG. 6. Accordingly, the gesture recognition module 211504 can be embodied as a set of computer-executable instructions stored in a memory 249 that, when executed by the processor 244, cause the computer system (e.g., a surgical hub 211801) to perform the described steps.

The gesture recognition system 211500 is programmed to receive image or video data from the image recognition hardware (e.g., the cameras 211802), recognize various gestures 211804 that can be performed by the surgical staff members 211803 (i.e., determine 211604, 211624 whether a gesture is being performed in the processes 211600, 211620 described in connection with FIGS. 65A and 65), and take a corresponding action or otherwise respond to the particular detected gesture 211804 (i.e., control 211606 a surgical device or save 211626 the data as metadata in the processes 211600, 211620 described in connection with FIGS. 65A and 65B). In one aspect, the gesture recognition module 211504 can include a feature extraction module 211506 and a gesture classification module 211508. The feature extract module 211506 is programmed to extract measurable, discriminative properties or characteristics (i.e., features) from the image/video data. The features can include edges (extracted via a Canny edge detector algorithm, for example), curvature, corners (extracted via a Harris & Stephens corner detector algorithm, for example), and so on. The gesture classification module 211508 determines whether the extracted features correspond to a gesture from a gesture set. In one aspect, the gesture classification module 211508 can include a machine learning model (e.g., an artificial neural network or a support vector machine) that has been trained via supervised or unsupervised learning techniques to correlate a feature vector of the extracted features to one or more output gestures. In another aspect, the gesture classification module 211508 can include a Hu invariant moment-based algorithm or a k-curvature algorithm to classify gestures. In yet another aspect, the gesture classification module 211508 can include a template-matching algorithm programmed to match the featurized image/video data (or portions thereof) to templates corresponding to predefined gestures. Other aspects can include various combinations of the aforementioned techniques and other techniques for classifying gestures.

Upon recognizing a gesture via the gesture recognition module 211504, the gesture recognition system 211500 can take an action 211510 or make a response that corresponds to the identified gesture. In one aspect, the action 211510 taken by the computer system includes controlling a surgical device within the OR 211800, as discussed above in connection with FIG. 65A. For example, the surgical hub 211801 executing the gesture recognition module 211504 can recognize a "brightness control" gesture and then correspondingly dim or brighten the overheard lights 211808 that are paired with the surgical hub 211801. As another example, the surgical hub 211801 executing the gesture recognition module 211504 can recognize a "generator on" gesture and then activate an energy generator paired with the surgical hub 211801, which can in turn power an ultrasonic surgical instrument or an electrosurgical instrument connected to the generator. Gestures can also be utilized to change the information being shown on displays 211806 (e.g., scroll through menus associated with a surgical instrument 211810 or alternate between video feeds being displayed); change the mode, function, or operational parameters of a surgical instrument 211810 (e.g., change an electrosurgical instrument from a sealing mode to a transecting mode); cause a scope to begin or stop recording video; change the power level of an energy generator; and so on. Gestures can be beneficial in order to control surgical devices that are outside the sterile barrier from within the sterile barrier without creating a risk for contamination, allow individuals who are not directly manipulating a surgical device or are not near the surgical device within the OR to control functions of the surgical device, and so on.

In another aspect, the action 211510 taken by the computer system includes saving the gestures made by the surgical staff as metadata associated with or linked to the perioperative data generated by the surgical devices during the course of the surgical procedure, as discussed above in connection with FIG. 65B. Such metadata can be useful in order to determine whether surgical staffs are manually controlling the surgical devices or controlling the surgical devices via gestures, which can in turn be correlated to performances of the surgical staff, procedure times, and other such metrics. In various other aspects, the computer system can both control one or more surgical devices and save the gesture data as metadata.

In another aspect, the gesture recognition system 211500 utilizes a magnetic sensing system for receiving non-contact input from users, in addition to or in lieu of cameras 211802 to visually identify gestures. In this aspect, the gesture recognition system 211500 can include, for example, a magnetic sensing array that can be positioned within the OR 211800. The magnetic sensing array can be configured to monitor for the positions of magnetic elements that can be controlled by the surgical staff members 211803. In one aspect, the magnetic elements can be built into a surgical glove or another such article of clothing. In another aspect, the magnetic elements can be located within an object or token that is manipulable by the surgical staff members 211803. Accordingly, the magnetic sensing array can be configured to detect the position of the magnetic sensing elements over time and identify any gestures that are performed by the individual controlling the magnetic elements. As with the gesture recognition system 211500, users can scroll through menus or selected items from menus displayed on displays 211806 within the OR 211800 or make other gestures to control the functions of various surgical devices within the OR 211800. Accordingly, the position, movement, and/or orientation of the magnetic element can be utilized as a tracking marker for controlling displays 211806 or other surgical devices that are connected by the surgical hub 211801, whether they are located within or outside of the sterile field.

In one prophetic implementation of the processes 211600, 211620 described in connection with FIGS. 65A and 65B, the computer system (e.g., a surgical hub 211801) can be configured to determine the pose of a surgical instrument 211654, as shown in FIG. 63, and control 211606 the surgical instrument 211654 accordingly or save 211626 the wrist angle as metadata for analysis. In this particular implementation, the angle of the individual's wrist 211650 is defined as the angle $\alpha$ between the longitudinal axis 211656 of the surgical instrument 211654 being held by the surgeon and the longitudinal axis 211652 (i.e., the proximal-to-distal axis) of the individual's hand In other implementations, wrist angle can be defined as the angle between the individual's hand and forearm, for example. The surgical hub 211801 can determine the wrist angle $\alpha$ by visually identifying the surgical instrument 211654 being manipulated by the surgeon and the hand of the surgeon, using object recognition techniques described above, for example.

In one aspect of the process 211620 described in FIG. 65B, the wrist angle $\alpha$ can be saved 211626 as metadata and utilized to perform analyses on recommended surgical techniques. For example, the scatterplot 211700 of FIG. 64 represents one such prophetic analysis on the relationship between wrist angle $\alpha$ and surgical procedure outcomes. In the scatterplot 211700, the vertical axis 211702 represents wrist angle α and the horizontal axis 211704 represents procedural outcomes. The portions of the horizontal axis 211704 to the right and left of the vertical axis 211702 can correspond to positive and negative procedural outcomes, respectively, for example. A variety of different procedural outcomes can be compared to the wrist angle α of the surgeon, such as whether a particular procedural step or firing of the surgical instrument 211654 resulted in excessive bleeding, the incidence of reoperation for the surgical procedure, and so on. Further, procedural outcomes can be quantified in a variety of different manners depending upon the particular type of procedural outcome that is being compared with the wrist angle α of the surgeon. For example, if the procedural outcome is bleeding occurring after a particular firing of the surgical instrument 211654, the horizontal axis 211704 can represent the degree or amount of blood along the incision line from the firing of the surgical instrument 211654. Further, the wrist angle α of each plotted point in the scatterplot 211700 can represent the wrist angle α at a particular instant in the surgical procedure, the average wrist angle α during a particular step of the surgical procedure, the overall average wrist angle during the surgical procedure, and so on. Further, whether the wrist angle α corresponds to an average wrist angle α or a wrist angle α at a particular instant in time can correspond to the type of procedural outcome against which the wrist angle α is being compared. For example, if the procedural outcome represented by the horizontal axis 211704 is the amount of bleeding from a firing of the surgical instrument 211654, the vertical axis 211702 can represent the wrist angle α at the instant that the surgical instrument 211654 was fired. As another example, if the procedural outcome represented by the horizontal axis 211704 is the incidence of reoperation for a particular procedure type, the vertical axis 211702 can represent the average wrist angle α during the surgical procedure.

Further, this data can then be utilized to establish thresholds or baselines, which can in turn be utilized to provide recommendations to surgical staff members 211803 during or after the completion of a surgical procedure, as described in U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES, filed on Nov. 6, 2018. For example, as illustrated in FIG. 63, the computer system can calculate a first threshold 211708 *a* and a second threshold 211708 *b* delineating the range of wrist angles α that are most highly correlated with positive procedural outcomes. The first and second thresholds 211708 *a*, 211708 *b* can thus define a first or preferred operating range. If the surgeon's wrist angle α is within this range when utilizing the surgical instrument 211654, the computer system may not take any action, for example. Further, the computer system can calculate a third threshold 211706 *a* and a fourth threshold 211706 *b* delineating the range of wrist angles α that are at least moderately correlated with positive procedural outcomes. The third and fourth thresholds 211706 *a*, 211706 *b* can thus define a second or cautionary operating range in conjunction with the first and second thresholds 211708 *a*, 211708 *b*, where the cautionary range is defined as the area between respect pairs of the first and second thresholds 211708 *a*, 211708 *b* and the third and fourth thresholds 211706 *a*, 211706 *b*. If the surgeon's wrist angle α is within the cautionary range when utilizing the surgical instrument 211654, the computer system may provide a first recommendation for the surgeon to adjust his or her technique, for example. The range outside of the third and fourth thresholds 211706 *a*, 211706 *b* can define a third or dangerous operating range that is highly correlated with negative procedural outcomes. If the surgeon's wrist angle α is within the dangerous range when utilizing the surgical instrument 211654, the computer system may provide a second recommendation for the surgeon to adjust his or her technique or deactivate the surgical instrument 211654, for example.

In one aspect of the process 211600 described in FIG. 65A, a surgical instrument 211810 can be controlled 211606 according to the determined wrist angle α. For example, the surgical hub 211801 can adjust the control program parameters of the surgical instrument 211810, such as the force to fire, force to close, or the maximum permitted articulation angle, to compensate for the orientation of the surgical instrument 211810. Such compensation can ensure that the end effector of the surgical instrument 211810 applies the same force that would have been applied had the surgical instrument 211810 been oriented more properly, for example.

In one aspect, the computer system can be programmed to create an orientation index that defines the pose of a surgical instrument 211810 with respect to a predefined or normalized reference frame. This can allow data captured in ORs of differing dimensions to be compared seamlessly. The orientation index can be defined when the surgical hub 206 scans its surroundings utilizing a non-contact sensor module 242, as described under the heading SURGICAL HUBS, for example. Accordingly, the computer system can detect and save the pose of the surgical instrument 211810 as a function of the predefined reference frame.

In other implementations, the computer system can track the locations and orientations of trocars utilized for a particular surgical procedure type, which can then be saved as metadata and/or utilized to control the displays 211806 or other surgical devices to provide recommendations to the surgical staff. The trocar positions can be analyzed to determine which range of positions (or combination of positions for surgical procedures utilized multiple trocars) is correlated most highly with positive procedural outcomes. Accordingly, the computer system can then provide recommendations for trocar placements in future surgical procedures.

In other implementations, the computer system can track the location of the handle with respect to surrounding objects (e.g., the surgical table or other equipment), which can then be saved as metadata and/or utilized to control the displays 211806 or other surgical devices to provide recommendations to the surgical staff. For example, the computer system can provide recommendations on the placement of trocars to avoid issues in previous procedures where particular placements caused the surgical instruments 211810 inserted throughout those trocars to be obstructed by various objects, resulting in more challenging procedures (which can be correlated with worse surgical outcomes or longer procedure times, for example).

In other implementations, the computer system can identify the surgical instruments 211810 and other surgical devices in the setup located on the preoperative back table to provide additional context to the surgical procedure data and/or the inferences made by the situational awareness system, as described under the heading SITUATIONAL AWARENESS. Identifying which surgical devices are (or are not) in the preoperative setup can inform the later inferences made by the situational awareness system.

In other implementations, the computer system can identify the circulating nurses and/or scrub nurses from the surgical staff members 211803 and track their locations and activities to assist in informing what the next step of the surgical procedure may be. The activities of the scrub nurse can be informative because the scrub nurse usually retrieves the surgical instrument 211810 that is expected to be needed next and then transfers that surgical instrument 211810 to the surgeon when needed. Further, some surgical instruments 211810 or other devices need preparation before they are utilized (e.g., when dictated by the tissue conditions, buttress may be placed on a surgical stapler). Accordingly, when the scrub nurse is holding a surgical instrument 211810, which surgical instrument 211810 is being held by the scrub nurse and what preparations are being performed by the scrub nurse can assist in inferring which steps of the surgical procedure are being performed or will be performed. Still further, new equipment being transferred from the circulating nurse to the scrub nurse can generally inform how the procedure is going, inform which procedure steps are being performed, and indicate the possibility of complications. For example, if additional adjunctive hemostats are being transferred to the scrub nurse, that can indicate that the surgical procedure is not proceeding well because there is more bleeding than was initially anticipated. Still further, circulating nurses bring materials into the OR, adjust the settings of surgical devices outside the sterile field, and so on. Accordingly, these activities can be monitored and also be used to inform which steps of the surgical procedure are being performed.

Configurable cooperative displays may be provided. For example, configurable cooperative displays between a primary display and one or more coupled displays, such as a secondary display, may be provided. An adaptation of one or more functional linked displays based on situational awareness of instruments in-use in the surgical site may be provided. An adaptation of one or more functional linked displays based on situational awareness of stapler instrument instructions and/or previous instructions may be provided. A relocation of display information (e.g. key display information) based on monitoring surgeon visual focus location may be provided. Superimposing, replacement, resizing of images resulting from a user instruction to move a display information onto another display may be provided. Control of a zoom and/or magnification of a selectable operation room display from within a sterile field or through a secondary display may be provided.

A surgical hub and/or medical instrument may be provided for controlling a display using situational awareness. The surgical hub may comprise a memory and a processor. The processor may be configured to perform a number of actions. A user, a medical instrument, and a location within an operating room may be determined. Contextual data (e.g. contextual information) associated with the medical instrument may be determined based on the user, the medical instrument, and the location within the operating room. A display instruction may be sent to a display that may instruct the display to be configured in accordance with contextual data (e.g. contextual information) associated with the medical instrument. The display may be a primary display or a secondary display.

A surgical hub and/or medical instrument may be provided for controlling a display using situational awareness. The surgical hub and/or medical instrument may comprise a memory and a processor. The processor may be configured to perform a number of actions. A first user, a medical instrument, and a location within an operating room may be determined. Contextual data (e.g. contextual information) associated with the medical instrument may be determined based on the first user, the medical instrument, and the location within the operating room. The surgical hub may determine that the medical instrument is being moved from a second user to the first user within or at a threshold distance of the location. The surgical hub may determine that that the location is near a patient. The surgical hub may set a display instruction to indicate that the first user is controlling the medical instrument and that the medical instrument will be used to perform a task of a surgical procedure. A display instruction may be sent to a display that may instruct the display to be configured in accordance with contextual data (e.g. contextual information) associated with the medical instrument. The primary display may be a primary display or a secondary display.

A surgical hub and/or medical instrument may be provided for controlling a display using situational awareness. The surgical hub may comprise a memory and a processor. The processor may be configured to perform a number of actions. A user, a first medical instrument, and a location within an operating room may be determined. A contextual data (e.g. contextual information) associated with the first medical instrument may be determined based on the user, the first medical instrument, and the location within the operating room. The surgical hub may determine that the first medical instrument, a second medical instrument, and the user within a threshold distance of the location. The surgical hub may determine that the user is exchanging the second medical instrument for the first medical instrument. The surgical hub may set the display instruction to indicate that the second medical instrument is being exchanged with the first medical instrument. In an example, a display instruction may be sent to the display that may instruct the display to be configured in accordance with contextual data (e.g. contextual information) associated with the medical instrument. The display may be a primary display or a secondary display.

A surgical hub and/or medical instrument may be provided for controlling a display using situational awareness. The surgical hub may comprise a memory and a processor. The processor may be configured to perform a number of actions. A user, a first medical instrument, and a location within an operating room may be determined. A first contextual data (e.g. contextual information) associated with the first medical instrument may be determined based on the user, the first medical instrument, and the location within the operating room. The surgical hub may determine that the first medical instrument, a second medical instrument, and the user within a threshold distance of the location. The surgical hub may determine that the user is exchanging the second medical instrument for the first medical instrument. The surgical hub may determine a second contextual data (e.g. contextual information) associated with the second medical instrument based on the user, the second medical instrument, and the location within the operating room. The surgical hub may set the first display instruction to indicate that the second medical instrument is being exchanged with the first medical instrument. A display instruction may be sent to the first display that may instruct the first display to be configured in accordance with first contextual data (e.g. contextual information) associated with the first medical instrument by displaying instrument data or an instruction for using the first medical instrument. The surgical hub send a second display instruction to a second display that instructs the second display to be configured in accordance with the second contextual data (e.g. contextual information) by turning off the second display or displaying one or more of a reloading instruction for the second medical instrument, a cleaning instruction for the second medical instrument, or an instrument instruction for the second medical instrument. The first display and the second display may be a primary display or a secondary display.

A surgical hub and/or medical instrument for prioritizing data on a display using situational awareness may be provided. The surgical hub and/or medical instrument may comprise a memory and a processor. The processor may be configured to perform a number of actions. A surgical procedure may be determined. A first surgical task that uses a medical instrument during a surgical procedure may be determined based on a contextual data. A second surgical task that uses the medical instrument may be determined based on the first surgical task and the contextual data. A message that may instruct a display to prioritize a display data associated with the second surgical task may be sent. The message may be a first message and a second message may be sent to the medical instrument to instruct the medical instrument to be configured in accordance with the second surgical task.

A surgical hub and/or medical instrument for prioritizing data on a display using situational awareness may be provided. The surgical hub and/or medical instrument may comprise a memory and a processor. The processor may be configured to perform a number of actions. A first surgical task that uses a medical instrument during a surgical procedure may be determined based on a contextual data. Instrument data may receive from the medical instrument and may be associated with the first surgical task. A second surgical task that uses the medical instrument may be determined based on the first surgical task, the instrument data, and the surgical procedure. A message may be sent that may instruct a display prioritize a display data associated with the second surgical task.

A surgical hub and/or medical instrument for prioritizing data on a display using situational awareness may be provided. The surgical hub and/or medical instrument may comprise a memory and a processor. The processor may be configured to perform a number of actions. A first surgical task that uses a medical instrument during a surgical procedure may be determined based on a contextual data. Instrument data may receive from the medical instrument and may be associated with the first surgical task. An error may be determined by analyzing the instrument data from the medical instrument using the contextual data. A second surgical task that uses the medical instrument may be determined based on the first surgical task, the instrument data, and the surgical procedure. A message may be sent that may instruct a display prioritize a display data associated with the second surgical task. The display data may indicate the error.

A surgical hub and/or medical instrument for prioritizing data on a display using situational awareness may be provided. The surgical hub and/or medical instrument may comprise a memory and a processor. A first surgical task that uses a medical instrument during a surgical procedure may be determined. An error that has occurred during the surgical procedure may be determined based on a contextual data. A second surgical task that uses the medical instrument may be determined based on the error, the contextual data, and the surgical procedure. A first message that may instruct a first display to display an indication of the error may be sent. A second message that may instruct a second display to a display data associated with the second surgical task may be sent. The first display may be a primary display, and the second display may be a secondary display associated with the medical instrument.

A surgical hub and/or medical instrument for prioritizing data on a display using situational awareness may be provided. The medical instrument may comprise a display and a memory. A contextual data may be determined. A surgical procedure may be determined. A surgical task that uses the medical instrument during a surgical procedure may be determined based on the contextual data. Display data may be determined. The display data may be associated with the surgical task and may be relevant to a user that may perform the surgical task that uses the medical instrument. A message may be sent. The message may instruct the display to prioritize the display data associated with the surgical task.

A surgical hub and/or medical instrument for prioritizing data on a display using situational awareness may be provided. The medical instrument may comprise a display and a memory. A first contextual data may be determined. A surgical procedure may be determined. A surgical task that uses the medical instrument during a surgical procedure may be determined based on the contextual data. A first display data may be determined. The first display data may be associated with the surgical task and may be relevant to a user that may perform the surgical task that uses the medical instrument. A first message may be sent. The first message may instruct the display to prioritize the first display data associated with the surgical task. An error that may have occurred during the surgical procedure may be determined based on a second contextual data. A second surgical task that uses the medical instrument may be determined based on the error. A second display data may be determined. The second display data that may be associated with the second surgical task and that may be relevant to the user that will perform the second surgical task that uses the medical instrument. A second message may be sent. The second message may instruct the display to reprioritize the second display data over the first display data.

A surgical hub and/or medical instrument for displaying information on a display based on a visual focus of a user may be provided. The surgical hub and/or medical instrument may comprise a memory and a processor. The processor may be configured to perform a number of actions. A display that is within a visual focus of the user may be determined. A surgical task that uses a medical instrument during a surgical procedure may be determined. Display data may be determined. The display data may be relevant to the user based on contextual data and the surgical task. A message may be sent that instructs the display to display the display data.

A surgical hub and/or medical instrument for displaying information on a display based on a visual focus of a user may be provided. The surgical hub and/or medical instrument may comprise a memory and a processor. The processor may be configured to perform a number of actions. A display that is within a visual focus of the user may be determined. An image or a video may be received from a camera. A geometric three-dimensional data set may be generated from the image or the video. One or more of a head orientation for the user and a line of sight for the user may be determined using the geometric three-dimensional data set. The visual focus of the user may be determined by using one or more of the head orientation for the user and the line of sight for the user. A surgical task that uses a medical instrument during a surgical procedure may be determined. Display data may be determined. The display data may be relevant to the user based on contextual data and the surgical task. A message may be sent that instructs the display to display the display data.

A surgical hub and/or medical instrument for displaying information on a display based on a visual focus of a user may be provided. The surgical hub and/or medical instrument may comprise a memory and a processor. The processor may be configured to perform a number of actions. A display that is within a visual focus of a first user may be determined. A surgical task that uses a medical instrument during a surgical procedure may be determined. Display data may be determined. The display data may be relevant to the first user based on contextual data and the surgical task. A message may be sent that instructs the display to display the display data.

A surgical hub and/or medical instrument for displaying information on a display based on a visual focus of a user may be provided. The surgical hub and/or medical instrument may comprise a memory and a processor. The processor may be configured to perform a number of actions. It may be determined that the display may be within a first focus of a first user and a second focus of a second user. Display data for the display may be determined based on a first surgical task for the first user and a second surgical task for the second user. A message instructing the display to display the display data may be sent.

A surgical hub and/or medical instrument for displaying information on a display based on a visual focus of a user may be provided. The surgical hub and/or medical instrument may comprise a memory and a processor. The processor may be configured to perform a number of actions. A first display and a second display that may be within a first focus of a first user and a second focus of a second user may be determined. It may be determined that that a first surgical task associated with the first user has a higher priority than a second surgical task associated with the second user. A first contextual data may be determined based on the first surgical task and a second contextual data may be determined based on the second surgical task. A first message instructing the first display to display the first contextual data may be sent and a second message instructing the second display to display the second contextual data may be sent.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first data based on the surgical task may be determined. A command from the user that indicates a preference for a second data may be determined. The command may be one or more of a voice command, a gesture, and a tactile control command. A display data may be determined. The display data may include the first data and the second data and may provide priority to the second data over the first data. A message comprising instructions for a display to display the display data may be sent. The message may be sent to the display. The display and/or an identity of the display may be determined based on the command from the user that indicates the preference for the second data. The first data may be a first contextual data and the second data may be a second contextual data.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first contextual data to be displayed on a first display may be determined. A command from a user may be determined. The command is one or more of a voice command, a command gesture, and a tactile control command. The command may indicate a preference for a second contextual data to be displayed on a second display.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first contextual data to be displayed on a first display may be determined. A command from a user may be determined. The command is one or more of a voice command, a command gesture, and a tactile control command. The command may indicate a preference for a second contextual data to be displayed on a second display. A visual focus of the user may be determined. It may be determined that the second display is within the visual focus of the user. A message instructing the second display to display the second contextual data may be sent.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first contextual data to be displayed on a first display may be determined. A command from a user may be determined. The command is one or more of a voice command, a command gesture, and a tactile control command. The command may indicate a preference for a second contextual data to be displayed on a second display. An image or a video may be received from a camera. A geometric three-dimensional data may be generated from the image or the video. One or more of a head orientation for the user and a line of sight for the user using the geometric three-dimensional data may be determined. A visual focus of the user by using one or more of the head orientation for the user and the line of sight for the user may be determined. The second display may be determined using the visual focus. A message instructing the second display to display the second contextual data may be sent. It may be determined that the second display is displaying a third contextual data associated with a second user. The message may instruct the second display to remove the third contextual data and display the second contextual data.

A surgical hub and/or medical instrument for controlling a display outside a sterile field may be provided. The surgical hub and/or medical instrument may comprise a memory and a processor. A first message that instructs a first display that is located within the sterile field to display a first contextual data may be sent. A user gesture may be determined from a device associated with the first display. The user gesture may indicate that a second contextual data is to be displayed on a second display outside the sterile field. A second message that instructs the second display to show the second contextual data may be sent.

A surgical hub and/or medical instrument may be provided. The surgical hub and/or the medical instrument may comprise a memory and a processor. The processor may be configured to perform a number of actions. A user gesture may be determined. The user gesture may indicate a visual effect to be applied to a focal point on the display that is outside the sterile field. A focal point may be determined. For example, the focal point on the display may be a place on the display that a user is viewing or focusing upon. The focal point on the display may be associated with a contextual data that may be displayed on the display. A second message may be sent. A second message may be sent to the display that may instruct the display to apply the visual effect to the contextual data at the focal point on the display that is outside the sterile field.

A surgical hub and/or a medical instrument for controlling a display outside a sterile field may be provided. The surgical hub and/or medical instrument may comprise a memory and a processor. A user gesture may be provided. The user gesture may indicate that a visual effect is to be applied to a focal point on the display that is outside the sterile field. The focal point on the display may be determined. The focal point on the display may be associated with a first display data and may be determined based on a contextual data. A second display data may be generated by applying the visual effect to the first display data. A second message may be sent. The second message may instruct the display to display the second display data.

Cooperative displays may be provided, for example, cooperative displays may be displays that may work in concert with each other. In an aspect, a medical instrument with a display may know which user may be handling the medical instrument. The medical instrument may know which surgical task in a procedure may be being performed. The medical instrument may display one or more data related to the surgical procedure. For example, the medical instrument may display patient data, medical instrument data, data associated with another medical instrument, EMR data, and the like.

In an aspect, a surgical hub may control a display and may know which user may be handling the display. The surgical hub may know which surgical task in a procedure may be being performed. The surgical hub may instruct the display to display one or more data related to the surgical procedure. For example, the surgical hub may instruct the display to display patient data, medical instrument data, data associated with another medical instrument, EMR data, and the like.

The medical instrument and/or surgical hub may know which surgical task in a procedure may be performed. The surgical task may be a reloading task, the cleaning task, a task performed on a patient, and the like. For example, it may be determined that a medical instrument may be in the process of being reloaded and may provide a user with instructions on how to reload it. As another example, it may be determined that a medical instrument is being handed to a surgeon, that the medical instrument is in a trocar, and the like. A display associated with the medical instrument may be instructed to show a staple line length and a speed. The display may be instructed to indicate how the user is interacting with the medical instrument, the staple line length, and/or the speed.

The medical instrument and/or surgical hub may be capable of determining an error. When an error is determined, a user that may be able to resolve the error may be determined. A display may be instructed to display data related to the error.

The medical instrument and/or surgical hub may be capable of displaying data associated with a number of surgical tasks, for example, at a same time. A display may be instructed to display data based on a priority. The medical instrument and/or surgical data may determine the priority and may prioritize data. For example, data may be prioritized based on which of the number of surgical tasks may be higher in priority and/or importance.

A medical instrument and/or a surgical hub may be able to instruct a display to display data. A display, such as a display of a medical instrument, may be able to display data based on a situational awareness. For example, the display, which may be a secondary display, may be able to display data based on an understanding of is going on during a surgical task and/or a surgical procedure. As another example, the display, which may be a secondary display, may be able to display data based on a location for the medical instrument. The display may belong to a medical instrument. The display may be associated with a surgical hub.

A medical instrument and/or surgical hub may be able to analyze a surgical procedure and may be able to determine one or more surgical tasks that are related to the surgical procedure. For example, a current surgical task may be determined, and a previous surgical task may be determined. The previous surgical task may be analyzed, for example, to determine if an error may have occurred. When an error has occurred, a display of a medical instrument, which may be a secondary display, may be instructed to display an error mode. The medical instrument may change from an operational mode to a failure mode. The medical instrument may be instructed to change from an operational mode to a failure mode.

For example, a medical instrument may be a stapler and may be used during a surgery. A current surgical task may request the surgeon to fire through a thing long firing. It may be determined that the force to fire is irregularly high. The display of the medical instrument may be instructed to display the force to fire to notify the surgeon that the force to fore to fire is irregularly high. The display of the medical instrument may be instructed to display a warning message, an error message, and the like. This may allow a medical instrument and/or surgical hub to provide feedback. For example, this may allow the medical instrument and/or surgical hub to provide feedback to the surgeon such that the surgeon may understand how hard an end effector.

A mechanical medical instrument may provide feedback to a surgeon by causing a surgeon to use more manual force to actuate the mechanical medical instrument. For example, a mechanical stapler may cause the surgeon to squeeze harder in order for the mechanical staplers to exert more force when stapling. An electronic medical instrument may use electric motors and may prevent a surgeon from receiving some feedback from the medical instrument. As disclosed herein, medical instruments may include a display to provide a surgeon with feedback as to a force used by the medical instrument. For example, a display of a medical instrument may display the force to fire such that a surgeon may understand the amount of force that was used for a stapler to fire.

With the use of robotics, a surgeon may not be able to feel and/or directly see what is happening with a medical instrument. For example, robotics may prevent tactile feedback. As described herein, embodiments may provide feedback that may assist a surgeon in understanding what is occurring in a surgery. The feedback may include data that may be displayed on a primary display and/or a secondary display. The feedback may include contextual data. For example, the feedback may include graphs of forced fire, data related to speeds, data related to tissue impedances, cartridge color, cartridge data, data related to grip load, and the like.

A surgical hub and/or medical instrument may be able to control a secondary display, which may be a tablet (e.g. an iPad). The secondary display may be located near or next to a surgeon. The secondary display may be located within a sterile field. The secondary display, the medical instrument, and/or the surgical hub may be used to control one or more displays, that may include primary displays and/or secondary displays, that may be outside the sterile field. For example, a surgeon may be able to use the secondary display to change from a multispectral image to a regular lit image. As another example, a surgeon may change the contrast of an image being displayed on a display using the secondary display. For example, the secondary display may provide the surgeon with an interface that may allow the surgeon to change the zoom on a display that is outside the sterile field. In an embodiment, the surgeon may use his fingers to manipulate the zoom on the display, may use his voice to issue a command that may manipulate the zoom on the display, and/or may use a gesture that may manipulate the zoom on the display. This may allow the surgeon to control (e.g. directly control) a display outside the sterile field without violating sterility as a surgeon in a sterile environment would not be able to contact an object outside the sterile field during a surgery.

During the surgery, an artificial barrier may be created around the patient to distinguish between a sterile field and a nonsterile field. This may be done, for example, to protect the patient from infection. In during the preparation for surgery, health care providers may clean a patient (e.g. scrub a patient) to eliminate and/or minimize bacteria on the outside of a patient that may infect the patient during a surgery. The patient may then be placed within the sterile field. Medical instruments within the sterile fields may also be sterile. items that are nonsterile may be excluded from the sterile field.

A surgeon or nurse may scrub in before entering into the sterile field. The surgeon or nurse within the sterile field may scrub in at a different level than health care providers that may be circulating outside the sterile field. A medical instrument that may enter the sterile field may be cleaned at a different level than a medical instrument that may not be within the sterile field but may be within the operating room.

A surgeon within the sterile fields may avoid coming in contact with a nonsterile object or item. For example, a surgeon may not be able to come in contact with a person in the nonsterile field. When a surgeon comes in contact with a person in or from the nonsterile field, the surgeon may have to leave the sterile field and rescrub in, as another example, a surgeon may not be able to come in contact with a medical instrument and/or display in the nonsterile field. If a surgeon comes in contact with the medical instrument and/or display in the nonsterile field, the surgeon may have to leave the sterile field and rescrub in. For example, if a surgeon touched a display in the nonsterile field to control the display, the surgeon would violate sterility and would have to rescrub in.

A surgical hub and/or a secondary display may be used to configure a medical instrument. For example, a first medical instrument, such as an endo cutter, may fail and may be replaced with a second medical instrument, which may be a new medical instrument. The surgical hub and/or medical instrument may receive an instruction from a user, such as a surgeon, to use the configuration and setup from the first medical instrument that failed and apply it to the second medical instrument. The surgical hub and/or secondary display may then send one or more instructions to the second medical instrument to provide medical instrument with the configuration and setup from the first medical instrument.

A surgical hub may be used to configure a medical instrument. For example, the surgical hub may send an instruction to a medical instrument that instructs the instruments as to how it may configure itself. The surgical hub may allow for advanced imaging to be provided on one or more displays using a user preference. For example, the surgical hub may retrieve a user preference that indicates an established set of parameters that may be applied to an image. The surgical hub may apply the established set of parameters to the image. The surgical hub may send an instruction to one or more displays to display the image with the established set of parameters applied. As another example, a surgical hub may determine that a surgeon may prefer to see a regular light imaging overlayed with an infrared blood flow imaging.

A surgical hub may be able to automatically determine and load (e.g. boot up) a user preferences. In an embodiment, surgical hub capabilities may be provided on a tier basis. For example, a surgical hub in a lower tier may have less capabilities than a surgical hub in a higher tier. A surgical hub in a higher tier, such as a third tier, may automatically determine and load user preferences. A surgical hub may in a lower tier, such as a first tier and/or a second tier, may not be able to automatically determine and load user preferences. A surgical hub in a higher tier, such as a third tier, may be able to provide bidirectional communication with one or more displays, and/or medical instruments. A surgical hub in a lower tier, such as first tier and/or a second tier, may not be able to provide bidirectional communication with one or more displays, and/or medical instruments.

A secondary display may be configured with at least three different operational configurations. The surgical hub may configure the secondary display in the different operational configuration based on a tier for the surgical hub. For example, the surgical hub may determine what tier it may be and may configured the secondary display with an appropriate operational configuration.

A surgical hub may be able to control one or more devices within an OR. The one or more devices may include primary displays and/or secondary displays. The one or more devices may include medical instruments and/or displays associated with the medical instruments. For example, a medical instrument may include a number of displays, which may be secondary displays. The one or more device may include wearable devices and/or displays that may be associated with the wearable devices. A wearable device may be associated with a user, such as a patient, a nurse, a surgeon, and the like. The one or more devices may include augmented reality glasses.

A surgical hub may be used to identify user, may be able to understand what tasks are being performed by different users within an OR, and may be able to configure medical instruments for the tasks being performed by the different users. For example, a surgical hub may track where users are looking and may be able to present relevant information to whatever job that a user may be doing. For example, a surgical hub may identify a user, determine what job the user is doing, may determine where the user is looking, and may instruct a display where the user is looking to display information relevant to the job the user is doing. The surgical hub may assist a surgeon in focusing on a surgical task by reducing extraneous data from being presented to the surgeon. The surgical hub may present data with a high priority (e.g. critical data) to a surgeon. For example, the surgical hub may detect an irregularity with the surgery, and error in the surgery, an error in a medical instrument, an issue with the patient, and may notify the surgeon of such.

The surgical hub may monitor data to make sure that data is within a parameter (e.g. normal parameters) and may notify a surgeon when an issue with the data is detected. For example, the surgical hub may monitor heart rate, drug delivery, a sedation level, and oxygenation level, and may notify a surgeon when the monitored data is outside of a parameter.

The surgical hub may track a user to predict what information the user may request and to deliver the information to the user before it is requested.

The surgical hub may be able to track a pupil of a user using a camera that may be mounted to a headset. The surgical hub may be able to track the hands of a user using a camera that may within the OR and/or placed on headset. For example, a camera may be located on a headset of a user and may be directed towards the hands of the user. The surgical hub may receive images from the headset and may use the images to track the hands of the user. The headset may use the camera to track the hands of the user and may provide the tracking data to the surgical hub.

An OR have one or more displays. A surgical hub may use the displays to show imaging from an internal camera, such as a camera on a medical instrument. The surgical hub may be used to augment the images using data from one or more medical instruments.

In an OR, there is an area around the patient that is consider a sterile barrier and things within the sterile barrier may not be allowed to interact with things outside the sterile barrier to ensure that the area remains sterile. For example, if a user within the sterile area were to touch a display outside the sterile area, the user would no longer be considered sterile as the contact would violate sterility.

In some cases, a medical instrument may have to pass across the line of sterility. For example, a medical instrument may be passed to a back table and across the line of sterility to be reloaded and cleaned. A surgical hub may control the display of the medical instrument such that the medical instrument may reflect its position and orientation.

A surgical hub may determine the location and orientation of a medical instrument. The surgical hub may report the location and orientation of a medical instrument to another medical instrument. The surgical hub may configure a display associated with a medical instrument to reflect a location and orientation of the medical instrument. The surgical hub may configure a display associated with a medical instrument to reflect a location and orientation of another medical instrument. For example, a surgical hub may update the display of a first medical instrument when another medical instrument is determined to be in a trocar.

A surgical hub may be use one or more cameras to determine a display that is being viewed by a user and to apply a visual effect to that display. A user within a sterile field may be viewing a display that may be outside the sterile field. The user may wish to apply a visual effect to the display, such as zooming in on an image, zooming out of the image, highlighting the image, applying an overlay to the image, rotating the images, and the like. Since the user is within the sterile field, the user is not permitted to physically touch the display. The surgical hub may use a camera to determine a gaze of the user and/or a line of sight for the user. For example, the surgical hub may use the camera to determine 3D geometric data to be used to determine the gaze of the user and/or the line of sight of the user. The surgical hub may determine a display that is within the user gaze. The surgical hub may determine a gesture from the user that may indicate the visual effect to be applied. The gesture may be a hand gesture, finger gesture, head movement, verbal command, pupil movement, and the light. For example, the surgical hub may determine that the user wants to superimpose, replace, and/or resize an image on a display that they are viewing.

The surgical hub may determine the gesture from the user that may indicate that the user may wish to display a data on the display. For example, a user may wish to see image and/or data. Of an image of a staple line, a staple line progression, a generator power level, a tissue impedance, and the like. The gesture from the user may be audible.

The surgical hub may determine from a gesture from the user that a camera may need to be refocused on an end effector in a scope. For example, a user may provide a gesture, such as a head movement, a hand motion, a finger motion, a motion with a medical instrument, a touch on the medical instrument, a touch on a secondary display, and the like. The surgical hub may interpret the gesture as an indication that a camera may need to be refocused on the end of the end effector in the scope. the surgical hub may send a message to the camera instructing the camera to refocus.

The surgical hub may determine from a gesture from the user a percentage that an image needs to be zoomed in on or out of. For example, the surgical hub may determine that the user gesture indicates that the user wants to zoom on the image being displayed by 50%. As another example, the surgical hub may determine that the user gesture indicates that the user wants to zoom out of the image by 25%. Surgical hub may determine from a gesture from the user that's a camera may need to be refocused.

The surgical hub may determine that the user gesture indicates that a camera needs to refocus. The camera may be a camera within the OR, or a camera that may be used for a surgical procedure, such as a scope camera. For example, the surgical hub may determine that the user gesture indicates that a scope camera should be refocused on a medical instrument.

The surgical hub may allow a secondary display to control another secondary display and/or a primary display. The surgical hub may allow a secondary display to control a display of another device that may not be able to be sterilized. For example, some electronics may not be able to be sterilized as the electronics may be sensitive to chemicals, may not be able to hold up to heat from an autoclave, and/or may not be compatible with gamma radiation. These electronics may be useful for a surgery, but may not be permitted within the sterile field. As described herein, the surgical hub may allow a secondary display to control these electronics, which may be outside the sterile field.

The surgical hub may allow for control (e.g. precise control) of a scope camera. For example, the surgical hub may allow for a surgeon within a sterile field to control zooming of the scope camera, resizing of images from the scope camera, replacing of images from the scope camera, super imposing other images with the images from the scope camera, and the like.

An adaptation of one or more functional linked displays based on situational awareness of instruments in-use in the surgical site may be provided. For example, situational awareness of instrument location and an individualization of users may be used to control displays. A surgical hub may have the ability to determine the user and a location for the user within the OR. The surgical hub may have the ability to determine a medical instrument and where the instrument may be location within the OR. The surgical hub may use the identity of the user and the location of the medical instrument to reconfigure one or more displays, such as coupled display units between the primary display and the systems in use. This reconfiguration may be a sharing of data with or removing shared data from primary room displays. For example, data may be displayed on a primary display and a secondary display.

Locally displayed information, which may be displayed on a secondary display, may shift between in-use control and status displays to one or more tasks, steps-for-use, or even reconfigure orientation based on handedness of the user and level of inversion. For example, a display on a medical instrument, which may be a secondary display, may be reconfigured for a left-handed user when the surgical hub determines that the medical instrument is being used and is being used by a user that is left-handed. As another example, the surgical hub may determine that the medical instrument is being transferred from one user to another for cleaning and/or reloading, and the surgical hub may instruct the display of the medical instrument to present cleaning instructions and/or reloading instructions.

As another example, the surgical hub may determine that the medical instrument may have to be inverted to perform a task of a surgical procedure. The surgical hub may instruct the display of the medical instrument (e.g. a secondary display) to reorient instructions for the performance of the task such that the user may be able to read the instructions while the medical instrument is inverted.

In an OR with connected (e.g. digital connected) instruments, it may be possible that more than one instrument may display information on more than one displays. It may be desirable to provide an ability to control and simplify the available information to what may be useful to the user. The surgical hub may control and/or simply information for a user. The surgical hub may identify a device that is in control of a user (e.g. a primary user) and may ensure that information from that device is displayed where it is most useful. For example, the surgical hub may display the information one or more primary and/or secondary displays.

As disclosed herein, cameras within the OR may be used such that the motions/actions of a user may be monitored and tracked. Sensors on the user or associated with the user may help with identification as well. The cameras may be used to identify the user. The cameras may be used to identify the instrument that is being controlled by the user. If present, the camera within the patient (e.g., laparoscope, etc.) may be used to provide additional confirmation. Displays on the instrument or controlled through the instrument, which may be secondary displays, may prioritize the information to be shared with the surgeon based on the situational awareness of the procedure (e.g., mode of operation of the device, status of the device, etc.). The surgical hub may instruct displays on the instrument or controlled through the instrument, which may be secondary displays, which information to prioritize for sharing with the surgeon based on the situational awareness of the procedure. To conserve power, simplify use, and/or to ensure relevant information is shared, when the device is no longer being used by the user, the device may stop sharing information to the display, power down, provide status, provide information for a secondary user (e.g., scrub nurse), etc. In an example, the device may determine when to stop sharing information. In another example, the device may be instructed by the surgical hub to stop sharing information.

A display may adapt based on a situational awareness of one or more instruments in use at a location, such as a surgical site, OR, and the like. One or more devices within the in-situ instrumentation may be identified. One or more users using that may be using the one or more devices may be identified. One or more devices in-situ may be identified, for example, using a scope. One or more users may be identified, for example, using a camera within the OR. Determine that a user has exchanged a first in-situ instrument for a second in-situ instrument. The first instrument and/or the second in-situ instrument may be instructed to reconfigure its display based on an in-situ presence for the device. For example, a display of an instrument going to a back table may change its display by turning off, showing reload instructions, showing cleaning instructions, showing reconfiguration instructions, and the like. As another example, a display of an instrument going into in-situ use may configure itself as a shared display, such as a secondary display, between the surgical hub and instrument parameters as the previous instrument may have been instructed to do. As another example, a display of an instrument may change based on an actuation by a user of one or more controls and the display may display data that may be related to a current control actuator use.

A surgical hub for controlling a display using situational awareness of a medical instrument may be provided. The surgical hub may comprise a memory and a processor. The processor may be configured to perform a number of actions. A user, a medical instrument, and a location within an operating room may be determined. Contextual data (e.g. contextual information) associated with the medical instrument may be determined based on the user, the medical instrument, and the location within the operating room. A display instruction may be sent to a display that may instruct the display to be configured in accordance with contextual data (e.g. contextual information) associated with the medical instrument. The display may be a primary display or a secondary display.

In an example, the contextual data (e.g. contextual information) may indicate that the user is controlling the medical instrument. The display instruction may comprise an instruction that causes the display to show one or more of an instrument data, a medical instrument instruction, and a surgical procedure instruction.

In an example, the contextual data (e.g. contextual information) may indicate that the user is controlling the medical instrument. The display instruction may comprise an instruction that causes the display to show instrument data based on one or more of an orientation of the medical instrument, a handedness of the user, and a level of inversion of the medical instrument.

The surgical hub may be configured to determine the user, the medical instrument, and the location within the operating room using one or more of a camera, a sensor within the operating room, a sensor associated with the user, a sensor associated with the medical instrument, and a wearable device.

The surgical hub (e.g. the processor) may determine display content that may relate to the contextual data (e.g. contextual information) associated with the medical instrument. The surgical hub may send display instructions to the display to display the display content. The surgical hub may include the display content within display instruction. For example, the display instruction may comprise the display content.

The surgical hub may determine a user. The user may be one or more of a patient, a health care provider, a doctor, a nurse, a scrub nurse, and a medical technician. In an example, the surgical hub may use a camera that may be located in the OR to identify a user. In another example, the surgical hub may detect a device that may be associated with a user, such as a medical instrument, a primary display, a secondary display, and a wearable device. The surgical hub may use the detection of the device to determine that a user and/or a user identity. The surgical hub may determine a user based on where a user may be standing within an OR. For example, the surgical hub may determine that a user standing next to a patient may be a surgeon. The surgical hub may determine a user based on a voice of the user. For example, the surgical hub may use a microphone to detect a voice and identify a user that is associated with the voice using voice recognition software and/or modules. The surgical hub may determine a user using RFID. For example, the surgical hub may determine that an RFID is present in the OR and may determine that the RFID is associated with a user.

The surgical hub may determine a location within the operating room. For example, the surgical hub may have spatial awareness and may use spatial awareness to map an operating room. The surgical hub may use the spatial awareness and/or map of the operating room to determine or one more locations within the operating room. The surgical hub may use spatial awareness to map an operating room for one or more potential components, which may allow the surgical hub to make autonomous decisions about whether to include or exclude such potential components as part of a surgical system and/or surgical procedure. The surgical hub may also be configured to make the type of surgical procedure to be performed in the operating room based on information gathered prior to, during, and/or after the performance of the surgical procedure. Examples of gathered information include the types of devices that are brought into the operating room, time of introduction of such devices into the operating room, and/or the devices sequence of activation. The spatial awareness of the surgical hub may also be used to update one of more displays within an operating room. For example, the spatial awareness of the surgical hub may display data on a primary display, may display data on a secondary display, and/or may move data between the primary display and secondary display based on at least one of a detection of an instrument, a mapping of the operating room, a detection of a user, a change in a location of the surgical hub, a disconnection of an instrument, and the like.

A determined location within the operating room may be a location within sterile field, or may be a location within a nonsterile field. The surgical hub may use the location to determine that a user is within the sterile field or is within the nonsterile field.

In an example, the surgical hub may be configured to determine the contextual data (e.g. contextual information) associated with the medical instrument based on the user, the medical instrument, and the location within the operating room. For example, the surgical hub may determine that the medical instrument is at the location. The surgical hub may determine that the user is at or beyond a threshold distance away from the location. The surgical hub may determine that the location indicates that the medical instrument is to be powered off. For example, the location may be a storage area, a preparation area, an area away from a patient, a surgical table, a cleaning station, and the like. The surgical hub may set the display instruction to indicate that the medical instrument should be powered off. The display instruction to the display that instructs the display to be configured in accordance with the contextual data (e.g. contextual information) associated with the medical instrument may causes the display to turn off or remove instrument data.

In an example, the surgical hub may be configured to determine the contextual data (e.g. contextual information) associated with the medical instrument based on the user, the medical instrument, and the location within the operating room. For example, the surgical hub may determine that the medical instrument and/or the user are at or within a threshold distance of the location. The surgical hub may determine that the location indicates that the medical instrument is to be cleaned. The surgical hub may set the display instruction to indicate that the medical instrument should be in a cleaning mode.

The display instruction to the display may instructs the display to be configured in accordance with the contextual data (e.g. contextual information) associated with the medical instrument causes the display to provide the user with a cleaning instruction for the medical instrument.

A surgical hub for controlling a display using situational awareness of a medical instrument may be provided. A first user, a medical instrument, and a location within an operating room may be determined. Contextual data (e.g. contextual information) associated with the medical instrument may be determined based on the first user, the medical instrument, and the location within the operating room. The surgical hub may determine that the medical instrument is being moved from a second user to the first user within or at a threshold distance of the location. The surgical hub may determine that that the location is near a patient. The surgical hub may set a display instruction to indicate that the first user is controlling the medical instrument and that the medical instrument will be used to perform a task of a surgical procedure. A display instruction may be sent to a display that may instruct the display to be configured in accordance with contextual data (e.g. contextual information) associated with the medical instrument. The primary display may be a primary display or a secondary display.

A surgical hub for controlling a display using situational awareness of a medical instrument may be provided. A user, a first medical instrument, and a location within an operating room may be determined. A contextual data (e.g. contextual information) associated with the first medical instrument may be determined based on the user, the first medical instrument, and the location within the operating room. The surgical hub may determine that the first medical instrument, a second medical instrument, and the user within a threshold distance of the location. The surgical hub may determine that the user is exchanging the second medical instrument for the first medical instrument. The surgical hub may set the display instruction to indicate that the second medical instrument is being exchanged with the first medical instrument. In an example, a display instruction may be sent to the display that may instruct the display to be configured in accordance with contextual data (e.g. contextual information) associated with the medical instrument. The display may be a primary display or a secondary display.

In an example, the display instruction to the display that may instruct the display to be configured in accordance with the contextual data (e.g. contextual information) associated with the first medical instrument causes the display to add a first instrument data associated with the first medical instrument and remove a second instrument data associated with the second medical instrument.

A surgical hub for controlling one or more displays using situational awareness of a medical instrument may be provided. A user, a first medical instrument, and a location within an operating room may be determined. A first contextual data (e.g. contextual information) associated with the first medical instrument may be determined based on the user, the first medical instrument, and the location within the operating room. The surgical hub may determine that the first medical instrument, a second medical instrument, and the user within a threshold distance of the location. The surgical hub may determine that the user is exchanging the second medical instrument for the first medical instrument. The surgical hub may determine a second contextual data (e.g. contextual information) associated with the second medical instrument based on the user, the second medical instrument, and the location within the operating room. The surgical hub may set the first display instruction to indicate that the second medical instrument is being exchanged with the first medical instrument. A display instruction may be sent to the first display that may instruct the first display to be configured in accordance with first contextual data (e.g. contextual information) associated with the first medical instrument by displaying instrument data or an instruction for using the first medical instrument. The surgical hub send a second display instruction to a second display that instructs the second display to be configured in accordance with the second contextual data (e.g. contextual information) by turning off the second display or displaying one or more of a reloading instruction for the second medical instrument, a cleaning instruction for the second medical instrument, or an instrument instruction for the second medical instrument. The first display and the second display may be a primary display or a secondary display.

Figure 67:
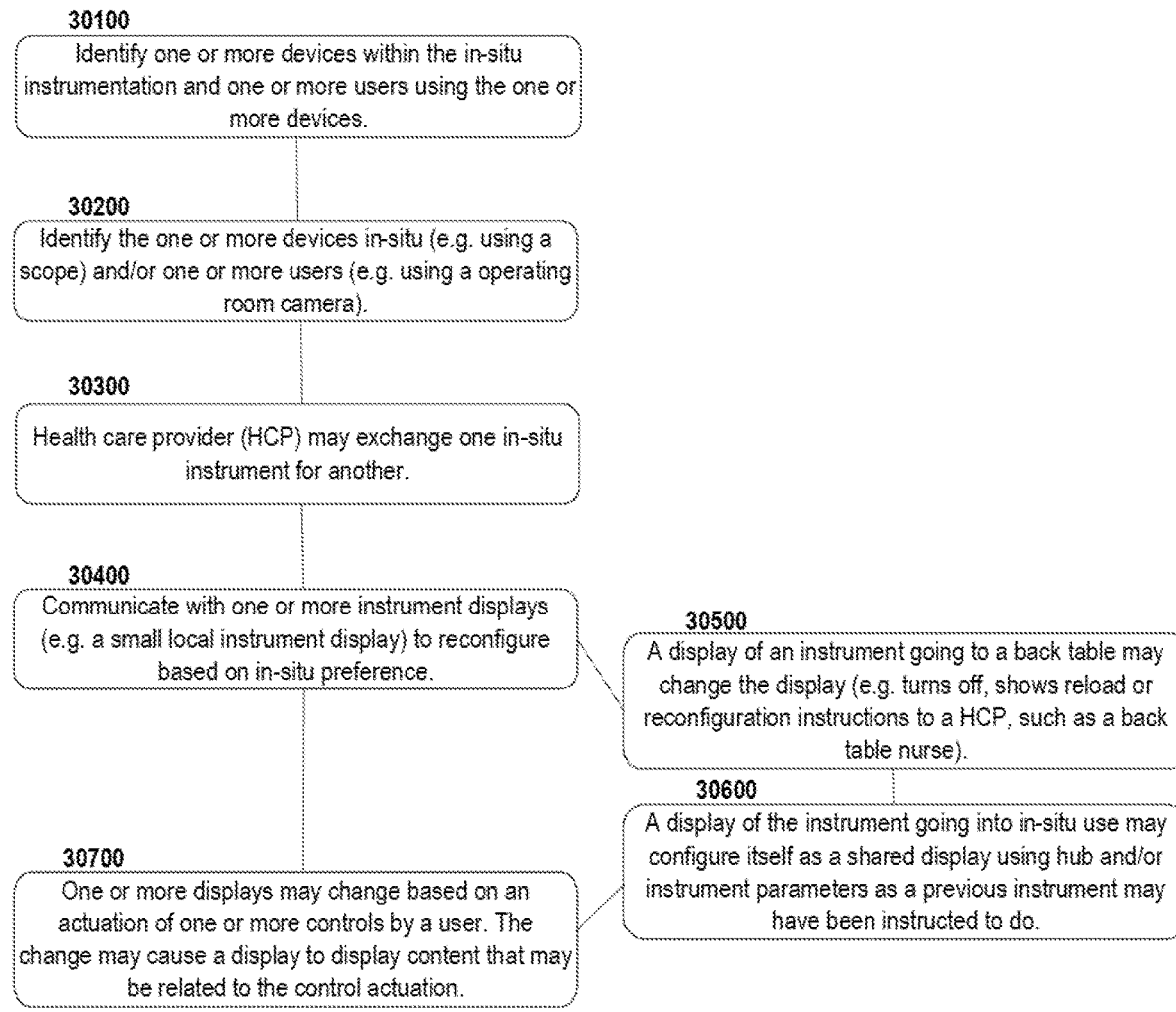
FIG. 67 is a logic flow diagram of a process for controlling a display using situational awareness of a medical instrument.

FIG. 67 is a logic flow diagram of a process for controlling a display using situational awareness of a medical instrument.

At 30100, one or more devices may be identified with in the in-situ instrumentation. One or more users using the one or more devices may be determined. For example, a surgical hub may identify one or more devices, such as medical instruments, that may be use during a surgery. The medical instruments may be located within an operating room.

A surgical hub may detect the one or more devices using any of the methods described herein. For example, a surgical hub may detect the one or more devices by detecting a connection to the surgical hub via Bluetooth, Wi-Fi, and the like. As another example, the surgical hub may detect a sensor associated with the one or more devices, such as an RFID.

The surgical hub may use a camera to identify the one or more devices. The surgical hub may be connected to one or more cameras. The one or more cameras may be located within the OR; may be a camera used for surgery, such as a scope camera; may be a camera that belongs to safety glasses; and the like. The camera may send an image or video to the surgical hub. The surgical hub may detect a medical instrument by analyzing the video or image. For example, the surgical hub may use artificial intelligence to identify a medical instrument in the video or image. The surgical hub may then access a database to determine more information regarding the medical instrument that has been identified, may attempt to connect to the medical instrument that has been identified, may prompt a user for information regarding new medical instrument, and the like.

The surgical hub made determine a position and orientation of a medical instrument using a camera. The surgical hub may use an image or video from a camera to determine what position a medical instrument may be in, how the medical instrument may be used, the context in which the medical instrument may be used, where the instrument may be located within the medical instrument, and the like. For example, the surgical hub may use an image or video along with contextual data to determine that a surgeon is holding the medical instrument upside down while using the medical instrument to perform a surgical task on a patient. The surgical hub may send a message instructing a display of the medical instrument to rotate a display of data in accordance with orientation of the medical instrument.

The surgical hub may determine one or more users within the OR. The surgical have may determine one or more users that may be using one or more devices located within the OR. The surgical hub may determine and/or identify a user using camera, a sensor associated with a user, a medical instrument that may be associated with the user, an ultrasonic sensor, a RFID (which may be embedded in an employee tag), and the like.

The surgical hub may use artificial intelligence along with images captured from a camera to identify a user and an identity of the user. For example, the surgical hub may identify a surgeon that may be the head surgeon of a surgical procedure being performed on a patient by using image processing, image recognition, artificial intelligence, and the like to recognize the identity of the surgeon from an image captured from a camera within the operating room.

At 30200, one or more devices, such as medical instruments, may be identified in-situ. For example, a surgical hub may use a camera from a scope to determine one or more medical instruments that may be used on a patient, during the surgery, a scope may be used on a patient. The surgical hub may have a connection to the scope. The surgical hub may be able to receive images and/or video from the scope. Surgical hub may use artificial intelligence to identify and/or detect a medical instrument from an image and/or video from the scope. For example, the surgical hub may identify a stapler in an image and/or video received from the scope.

The surgical hub may identify a medical instrument in-situ using a sensor associated with the medical instrument and/or the sensor associated with another medical instrument. For example, the surgical hub may detect a sensor associated with the medical instrument and may identify the medical instrument. There's another example, a sensor from another medical instrument make detect a medical instrument and may report the medical instrument to the surgical hub such that the surgical hub may identify the medical instrument.

The surgical hub may identify one for more users. Surgical hub may determine if the one or more users are associated with a detected medical instrument. For example, the surgical hub may detect a medical instrument in-situ and may identify a surgeon that may be using the medical instrument. As another example, the surgical hub may detect a medical instrument that may be used on a patient and may use a camera within the OR to determine the user that is using the medical instrument.

At 30300, The surgical hub may determine that a health care provider may be exchanging one medical instrument for another medical instrument. During the surgery, a surgeon may need to use several medical instruments. The surgeon may exchange one medical instrument for another medical instrument. Cameras within the operating room may view the surgery and may view the exchange of the medical instruments. A surgical hub connected to the camera may detect the exchange using images and/or videos from the cameras within the operating room. For example, the surgical hub may detect that a medical instrument that a surgeon is using was handed off to another user.

The surgical hub may use the camera from a scope to determine that a health care provider, such as the surgeon, may be exchanging one medical instrument for another medical instrument. The surgical hub may receive video and/or images from the scope camera. The video and/or images from the scope camera may be analyzed to determine that a first medical instrument is being removed. The video and/or images from the scope camera may be analyzed to determine that a second medical instrument is being introduced. For example, as a surgeon removes the first medical instrument, the surgeon may introduce a second medical instrument in-situ, and images/video from the scope camera may show the introduction of the second medical instrument. Using artificial intelligence, the surgical hub may detect the introduction of the second medical instruments from the scope camera images/video.

At 30400, the surgical hub may communicate with one or more displays to configure the displays based on a user preference. The one or more displays may be medical instrument displays, such as small medical instrument display that is local to the medical instrument. The one or more displays may include a secondary display. The surgical hub may configure the displays based on a determination of the identity of the one or more medical instruments. For example, the surgical hub may determine that a stapler has been introduced in-situ then may instruct a display of the stapler to provide instructions and/or data related to you a surgical task to be performed using the stapler. As another example, the surgical hub may determine that an endo cutter has been introduced in-situ; the surgical hub may retrieve the configuration for the endo cutter using contextual data, the user preference, and the like; and the surgical hub may send a message to the endo cutter to instruct the endo cutter and/or a display of the endo cutter to be configure in accordance with the configuration.

The display of the medical instrument, which may be a secondary display, may be configured by the surgical hub such that it displays data that may be preferred by a user, such as a surgeon. For example, a surgeon may prefer to see data related to a tissue impedance while performing a surgical task on a patient. The surgical hub may detect that the surgical task is about to be performed on a patient and the surgical hub may instruct a medical instrument to display the tissue impedance on a display of the medical instrument. As another example, a surgeon may prefer to set a stapler to a particular forced to fire for a surgical task to be performed on a patient. The surgical hub may determine that the surgical task may be the current surgical task and may send a message to a medical instrument to configure the stapler to the preferred force to fire for the surgeon.

The preferences for a medical instrument may be stored in a database and may be retrieved by a surgical hub and/or a medical instrument. The preferences for a medical instrument may be predicted, by using artificial intelligence for example, at a surgical hub and/or a medical instrument. The preferences for a medical instrument may be predicted by analyzing a prior usage of the medical instrument by one or more users.

At 30500, it may be determined that a medical instrument may be sent to a back table to be used for a surgical task such as being reloaded, being cleaned, being reconfigured, and the like. The surgical hub and/or the medical instrument may instruct a display of the medical instrument according to the surgical task. The display of the medical instrument may be instructed to display data and/or instructions for or associated to the surgical task. For example, it may be determined that the medical instrument may need to be reloaded, it may be determined that the medical instrument is at a back table, and the display of the medical instrument may be instructed to display instructions for reloading the medical instrument. The medical instrument may be instructed to enter a reload mode. As another example, it may be determined that the medical instrument may need to be cleaned, it may be determined that the medical instrument is at a back table, and the display of the medical instrument may be instructed to display instructions for cleaning the medical instrument. The medical instrument may be instructed to enter a cleaning mode. As another example, it may be determined that the medical instrument may not be used for a further surgical task during a surgical procedure, it may be determined that the medical instrument may is at a back table, and the display of the medical instrument may be instructed to turn off. The medical instrument may be instructed to enter a power off mode.

At the back table, a user may view the instructions that are being displayed to perform a surgical task (e.g. the current surgical task) for the medical instrument. For example, the medical instrument may need to be cleaned and/or reloaded, and the user may use the displayed instructions to clean and/or reload the medical instrument.

At 30600, a display of a medical instrument that may be going into in-situ use may be configured to be used as a shared display and/or may be configured with the parameters of a previous instrument. A number of medical instruments may be in in-situ use. For example, a scope with the camera may be used along with an endo cutter and/or a stapler. A surgical hub may detect a first medical instrument and a second medical instrument that may be used by a surgeon.

The surgical hub may instruct a first medical instrument to reconfigure its display to display data from a second medical instrument. The surgical hub may determine that the first medical instrument is being used in-situ along with the second medical instrument. The first medical instrument may be instructed to reconfigure its display to show a video and/or image from the second medical instrument. For example, the first medical instrument may be instructed to reconfigure its display to show a video of the surgical site taken from a camera of the second medical instrument. As another example, the first medical instrument may be instructed to reconfigure its display to show an image of the surgical site that may be overlaid with additional data. The image of the surgical site and/or the additional data may come from second medical instrument.

The surgical hub may determine that a first medical instrument is being used in-situ along with a second medical instrument. The surgical hub may instruct the first medical instrument to reconfigure its display to show data from the second medical instrument and/or show data that may assist a user in using the second medical instrument. For example, the surgical hub may instruct the first medical instrument to reconfigure its display to show the forced to fire for the second medical instrument. As another example, the surgical hub may determine the surgical task that the second medical instrument is to be used for may determine contextual data related to the surgical task for the second medical instrument and may instruct the first medical instrument to display that contextual data.

A first medical instrument may reconfigure its display to display data from a second medical instrument. The first medical instrument may determine that it is being used in-situ along with the second medical instrument. The first medical instrument may reconfigure its display to show a video and/or image from the second medical instrument. For example, the first medical instrument may reconfigure its display to show a video of the surgical site taken from a camera of the second medical instrument. As another example, the first medical instrument may reconfigure its display to show an image of the surgical site that may be overlaid with additional data. The image of the surgical site and/or the additional data may come from the second medical instrument.

The first medical instrument may determine that it is being used in-situ along with the second medical instrument. The first medical instrument may reconfigure its display to show data from the second medical instrument and/or may show data that may assist a user in using the second medical instrument. For example, the first medical instrument may figure its display to show the forced to fire for the second medical instrument. As another example, the first medical instrument may determine the surgical task that the second medical instrument is to be used for an may determine contextual data related to the surgical task for the second medical instrument and may display that contextual data.

At 30700, one or more displays may change a displayed data. The display data may be changed based on an actuation one or more controls by a user and may display content that related to the controller actuation. A display may be a primary display under secondary display. The display may be a display of a medical instrument. The medical instrument display may be displaying information to a user. The information to the user may be related to a surgical task. For example, contextual data may be displayed to a user that is related to the surgical task.

Figure 68:
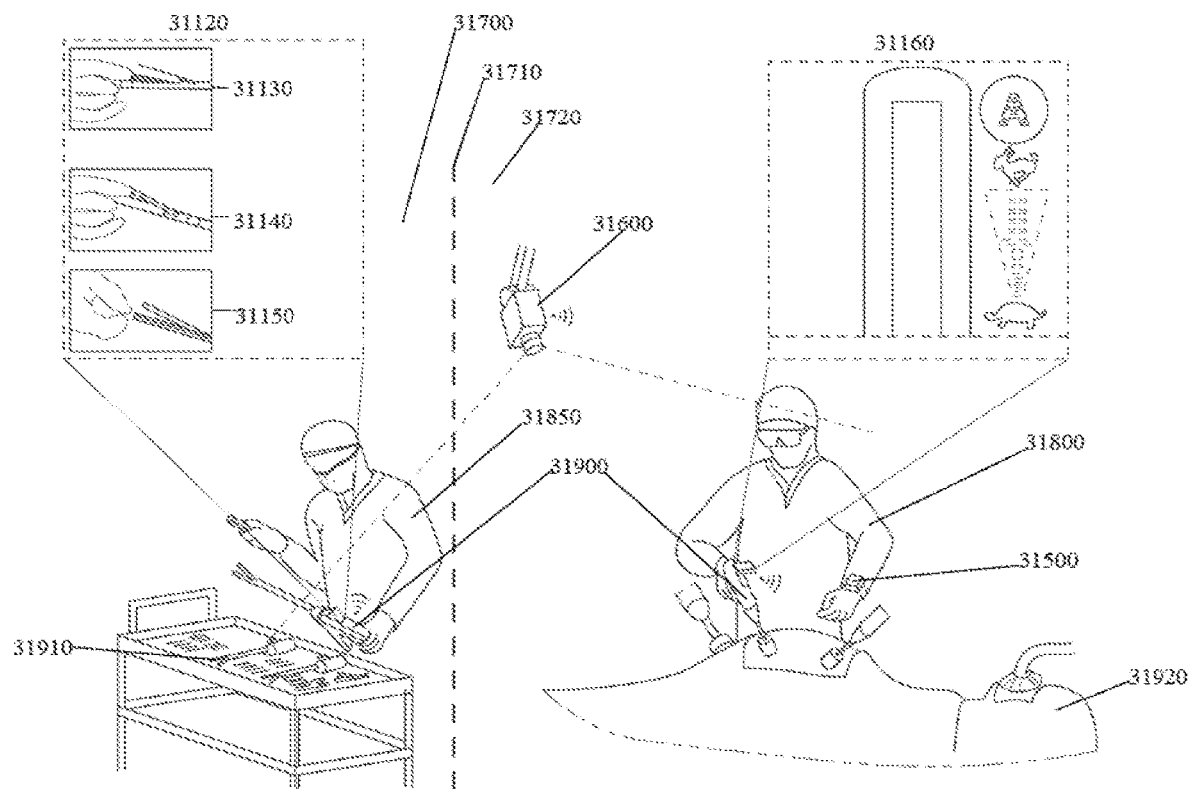
FIG. 68 is a diagram illustrating one or more displays that may be controlled using situational awareness of one or more medical instruments during the course of a surgical procedure.

The user may actuate one or more controls of the medical instrument. The actuation of a control may cause the medical instrument to change its display. The medical instrument may be displaying a first contextual data and when a user actuates a control of medical instrument, the medical instrument may display a second contextual data. The second contextual data may be FIG. 68 is a diagram illustrating one or more displays that may be controlled using situational awareness of one or more medical instruments during the course of a surgical procedure. An OR may include one or more displays. The one or more displays may include primary display and/or secondary displays. For example, the one or more display may include a display of medical instrument 31900, which may be a first secondary display, and a display of medical instrument 31910, which may be a second secondary display.

Camera 31600 may be within the OR. Camera 31600 may be used to track one or more users such as surgeon 31900 and nurse 31850. Camera 31600 may be used to track one or more instruments. For example, camera 31600 may be used to track medical instrument 31900 and medical instrument 31910. Camera 31600 may be used to capture images and/or videos of the OR, which may be sent to a surgical hub. The images and/or videos of the R may be used by the surgical hub and/or a medical instrument to identify users, medical instruments, interactions between users and medical instruments, and the like.

An OR may be separated by a sterile border 31710. The sterile border 31710 may be used to designate a sterile field 31720 and a nonsterile field 31700. The sterile field 31720 may include a patient, such as patient 31920. The sterile field 31720 may be a portion of the OR that may be sterile for a surgical procedure. Sterility may be used to prevent infection to occur into the patient 31920. The nonsterile field 31700 may be a portion of the OR that may not be sterile for the surgical procedure. The nonsterile field 31700 may be an area where preparation for the surgical procedure may be performed. For example, nurse 31850 may be in the nonsterile field 31700 And may prepare one or more medical instruments, such as medical instrument 31910 and medical instrument 31900.

During a surgical procedure, caution may be taken to ensure that sterility of the sterile field 31720 is not violated. For example, a surgical hub may track whether a medical instrument may pass over the sterile border 31710, such as when a medical instrument leaves nonsterile field 317002 and enters sterile field 31720, or when a medical instrument leaves sterile field 31720 into sterile field 31700. As another example, a medical instrument may track whether it or another medical instrument may pass over the sterile border 31710. Tracking the location of a medical instrument may be performed using camera 31600 or a sensor located on a medical instrument, such as a sensor located on medical instrument 31900 or a sensor located on medical instrument 31910.

It may be determined that medical instrument 31900 is in sterile field 31720. It may be determined that medical instrument 31900 is being held by surgeon 31800. And may be determined at medical instrument 31900 may be used to perform a surgical task on patient 31920. For example, a surgical hub may use camera 31600 to determine that medical instrument 31900 is in the hand of surgeon 31800 and may be used for a surgical task. As another example, medical instrument 31900 may determine it is in the sterile field 31720 using an internal sensor to the medical instrument 31900 or the camera 31600. The medical instrument 31900 may determine a surgical task and make configure itself for the medical surgical.

The medical hub may configure a display of medical instrument 31900 using contextual data and a determined surgical task for the medical instrument 31900. For example, the surgical hub may determine that medical instrument 31900 is a stapler that will be used by the surgeon 31800 to fire a staple. The surgical hub may send a message to the medical instrument 31900 to instruct the medical instrument 31900 configure itself for stapling. The surgical hub may send a message to the medical instrument 31900 to instruct the medical instrument 31900 to display data for the medical task such as shown on data display 31160.

The data display 31160 may be data that is displayed on the display of medical instrument 31900. The display of medical instrument 31900 may be a secondary display. The date of display 31160 may be configured with data that may be relevant to a surgical task of a surgical procedure. The surgical task of the surgical procedure may be the current surgical task that the surgeon 31500 may be performing on a patient 31920. The data display 31160 may be determined by a surgical hub and/or the medical instrument 31900. It may be determined that the medical task is for the surgeon 31800 to use the medical instrument 31900 to staple tissue. The display of the medical instrument 31900 may be instructed to display the data display 31160. The data display 31160 may show a configuration of the medical instrument 31900, which may be a stapler, for the stapling task. For example, the data display 31160 may show the speed of the stapler, a forced to fire of the stapler, and a number of staples remaining.

The medical instrument 31900 may be transferred from the surgeon 318002 the nurse 31850. The medical instrument 31900 may be transferred from the sterile field 317202 the nonsterile field 31700. The medical instrument 39100 may be a stapler an may have to be reloaded. For example, the medical instrument 39100 may be out of staples and may have to be reloaded.

It may be determined that the medical instrument 31900 may have to be reloaded. For example, the surgical hub may determine that medical instrument 31900 may have to be reloaded to perform a future surgical task. As another example, the medical instrument 31900 may determine that it is out of staples and needs to be reloaded.

It may be determined that the medical instrument 31900 may be located at a back table in the nonsterile field 31700. It may be determined that the medical instrument 31900 may be held by nurse 31850. For example, a surgical hub may use images or video from camera 31600 to determine that the medical instrument 31900 may have been transferred from the hand of the surgeon 31800 in sterile field 31720 to the hand of the nurse 31850 that is in the nonsterile field 31700. As another example, the medical instrument 31900 may use one or more sensors to determine that it may have been transferred from surgeon 31800 in the sterile field 31720 to the nurse 31850 that is in the nonsterile field 31700. As another example, the medical instrument 31910 use one of its sensors to determine that medical instrument 31900 is located near it and may determine that medical instrument 31900 may have to be reloaded.

Surgical task for the medical instrument 31900 which may be located in the nonsterile field 31700 may be determined. For example, the surgical task may be a cleaning task, a reloading task, and the like. It may be determined that nurse 31850 may use the medical instrument 31900 to perform the surgical task. The display of the medical instrument 31900 may be instructed to display data display 31120, which may provide instructions to the nurse 31850 to perform the medical task. For example, it may be determined that medical instrument 31900 may need to be reloaded, and instructions to reload medical instrument 31900 included in data display 31120.

Data display 31120 may include one or more instructions for a surgical task such as reloading, cleaning, powering off, correcting an error, and the like. For example, Title display 31120 may include reloading instructions for the medical instrument 31900. Data display 31120 may include instruction 31130, instruction 31140, and instruction 31150. Instruction 31130 may instruct a user to insert a cartridge. Instruction 31140 may instruct the user to firmly press on a staple retainer to snap in. Instruction 31150 may instruct a user to remove staple retainer.

An adaptation of one or more functional linked displays based on situational awareness of stapler instrument instructions and/or previous instructions may be provided. For example, shared situational awareness of a device actuator activity to prioritize aspects of displayed information may be provided. The order of actuator operation, instrument status, and procedural tasks may be shared between a surgical hub and a medical instrument to determine the priority of different aspects of the medical instrument data and display relevant information (e.g. the most relevant information) of the actuation of the medical instrument on the primary display and/or a secondary display (e.g. highlighted on the secondary display that belongs to the instrument). The location and highlight of the information may also determines reprioritization of that information on secondary display of the medical instrument or other secondary displays. The medical instrument data may take up an amount (e.g. a substantial amount) of the primary display when it is in use in the process of performing a critical or dangerous job.

The surgical hub with context from, for example, one or more external data sources such as the patient EMR may determine the procedure that is being performed. From a variety of data sources such as from cameras within the OR/patient, device utilization and status, activity of the surgical staff, etc. the current task in the procedure may be identified. With knowledge of the procedure, the subsequent or next task in the procedure may also be determined. Based on this information, the surgical hub may supply the smart instrument with the necessary information to display on the device (if capable) and/or on the appropriate screen within the OR. Appropriate information may be displayed on a device (e.g. each device) that is being handled by a user (e.g., surgeon, scrub nurse, etc.) as well as devices that may be anticipated to be used next (e.g., a device that should be loaded, or ready to be transferred from the back table to the surgeon). Appropriate information may include instrument status and settings, recommended usage information (e.g., wait time), error resolution, and the like.

A surgical hub may identify a procedure, a current surgical task, and a next surgical task. The surgical hub may supply a medical instrument (e.g. a smart medical instrument) with information regarding the current surgical task and/or the next surgical task. The medical instrument may have a display and may display information regarding the current surgical task and/or the next surgical task. The medical instrument may combine data such as the situational awareness of the procedure, the surgical current surgical step, the next surgical step, the device status, the status of a subsystem, the status of a component (e.g. a motor, reload, end-effector orientation, and the like), a user actuation information, and the like. The combined data may be used to determine what may should be displayed. The instrument may identify a one or more significant (e.g. critical) data sources that are relevant to the current surgical task and/or the next surgical tasks. The medical instrument and/or the surgical hub may monitor the identified data sources. The medical instrument and/or surgical hub may monitor one or more instrument parameters (e.g. wait time, force-to-fire, clamp compression) that may be adjusted and/or modified by a user (e.g. a surgeon). The adjusted parameters may be displayed such that the adjusted parameters display displayed data from a previous surgical task on a display, such as the primary display and/or the secondary display. A local display may update to a system status tracking or an error resolution for the current surgical task (e.g. cartridge color loaded, spent new cartridge status, a control that is enabled, a control that is disabled, a batter power level, a control that is prohibited, and the like).

A surgical hub and/or a medical instrument may determine that an error may have occurred. A primary display may change to indicate that the error may have occurred. For example, the primary display may indicate that an error occurred in a stapler operation. A secondary display, which may be local to the medical instrument, may updated to provide details of the error that occurred. The secondary display may display one or more error resolution instructions and/or options to assist in resolving the error.

A surgical hub for prioritizing data on a display using situational awareness of a medical instrument may be provided. The surgical hub and/or medical instrument may comprise a memory and a processor. The processor may be configured to perform a number of actions. A surgical procedure may be determined. A first surgical task that uses a medical instrument during a surgical procedure may be determined based on a contextual data. A second surgical task that uses the medical instrument may be determined based on the first surgical task and the contextual data. A message that may instruct a display to prioritize a display data associated with the second surgical task may be sent. The message may be a first message and a second message may be sent to the medical instrument to instruct the medical instrument to be configured in accordance with the second surgical task.

In an example, the display data may be relevant to the second surgical task that uses the medical instrument and may be determined based on a user identity and the contextual data. The display data that may be relevant to a user that may perform the second surgical task that uses the medical instrument. The second surgical task may be performed after a completion of the first surgical task of the surgical procedure. The second surgical task that uses the medical instrument may be one or more of a significant task, a critical task, a dangerous task, or an error correction task.

In an example, the contextual data may comprise one or more of data received from the medical instrument, one or more of a status of the medical instrument, a status of a subsystem of the medical instrument, a status of a component of the medical instrument, a status of a motor of the medical instrument, an end-effector orientation, a reload status, a configuration of the medical instrument, and actuation information.

A surgical hub for prioritizing data on a display using situational awareness of a medical instrument may be provided. The surgical hub and/or medical instrument may comprise a memory and a processor. The processor may be configured to perform a number of actions. A first surgical task that uses a medical instrument during a surgical procedure may be determined based on a contextual data. Instrument data may be received from the medical instrument and may be associated with the first surgical task. A second surgical task that uses the medical instrument may be determined based on the first surgical task, the instrument data, and the surgical procedure. A message may be sent that may instruct a display prioritize a display data associated with the second surgical task.

In an example, the instrument data may comprise one or more of a user feedback, a parameter for the medical instrument that was adjusted by a user, a wait time, a force-to-fire parameter (FTF), a clamp compression parameter, an indication that a cartridge was loaded, a cartridge status, an indication of a control that is enabled, an indication of a medical instrument control that was disabled, a battery power level, and a status of the medical instrument.

A surgical hub for prioritizing data on a display using situational awareness of a medical instrument may be provided. The surgical hub and/or medical instrument may comprise a memory and a processor. The processor may be configured to perform a number of actions. A first surgical task that uses a medical instrument during a surgical procedure may be determined based on a contextual data. Instrument data may be received from the medical instrument and may be associated with the first surgical task. An error may be determined by analyzing the instrument data from the medical instrument using the contextual data. A second surgical task that uses the medical instrument may be determined based on the first surgical task, the instrument data, and the surgical procedure. A message may be sent that may instruct a display prioritize a display data associated with the second surgical task. The display data may indicate the error.

In an example, one or more instructions to resolve the error may be determined. The display data may comprise the one or more instructions to resolve to the error.

In an example, the contextual data may be a first contextual data. A second contextual data may be received. An error that occurred during the surgical procedure may be determined based on the second contextual data.

In an example, the second surgical task may be a corrective surgical task for correcting the error that occurred during the surgical procedure. One or more instructions to assist a user in performing the corrective surgical task may be determined. The display data may comprise the one or more instructions to assist the user in performing the corrective surgical task.

A surgical hub for prioritizing data on a display using situational awareness of a medical instrument may be provided. The surgical hub and/or medical instrument may comprise a memory and a processor. A first surgical task that uses a medical instrument during a surgical procedure may be determined. An error that has occurred during the surgical procedure may be determined based on a contextual data. A second surgical task that uses the medical instrument may be determined based on the error, the contextual data, and the surgical procedure. A first message that may instruct a first display to display an indication of the error may be sent. A second message that may instruct a second display to a display data associated with the second surgical task may be sent. The first display may be a primary display, and the second display may be a secondary display associated with the medical instrument.

In an example, a resolution to the error may be determined. The display data may comprise the resolution to the error.

In an example, the second surgical task may be a corrective surgical task for correcting the error. One or more instructions to assist a user in performing the corrective surgical task may be determined. The display data may comprise the one or more instructions to assist the user in performing the corrective surgical task.

In an example, the second message may instruct the display to display an instruction to a user to assist the user in resolving the error. In an example, the second message may instruct the display to display a corrective instruction a user. The corrective instruction may comprise one or more of a cleaning instruction for the medical instrument, a reloading instruction for the medical instrument, and a repair instruction for the medical instrument.

A medical instrument for prioritizing data on a display using situational awareness may be provided. The medical instrument may comprise a display and a memory. A contextual data may be determined. A surgical procedure may be determined. A surgical task that uses the medical instrument during a surgical procedure may be determined based on the contextual data. Display data may be determined. The display data may be associated with the surgical task and may be relevant to a user that may perform the surgical task that uses the medical instrument. A message may be sent. The message may instruct the display to prioritize the display data associated with the surgical task.

The surgical task may be one or more of a task for reloading the medical instrument, a task for preparing the medical instrument, a task for cleaning the medical instrument, a task for testing the medical instrument, a task for handing off the medical instrument to another user, a task for repairing the medical instrument, a task for determining a medical instrument error, and a task for performing a procedure on a patient using the medical instrument. The surgical task may be one or more of a significant task, a critical task, a dangerous task, or an error correction task.

The display data may comprise one or more of a parameter for the medical instrument that was adjusted by a user, a wait time, a force-to-fire parameter (FTF), a clamp compression parameter, an indication that a cartridge was loaded, a cartridge status, an indication of a control that is enabled, an indication of a medical instrument control that was disabled, a battery power level, and a status of the medical instrument. The display data may comprise one or more of instructions to instruct or assist the user with performing the surgical task that uses the medical instrument.

In an example, the surgical task may be a first surgical task. A second surgical task that uses the medical instrument may be determined.

In an example, the contextual data is may be first contextual data. The surgical task may be a first surgical task. A second surgical task that uses the medical instrument may be determined during the surgical procedure based on a second contextual data.

In an example, the message is may be first message. The display data may be a first display data. A second display data may be determined. The second display data may be associated with the second surgical task and that may be relevant to a user that may perform the second surgical task that uses the medical instrument based. The second display data may be determined based on a user identity and the second contextual data. A second message instructing the display to prioritize the second display data over the first display data may be sent.

In an example, the contextual data may be a first contextual data. The surgical task may be a first surgical task. A second surgical task that uses the medical instrument during the surgical procedure may be determined based on the first surgical task, a second contextual data, and the surgical procedure.

A medical instrument for prioritizing data on a display using situational awareness may be provided. The medical instrument may comprise a display and a memory. A first contextual data may be determined. A surgical procedure may be determined. A surgical task that uses the medical instrument during a surgical procedure may be determined based on the contextual data. A first display data may be determined. The first display data may be associated with the surgical task and may be relevant to a user that may perform the surgical task that uses the medical instrument. A first message may be sent. The first message may instruct the display to prioritize the first display data associated with the surgical task. An error that may have occurred during the surgical procedure may be determined based on a second contextual data. A second surgical task that uses the medical instrument may be determined based on the error. A second display data may be determined. The second display data that may be associated with the second surgical task and that may be relevant to the user that will perform the second surgical task that uses the medical instrument. A second message may be sent. The second message may instruct the display to reprioritize the second display data over the first display data.

In an example, the second surgical task may be a corrective surgical task for correcting the error. One or more instructions to assist the user in performing the corrective surgical task may be determined. The second display data may comprise the one or more instructions to assist the user in performing the corrective surgical task.

Figure 69:
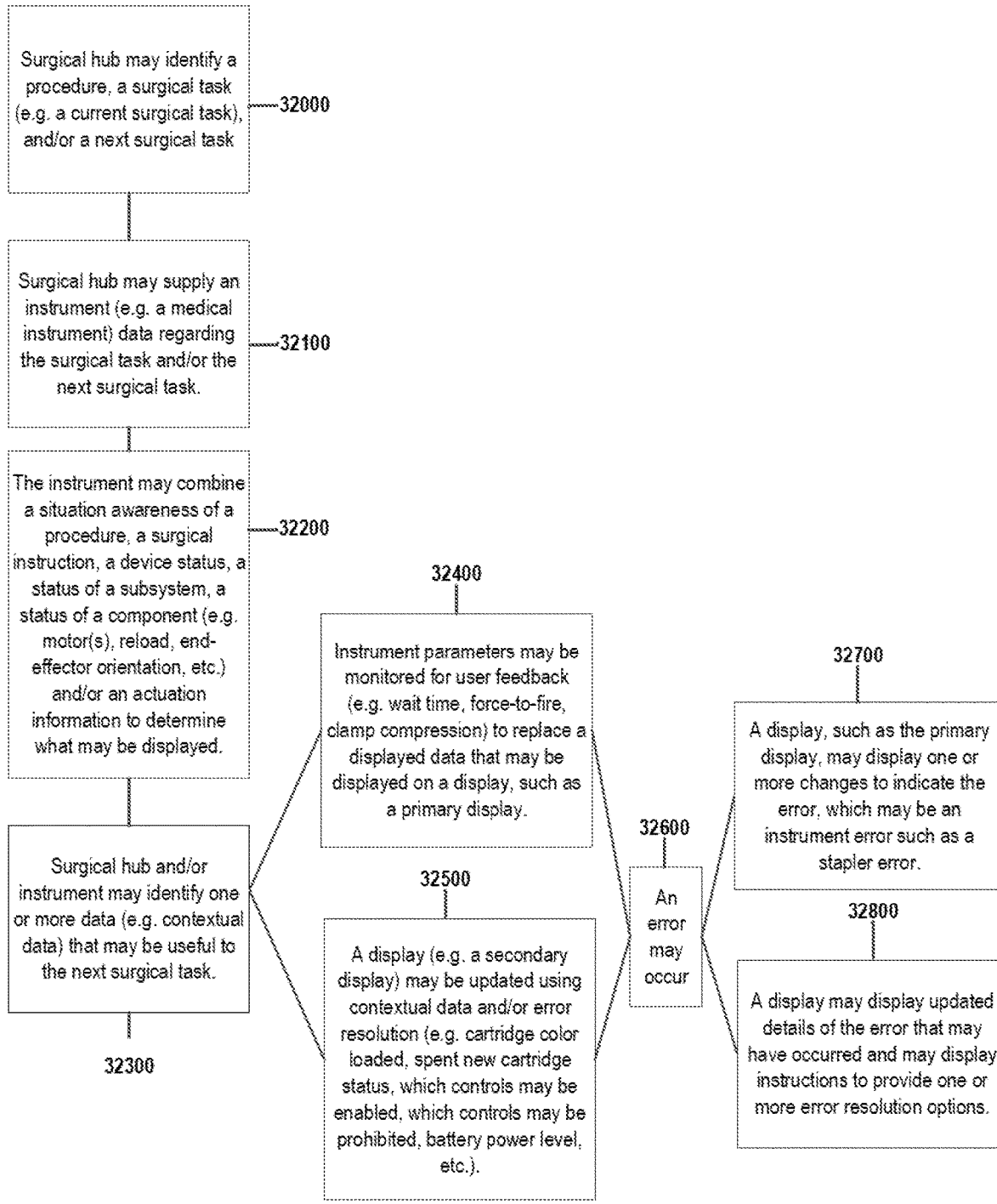
FIG. 69 is a logical flow diagram of a process for controlling a display using situational awareness to prioritize data displayed to a user.

FIG. 69 is a logical flow diagram of a process for controlling a display using situational awareness to prioritize data displayed to a user. At 32000, a surgical hub may identify a procedure, a surgical task, and/or a next surgical task. The procedure may be a surgical procedure that may be performed on a patient. For example, a surgeon may perform the surgical procedure on the patent. A surgical task may be a task to be performed during the surgical procedure. A next surgical task may be a task to be to be performed during the surgical procedure that is subsequent to another surgical task.

A surgical hub may use contextual data to determine a surgical procedure, a surgical task, a next surgical task, and the like. Contextual data may allow the surgical hub to become situationally aware. For example, the surgical hub may use contextual data to become surgically aware of a surgical procedure, and what may be occurring during the surgical procedure. FIG. 10 illustrates a timeline of an illustrative surgical procedure and the inferences that the surgical hub can make from the data detected at each step or task in the surgical procedure, in accordance with at least one aspect of the present disclosure.

For example, patient data from EMR database(s) may be utilized to infer the type of surgical procedure that is to be performed. As illustrated in the first step 5202 of the timeline 5200 depicted in FIG. 10, the patient data can also be utilized by a situationally aware surgical hub 5104 to generate control adjustments for the paired modular devices 5102. As another example, the surgical hub 106 may be configured to establish and sever pairings between components of the surgical system 102 based on operator request or situational and/or spatial awareness. The hub situational awareness is described in greater detail herein with respect to FIG. 10. As another example, the surgical hub 106 may selectively connect or disconnect devices of the surgical system 102 within an operating room based on the type of surgical procedure being performed or based on a determination of an upcoming task of the surgical procedure that requires the devices to be connected or disconnected. The hub situational awareness is described herein, for example with respect to FIG. 10.

Referring again to FIG. 69, at 32200, a surgical hub may supply save medical instrument with data. The data may be associated or regarding a surgical task, a current surgical task, and/or a next surgical task. The surgical hub may retrieve contextual data may determine that the textual data relates to a current surgical task that may be performed using the medical instrument. The surgical hub may send the contextual data to the medical instrument. The surgical hub Bay used the contextual data to determine a data display that may be provided to the medical instrument. The surgical hub may use the contextual data to generate a message that may instruct a medical instrument to display a data display. The surgical hub may use the contextual data too generate a data display for medical instrument that may be sent to a display that is external to the medical instrument, such as a primary display and/or a secondary display.

In an aspect, the medical instrument may retrieve contextual data, or may be supplied with contextual data. The medical instrument may use the contextual data to determine a surgical procedure, a surgical task, a current surgical task, and/or a next surgical task. The medical instrument may use the contextual data to determine a data display that may be related to or associated with the surgical task, a current surgical task, and/or the next surgical task.

For example, the medical instrument may use contextual data to determine a surgical task where the surgeon may use the medical instrument to fire a staple. The medical instrument may instruct a display to show data that may be relevant to the surgeon while the surgeon is using the medical instrument to fire the staple.

At 32300, the surgical hub and/or the medical instrument may identify one or more data, such as contextual data, that may be useful to the next surgical task. It may be determined that a surgeon is performing a first surgical task. It may be predicted that a surgeon will perform a second surgical task based on the surgical procedure. Contextual data that may be useful to the surgeon performing the second surgical task may be determined. The contextual data may include perioperative data, instrument data, image data, medical instrument data, biometric data, patent data, EMR data, video data, and the like. The contextual data may include data regarding the patient, the status of the medical instrument, a parameter of the medical instrument, an image of a surgical site, a video of a surgical site, instructions for performing the surgical tasks, and the like.

At 32400, data related to the medical instrument, data related to the surgical task, contextual data, and star like may be monitored for user feedback. For example, one or more parameters of the medical instrument may be monitored determine if a user may have changed one of the parameters. When one of the parameters has been detected as being changed by the user, it may be considered user feedback. The user feedback may indicate that the medical instrument may be configured in a different way than what may have been suggested by the medical instrument and/or the surgical hub. The parameters may include a wait time, a forced to fire, a clamp compression, a speed, and the like.

The display of the medical instrument may be reconfigured to indicate that the user feedback may have been detected. The display of the medical instrument may be reconfigured to indicate that the parameter of the medical instrument may have been changed by the user. The display of the medical instrument may be reconfigured to indicate that a user feedback has been received. For example, the display of a medical device may highlight a parameter that may have been changed by user to indicate to the user that the parameter may have been changed. As another example, the display of the medical instrument may highlight a parameter that may have been changed by the user but may result in a surgical error to warn the user that the surgical error may occur. As another example, the display of the medical instrument may change the data that may be displayed as the feedback from the user may indicate that the user may prefer to view different data.

At 32500, a display may be updated using contextual data. The display may be a primary display and/or a secondary display. A medical instrument and/or a surgical hub may cause the display to be updated. The display may be updated to indicate contextual data that may be relevant to the user during the surgical procedure. For example, a surgical hub may detect that a patient may be experiencing an increased heart rate and may instruct a secondary display, which may belong to a medical instrument, to display the increased heart rate to a surgeon. As another example, a surgical hub may detect that an error may have occurred with a medical instrument and may instruct the display of the medical instrument to indicate that the error may have occurred.

The contextual data that may be used to update the display may include a status of a medical instrument, a status of a resource used by the medical instrument, a patient status, EMR data, cartridge color loaded, spent new cartridge status, which controls may be enabled on a medical instrument, which controls may be enabled on a medical hub, which controls may be prohibited from being used on the medical instrument, which controls may be prohibited from being used on a surgical hub, a battery power level, and the like.

At 32600, it may be determined that an error may have occurred. A surgical hub and/or a medical instrument may have detected the error. The error may be a surgical error, a medical instrument error, a surgical hub error, a device error, and the like. The error may be a critical status of patent, a biometric data that may be out of a range, and the like. The error may be an indication that one or more devices are within a proximity that may result in an impact.

The error may indicate that an event may have occurred which may be probably problematic for the surgical procedure. For example, the error may indicate that a bleeding event may have occurred. There error may reflect a determination by the surgical hub that the surgical procedure may not be successful unless one or more corrective procedures may be performed.

At 32700, The primary display and/or the secondary display may be used to display the error. For example, a primary display may be instructed to display the information regarding error. The primary display may be outside a sterile field. The primary display may be external to the medical instrument. As another example, the secondary display may be instructed to display information regarding the error. The secondary display may be within the sterile field. The secondary display may be a display that belonged to the medical instrument. As another example, the primary display and the secondary display may be used to display information regarding error.

In an aspect, the primary display may be used to display information that may explain the error and the secondary display may be used to indicate that the error occurred on the medical instrument. For example, the secondary display, which may belong to the medical instrument, may be used to indicate that a stapling error occurred.

The primary display may be used to indicate to the surgeon how the error may have may affected the surgery, where the error may have occurred, and what instrument may have experienced the error instrument. The primary display may display data that may be relevant to the surgeon in correcting the error. The primary display may display data that may be relevant to the surgeon to understand the error.

The secondary display may indicate that the error to the medical instrument that includes the secondary display. The secondary display may indicate the type of error that may have occurred to the medical instrument, such as a stapling error.

At 32800, a display may provide a user with instructions as to how to correct an error that may have occurred. The instructions may have been determined by a surgical hub and/or medical instrument using contextual data and an understanding of the surgical task. For example, a surgical hub may determine how the surgical task may have affected the surgical procedure then may determine what course of action may be used to correct the error. As another example, a surgical hub may determine that the medical instrument has experienced an error and may determine instructions as to how to fix the error on the medical instrument.

In an aspect, the surgical hub may send one or more error resolution options to a primary display. The surgical options may present the user with a number of ways of correcting the error. In an aspect, the surgical hub may provide a surgeon with instructions as to how correct a surgical error. The instructions may guide and/or assist the surgeon and performing a surgical task to correct the surgical error.

The surgical hub may provide a user with instructions as to how to correct a medical instrument error. The surgical hub may send the instructions to a primary display and/or a secondary display, and the user follow the instructions to correct the error with the medical instrument. For example, the surgical hub may determine that a stapler may have experienced a misfire and is jammed. The surgical hub may provide instructions on a display that may assist a user in clearing the staple from the stapler. As another example, a medical instrument may determine that it has experienced a failure and may provide a health care provider with instructions as to how to repair a component of the medical instrument so that the medical instrument may function properly.

A relocation of display information (e.g. key display information) based on monitoring surgeon visual focus location may be provided. One or more devices may be identified within the in-situ instrumentation. One or more users that may use the devices may be identified. Devices may be identified in-situ using, for example, a scope and/or a camera. Users may be identified using, for example, a camera.

A surgeon may be monitored. The surgeon may be monitored, for example, when the surging is using a specific device. An instrument that may be used by the surgeon may be identified. A visual focus of a user, such as the surgeon may be identified. For example, it may be determined where the surgeon is looking. As another example, an identity of a device, primary display, secondary display, medical instrument, and the like may be identified using the visual focus of the user.

Communication between a primary screen, a secondary screen, and/or a surgical hub may occur. This communication may assist in determining where data, such as primary data, may be displayed. For example, a surgical hub may determine that a visual focus of a user indicates that the user is looking at a primary display. The surgical hub may then send a first instruction to the primary display to display data. The surgical hub may then then send a second instruction to a secondary display to cease displaying data, to remove data, or display another data. The surgical hub may send one or more messages to cause data that is being displayed on a primary display to be displayed on a secondary display. The surgical hub may send one or more messages to cause data that is being displayed on a secondary display to be displayed on a primary display.

A data, such a primary data, contextual data, perioperative data, instrument data, image data, medical instrument data, biometric data, patent data, EMR data, video data, and the like may be displayed on a primary display and/or a secondary display. Primary data may include medical instrument data, key medical instrument data, an error, an error of another device, an indication a proximity of one or more devices that may result in an impact, biometric data, image data, camera data, and the like.

In an example, a surgical event, such as a bleeding event, may be determined. Display data associated or related to the bleeding event, such a live video image, biometrics, and the like may be determined. A visual focus of a user, such as a surgeon may be determined. A display may be determined based on the visual focus of the user. Display data may be sent to the display. The display data may be sent to a primary display and/or a secondary display. Display data may also be sent to a secondary display.

In an example, upon detecting a bleeding event, the visual focus of the user may be used to determine a primary display and a secondary display. A first message may be sent that instructs the primary display to display the patent biometrics. A second message may be sent that instructs the secondary display to display a video of a surgical area where bleeding may be occurring.

One or more control devices, such as a secondary control array, may be used to control a display and/or what is shown on the display. A control device may be a smart device, such as a tablet, iPad, smart phone, a camera, a wearable device, an RFID, and the like. The control device may be used inside or outside the OR. The control device may be used within a sterile field, or within a nonsterile field.

A control device may be a camera. The camera may track one or more users. For example, the camera may track one or more staff within an operating room. The camera may be used to generate geometric 3D information that may be analyzed to determine a head orientation and/or a line of sight for a user. For example, the camera may be used to generate 3D information related to a user, such as a surgeon. The geometric 3D information may be used to determine a visual focus of the user. The camera may be used to identify one or more users. For example, the camera may identify a surgeon.

An RFID and/or a wearable device may be used to identify a User. For example, a surgical hub may identify a user by detecting the presence of a wearable device associated with the user. As another example, the surgical hub may identify a user by detecting the presence of a RFID associated with a user. The RF ID may be part of an employee ID tag, which may be worn by a user.

One or more displays may be used to show data that may be relevant to a user. For example, a display may be controlled such that the monitor may display relevant information to a user based on the user that looks at the display. The relevant information may be based on the user, a surgical procedure, a medical instrument, a surgical task, a patient biometric, a user biometric, contextual data, and the like.

The camera may monitor a line of sight, or a visual focus, for one or more users. For example, the camera may monitor the line of sight for each user within an OR. The line of sight for a user may be used to control the information that may be displayed on a primary display and/or a secondary display.

The location of a display may be used to determine what information may be relevant to a user that may be viewing the display. For example, a display, such as a smart device display, which may be a secondary display, may be located near a patient. When a surgical hub detects that a first user is viewing the smart device display, the smart hub may instruct the smart device display to show patient information. When a smart hub detects that a second user, such as a surgeon, is viewing the smart device display, the smart hub may instruct a smart device display to show one or more instructions related to a surgical task.

As another example, a display, which may be a handheld device display and/or a wearable device display, may be located on a surgeon. When a surgical hub detects that a surgeon is viewing the wearable display, the surgical hub may instruct the display to show data related to a surgical task. When a surgical help detects that another user is viewing the wearable display that belongs to the surgeon, the surgical hub may instruct the display to show biometric data that may be associated with the surgeon.

As another example, displayed information may be shared between sterile field and a nonsterile field to highlight pertinent information. For example, a first user may be viewing a first display in a nonsterile field. The first display may be showing data that may be relevant to the first user. A second user may be viewing a second display in a sterile field. The second display may be showing data that may be relevant to the second user. When the first user begins viewing the second display, a surgical hub may instruct the second display to show both the data that may be relevant to the first user and the data that may be relevant to the second user. When the second user beings viewing the first display, a surgical hub may instruct the second display to show both the data that may be relevant to the first user and the data that may be relevant to the second user.

When it is determined that more than one user is viewing a display, the display may be instructed emphasize some data. For example, it may be determined that the one or more users may be interested in similar data, and the display may be instructed to emphasize the similar data. The display may also be instructed to deemphasize other data.

When it is determined that more than one user is viewing a display, the display may be instructed to show data that may have a higher priority. For example, the one or more users may be identified. The identifies of the one or more users and contextual data may be used to determine a surgical procedure and a current medical task. Data associated with the current medical task may then be given a priority such that the display is instructed to show the data associated with the current medical task.

Monitoring of a user visual focus may be provided, for example, to control which display and/or display systems may show information (e.g. primary information). One or more cameras may be used to determine a location of a gaze of a user, such as a surgeon. The gaze of the user may be used to identify a display and populate the display with data that may have a high priority.

One or more cameras in the OR may be used to help monitor activities of staff. These cameras may be used to determine which device is being used by which user. Primary users may be identified by the cameras and/or sensed based on sensors worn by the user. These cameras may monitor the relative orientation of the user's head (or user for which the information may be valuable) relative to displays in the OR and may allow this orientation to control the location of information. The information may be tailored for the user based on the instrument that may be controlled by the user and may be based on situational awareness of the procedure to help prioritize the relevant information from the device for the user at that moment in the procedure. The displayed information may include patient information, safety information, device information, medical instrument information, information about other devices in use at the time, and the like.

A surgical hub for displaying information on a display based on a visual focus of a user may be provided. The surgical hub and/or medical instrument may comprise a memory and a processor. The processor may be configured to perform a number of actions. A display that is within a visual focus of the user may be determined. A surgical task that uses a medical instrument during a surgical procedure may be determined. Display data may be determined. The display data may be relevant to the user based on contextual data and the surgical task. A message may be sent that instructs the display to display the display data.

The visual focus of the user by may be determined using one or more of wearable device data, sensor data associated with the user, an image from a camera within an operating room, and a video from the camera within the operating room. The display data may comprise one or more of an instrument data, a device error, a device proximity likely to result in an impact, a biometric data, an image, a video, and a camera display.

In an example, the display may be a first display, the display data may be a first display data, and the message may be a first message. It may be determined that the display is displaying a second display data. It may be determined that the first display data has a higher priority that the second display data based on an identity of the user, the surgical task, and the contextual data. A second message instructing the second display to display the second display data may be sent.

In an example, the display may be a first display, the display data may be a first display data, and the message may be a first message. A second display that may be within the visual focus of the user may be determined. A second display data from the contextual data may be determined based on the surgical task. The second display data may be of a lower priority to the user than the first display data. A second message instructing the second display to display the second display data may be sent.

In an example, determining the display data that may be relevant to the user based on the contextual data and the surgical task may be performed. A ranked data set may be determined by ranking the contextual data based on a likelihood of being requested by the user during surgical task. An amount of display space for the display may be determined. A subset of the ranked data may be assigned as the display data based on the amount of display space for the display.

A surgical hub for displaying information on a display based on a visual focus of a user may be provided. The surgical hub and/or medical instrument may comprise a memory and a processor. The processor may be configured to perform a number of actions. A display that is within a visual focus of the user may be determined. An image or a video may be received from a camera. A geometric three-dimensional data set may be generated from the image or the video. One or more of a head orientation for the user and a line of sight for the user may be determined using the geometric three-dimensional data set. The visual focus of the user may be determined by using one or more of the head orientation for the user and the line of sight for the user. A surgical task that uses a medical instrument during a surgical procedure may be determined. Display data may be determined. The display data may be relevant to the user based on contextual data and the surgical task. A message may be sent that instructs the display to display the display data.

A surgical hub for displaying information on a display based on a visual focus of a user may be provided. The surgical hub and/or medical instrument may comprise a memory and a processor. The processor may be configured to perform a number of actions. A display that is within a visual focus of a first user may be determined. A surgical task that uses a medical instrument during a surgical procedure may be determined. Display data may be determined. The display data may be relevant to the first user based on contextual data and the surgical task. A message may be sent that instructs the display to display the display data.

In an example, the display may be a first display, and the display data may be a first display data. It may be determined that the display is displaying a second display data that may be associated with a second user. The message may be sent to the display. The message may comprise instructions to the display to display the first display and may comprise instructions to display the first display data along with the second display data.

In an example, determining the display data that may be relevant to the first user based on the contextual data and the surgical task may be performed. It may be determined that a second user is viewing the display. An amount of available display space for the display may be determined. A data priority for the contextual data may be determined based on the surgical task and a relation between the first user and the second user. A subset of the contextual data may be assigned as the display data based on the first data priority and the second data priority.

A surgical hub for displaying information on a display based on a visual focus of a user may be provided. The surgical hub and/or medical instrument may comprise a memory and a processor. The processor may be configured to perform a number of actions. It may be determined that the display may be within a first focus of a first user and a second focus of a second user. Display data for the display may be determined based on a first surgical task for the first user and a second surgical task for the second user. A message instructing the display to display the display data may be sent.

The display data may comprise one or more of an instrument data, a device error, a device proximity likely to result in an impact, a biometric data, an image, a video, and a camera display.

In an example, the first surgical task may indicate that a first medical instrument is being used by the first user during a surgical procedure. The second surgical task may indicate that a second medical instrument is being used by the second user during the surgical procedure.

In an example, the display data for the display based on the first surgical task for the first user and the second surgical task for the second user may be determined. A priority between the first surgical task and the second surgical task may be determined. The display data may be determined from contextual data using the priority, the first surgical task, and the second surgical task.

In an example, the display data for the display may be determined based on the first surgical task for the first user and the second surgical task for the second user. A priority between the first user and the second user may be determined. The display data may be determined from contextual data using the priority, the first surgical task, and the second surgical task.

A surgical hub for displaying information on a display based on a visual focus of a user may be provided. The surgical hub and/or medical instrument may comprise a memory and a processor. The processor may be configured to perform a number of actions. A first display and a second display that may be within a first focus of a first user and a second focus of a second user may be determined. It may be determined that that a first surgical task associated with the first user has a higher priority than a second surgical task associated with the second user. A first contextual data may be determined based on the first surgical task and a second contextual data may be determined based on the second surgical task. A first message instructing the first display to display the first contextual data may be sent and a second message instructing the second display to display the second contextual data may be sent.

In an example, the first surgical task may indicate that a first medical instrument is being used by the first user during a surgical procedure. The second surgical task may indicate that a second medical instrument is being used by the second user during the surgical procedure.

In an example, the first message may instruct (e.g. further instruct) the first display to remove display data that is associated with the second user.

In an example, it may be determined that the first surgical task associated with the first user may have the higher priority than the second surgical task associated with the second user. It may be determined that the first surgical task indicates that the first medical instrument is being used on a patient. It may be determined that the second surgical task indicates that the second medical instrument is being cleaned, reloaded, or prepared. A priority may be assigned to the first surgical task such that the first surgical task is given a higher priority than the second surgical task.

In an example, it may be determined that the first surgical task associated with the first user has a higher priority than the second surgical task associated with the second user. A surgical procedure may be determined. A first priority for the first surgical task based on the surgical procedure. A second priority for the second surgical task based on the surgical procedure. It may be determined that the first priority for the first surgical task is higher than the second priority for the second surgical task.

In an example, it may be determined that the first surgical task associated with the first user may have a higher priority than the second surgical task associated with the second user by determining that the first surgical task is associated with a higher level of danger than the second surgical task.

Figure 70:
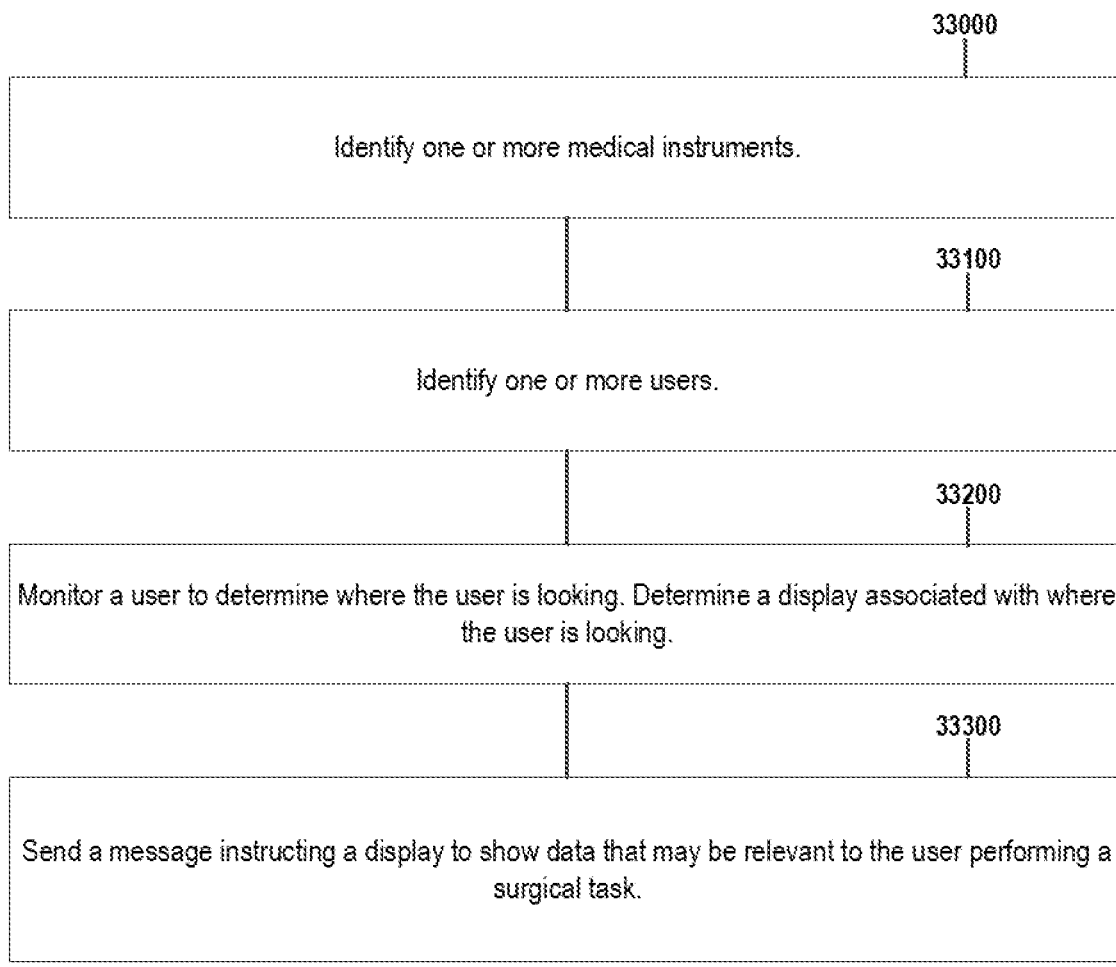
FIG. 70 is a logical flow diagram of a process for displaying information on a display based on a visual focus of a user.

FIG. 70 is a logical flow diagram of a process for displaying information on a display based on a visual focus of a user. The surgical hub may determine a visual focus of the user to determine which display a user may be viewing. The surgical hub may use the determination of the visual focus of the user to display information at the display that the user may be viewing. The surgical hub may present the user with information that may be relevant to a task that a user may be performing during a surgery at the display that the user may be viewing.

To determine the visual focus of the user, a surgical hub may use a sensor and/or a camera to determine a line of sight for a user. For example, a user may be outfitted with one or more sensors that may be detected by the surgical hub such that the surgical hub may generate 3D geometric data and may determine a line of sight using the 3D geometric data. Another example, the user may be wearing safety glasses that may be able to track the visual focus of a user or may be able to provide data regarding the visual focus of the user, such as head motion, head tilt, and the like. The safety glasses, which may be referred to as smart safety glasses, are described herein. Safety glasses may include one or more sensors, and/or electronics to monitor movement of the user. The safety glasses may also include a camera that may be used to monitor pupil movements for the user. The safety glasses may also include a screen that may be used to present information such as contextual data to the user.

At 33000, one or more medical instruments may be identified. The one or more medical instruments may be in the OR. The one or more medical instruments may be in-situ. The one or more medical instruments may be identified using a camera, a sensor, ultrasonic detection, RFID tracking, Bluetooth tracking, Wi-Fi tracking, and the like.

A camera within the OR may be used to track and/or identify the one or more medical instruments. The camera may record images and/or video of the OR. The video and/or images of the OR may be sent to the surgical hub. The surgical hub may analyze the images and video. For example, the surgical hub may analyze the images and/or video using artificial intelligence to identify the one or more medical instruments.

A surgical hub may use data from the camera to track movement of a medical instrument around the OR. For example, the surgical hub may use the camera to track a medical instrument that may move from a sterile field to a nonsterile field, or from a sterile field to a nonsterile field. A surgical hub may use tracking information for a medical instrument too instruct a medical instrument to enter into one of a number of modes, such as a usage mode, a power off mode, a cleaning mode, a reloading mode, and the like.

A camera that may belong to a scope may be used to track and/or identify the one or more medical instruments. The scope camera may be used to track medical instruments as they enter and/or leave a surgical area. The surgical hub may use the camera from a scope to determine that a health care provider, such as the surgeon, may be exchanging one medical instrument for another medical instrument. The surgical hub may receive video and/or images from the scope camera. The video and/or images from the scope camera may be analyzed to determine that a first medical instrument is being removed. The video and/or images from the scope camera may be analyzed to determine that a second medical instrument is being introduced. For example, as a surgeon removes the first medical instrument, the surgeon may introduce a second medical instrument in-situ, and images/video from the scope camera may show the introduction of the second medical instrument. Using artificial intelligence, the surgical hub may detect the introduction of the second medical instruments from the scope camera images/video.

At 33100, a surgical hub may use data from one or more cameras to identify one or more users. Camera data, such as image and/or video data, may be captured by the camera. The camera data may be sent to the surgical hub. The surgical hub may receive the camera data and may analyze the camera data to identify a user. The surgical hub may identify a user from the camera data using, for example, artificial intelligence.

A surgical hub may be able to determine the identity of a user by detecting a device that may be associated with the user. For example, the surgical hub may detect a RFID that may be embedded in an employee tag that may be associated with the user. As another example, the surgical hub may detect a wearable device that may be associated with a user. As another example, the surgical hub may detect that a medical instrument associated with a user is present in the operating room. As another example, the surgical hub may use contextual data to determine an identity of a user.

The surgical hub may use camera data to determine where a user is located within an OR. The surgical hub may receive camera data and may use the camera data to generate a map of OR. The surgical hub may receive camera data that may include a user. The surgical hub may compare the camera data that includes the user to the map of the OR to determine the location of the user. The surgical hub may determine a surgical procedure and may correlate the location of the user within the OR to the surgical procedure to determine a task that the user may be performing or may be about to perform. The surgical hub may determine a surgical task to be performed by a user using contextual data.

A surgical hub may be able to determine where are user is located within an OR using a device that may be associated with the user. The surgical hub may detect an RFID in the location within the OR an may associate that location with a user associated with the RFID. The surgical hub may detect a wearable device associated with a user is at a location within the OR and may associate that location with the user associated with the wearable device. Surgical hub may use ultrasonic sensors, Wi-Fi, Bluetooth, radar, lidar, and the like to track user movement.

An operating room may be separated into a sterile field in a nonsterile field. The surgical hub may determine that the location of a user may indicate that the user is within a sterile field. The surgical hub may determine that the location of a user may indicate that the user is within a nonsterile field. The surgical hub may determine that a user may have passed from the sterile field to the nonsterile field. Surgical hub may determine that the user may have passed from the nonsterile field to the sterile field.

For example, a surgical hub may track where users are looking and may be able to present relevant information to whatever job that a user may be doing. For example, a surgical hub may identify a user, determine what job the user is doing, may determine where the user is looking, and may instruct a display where the user is looking to display information relevant to the job the user is doing. The surgical hub may assist a surgeon in focusing on a surgical task by reducing extraneous data from being presented to the surgeon. The surgical hub may present data with a high priority (e.g. critical data) to a surgeon. For example, the surgical hub may detect an irregularity with the surgery, and error in the surgery, an error in a medical instrument, an issue with the patient, and may notify the surgeon of such.

At 33200, the user may be monitored to determine where the user may be looking. A surgical hub may receive data from safety glasses that may be worn by a user. The safety glasses (see FIG. 29) may use one or more sensors to track the head movement of the user to determine where the user is viewing (e.g. the surgeon is viewing the monitor). In an aspect, the safety glasses may inform the surgical hub as to where the user is looking after the safety glasses determines where the user is looking. In an aspect, the safety glasses may data from its sensors to allow the surgical hub to determine where the user is looking.

A surgical hub may use a camera to track the head movement of a user to determine a line of sight or a gaze of the user. The camera may capture one or more images of a user. The images may be analyzed to determine a physical characteristic of a user from the captured image(s). For example, the physical characteristic may include posture, as discussed in connection with FIGS. 61-62, or wrist angle, as discussed in connection with FIGS. 63-64. As another example, the physical characteristic may include the position, orientation, angle, or rotation of an individual's head, shoulders, torso, elbows, legs, hips, and so on. The physical characteristic may be determined utilizing a variety of machine vision, image processing, object recognition, and optical tracking techniques. In an aspect, the physical characteristic may be determined by processing the captured images to detect the edges of the objects in the images and comparing the detected images to a template of the body part being evaluated. Once the body part being evaluated has been recognized, its position, orientation, and other characteristics may be tracked by comparing the movement of the tracked body part relative to the known positions of the cameras. In another aspect, the physical characteristic can be determined utilizing marker-based optical systems (e.g., active markers embedded in the surgical staff members' uniforms emitting electromagnetic radiation or other signals that can be received by the cameras or other sensors connected to the surgical hubs. By tracking the movement of the markers relative to the cameras, the processor may determine the head position of a user to determine where the user may be looking.

The surgical hub may determine where a user is looking. Surgical hub they determine where a user is looking to determine one or more displays. Surgical hub may monitor the user using the camera to determine a line of sight for the user. The line of sight may be determined using geometric data that may be generated using data from the camera. For example, a line of sight for the user may be determined using geometric data generated from one or more images taken from the camera. The surgical hub may use a line of sight or visual focus for the user to determine an area or location within an OR that a user may be viewing. The surgical hub may use a line of sight or visual focus for the user to determine a direction or vector where a user is looking. The surgical hub may use a line of sight or visual focus to determine an area or location within an OR that may be associated with one or more displays that may include primary displays and/or secondary displays.

A surgical hub may determine that a user is viewing a display using a line of sight. The display may be a primary display and/or a secondary display. For example, the surgical hub may use a line of sight or visual focus for the user to determine that a surgeon may be viewing a primary display that may be within a sterile field. As another example, the surgical hub may use a visual focus for the user to determine that a surgeon may be viewing a primary display that may be within a nonsterile field. The surgical hub may determine that a user is viewing a secondary display using a line of sight. For example, the surgical hub may determine a visual focus or line aside for the user and may determine that the user is viewing a secondary display, such as a display of a wearable device, a display of a tablet device, a display of a computing device, a display of a medical instrument, and the like.

A surgical hub may determine that a first display and a second display may be within a visual focus or a line of sight of the user. The surgical hub may prioritize data such that higher priority data may be displayed on the first display and lower priority data may be displayed on the second display. The first display may be a primary display and/or a secondary display. The second display may be a primary display and/or a secondary display. For example, a surgical hub may determine that a primary display in a secondary display may be within a visual focus of the user. The surgical hub may send higher priority data to the primary display and may send lower priority data to the secondary display such that the surgeon may be able to view both.

The surgical hub may determine that a first user and a second user may be viewing a display. For example, the surgical hub may determine that a first visual focus for first user may indicate that the first user is viewing a display. The surgical hub may determine that a second visual focus for the second visual user may indicate that the second user is viewing the display. In an example, the surgical hub may determine that the first user has priority over the second user and may show data for the first user on the display. In an example, the surgical hub may determine that the first user has less priority than the second user and may show data for the second user on the display. In an example, the surgical hub may display a first data for the first user and a second data for the second user on the display. In an example, the surgical hub may determine that the first user has a higher priority than a second user and may display a first data for the first user more prominently on the display than a second data for the second user.

The surgical hub may determine a first visual focus for a first user and a second visual focus for a second user. The surgical hub may determine that the first user and the second user may be viewing a first monitor and the second monitor. The surgical hub may determine that the first user and the second user may be viewing the first monitor and the second monitor using the first visual focus and the second visual focus. The first display may be a primary display and/or a secondary display. The second display may be a primary display and/or a secondary display. In an example, the surgical hub may determine that the first user has a higher priority than the second user and may display data for the first user on the 1st display and may display data for the second user on the second display. In an example, the surgical hub may determine that the first user has a higher priority than the second user and may display data for the first user on the first display and may display data for the first user on the second display. In an example, the surgical hub may determine that priority data is to be displayed without consideration to a priority of a first user and a second user, and the priority data may be displayed on the first display, the second display, or the first display and the second display. In an example, the surgical hub may show a first data for a first user on the first display, a second data for a second user on the second display, a third data for the first user on the second display, a fourth data for the second user on the second display, or any combination thereof.

At 333000, the surgical hub may send a message to a display, which may be a primary display and/or a secondary display. The message may instruct a display to show a display data. The display data may include contextual data, a format for showing data, an error message, instructions, medical instrument related data, the proximity of one or more devices, a warning that one or more devices may impact each other, a biometric data, a camera display, an image, a video, and the like.

In an example, a message may be sent to a display to show data that may be relevant to a surgical task being performed by a user. The data may be data for a medical instrument that is being used by the user. The message may instruct the display that is being viewed by the user to show the data for the medical instrument that is being used by the user.

In an example, the message may be sent to a display to show relevant data from contextual data for a user. The contextual data may be for a surgical task that may be performed by the user. The display may be determined according to where a user is viewing. The message may be sent to display to allow relevant data to be presented to the user on a display that a user is viewing while the user is performing a surgical task.

Figure 71:
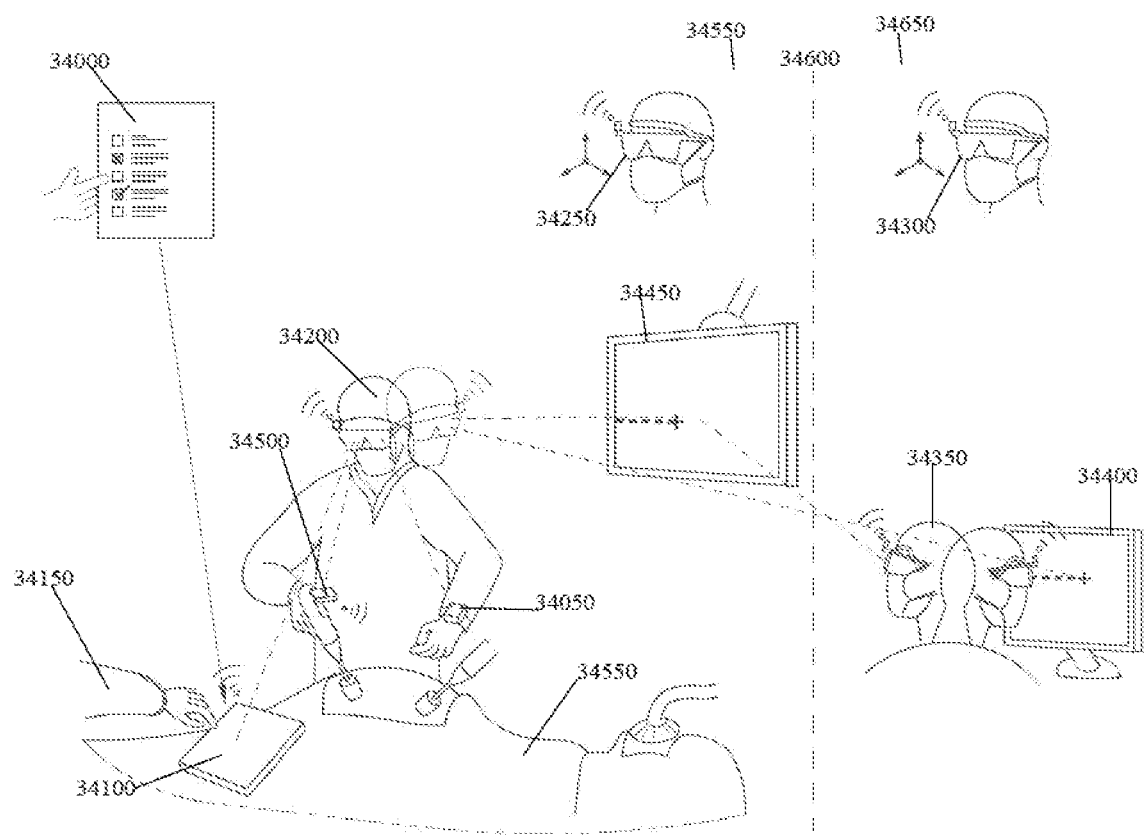
FIG. 71 shows a diagram illustrating one or more displays that may display information based on a visual focus of a user.

FIG. 71 shows a diagram illustrating one or more displays that may display information based on a visual focus of a user. During the surgery, an artificial barrier may be created around the patient to distinguish between a sterile field, such as sterile field 34550, and a nonsterile field, such as non-sterile field 34650. This barrier may be referred to as a sterile barrier, such as sterile barrier 34600. This may be done, for example, to protect the patient from infection. In during the preparation for surgery, health care providers may clean a patient (e.g. scrub a patient) to eliminate and/or minimize bacteria on the outside of a patient that may infect the patient during a surgery. Patient 34550 may be placed within sterile field 34550. Medical instruments within the sterile field 34550 may also be sterile. Items that are nonsterile may be excluded from the sterile field. For example, nonsterile items may be found in nonsterile field 34650.

Surgeon 34200 may scrub in before entering into sterile field 34550. Surgeon 34550 within sterile field 34550 may scrub in at a different level than surgical staff member 34350 that may be located in nonsterile field 34650. A medical instrument that may enter the sterile field may be cleaned at a different level than a medical instrument that may not be within the sterile field but may be within the operating room. For example, the medical instrument that may include secondary display 34500 May be within sterile field 34550 and may be cleaned at a different level than a medical instrument that may not be within the sterile field.

Surgeon 34200 within sterile field 34550 may avoid coming in contact with a nonsterile object or item. For example, surgeon 34200 may not be able to come in contact with surgical staff member 34350 in nonsterile field 34650. If surgeon 34200 comes in contact a nonsterile item, such as primary display 34400 located in nonsterile field 34650, surgeon 34200 may have to leave sterile field 34550 and rescrub in.

The head movement of surgeon 34200 may be tracked to determine where surgeon 34200 may be looking. This may be done, for example, to determine where surgeon 34220 may be looking, determine one or more displays that surgeon 34220 may be viewing, determine one or more displays within proximity to a line of sight or a visual focus of surgeon 34220, and the like. The head movement of surgeon 34200 may be tracked using safety glasses 34250. Safety glasses 34250 may include one or more sensors that may be used to generate geometric 3D data, which may be used to determine a line of sight for surgeon 34200 and/or the visual focus of surgeon 34200. Safety glasses 34250 may be safety glasses 6991 reference with respect to FIG. 29.

The head movement of surgical staff member 34350 may be tracked to determine where surgical staff member 34350 may be looking. This may be done, for example to determine where surgical staff member 34350 may be looking, determine one or more displays that surgical staff member 34350 may be viewing, determine one or more displays within proximity to a line of sight or a visual focus of surgical staff member 34350, and the like. The head movement of staff member 34350 may be track using safety glasses 34300. Safety glasses 34300 it may include one or more sensors that may be used to generate geometric 3D data, which may be used to determine a line of sight for surgical staff member 34350 and/or the visual focus of surgical member 34350. Safety glasses 34350 may be safety glasses 6991 with respect to FIG. 29.

Referring again to FIG. 71, a surgical hub may for displaying information on a display based on a visual focus of a user may be provided. The user may be surgeon 34200, surgical staff member 34350, and/or surgical staff member 34150.

The surgical hub may determine using data from safety glasses 34250 that one or more displays are within a visual focus of a user. The one or more displays may be primary display 34450, primary display 34400, secondary display 34050 that may be part of a wearable device, secondary display 34500 that may be part of a medical instrument, or secondary display 34100 that may be part of a tablet computing device.

The surgical hub may determine using data from safety glasses 34250 that the visual focus of surgeon 34200 may indicate that surgeon 34200 may be viewing primary display 34450. The surgical hub may determine a surgical task that is being performed by surgeon 34200. The surgical hub may determine contextual data associated with the surgical task, and the surgical hub may send a message to primary display 34450 that may instruct primary display 34450 to display the contextual data.

In an example, the surgical hub may determine using data from safety glasses 34250 that surgeon 34200 may have been viewing secondary display 34500 prior to displaying primary display 34450. The surgical hub may move contextual data from secondary display 34500 to primary display 34450 such that contextual data that may be relevant to a surgical task is within the visual focus of the surgeon.

The surgical hub may determine using data from safety glasses 34250 that the visual focus of surgeon 34200 may indicate that surgeon 34200 may be viewing primary display 34400. The surgical hub may determine contextual data related to a surgical task that may be performed by the surgeon and may display the contextual data at primary display 34400.

The surgical hub may determine using data from safety glasses 34250 that the visual focus of surgeon 34200 may indicate that surgeon 34200 may be viewing secondary display 34050. The surgical hub may determine that secondary display 34050 may belong to a wearable device that is on the surgeon. The surgical hub may determine contextual data that may be relevant to the surgeon when viewing the wearable device. For example, the surgical hub may show the surgeon data that may include a time, an elapsed time of the surgery, a message, biometric data for the patent, and the like.

The surgical hub may determine using data from safety glasses 34250 that the visual focus of surgeon 34200 may indicate that surgeon 34200 may be viewing secondary display 341000. The secondary display 341000 may be a tablet computing device. The surgical hub may display contextual data associated with a surgical task to be performed by the surgeon. For example, as shown at 34000, the surgical hub may instruct the secondary display 34200 to display a check list for the surgical task and/or instructions to assist surgeon 34200 in performing the surgical task. In another example, the surgical hub may display an image on secondary 34100 that may also be displayed on primary display 34400 to allow surgeon 342000 to control the image on primary display 34400, which is in nonsterile field 34650.

The surgical hub may determine using data from safety glasses 34250 that the visual focus of surgeon 34200 may indicate that surgeon 34200 may be viewing secondary display 34500. The secondary display 34500 may be part of a medical instrument. The surgical hub may instruct the secondary display 34500 to display contextual data associated with a surgical task to be performed using the medical instrument. For example, the surgical hot may instruct the medical instrument to display a status of the medical instrument.

The surgical hub may determine that at least two users may be viewing a display and may allow the display to be shared by instructing the display to display data for a first user and data for a second user. The surgical hub may determine a first visual focus for surgeon 34200 using data from safety glasses 34250. The surgical hub may determine a second visual focus for medical staff member 34350 using safety glasses 34300. The surgical hub may determine that the first visual focus for surgeon 34200 and the second visual focus for medical staff member 34350 may indicate that both surgeon 34200 and surgical staff member 34350 are viewing primary display 34450. The surgical hub may determine a first surgical task to be performed by surgeon 34200. The surgical hub may determine a second surgical task to be performed by surgical staff member 34350. The surgical hub may instruct primary display 34450 to display a first contextual data for surgeon 34200 and a second contextual data for surgeon 34350.

The surgical hub may determine that at least two users may be viewing a display and may allow the display to be shared by instructing the display to display data for a first user and data for a second user while prioritizing the data for the first user. The surgical hub may determine a first visual focus for surgeon 34200 using data from safety glasses 34250. The surgical hub may determine a second visual focus for medical staff member 34350 using safety glasses 34300. The surgical hub may determine that the first visual focus for surgeon 34200 and the second visual focus for medical staff member 34500 may indicate that both surgeon 34200 and surgical staff member 34350 are viewing primary display 34450. The surgical hub may determine that surgeon 34200 may have priority over surgical staff member 34350 based on at least one of a priority of data requested, a priority of surgical tasks being performed, a priority based on a hierarchy of users, and the like. The surgical hub may instruct primary display 34450 to display a first contextual data for surgeon 34200 and a second contextual data for surgeon 34350 while prioritizing the first contextual data. For example, the first contextual data may be allowed to take up more space of display 34450 than the second contextual data. As another example, the first contextual data may be displayed more prominently than the second contextual data.

The surgical hub may determine that a first user is viewing a display and that a second user has begun viewing the display. The surgical hub may determine that surgical staff member 34150 may be viewing secondary display 34100 and that secondary display may be displaying a first contextual data for surgical staff member 34150. The surgical hub may determine that surgeon 34200 may be viewing secondary display 34100. The surgical hub may determine that surgeon 34200 may have priority over surgical staff member 34150. The surgical hub may determine that surgeon 34200 may have priority over surgical staff member 34150 based on at least one of a priority of data requested, a priority of surgical tasks being performed, a priority based on a hierarchy of users, and the like. The surgical hub may determine that a second contextual data for surgeon 34200 may have priority over the first contextual data. The surgical hub may instruct secondary display 34100 to remove the first contextual data and/or to stop displaying the first contextual data. The surgical hub may instruct secondary display 34100 to display the second contextual data.

The surgical hub may determine that a first user is viewing a display and that a second user has begun viewing the display. The surgical hub may determine that surgical staff member 34150 may be viewing secondary display 34100 and that secondary display may be displaying a contextual data for surgical staff member 34150. The surgical hub may determine that surgeon 34200 may be viewing secondary display 34100. The surgical hub may determine that the contextual data should continue to be displayed, determine that the surgeon 34200 may wish to view the contextual data, determining that the surgeon 34200 may be reviewing the contextual data, determine that the contextual data may be relevant to the surgeon 34200 based on a surgical task that surgeon 34200 may be performing, or determine that a user has requested to keep the contextual data on the secondary display 34100. The surgical hub may send a message instructing the secondary display 34100 to display the contextual data, or the surgical hub may prevent sending a message to the secondary display 34100 that may cause the secondary display 34100 to stop displaying the contextual data.

The surgical hub may determine that a first user and a second user is viewing a display and may provide priority to the first user based on the priority of data for the first user. The surgical hub may determine a first visual focus for surgeon 34200 using data from safety glasses 34250. The surgical hub may determine a second visual focus for medical staff member 34350 using safety glasses 34300. The surgical hub may determine that the first visual focus may indicate that surgeon 34200 may be viewing primary display 34400. The surgical hub may determine that the second visual focus indicates that surgical staff member 34350 may be viewing primary display 34400. The surgical hub may determine a first contextual data for surgeon 34200 based on a surgical task to be performed by surgeon 34200. The surgical hub may determine a second contextual data for surgical staff member 34350 based on a surgical task to be performed by surgical staff member 34350. The surgical hub may determine that the first contextual data has a higher priority than the second surgical data based on at least one of the contextual data, the surgical tasks performed, an importance of the data, an error detection, and the like. The surgical hub may instruct primary display 34400 to display the first contextual data.

The surgical hub may determine that a user may be viewing one or more displays. The surgical hub may determine a visual focus of surgeon 34200 using data from safety 34250. The surgical hub may determine that secondary display 34500 and secondary display 34100 may be within the visual focus of surgeon 34200. In an example, the surgical hub may determine a contextual data for surgeon 34200 based on a surgical task to be performed by surgeon 34200. The surgical hub may send a message instructing secondary display 34500 to display the contextual data and/or may send a message instructing secondary display 34100 to display the contextual data. In another example, the surgical hub may determine a first contextual data based on the surgical task and a second contextual data based on the surgical task. The surgical hub may send a first message instructing secondary display 34500 to display the first contextual data and may send a second message instructing secondary display 34100 to display a second contextual data.

The surgical hub may determine that a user may be viewing one or more displays. The surgical hub may determine a visual focus of surgeon 34200 using data from safety glasses 34250. The surgical hub may determine that primary display 34450 and primary display 34400 may be within the visual focus of surgeon 34200. In an example, the surgical hub may determine a contextual data for surgeon 34200 based on a surgical task to be performed by surgeon 34200. The surgical hub may send a message instructing primary display 34450 to display the contextual data and/or may send a message instructing primary display 34400 to display the contextual data. In another example, the surgical hub may determine a first contextual context data based on the surgical task and a second contextual data based on the surgical task. The surgical hub may send a first message instructing primary display 344500 to display the first contextual data. The surgical hub may send a second message instructing primary display 34350 to display the second contextual data.

The surgical hub may determine that a user of may be viewing one or more displays. The surgical hub may determine a visual focus of surgeon 34200 using data from safety glasses 34250. The surgical hub may determine that primary display 34450 and secondary display 34050 may be within the visual focus of surgeon 34200. In an example, the surgical hub may determine a contextual data for surgeon 34200 based on a surgical task to be performed by surgeon 34200. The surgical hub may send a message instructing primary display 34450 to display the contextual data and/or may send a message instructing secondary display 34050 to display the contextual data. In another example, the surgical hub may determine a first contextual data based on the surgical task and a second contextual data based on the surgical task. The surgical hub may send a first message instructing primary display 344500 to display the first contextual data. The surgical hub may send a second message instructing secondary display 34050 to display the second contextual data.

The surgical hub may determine that at least two users may be viewing one or more displays. The surgical hub may determine a visual focus of surgeon 34200 using data from safety glasses 34250. The surgical hub may determine a visual focus of surgical staff member 34350 from safety glasses 34300. The surgical hub may determine that primary display 34450 and primary display 34400 may be within the visual focus of surgeon 34200. The surgical hub may determine that primary display 34450 and primary display 34400 may be within the visual focus of surgical staff member 34350. Surgical hub may determine a first contextual data for surgeon 34200 based on a surgical task to be performed by surgeon 34200. The surgical hub may determine a second contextual data for surgical staff member 34350 based on a surgical task to be performed by surgical staff member 34350.

In an example, the surgical hub may determine that surgeon 34200 may be in a location that may be closer to primary display 34450. Surgical hub may determine that surgical staff member 34200 may be in a location that may be closer to primary display 34400. The surgical hub may send a first message instructing primary display 34450 to display the first contextual data. The surgical hub may send a second message instructing primary display 34400 to display the second contextual data.

In an example, the surgical hub may determine that surgeon 34200 may have priority over surgical staff member 34350. The surgical hub may send a first message instructing primary display 34450 to display the first contextual data. The surgical hub may send a second message instructing primary display 34400 to display the second contextual data.

In an example, the surgical hub may determine that the first contextual data may have priority over the second contextual data. The surgical hub may send a first message instructing primary display 34450 to display the first contextual data. The surgical hub may send a second message instructing primary display 34400 to display the second contextual data.

The surgical hub may determine that at least two users may be viewing one or more displays. The surgical hub may determine a visual focus of surgeon 34200 using data from safety glasses 34250. The surgical hub may determine a visual focus of surgical staff member 34350 from safety glasses. The surgical hub may determine that secondary display 34500 and secondary display 34100 may be within the visual focus of surgeon 34200. The surgical hub may determine that secondary display 34500 and secondary display 34100 may be within the visual focus of surgical staff member 34150. Surgical hub may determine a first contextual data for surgeon 34200 based on a surgical task to be performed by surgeon 34200. The surgical hub may determine a second contextual data for surgical staff member 34150 based on a surgical task to be performed by surgical staff member 34150. The surgical hub may determine that surgeon 34200 may be using the medical instrument associated with secondary display 34500. The medical hub may determine that surgical medical staff member 34100 may be using the device associated with secondary display 34100. The surgical hub may send a first message instructing secondary display 34500 to display the first contextual data. The surgical hub may send a second message instructing secondary display 34100 to display the second contextual data.

Figure 72:
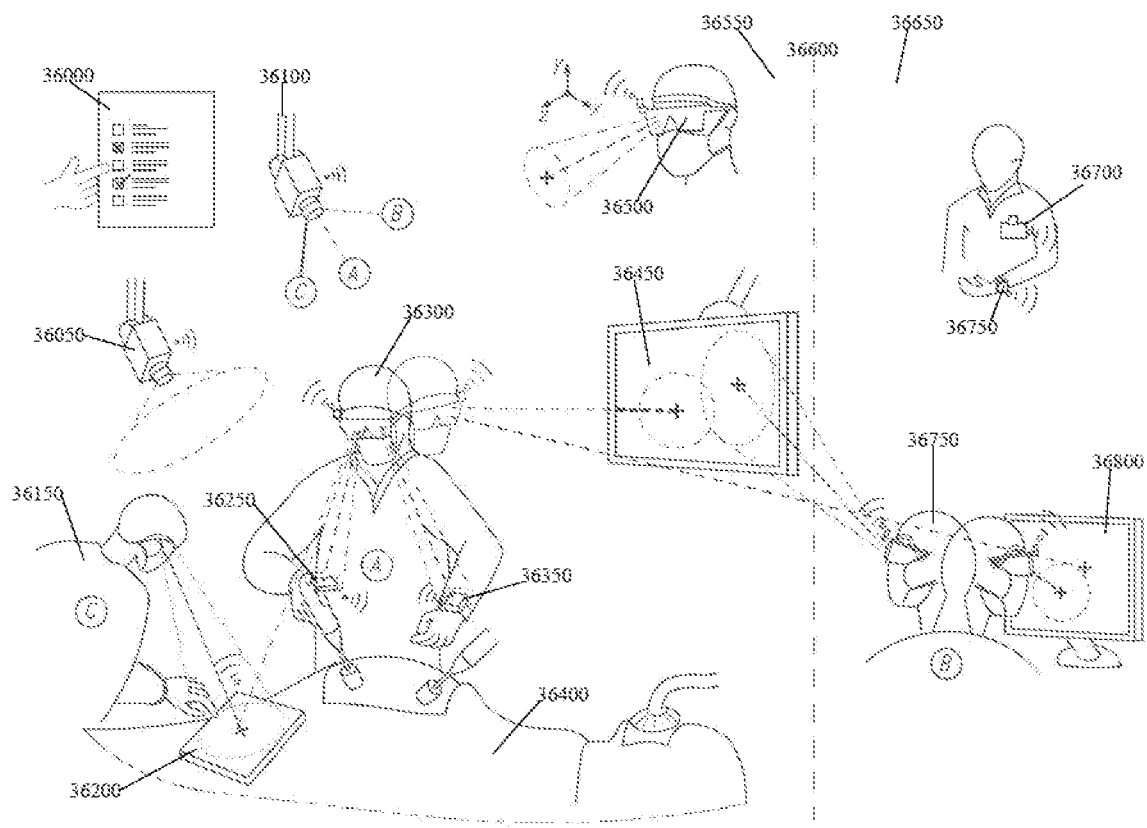
FIG. 72 shows a diagram illustrating one or more displays that may display information based on a visual focus of one or more users.

FIG. 72 shows a diagram illustrating one or more displays that may display information based on a visual focus of one or more users. During the surgery, an artificial barrier may be created around the patient to distinguish between a sterile field, such as sterile field 36550, and a nonsterile field, such as nonsterile field 36650. This barrier may be referred to as a sterile barrier, such as sterile barrier 36600. This may be done, for example, to protect the patient from infection. In preparation for surgery, health care providers may clean a patient (e.g. scrub a patient) to eliminate and/or minimize bacteria on the outside of a patient that may infect the patient during a surgery. Patient 36400 may be placed within sterile field 36550. Medical instruments within the sterile field 36550 may also be sterile. Items that are nonsterile may be excluded from the sterile field. For example, nonsterile items may be found in nonsterile field 36650.

Users within the OR may be identified. For example, the surgical hub may identify users with the OR using data from a wearable device, such as wearable device 36750; data from a RFID, such as RFID 36700 that may be embedded within an employee identification; images and/or video from a camera; data from safety glasses; data from a medical instrument; and the like.

A camera may be used by a surgical hub to identify the users within the OR. The camera may be camera 36100, camera 36050, and/or a camera within a safety glasses. Data, such as images and/or video, may be Received from the camera. The data may be analyzed by the surgical hub to identify one or more users. For example, the surgical hub may use artificial intelligence, and/or image processing algorithms to identify one or more users, such as surgeon 36300, As illustrated in FIG. 72, the surgical hub may identify and track users using camera 36100. For example, as indicated by "A", the surgical hub may have identified surgeon 3600 using camera 36100. As another example, as indicated by "B", the surgical hub may have identified surgical staff member 36750 using camera 36100. As another example, as indicated by "C", the surgical hub may have identified surgical staff member 36150.

The head movement of surgeon 36300 may be tracked to determine where surgeon 36300 may be looking. This may be done, for example, to determine where surgeon 36300 may be looking, determine one or more displays that surgeon 36300 may be viewing, determine one or more displays within proximity to a line of sight or a visual focus of surgeon 36300, and the like.

The head movement of surgeon 36300 may be tracked using safety glasses 36300. Safety glasses 34250 may include one or more sensors that may be used to generate geometric 3D data, which may be used to determine a line of sight for surgeon 36300 and/or the visual focus of surgeon 34200. Safety glasses 36500 may be safety glasses 6991 reference with respect to FIG. 29. Referring again to FIG. 72, safety glasses 36500 may include a camera. Safety glasses 36500 may use the camera to determine where surgeon 36300 may be looking and data from the camera included in safety glasses 36500 may be used to determine a visual focus of surgeon 36300. Safety glasses, similar to safety glasses 36500, may be used to track the head movement of medical staff member 36750 and/or medical staff member 36150.

The head movement of surgeon 36300 may be tracked using one or more cameras that may include camera 36100, camera 36050, and/or a camera within the safety glasses being worn by surgeon 36300. The camera bay be the cameras 211802 in FIG. 59. Referring again to FIG. 72, a camera may be oriented to capture images and/or video of the users within the OR such as surgical staff member 36159, surgeon 36300, and surgical staff member 36750. The camera may be used to visually analyze the techniques or physical characteristics of the users during the surgical procedure. The camera may be used to visually identify the users in the OR, visually track the users in the OR, visually identify medical instruments in the OR, and/or visually track medical instruments in the OR. For example, as indicated by "A", the surgical hub may identify and track surgeon 3600 using camera 36100. As another example, as indicated by "B", the surgical hub may identify and track surgical staff member 36750 using camera 36100. As another example, as indicated by "C", the surgical hub may identify and track surgical staff member 36150.

The surgical hub may determine data from a camera and/or safety glasses one or more displays are within a visual focus of a user. The one or more displays may be primary display 36450, primary display 36800, secondary display 36350 that may be part of a wearable device, secondary display 36250 that may be part of a medical instrument, or secondary display 36200 that may be part of a tablet computing device.

The surgical hub may determine using data from a camera and/or safety glasses that the visual focus of surgeon 36300 may indicate that surgeon 36300 may be viewing primary display 36450. For example, the surgical hub may receive one or more images from the camera, may analyze the one or more images to determine a visual focus of the surgeon 36300. The surgical hub may determine a surgical task that is being performed by surgeon 36300. The surgical hub may determine contextual data associated with the surgical task, and the surgical hub may send a message to primary display 36450 that may instruct primary display 36450 to display the contextual data.

In an example, the surgical hub may determine using data from a camera and/or safety glasses that surgeon 36300 may have been viewing secondary display 36250 prior to displaying primary display 36450. The surgical hub may move contextual data from secondary display 36250 to primary display 36450 such that contextual data that may be relevant to a surgical task is within the visual focus of the surgeon.

The surgical hub may determine using data from a camera and/or safety glasses that the visual focus of surgeon 36300 may indicate that surgeon 36300 may be viewing primary display 36800. The surgical hub may receive one or more images from camera 36100, may analyze the one or more images to determine a visual focus of the surgeon 36300. The surgical hub may determine contextual data related to a surgical task that may be performed by the surgeon and may display the contextual data at primary display 36800.

The surgical hub may determine using data from a camera and/or safety glasses that the visual focus of surgeon 36300 may indicate that surgeon 36300 may be viewing secondary display 36350. The surgical hub may receive one or more images from camera 36100, may analyze the one or more images to determine a visual focus of the surgeon 36300. The surgical hub may determine that the visual focus of surgeon 36300 indicates that surgeon 36300 may be viewing secondary display 36350. The surgical hub may determine that secondary display 36350 may belong to a wearable device that is on the surgeon. The surgical hub may determine contextual data that may be relevant to the surgeon when viewing the wearable device. For example, the surgical hub may show the surgeon data that may include a time, an elapsed time of the surgery, a message, biometric data for the patent, and the like.

The surgical hub may determine using data from a camera and/or safety glasses that the visual focus of surgeon 36300 may indicate that surgeon 36300 may be viewing secondary display 36200. The surgical hub may receive one or more images from camera 36100, may analyze the one or more images to determine a visual focus of the surgeon 36300. The visual focus of the surgeon 36300 may indicate that the surgeon is viewing the secondary display 362000. The secondary display 362000 may be a tablet computing device. The surgical hub may display contextual data associated with a surgical task to be performed by the surgeon. For example, as shown at 36000, the surgical hub may instruct the secondary display 36800 to display a check list for the surgical task and/or instructions to assist surgeon 36300 in performing the surgical task. In another example, the surgical hub may display an image on secondary 36200 that may also be displayed on primary display 36800 to allow surgeon 363000 to control the image on primary display 36800, which is in nonsterile field 36650.

The surgical hub may determine using data from a camera and/or safety glasses that the visual focus of surgeon 36300 may indicate that surgeon 36300 may be viewing secondary display 36250. The surgical hub may receive one or more images from camera 36100, may analyze the one or more images to determine a visual focus of the surgeon 36300. The visual focus of the surgeon 36300 may indicate that the surgeon 36300 may be viewing the secondary display 36250. The secondary display 36250 may be part of a medical instrument. The surgical hub may instruct the secondary display 36250 to display contextual data associated with a surgical task to be performed using the medical instrument. For example, the surgical hot may instruct the medical instrument to display a status of the medical instrument.

The surgical hub may determine that at least two users may be viewing a display and may allow the display to be shared by instructing the display to display data for a first user and data for a second user. The surgical hub may determine a first visual focus for surgeon 36300 using data from camera 36100 and/or a camera from the safety glasses. The surgical hub may determine a second visual focus for medical staff member 36750 using camera 36100 and/or a camera from the safety glasses. The surgical hub may determine that the first visual focus for surgeon 36300 and the second visual focus for medical staff member 36750 may indicate that both surgeon 36300 and surgical staff member 36750 are viewing primary display 36450. The surgical hub may determine a first surgical task to be performed by surgeon 36300. The surgical hub may determine a second surgical task to be performed by surgical staff member 36750. The surgical hub may instruct primary display 36450 to display a first contextual data for surgeon 36300 and a second contextual data for surgeon 36750.

The surgical hub may determine that at least two users may be viewing a display and may allow the display to be shared by instructing the display to display data for a first user and data for a second user while prioritizing the data for the first user. The surgical hub may determine a first visual focus for surgeon 36300 using data from camera 36100 and/or a safety glasses camera. The surgical hub may determine a second visual focus for medical staff member 36750 using data from camera 36100 and/or a safety glasses camera. The surgical hub may determine that the first visual focus for surgeon 36300 and the second visual focus for medical staff member 36250 may indicate that both surgeon 36300 and surgical staff member 36750 are viewing primary display 36450. The surgical hub may determine that surgeon 36300 may have priority over surgical staff member 36750 based on at least one of a priority of data requested, a priority of surgical tasks being performed, a priority based on a hierarchy of users, and the like. The surgical hub may instruct primary display 36450 to display a first contextual data for surgeon 36300 and a second contextual data for surgeon 36750 while prioritizing the first contextual data. For example, the first contextual data may be allowed to take up more space of display 36450 than the second contextual data. As another example, the first contextual data may be displayed more prominently than the second contextual data.

The surgical hub may determine that a first user is viewing a display and that a second user has begun viewing the display. The surgical hub may determine a first visual focus for surgical staff member 36150 using data from camera 36100 and/or a safety glasses camera. The surgical hub may determine a second visual focus for surgeon 36150 using data from camera 36100 and/or a safety glasses. The surgical hub may use the first visual focus to determine that surgical staff member 36150 may be viewing secondary display 36200. The surgical hub may determine that secondary display may be displaying a first contextual data for surgical staff member 36150. The surgical hub may use the second visual focus to determine that surgeon 36300 may be viewing secondary display 36200. The surgical hub may determine that surgeon 36300 may have priority over surgical staff member 36150. The surgical hub may determine that surgeon 36300 may have priority over surgical staff member 36150 based on at least one of a priority of data requested, a priority of surgical tasks being performed, a priority based on a hierarchy of users, and the like. The surgical hub may determine that a second contextual data for surgeon 36300 may have priority over the first contextual data. The surgical hub may instruct secondary display 36200 to remove the first contextual data and/or to stop displaying the first contextual data. The surgical hub may instruct secondary display 36200 to display the second contextual data.

The surgical hub may determine that a first user is viewing a display and that a second user has begun viewing the display. The surgical hub may determine a first visual focus for surgical staff member 36150 using data from camera 36100 and/or a safety glasses camera. The surgical hub may determine a second visual focus for surgeon 36150 using data from camera 36100 and/or a safety glasses. The surgical hub may use the first visual focus to determine that surgical staff member 36150 may be viewing secondary display 36200. The surgical hub may determine that secondary display 36200 may be displaying a contextual data for surgical staff member 36150. The surgical hub may use the second visual focus to determine that surgeon 36300 may be viewing secondary display 36200. The surgical hub may determine that the contextual data should continue to be displayed, determine that the surgeon 36300 may wish to view the contextual data, determining that the surgeon 36300 may be reviewing the contextual data, determine that the contextual data may be relevant to the surgeon 34200 based on a surgical task that surgeon 36300 may be performing, or determine that a user has requested to keep the contextual data on the secondary display 36200. The surgical hub may send a message instructing the secondary display 36200 to display the contextual data, or the surgical hub may prevent sending a message to the secondary display 36200 that may cause the secondary display 36200 to stop displaying the contextual data.

The surgical hub may determine that a first user and a second user is viewing a display and may provide priority to the first user based on the priority of data for the first user. The surgical hub may determine a first visual focus for surgeon 36300 using data from camera 36110 and/or safety glasses camera. The surgical hub may determine a second visual focus for medical staff member 36750 using data from camera 36100 and/or a safety glasses camera. The surgical hub may determine that the first visual focus may indicate that surgeon 36300 may be viewing primary display 36800. The surgical hub may determine that the second visual focus indicates that surgical staff member 36750 may be viewing primary display 36800. The surgical hub may determine a first contextual data for surgeon 36300 based on a surgical task to be performed by surgeon 36300. The surgical hub may determine a second contextual data for surgical staff member 36750 based on a surgical task to be performed by surgical staff member 36750. The surgical hub may determine that the first contextual data has a higher priority than the second surgical data based on at least one of the contextual data, the surgical tasks performed, an importance of the data, an error detection, and the like. The surgical hub may instruct primary display 36800 to display the first contextual data.

The surgical hub may determine that a user may be viewing one or more displays. The surgical hub may determine a visual focus of surgeon 36300 using data from camera 36100 and/or a safety glasses camera. The surgical hub may determine that secondary display 36250 and secondary display 36200 may be within the visual focus of surgeon 36300. In an example, the surgical hub may determine a contextual data for surgeon 36300 based on a surgical task to be performed by surgeon 36300. The surgical hub may send a message instructing secondary display 36250 to display the contextual data and/or may send a message instructing secondary display 36200 to display the contextual data. In another example, the surgical hub may determine a first contextual data based on the surgical task and a second contextual data based on the surgical task. The surgical hub may send a first message instructing secondary display 36250 to display the first contextual data and may send a second message instructing secondary display 36200 to display a second contextual data.

The surgical hub may determine that a user may be viewing one or more displays. The surgical hub may determine a visual focus of surgeon 36300 using data from camera 36100 and/or a safety glasses camera. The surgical hub may determine that primary display 36450 and primary display 36800 may be within the visual focus of surgeon 36300. In an example, the surgical hub may determine a contextual data for surgeon 36300 based on a surgical task to be performed by surgeon 36300. The surgical hub may send a message instructing primary display 36450 to display the contextual data and/or may send a message instructing primary display 36800 to display the contextual data. In another example, the surgical hub may determine a first contextual context data based on the surgical task and a second contextual data based on the surgical task. The surgical hub may send a first message instructing primary display 364500 to display the first contextual data. The surgical hub may send a second message instructing primary display 36750 to display the second contextual data.

The surgical hub may determine that a user of may be viewing one or more displays. The surgical hub may determine a visual focus of surgeon 36300 using data from camera 36100 and/or a safety glasses camera. The surgical hub may determine that primary display 36450 and secondary display 36350 may be within the visual focus of surgeon 36300. In an example, the surgical hub may determine a contextual data for surgeon 36300 based on a surgical task to be performed by surgeon 36300. The surgical hub may send a message instructing primary display 36450 to display the contextual data and/or may send a message instructing secondary display 36350 to display the contextual data. In another example, the surgical hub may determine a first contextual data based on the surgical task and a second contextual data based on the surgical task. The surgical hub may send a first message instructing primary display 364500 to display the first contextual data. The surgical hub may send a second message instructing secondary display 36350 to display the second contextual data.

The surgical hub may determine that at least two users may be viewing one or more displays. The surgical hub may determine a visual focus of surgeon 36300 using data from camera 36100 and/or a safety glasses camera. The surgical hub may determine a visual focus of surgical staff member 36750 using data from camera 36100 and/or a safety glasses camera. The surgical hub may determine that primary display 36450 and primary display 36800 may be within the visual focus of surgeon 36300. The surgical hub may determine that primary display 36450 and primary display 36800 may be within the visual focus of surgical staff member 36750. Surgical hub may determine a first contextual data for surgeon 36300 based on a surgical task to be performed by surgeon 36300. The surgical hub may determine a second contextual data for surgical staff member 36750 based on a surgical task to be performed by surgical staff member 36750.

In an example, the surgical hub may determine that surgeon 36300 may be in a location that may be closer to primary display 36450. Surgical hub may determine that surgical staff member 36300 may be in a location that may be closer to primary display 36800. The surgical hub may send a first message instructing primary display 36450 to display the first contextual data. The surgical hub may send a second message instructing primary display 36800 to display the second contextual data.

In an example, the surgical hub may determine that surgeon 36300 may have priority over surgical staff member 36750. The surgical hub may send a first message instructing primary display 36450 to display the first contextual data. The surgical hub may send a second message instructing primary display 36800 to display the second contextual data.

In an example, the surgical hub may determine that the first contextual data may have priority over the second contextual data. The surgical hub may send a first message instructing primary display 36450 to display the first contextual data. The surgical hub may send a second message instructing primary display 36800 to display the second contextual data.

The surgical hub may determine that at least two users may be viewing one or more displays. The surgical hub may determine a visual focus of surgeon 36300 using data from camera 36100 and/or a safety glasses camera. The surgical hub may determine a visual focus of surgical staff member 36750 using data from camera 36100 and/or a safety glasses camera. The surgical hub may determine that secondary display 36250 and secondary display 36200 may be within the visual focus of surgeon 36300. The surgical hub may determine that secondary display 36250 and secondary display 36200 may be within the visual focus of surgical staff member 36150. Surgical hub may determine a first contextual data for surgeon 36300 based on a surgical task to be performed by surgeon 36300. The surgical hub may determine a second contextual data for surgical staff member 36150 based on a surgical task to be performed by surgical staff member 36150. The surgical hub may determine that surgeon 36300 may be using the medical instrument associated with secondary display 36250. The medical hub may determine that surgical medical staff member 36200 may be using the device associated with secondary display 36200. The surgical hub may send a first message instructing secondary display 36250 to display the first contextual data. The surgical hub may send a second message instructing secondary display 36200 to display the second contextual data.

Superimposing, replacement, resizing of images resulting from a user instruction to move a display information onto another display may be provided. A medical instrument may monitor one or more instrument data, which may include an instrument parameter. The medical instrument may include a display, which may be a secondary display. The medical instrument may use the display to show one or more instrument data. The secondary display may show at least one of the one or more monitored instrument data prominently. For example, the secondary display may show at least one of the one or more instrument data more prominently than another instrument data. As another example, the medical instrument may prioritize the display of at least one of the one or more instrument data. As another example, the medical instrument may highlight at least one of the one or more instrument data. The secondary display may show the instrument data more prominently based on one or more of an instrument configuration (e.g. a current instrument configuration), contextual data, a surgical procedure, a surgical task (e.g. a surgical task that may be performed during a surgical procedure).

A user may instruct the medical instrument to not highlight, prioritize, and/or display prominently data on the display. A user may instruct the medical instrument to highlight, prioritize, and/or display prominently data on the display.

When a user may instruct the medical instrument to highlight, prioritize, and/or display prominently data on the display, the data may be become highlighted, prioritized, and/or displayed prominently data. For example, the user may select data being displayed on the medical instrument display. The selected data may be made larger, may be highlighted, may change in color, may be moved to a more prominent portion of the display, and the like. The data that was not selected by the user may become semi-transparent, may change in color, may be made smaller, moved to a less prominent portion of the display, and the like.

A user may request that the data be moved from a secondary display, which may be the medical instrument display, to a primary display and/or another secondary display. A device, such as a surgical hub and/or medical instruct, may determine that the user has requested the data to be moved to the primary and/or another secondary display using at least one of a voice command from the user, a gesture made by the user, an instruction via an interface, and the like. For example, a user may make a gesture, such as swiping data towards a display located within an OR, the surgical hub and/or medical instrument may detect the gesture, and a message may be sent to the display located within the OR to display the data.

Data selected by a user, which may be highlighted, prioritized, and/or displayed prominently, may be moved from a secondary display to another display, which may be a primary display and/or a secondary display. For example, a user may select data on a display of a medical instrument, which may be a secondary display, and may indicate that the data is to be moved to another display. The medical instrument and/or a surgical hub may determine the identity of another display and may send a message to another display to display the selected data. The selected data may be displayed and may or may not be highlighted, prioritized, and/or displayed prominently. For example, the selected data may be made larger, may be highlighted, may change in color, may be moved to a more prominent portion of the display, and the like. As another example, the selected data may become semi-transparent, may change in color, may be made smaller, moved to a less prominent portion of the display, and the like.

A user may actuate a control of the medical instrument. For example, the medical instrument may be a stapler and the user may actuate a control of the stapler that may cause the stapler to fire. As another example, user may touch a display that belongs to the medical instrument and the display may turn on, display data, and/or react to the user touch.

When user actuates a control of the medical instrument, the display of the medical instrument may display the data in a first format while displaying other data in a second format. The first format may cause data to be displayed more prominently than the data displayed using the second format.

A medical instrument and/or a surgical hub provide reconfiguration of a display and/or display sharing based on an actuation of a control, a user gesture, a user voice command, and the like. The user may be provided with a capability to display the data of interest on the display of choice. In an embodiment, the medical instrument and/or surgical hub may cause a display to display suggested data from contextual data and a user may be provided with a capability to override the suggested data and/or replace the suggested data with data preferred by the user. As disclosed herein, voice commands, gestures, or with tactile controls may be used to indicate which screen to display the data/status of the instrument currently being used.

One or more camera in the OR may be used to help monitor activities of staff. These cameras may be used to determine which device is being used by which user. Primary users may be identified by the cameras and/or sensed based on sensors worn by the user. Based on situational awareness of the procedure, device status, anticipated next step, and the like, the surgical hub and/or device displays the information that may be anticipated to useful (e.g. to be the most useful) and displays it on a screen. The user may to see additional or different information and may cause the instrument to display different information on the screen. For example, this may be accomplished with gestures. Using the cameras in the OR, motions from the lead user may be used to interpret swiping motions, selections, scrolling, and the like to control the flow on information. As another example, voice activated controls may be used to accomplish the same tasks. As another example, controls on a sterile instrument or sterile display, such as a secondary display (e.g., iPad), may be used for this control.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first data based on the surgical task may be determined. A command from the user that indicates a preference for a second data may be determined. The command may be one or more of a voice command, a gesture, and a tactile control command. A display data may be determined. The display data may include the first data and the second data and may provide priority to the second data over the first data. A message comprising instructions for a display to display the display data may be sent. The message may be sent to the display. The display and/or an identity of the display may be determined based on the command from the user that indicates the preference for the second data. The first data may be a first contextual data and the second data may be a second contextual data.

Determining the display data that includes the first data and the second data and provides priority to the second data over the first data may comprise a number of actions. For example, one or more of the following may be performed: superimposing the second data over the first data, replacing at least a portion of first data with at least a portion of the second data, and changing a size of an image associated with the first data or the second data. In an example, determine the display data that includes the first data and the second data and provides priority to the second data over the first data may comprise ensuring that the second data is more pronounced than the first data when displayed.

In an example, message may comprise one or more of an instruction to emphasize the second data when displaying the display data, an instruction to highlight the second data when displaying the display data, an instruction to decrease a first font size of the first data when displaying the display data, an instruction to increase a second font size of the second data when displaying the display data, an instruction to display the second data using a color when displaying the display data, an instruction to display the first data semi-transparently when displaying the data, an instruction to display the second data at a prominent location of the display when displaying the display data, instructions to display the first data at a first location of the display that is less prominent than a second location of the display. In an example, the message may comprise instructions to display the second data with a higher priority than the first data when displaying the display data.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first contextual data to be displayed on a first display may be determined. A command from a user may be determined. The command is one or more of a voice command, a command gesture, and a tactile control command. The command may indicate a preference for a second contextual data to be displayed on a second display.

In an example, a first message instructing the first display to display the first contextual data may be sent. A second message instructing the second display to display the second contextual data may be sent.

In an example, a second display may be determined from the command. It may be determined that the second contextual data is being displayed on the first display. A first message may be sent to the first display to remove the second contextual data from the first display. A second message may be sent to the second display to display the second contextual data.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first contextual data to be displayed on a first display may be determined. A command from a user may be determined. The command is one or more of a voice command, a command gesture, and a tactile control command. The command may indicate a preference for a second contextual data to be displayed on a second display. A visual focus of the user may be determined. It may be determined that the second display is within the visual focus of the user. A message instructing the second display to display the second contextual data may be sent.

In an example, the visual focus of the user by determined using one or more of wearable device data, sensor data associated with the user, an image from a camera within an operating room, and a video from the camera within the operating room.

A surgical hub and/or a medical instrument may be provided for configuring data to be displayed on a display. The surgical hub and/or medical instrument may comprise a memory and a processor. A surgical task that uses a medical instrument during a surgical procedure may be determined. A first contextual data to be displayed on a first display may be determined. A command from a user may be determined. The command is one or more of a voice command, a command gesture, and a tactile control command. The command may indicate a preference for a second contextual data to be displayed on a second display. An image or a video may be received from a camera. A geometric three-dimensional data may be generated from the image or the video. One or more of a head orientation for the user and a line of sight for the user using the geometric three-dimensional data may be determined. A visual focus of the user by using one or more of the head orientation for the user and the line of sight for the user may be determined. The second display may be determined using the visual focus. A message instructing the second display to display the second contextual data may be sent. It may be determined that the second display is displaying a third contextual data associated with a second user. The message may instruct the second display to remove the third contextual data and display the second contextual data.

Figure 73:
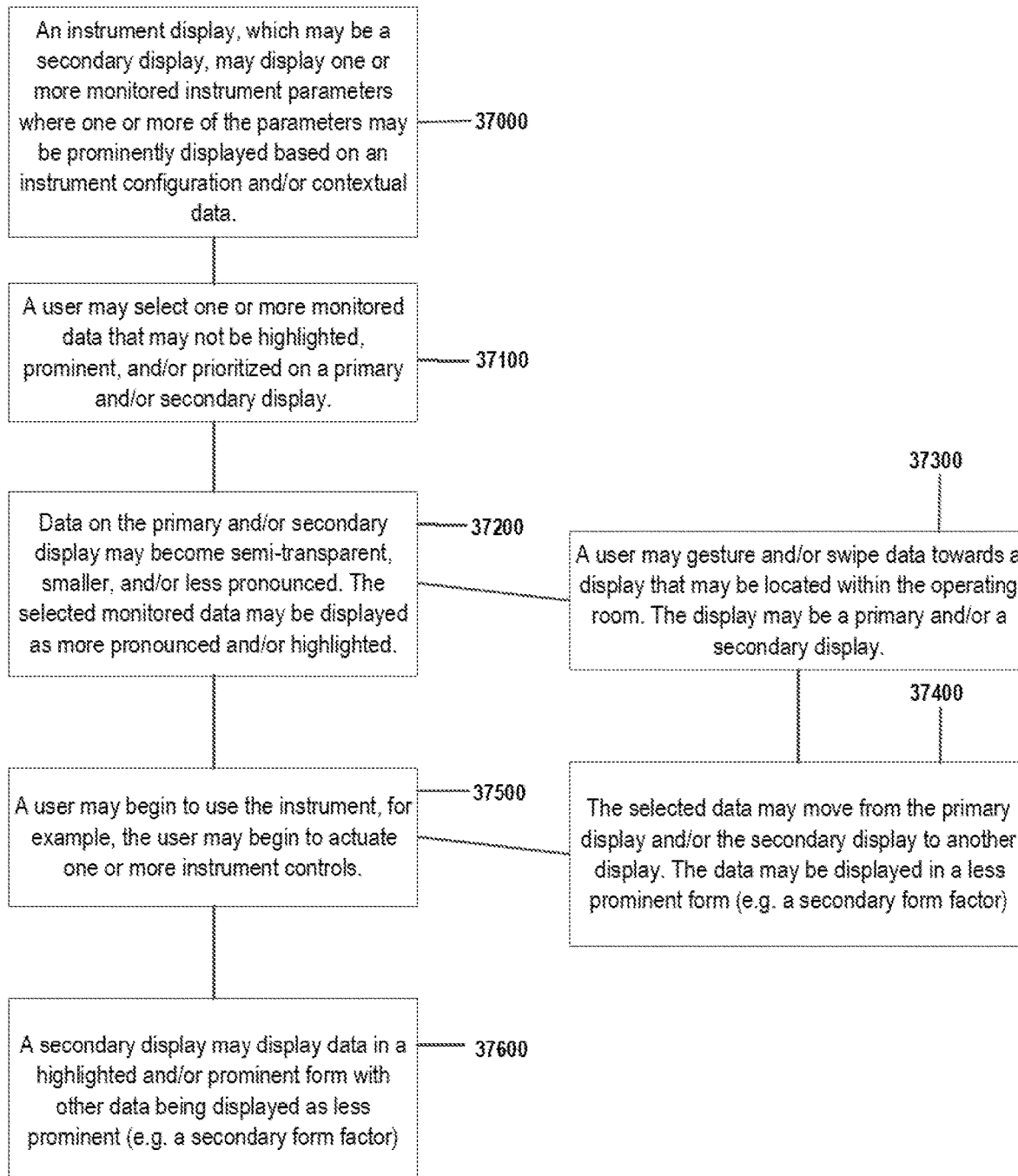
FIG. 73 is a logical flow diagram of a process for configuring data being displayed on a display.

FIG. 73 is a logical flow diagram of a process for configuring data being displayed on a display.

At 37000, an instrument display, which may be a secondary display, may display one or more instrument parameters. The instrument parameters may be medical instrument parameters. The instrument parameters may be monitored instrument parameters. For example, a user may identify one or more parameters that may be monitored by a surgical hub and/or a medical instrument. For example, a user may request that a force-to-fire for a stapler be monitored by the surgical hub, and the surgical hub may notify the user when a force to fire may be outside a range.

At 37000, a medical instrument parameter may be displayed more prominently based on an instrument configuration and/or a surgical instruction. The surgical hub may use contextual data to determine one or more parameters of a medical instrument that may be of interest to a user during a surgical task. The surgical task may be performed by a user during a surgical procedure. The surgical task may be performed by the user using the medical instrument during the surgical procedure.

The surgical hub may analyze contextual data to determine data that may be relevant to a user before or during this surgical task. The surgical hub may present the data to the user. For example, the surgical hub may send contextual data to a primary display and/or secondary display such that a user may view the contextual data. Surgical hub may choose to highlight, emphasize, or prioritize contextual data. For example, the surgical hub may determine that the contextual data may be highly relevant to a surgical task that a surgeon is performing and may choose to highlight the contextual data so that it may be easily viewable on a primary display. The contextual data may be a parameter related to the medical device, such as a forced to fire, a speed, an indication of a number of staples, and the like. The contextual data may be a parameter related to the patient such as biometric data, patient data from an EMR, and the like. The contextual data may include images and/or videos, such as medical images, X Rays, videos from a camera scope, and the like.

At 37100, a user may select one or more monitored data. The monitor data may be presented to the user on a primary display and/or a secondary display. The monitor data may not be highlighted, prominent, and/or prioritized on a primary and/or secondary display. For example, the surgical hub and/or a medical instrument may have analyzed contextual data and determined that a monitor data may not be a priority to a user. The user may still be interested in the monitor data and may wish to indicate that the monitor data should be made a priority. The user may select the monitored data and may indicate to a surgical hub and/or a medical device that the selected monitored data should be prioritized.

At 37200, data that may be displayed on a primary display end or a secondary display may become semitransparent, smaller, less pronounced, or less prioritized. It may be determined that data that may be presented to a user on a monitor may nor be a priority to the user. For example, a user may provide an indication that data that may not have been a priority should be made a priority. In an example, the user may select data that may not have been a priority to indicate that the data should be made a priority. The user may select the data using the secondary display, a gesture, a voice command, a control on a medical instrument, a visual focus, and the like.

The surgical hub and/or the medical device may determine that the user has selected data. The selected data may be prioritized on a primary display and/or secondary display. For example, the surgical hub may send a message to a primary display to instruct the primary display to highlight the selected data, to prioritize the selected data, or to make the selected data more prominent. As an example, the medical instrument may send a message to a secondary display to instruct the secondary display to highlight the selected data come up to prioritize the selected data or to make the selected data more prominent.

The surgical hub and/or the medical device may determine a format that may be applied to the selected data. The format may allow the selected data to appear more prominently on a display screen.

At 37300, a user may gesture and/or swipe selected data towards a display that may be located within an operating room period the display may be a primary display and/or secondary display. It may be determined that the gesture indicates that data should be moved from one display to a second display. For example, they may be determined that the user gesture may indicate that data that was selected on the secondary display should be moved to a primary display.

The gesture may be analyzed to determine a first display and a second. The first display may be a primary display and the second display may be a secondary display. For example, data may be moved from a display outside the sterile field to a display of a medical instrument inside the sterile field. The gesture may be analyzed to determine contextual data that is being displayed on the primary display. The gesture may be analyzed to determine the second display. For example, the gesture may indicate a direction where the second display may be located, and the direction may be analyzed to determine the identity of the second display such that the second screen display may be sent one or more instructions. The contextual data may be removed from the primary screen and sent to secondary screen using one or more messages. For example, a first message may be sent to the primary display to instruct the primary display to remove the data, and a second message may be sent to the secondary display to instruct the secondary display to display the data. As an example, the first message may instruct a display outside the sterile field to remove a video from a scope and the second message may instruct a display of a scope being used inside the sterile filed to display the video.

The gesture may be analyzed to determine a first display and a second display. The first display may be a first secondary display and the second display may be a second secondary display. For example, data may be moved from a wearable device to a tablet computing device. The gesture may be analyzed to determine contextual data that is being displayed on the first secondary display. The gesture may be analyzed to determine an identity of the second secondary display. For example, the gesture may indicate a line of sight for the surgeon, and the identity of the second secondary display may be determined using the line of sight such that second secondary display may be sent one or more instructions. The contextual data may be removed from the first secondary display and may be sent to the second secondary display using one or more message. For example, a first message may be sent to the first secondary display to instruct the first secondary display to remove the data, and a second message may be sent to the second secondary display to the instruct the second secondary display to display the data. As an example, the first message may instruct a wearable device to remove a heart rate that is being displayed on the wearable device and the second message may instruct a tablet computing device to display the heart rate.

The gesture may be analyzed to determine a first display and a second display. The first display may be a secondary display and the second display may be a primary display. For example, data may be moved from the secondary display to the tablet computing device. The gesture may be analyzed to determine contextual data that is being displayed on the secondary display. The gesture may be analyzed to determine an identity of the primary display. For example, the gesture may be a touch gesture toward an icon on the secondary display, and the gesture may indicate that data should be sent to the primary display associated with the icon. The contextual data may be removed from the secondary display and may be sent to the primary display using one or more message. For example, a first message may be sent to the secondary display to instruct the secondary display to remove the data, and a second message may be sent to the primary display to instruct the primary display to display the data. As an example, the first message may instruct a tablet computing device to remove a medical image that is being displayed and the second message may instruct a display outside of a sterile field to display the medical image.

At 37400, selected data may be moved between a first display and a second display. The first display may be primary display and/or a secondary display. The second display may be a primary display and/or a secondary display. The selected display may be displayed using a data format that may be a primary format that may emphasize the data, a secondary format that may deemphasize the data, and a standard format that may not emphasize or deemphasize the data.

A user may select data that is being displayed on the first display. The user may request that the data displayed on the first display also be displayed on the second display. The data may be contextual data. A message may be sent to the second display to instruct the second display to display the selected data. The selected data may be displayed on the first display and may be displayed on the second display. In an example, the selected data may be displayed on the first display using a secondary format to deemphasize the data and may be displayed on the second display using a primary format to emphasize the data. The selected data may be removed from the first display and may be displayed on the second display.

A user may select data that is being displayed on the second display. The user may request that data displayed on the second display also be displayed on the first display. The data may be contextual data. A message may be sent to the first display to instruct the first display to display the selected data. The selected data may be displayed on the first display and may be displayed on the second display. In an example, the selected data may be displayed on the second display using a secondary format to deemphasize the data and may be displayed on the first display using a primary format to emphasize the data. The selected data may be removed from the second display and may be displayed on the primary display.

At 37500, a user may begin to use a medical instrument. The surgical hub may determine that the user is using the medical instrument by determining that a control of the medical instrument has been actuated by a user. The surgical hub may receive data from the medical instrument and may send data indicating the usage of the medical instrument to one or more displays.

The medical instrument may determine that the user is using the medical instrument by determining that the control of the medical instrument has been actuated by a user. The medical instrument may send data related to the usage to a secondary display, which belong to the medical instrument. For example, the medical instrument may send data to a display off the medical instrument.

Usage of a medical instrument may be detected by another medical instrument. During a surgical task, a surgeon may be using a first medical instrument in a second medical instrument. The second medical instrument may detect that the surgeon is using the first medical instrument. For example, the second medical instrument may use a sensor to detect that the first medical instrument is nearby and/or in use. As another example, the second medical instrument may receive contextual data that may make the second medical instruments situationally aware, the situationally aware second medical instrument may perceive that the first medical instrument may be used. As another example, the second medical instrument may have a camera, may determine an image of the first medical instrument, and may determine that the first medical instrument may be used by the surgeon. As another example, the second medical instrument may receive data from a surgical hub that indicates that the first medical instrument may be used.

Usage of the medical instrument may be detected by the surgical hub using, for example, camera. The surgical hub may receive one or more images from the camera, which may be a camera that is located within an OR. The surgical hub may determine from the one or more images that a surgeon is performing a surgical task. The surgical help may determine from the one or more images that the medical instrument is being used for the surgical task. For example, the surgical hub may determine that the surgeon is holding the medical instruments and may be about two or may be performing the surgical task.

Usage of the medical instrument may be detected by the medical instrument using a sensor on the medical instrument. The medical instrument may determine a surgical task that may be performed. The medical instrument may have a sensor, such as the motion sensor, which may detect that it is being held by a surgeon.

Usage of the medical instrument may be detected by the medical instrument using a control of the medical instrument. Medical instrument may determine that a surgical task may be performed. The medical instrument may detect that one of its controls may be actuated by a user. For example, the medical instrument may detect that a surgeon actuated a control. As an example, the medical instrument may be a stapler, may detect that a surgeon actuated a control, and may fire a staple. As another example, the medical instrument may be an endo cutter, may detect that a surgeon activated a control, and may begin cutting. The medical instrument may send data to a surgical hub and/or another medical instrument to indicate that the medical instrument is being used.

At 37600, A secondary display may display data in a highlighted and/or prominent form with other data being displayed in a less prominent form. For example, data may be displayed using a data format that may be a primary format that may emphasize the data, a secondary format that may deemphasize the data, and a standard format that may not emphasize or deemphasize the data.

When a use of a medical instrument is detected, the medical instrument and/or the surgical hub may instruct one or more displays to change the data that is being displayed based on the use of the medical instrument. The one or more displays may include a primary display and/or secondary display.

In an example, the use of a medical instrument may be detected, and the secondary display of the medical instrument may be instructed to Be reconfigured to display data that may be relevant to the surgical task. The secondary display may be displaying data, such as data that may be selected by user. The data may or may not be relevant to the surgical task. The data that is being displayed may be replaced by contextual data when the medical instrument is being used. For example, the medical instrument tray replaced data that is being displayed with contextual data when the medical instrument is being used by a surgeon to perform a surgical task.

In an example, the use of the medical instrument may be detected and data from a primary display may be moved to a secondary display. The secondary display may belong to a medical instrument. The secondary display may belong to the medical instrument that may be used by the surgeon to perform a surgical task. It may be determined that data that may be displayed on a primary display may be relevant to the surgeon. It may be determined that the data would be better displayed on the secondary display than the primary display, for example, to be more useful to the surgeon. A message may be sent to the primary display to remove the data from the primary display. A message may be sent to the secondary display to instruct the secondary display to display the data.

In an example, the use of the medical instrument may be detected and data from a secondary display may be moved to a primary display. The primary display may be outside of a sterile field. The secondary display may belong to a medical instrument that may be used by the surgeon to perform a surgical task. The secondary display may be within the sterile field. It may be determined that data that may be displayed on the secondary display may be relevant to the surgeon. It may be determined that the data would be better displayed on the primary display than the secondary display, for example, to be more useful to the surgeon. A message may be sent to the secondary display to remove the data from the secondary display. The message may be sent to the primary display to instruct the primary display to display the data. An example, the use of the medical instrument may be detected and data from a secondary display may be mirrored on a primary display.

In an example, the use of the medical instrument may be detected, and data may be emphasized on a display. For example, the display may be instructed to display the data using a primary format. The display may be instructed to display other data using a secondary format.

An example, the use of the medical instrument may be detected, and data may be shared on a display, such as a primary display and/or a secondary display. May be determined that a display that is within the visual focus of a surgeon may be showing data. Instead of removing data from the display and may be determined that it may be helpful to split the display such that existing data and the new data regarding the usage of the medical instrument may be displayed.

Control of a zoom and/or magnification of a selectable operation room display from within a sterile field or through a secondary display may be provided. A secondary display, which may belong to a medical instrument may show a status for the instrument and may show an icon. The icon may be link to one or more displays, which may be primary displays secondary displays. The icon may allow a user to connect to another display. For example, when a user touches the icon, the user may be able to connect to the other display and may be able to manipulate order more controls that belong to the other display. As another example, when a user touches the icon, the user may be able to issue one or more commands to the other display.

The user may indicate which display they may want to control period for example, a user may indicate which display they want to zoom in on. This may be done, for example, using a secondary display. The secondary display may be within a sterile field. The user may use the secondary display to zoom in on a data being displayed on another display, which may be outside the sterile filed (e.g. within a nonsterile filed) and may be a primary and/or secondary display.

User may indicate a focal point on a display that they may want to highlight. For example, a user may use a secondary display to indicate a focal point of another display, such as a primary and/or secondary display, that they wish to highlight. As another example, the user may use a secondary display to indicate that a data being displayed on a primary display should be highlighted, prioritized, zoomed in, zoomed out, and/or the like. As another example, the user may use a secondary display to indicate that a visual effect may be applied to a focal point on another display, which may be a primary and/or secondary display.

Finger motion tracking may be performed using the secondary display and may be used to highlight or zoom a size of the highlighted portion. For example, one or more gestures from a user, such as finger motion gestures, may be used to manipulate data being displayed on the secondary display and/or data being displayed on a primary display. A gesture from a user may indicate that a visual effect may be applied portion of a primary display, which may be outside of the sterile field. A gesture from a user may be determined from a secondary display and the gesture may indicate that a visual effect may be applied to a portion of a primary display. A visual effect may also be referred to as a display effect.

Finger motion tracking an or gesture tracking may be used to determine when a user is no longer interested in a highlighted area. When the user is no longer interested in the highlighted area, the display may return to a normal mode. For example, when the user is no longer interested in the highlighted area, a secondary display, which may belong to a medical instrument, may display data that reflects a status of the medical instrument. Determining when a user is no longer interested in a highlighted area may comprise determining a gesture, determining a finger motion, determining that a timer has expired, determining that a medical instrument has been activated, determining that a medical instrument actuator has been operated, determining that the medical instrument has been used, determined that a medical instrument may be used, determining that a visual focus of the user is no longer directed at the highlighted area, and the like.

The user may instruct a display to return to a size, such as an original size. The display may be a secondary display, which may belong to a medical instrument. When the user instructs the display to return to a size, the display may return to a normal mode. For example, when the user instructs the display to return to a size, the display may display data that reflects a status of the medical instrument.

A sterile controller may reside within a sterile field and may have a touchscreen, which may be a secondary display, that may be operated by one or more users within a sterile field. This sterile controller may be in communication with a surgical hub, one or more medical instruments, one or more primary screens, and one or more secondary screens. The controller may be used to control a nonsterile display within an operating room. For example, much like an iPad, icons may be used to access medical instruments and/or displays. For example, the control and flow of information to a primary display within a nonsterile field may be driven from within a sterile field. Operations such as zooming in on an image, making selections for topics, marking the recording for a particular event, and the like may be controlled from this interface. Communication with people outside of the OR may also be controlled by the controller. Communication from outside the OR may be controlled by the controller. Communication to those within the sterile field may be controlled by the controller.

Control of a display aspect of a display outside the sterile field from a device within the sterile field may be provided. A medical instrument with a display may be in in communication with a surgical hub, a primary display, and/or a secondary display that may allow the user to zoom into a portion of the instrument display. For example, the user may indicate to the instrument to zoom with a coupled finger motion. As another example, the user may select a portion of the data to be displayed. A finger gesture may be used to enable the data to be displayed on the primary display rather than the medical instrument display, which may be a secondary display. The gestural commands also provide the user with a way to return the medical instrument display to its multi-element data display. A gesture may also be used to rotate the instrument display with respect to a user.

A surgical hub and/or medical instrument for controlling a display outside a sterile field may be provided. The surgical hub and/or medical instrument may comprise a memory and a processor. A first message that instructs a first display that is located within the sterile field to display a first contextual data may be sent. A user gesture may be determined from a device associated with the first display. The user gesture may indicate that a second contextual data is to be displayed on a second display outside the sterile field. A second message that instructs the second display to show the second contextual data may be sent.

In an example, a visual effect to be applied to the second contextual data may be determined based on the user gesture. The second message may instruct (e.g. further instruct) the second display to apply the visual effect to the second contextual data. The visual effect may be one or more of a highlighting effect to be applied to the second contextual data, a zoom-in effect to be applied to the second contextual data, and a zoom-out effect to be applied to the second contextual data.

In an example, a focal display may be determined. The focal point may be a focal point on the second display that is being viewed by a user.

In an example, a visual focus of a user may be determined. It may be displayed that the second display is within the visual focus of the user. The visual focus of the user may be determined by using one or more of wearable device data, sensor data associated with the user, an image from a camera within an operating room, and a video from the camera within the operating room.

In an example, the second message may further instruct the second display to show the second contextual data using a visual effect at a focal point. The user gesture may be a first user gesture. A second user gesture may be determined. The second user gesture may indicate that the second contextual data is to be displayed on the second display without the visual effect. A third message may be sent. The third message may instruct the second display to show the second contextual data without the visual effect.

In an example, a second user gesture may be determined. The second user gesture may indicate that the second contextual data is to be removed from the second display. A third message may be sent. The third message may instruct the second display to stop displaying the second contextual data.

In an example, a second user gesture may be determined. The second user gesture may indicate that the second contextual data on the second display should be rotated. A third message may be sent. The third message may instruct the second display to rotate the second contextual data.

In an example, the first display may a secondary display. The second display may be a primary display.

A surgical hub and/or medical instrument may be provided. The surgical hub and/or the medical instrument may comprise a memory and a processor. The processor may be configured to perform a number of actions. A user gesture may be determined. The user gesture may indicate a visual effect to be applied to a focal point on the display that is outside the sterile field. A focal point may be determined. For example, the focal point on the display may be a place on the display that a user is viewing or focusing upon. The focal point on the display may be associated with a contextual data that may be displayed on the display. A second message may be sent. A second message may be sent to the display that may instruct the display to apply the visual effect to the contextual data at the focal point on the display that is outside the sterile field.

In an example, the visual effect may indicate one or more of a highlighting effect to be applied to the contextual data, a zooming in effect to be applied to the contextual data, and a zoom-out effect to be applied to the contextual data.

In an example, the focal point on the display may be determined. The focal point may be on the display that is outside the sterile field.

In an example, user gesture may be a gesture detected by a camera, a gesture detected by a motion sensor, a gesture detected by a touch screen, a gesture detected by a microphone (e.g. a voice command), and the like. The user gesture may be a pinch zoom-in gesture (e.g. a pinch open gesture) and the visual effect may be a zoom-in effect. The user gesture may be a pinch zoom-out gesture (e.g. a pinch close gesture) and the visual effect may be a zoom-out effect.

A surgical hub and/or a medical instrument for controlling a display outside a sterile field may be provided. The surgical hub and/or medical instrument may comprise a memory and a processor. A user gesture may be provided. The user gesture may indicate that a visual effect is to be applied to a focal point on the display that is outside the sterile field. The focal point on the display may be determined. The focal point on the display may be associated with a first display data and may be determined based on a contextual data. A second display data may be generated by applying the visual effect to the first display data. A second message may be sent. The second message may instruct the display to display the second display data.

In an example, the visual effect may be one or more of a highlighting effect to be applied to the second display data, a zoom-in effect to be applied to the second display data, and a zoom-out effect to be applied to the second display data.

In an example, a visual focus of a user may be determined. It may be determined that the focal point is within the visual focus of the user.

In an example, the first display data may be an image or video, and the user gesture may be a pinch zoom-in gesture. The second display data may be generated by applying the visual effect to the first display data by determining that the visual effect is a zoom-in effect and generating the second display data by zooming in on the image or video.

In an example, the first display data may be an image or video and the user gesture may be a pinch zoom-out gesture. The second display data may be generated by applying the visual effect to the first display data by determining that the visual effect is a zoom-out effect and generating the second display data by zooming out of the image or video.

In an example, the first display data may be an image or video and the user gesture may be a rotation gesture. The second display data may be generated by applying the visual effect to the first display data by determining that the visual effect is a rotation effect and generating the second display data by rotating the image or video.

Figure 74:
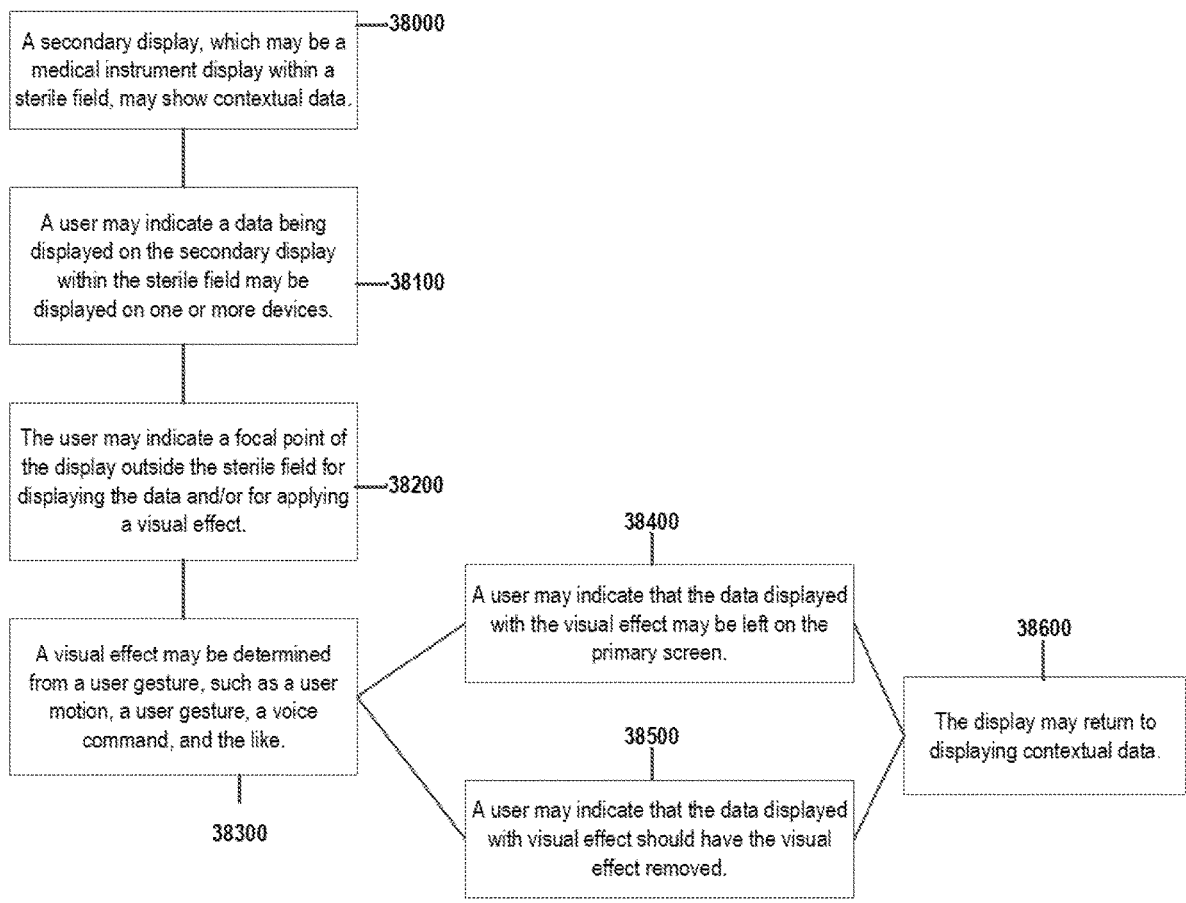
FIG. 74 is a logical flow diagram of a process for controlling a display that may be outside a sterile field.

FIG. 74 is a logical flow diagram of a process for controlling a display that may be outside a sterile field. During the surgery, an artificial barrier may be created around the patient to distinguish between a sterile field and a nonsterile field. This may be done, for example, to protect the patient from infection. In preparation for surgery, health care providers may clean a patient (e.g. scrub a patient) to eliminate and/or minimize bacteria on the outside of a patient that may infect the patient during a surgery. The patient may then be placed within the sterile field. Medical instruments within the sterile fields may also be sterile. Items that are nonsterile may be excluded from the sterile field.

A surgeon or nurse may scrub in before entering into the sterile field. The surgeon or nurse within the sterile field may scrub in at a different level than health care providers that may be outside the sterile field. A medical instrument that may enter the sterile field may be cleaned at a different level than a medical instrument that may not be within the sterile field but may be within the operating room.

A surgeon within the sterile fields may avoid coming in contact with a nonsterile object or item. For example, a surgeon may not be able to come in contact with a person in the nonsterile field. When a surgeon comes in contact with a person in or from the nonsterile field, the surgeon may have to leave the sterile field and rescrub in. As another example, a surgeon may not be able to come in contact with a medical instrument and/or display in the nonsterile field. If a surgeon comes in contact with the medical instrument and/or display in the nonsterile field, the surgeon may have to leave the sterile field and rescrub in. For example, if a surgeon touched a display in the nonsterile field to control the display, the surgeon would violate sterility and would have to rescrub in. It may be desirable to provide a surgeon in a sterile field with an ability to control one or more displays that may be outside the sterile field.

At 38000, a secondary display, which may be a display that belongs to a medical instrument and may be within a sterile field, may show contextual data. The contextual data may include an instrument status and the secondary display may show the instrument status. The contextual data may relate to a surgical task that may be performed.

A user may wish to send the contextual data to a primary display that may be outside the sterile field. This may be done, for example, to display the data on a display that may be larger than the secondary display.

At 38100, a user may indicate that data being displayed on the secondary display within the sterile field may be displayed on a display outside the sterile field. The display may be a primary display or another secondary display. The data may be contextual data. The user may select the data my interacting with the secondary display. For example, the user may touch the secondary display to select data that the user wants to send to the primary display. This may be possible within the sterile field as the secondary display is permitted within the sterile field without violating sterility.

When the user indicates that data on the secondary display may be displaced on the primary display, the secondary display or a device associated with the secondary display may send a message to the surgical hub. The device and/or the secondary display may be a tablet computing device, a medical instrument, and the like. The message may indicate that a user has selected data to be displayed on another display. The message may indicate the identity of the display to be used for displaying the selected data.

In an aspect, a surgical hub may receive a command that may indicate that data being displayed on the secondary display within the sterile field may be displayed on a display outside the sterile field. For example, the surgical hub may detect a hand gesture using a camera in the OR to determine that data should be sent to the primary display. In another example, the surgical hub may detect a voice command and determined that data should be sent to the primary display.

In an aspect, a medical instrument may determine that the user is indicating that data displayed on the secondary display within the sterile field may be displayed on a display outside the sterile field. For example, the medical instrument may include the secondary display medical display. The medical instrument may receive a command/or gesture from the user to send data to the primary display. The medical instrument may send a message to a surgical hub or may send a message to the primary display to indicate that selected data should be displayed on the primary display.

At 38200, the user may indicate a focal point of the display outside the sterile field for displaying the data and/or for applying a visual effect. The user may wish to have data shown at a focal point on a display that is outside the sterile field. The user may issue a command, touch the secondary display, or make a gesture to indicate the focal point of the display outside the sterile field. For example, the user may touch the secondary screen to indicate that data should be displayed at a focal point of the display outside the sterile field. As another example, the user may look at the display, and a surgical hub may determine, using a camera, that the user wishes to have the data displayed at the focal point on the display.

The focal point of the display may be a location of the primary display that a user may be interested in. For example, the focal point on the primary display may correlate to data being displayed on the primary display and may correlate to data on the secondary display. The user may use the secondary display to manipular the data at the focal point on the primary display, for example, by applying a visual effect to the data.

At 38200, the user may indicate that a visual effect may be applied to the focal point of the display outside the sterile field. A viewing data on the primary display may indicate, using a secondary display, that a visual effect at a focal point of the primary display may be applied. For example, surgeon may use a secondary display to indicate that a visual effect may be applied to a focal point of the primary display.

The secondary display may be mirroring an image being displayed on the primary display. The secondary display may allow the surgeon to use one or more gestures to manipulate the image being displayed on the primary display. The secondary display may allow the surgeon to indicate a focal point where a visual effect may be applied. For example, the surgeon may use the secondary display to rotate the image on the primary display. As another example, the surgeon may use a pinch gesture to zoom out of an image being displayed on a primary display such that the image on the primary display is zoomed out. As another example, the surgeon may use a pinch gesture to zoom in of an image being displayed on the primary display such that the image on the primary display is zoomed in. As another example, the surgeon may use the secondary display to select data that should be overlaid on an image that is being displayed on the primary display.

At 38300, a visual effect may be determined from a user gesture and may be applied to the focal point of the display outside the sterile field. Gesture tracking may be used to determine the visual effect to be applied to an image at a focal point. Gesture tracking may be used to determine a gesture made by a user. The gesture may be user motion, user gesture, voice command, and the like. The gesture may be made using a touch screen. The gesture may be detected using one or more images from a camera, such as a camera in the OR.

The gesture may be used to determine a visual effect that may be applied to a focal point of a display. For example, the gesture may be used to determine that a user may wish to zoom in on an image at a focal point on a primary display. The visual effect may be a zoom in effect, a zoom out effect, a rotation, a highlighting, an overlay of data, and the like. For example, the gesture may indicate that one or more images may be combined to produce an overlayed image, an enhanced image, and the like.

A user may indicate that a portion of the primary display may be zoomed in on and/or highlighted. During the surgery, the surgeon may be in the sterile field and may not be able to touch the primary display that may be in the nonsterile field. The surgeon being used a secondary display, which may be in a sterile field to control the primary display. The primary display may be showing an image. The surgeon may indicate that visual effect should be applied to a focal point on the primary display that may correlate to a portion of the image. For example, the surgeon may make a gesture on the secondary display that indicates that a portion of the image should be zoomed in on. The visual effect may be determined from the gesture and may be applied to the image.

In an example, the surgical hub may determine that the visual effect may be applied to the image and may send a message to the primary display to display the image with the visual effect. In an example, the surgical hub may generate an enhanced image by applying the visual effect to the image and may send the enhanced image to the primary display to display the image. In an example, the surgical hub may instruct the display to apply the visual effect to the portion of the image.

In an example, the medical instrument may determine that the visual effect may be applied to the image and may send a message to the primary display to display the image with the visual effect. In an example, the medical instrument may generate an enhanced image by applying the visual effect to the image and may send the enhanced image to the primary display to display the image. In an example, the medical instrument may instruct the display to apply the visual effect to the portion of the image.

At 38400, the user may view the data, such as an image, with the visual effect applied to the image on the primary screen. The user may indicate that the visual effect may remain applied to the image. For example, the user may use the secondary display to indicate to a surgical hub that the visual effect that has been applied to the image should continue to be applied to the image while the image is displayed on the primary screen. For example, this may allow the user to zoom into an area of an image and allow the image to remain zoomed in on. This may allow contextual data and/or images suggestions from the surgical hub to be overridden by the user selection. As another example, the surgeon may use the secondary display to overlay two images on to each other, may request that the overlaid images be left.

At 38500, the user may view the data, such as an image, with the visual effect applied on the primary screen. The user may indicate visual effects should be removed from the data. For example, the user may use the secondary display to indicate to a surgical hub that the visual effect that has been applied to the image should be removed. The surgical hub may send a message to the primary display that may return the image to a normal size and/or may display the image without a visual effect.

At 38600, the primary display may return to displaying contextual data. The contextual data may include data from a medical instrument, a status from a medical instrument, and the like. The primary display may be instructed to display the contextual data when it is determined that the user is using the medical instrument. For example, a user may be viewing a medical image, may zoom in on the medical image, may begin using a surgical stapler, and a primary display may be instructed to remove the medical image and to display contextual data related to the surgical image.

In an aspect, the primary display may return to displaying contextual data in response to a one or more of a user inputs, a predetermined time, a time threshold, a timer, an instrument actuation, and a user gesture. For example, a medical instrument and/or a surgical hub may set a timer and upon expiration of the timer, the medical instrument and/or the surgical hub may instruct the primary display to return to displaying contextual data.

The invention claimed is:

1. A surgical hub for controlling a display using situational awareness of a medical instrument, the surgical hub comprising:
   a memory; and
   a processor, the processor being configured to:
      determine a user, the medical instrument, and a location within an operating room;
      determine contextual data associated with the medical instrument based on the user, the medical instrument, and the location within the operating room; and send a display instruction to the display that instructs the display to be configured in accordance with the contextual data associated with the medical instrument, wherein the display is a primary display or a secondary display.

2. The surgical hub of claim 1, wherein the processor is further configured to determine a display content relating to the contextual data associated with the medical instrument.

3. The surgical hub of claim 2, wherein the display instruction further comprises the display content.

4. The surgical hub of claim 1, wherein the processor configured to determine the contextual data associated with the medical instrument based on the user, the medical instrument, and the location within the operating room by:
  determining that the medical instrument is at the location;
  determining that the user is beyond a threshold distance away from the location;
  determining that the location indicates that the medical instrument is to be powered off; and
  setting the display instruction to indicate that the medical instrument should be powered off.

5. The surgical hub of claim 4, wherein the display instruction to the display that instructs the display to be configured in accordance with the contextual data associated with the medical instrument causes the display to turn off or remove instrument data.

6. The surgical hub of claim 1, wherein the processor is configured to determine the contextual data associated with the medical instrument based on the user, the medical instrument, and the location within the operating room by:
  determining that the medical instrument and the user are within a threshold distance of the location;
  determining that the location indicates that the medical instrument is to be cleaned; and
  setting the display instruction to indicate that the medical instrument should be in a cleaning mode.

7. The surgical hub of claim 6, wherein the display instruction to the display that instructs the display to be configured in accordance with the contextual data associated with the medical instrument causes the display to provide the user with a cleaning instruction for the medical instrument.

8. The surgical hub of claim 1, wherein the medical instrument is a first medical instrument and wherein the processor is configured to determine the contextual data for the first medical instrument based on the user, the first medical instrument, and the location within the operating room by:
  determining that the first medical instrument, a second medical instrument, and the user are within a threshold distance of the location;
  determining that the user is exchanging the second medical instrument for the first medical instrument; and
  setting the display instruction to indicate that the second medical instrument is being exchanged with the first medical instrument.

9. The surgical hub of claim 8, wherein the display instruction to the display that instructs the display to be configured in accordance with the contextual data associated with the first medical instrument causes the display to remove a first instrument data associated with the first medical instrument and add a second instrument data associated with the second medical instrument.

10. The surgical hub of claim 9, wherein the contextual data is a first contextual data, the display instruction is a first display instruction, the display is a first display, and wherein the processor is further configured to:
  determine a second contextual data associated with the second medical instrument based on the user, the second medical instrument, and the location within the operating room; and
  send a second display instruction to a second display that instructs the second display to be configured in accordance with the second contextual data by turning off the second display or displaying at least one of a reloading instruction for the second medical instrument, a cleaning instruction for the second medical instrument, or a surgical instruction for using the second medical instrument.

11. The surgical hub of claim 9, wherein the display instruction is a first display instruction, and wherein the processor is further configured to send a second display instruction to the display that instructs the display to be configured in accordance with a contextual data of the second medical instrument.

12. The surgical hub of claim 1, wherein the user is a first user, and wherein the processor is configured to determine the contextual data for the medical instrument based on the first user, the medical instrument, and the location within the operating room by:
  determining that the medical instrument is being moved from a second user to the first user within a threshold distance of the location;
  determining that the location is near a patient; and
  setting the display instruction to indicate that the first user is controlling the medical instrument and that the medical instrument will be used to perform a task of a surgical procedure.

13. The surgical hub of claim 1, wherein the contextual data indicates that the user is controlling the medical instrument, and wherein the display instruction comprises an instruction that causes the display to show at least one of an instrument data, a medical instrument instruction, or a surgical procedure instruction.

14. The surgical hub of claim 1, wherein the contextual data indicates that the user is controlling the medical instrument, and wherein the display instruction comprises an instruction that causes the display to show instrument data based on at least one of an orientation of the medical instrument, a handedness of the user, or a level of inversion of the medical instrument.

15. The surgical hub of claim 1, wherein the processor is configured to determine the user, the medical instrument, and the location within the operating room using at least one of a camera, a sensor within the operating room, a sensor associated with the user, a sensor associated with the medical instrument, or a wearable device.

16. The surgical hub of claim 1, wherein the user is at least one of a patient, a health care provider, a doctor, a nurse, a scrub nurse, or a medical technician.

17. A method for a surgical hub to control a display using situational awareness of a medical instrument, the method comprising:
  determining a user, the medical instrument, and a location within an operating room;
  determining s-contextual data associated with the medical instrument based on the user, the medical instrument, and the location within the operating room; and
  sending a display instruction to the display that instructs the display to be configured in accordance with the contextual data associated with the medical instrument wherein the display is a primary display or a secondary display.

18. The method of claim 17, wherein the method further comprises determining a display content relating to the contextual data associated with the medical instrument.

19. The method of claim 18, wherein the display instruction further comprises the display content.

\* \* \* \* \*